(12) United States Patent
Daun et al.

(10) Patent No.: US 7,314,936 B2
(45) Date of Patent: *Jan. 1, 2008

(54) DEAZAPURINES AND USES THEREOF

(75) Inventors: Jane Daun, Dracut, MA (US); Heather A. Davis, Haverhill, MA (US); Bruce DeCosta, Salem, NH (US); Fabian Gusovsky, Andover, MA (US); Ieharu Hishinuma, Moriya (JP); Yimin Jiang, Londonderry, NH (US); Toshihiko Kaneko, Ushiku (JP); Kouichi Kikuchi, Tsuchiura (JP); Seiichi Kobayashi, Belmont, MA (US); André Lescarbeau, Somerville, MA (US); Xiang-Yi Li, Andover, MA (US); Kenzo Muramoto, Tsukuba (JP); Norihito Ohi, Ibaraki (JP); Marc Pesant, Andover, MA (US); Boris M. Seletsky, Andover, MA (US); Motohiro Soejima, Tsukuba (JP); Mark Spyvee, Hampstead, NH (US); Lynda Tremblay, Tewksbury, MA (US); Ye Yao, North Andover, MA (US); Hiromitsu Yokohama, Moriya (JP); Yan (Janet) Zhao, North Andover, MA (US); Wanjun Zheng, Londonderry, NH (US)

(73) Assignee: Eisai Co., Ltd., Tokyo (JP)

( * ) Notice: Subject to any disclaimer, the term of this patent is extended or adjusted under 35 U.S.C. 154(b) by 87 days.

This patent is subject to a terminal disclaimer.

(21) Appl. No.: 10/500,840
(22) PCT Filed: Jan. 7, 2003
(86) PCT No.: PCT/US03/00366

§ 371 (c)(1),
(2), (4) Date: Jan. 21, 2005

(87) PCT Pub. No.: WO03/057696

PCT Pub. Date: Jul. 17, 2003

(65) Prior Publication Data
US 2005/0124649 A1    Jun. 9, 2005

Related U.S. Application Data

(60) Provisional application No. 60/346,598, filed on Jan. 7, 2002.

(51) Int. Cl.
C07D 498/02 (2006.01)
C07D 513/02 (2006.01)
C07D 515/02 (2006.01)
C07D 471/02 (2006.01)

(52) U.S. Cl. .................................... 546/118
(58) Field of Classification Search ................ 546/118; 514/303
See application file for complete search history.

(56) References Cited

U.S. PATENT DOCUMENTS 3,891,660 A * 6/1975 Denzel et al. ............... 546/118
4,891,374 A   1/1990 Thorwart et al.
5,342,832 A   8/1994 Siren
5,360,794 A  11/1994 Arora
5,486,525 A   1/1996 Summers et al. ........... 514/303
5,492,915 A   2/1996 Dereu et al.
5,506,238 A   4/1996 Miyake et al. .............. 514/303
5,565,452 A  10/1996 Arndts et al.
5,632,991 A   5/1997 Gimbrone, Jr.
5,654,305 A   8/1997 Shepard et al. ............. 514/253
5,656,654 A   8/1997 Buzzetti et al.
5,880,141 A   3/1999 Tang et al.
5,981,536 A  11/1999 Mullner et al.
6,143,743 A  11/2000 Wilde et al. ................. 514/44
6,410,516 B1  6/2002 Baltimore et al. ....... 514/234.2
6,521,654 B2  2/2003 Wehner et al.
6,599,741 B1  7/2003 Hecker et al.
6,831,065 B2 12/2004 May et al.
RE39,464 E    1/2007 Cook et al.
2006/0194833 A1* 8/2006 Chase et al. ................ 514/303

FOREIGN PATENT DOCUMENTS

EP          0434405        6/1991

(Continued)

OTHER PUBLICATIONS

Krenitsky et al, Imidazo[4,5-c]pyridines (3-Deazapurines) and Their Nucleosides as Immunosuppressive and Antiinflammatory Agents, J. Med. Chem. 1986, 29, 138-143.*
International Search Report for PCT/US03/00366.

(Continued)

*Primary Examiner*—Janet Andres
*Assistant Examiner*—Niloofar Rahmani
(74) *Attorney, Agent, or Firm*—Myers Bigel Sibley & Sajovec, PA

(57) ABSTRACT

The present invention provides compounds having formula (I), wherein $R_1$, $R_2$, $R_3$ and n are as described generally and in classes and subclasses herein, and additionally provides pharmaceutical compositions thereof, and methods for the use thereof in the treatment of inflammatory or autoimmune and proliferative disorders and as inhibitors of cell adhesion molecule expression and inflammatory cytokine signal transduction generally

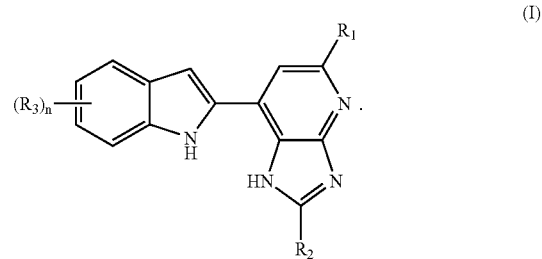

(I)

34 Claims, No Drawings

FOREIGN PATENT DOCUMENTS

| | | |
|---|---|---|
| EP | 0 945 422 A1 | 9/1999 |
| EP | 0 945 443 A1 | 9/1999 |
| EP | 0 399 731 B2 | 7/2001 |
| EP | 1 256 582 A1 | 11/2002 |
| WO | WO 99/01454 | 1/1999 |
| WO | WO 99/65909 | 12/1999 |
| WO | WO 00 76505 A1 | 12/2000 |
| WO | WO 01/00610 A1 | 1/2001 |
| WO | WO 01/30774 A1 | 5/2001 |
| WO | WO 01/30778 | 5/2001 |
| WO | WO 01/30778 A1 | 5/2001 |
| WO | WO 01/58900 | 8/2001 |

OTHER PUBLICATIONS

Abrahamsen, et al., "Cytokines and Bone Loss in a 5-Year Longitudinal Study—Hormone Replacement Therapy Suppresses Serum Soluble Interlukin-6 Receptor and Increases Interleukin-1-Receptor Antagonist: The Danish Osteoporosis Prevention Study" *Journal of Bone and Mineral Research*: 15 (8): 1545-1554, 2000.

Azuma, et al., "Tumor Necrosis Factor-α Induces Differentiation of and Bone Resorption by Osteoclasts" *Journal of Biological Chemistry* 275(7): 4858-4864, 2000.

Cain, et al., "p-38 MAPK Inhibition Decreases TNF-α Production and Enhances Postischemic Human Myocardial Function" *Journal of Surgical Research* 83 (1): 7-12, 1999.

Koyano, et al., "Effects of FR167653 on Ischemia-reperfusion Injury: Evaluation Through Preservation and Transplantation in Canine Hearts" *J. Heart Lung Transplant* 17 (12): 1247-54, 1998.

Souza, et al., "Effects of Inhibition of PDE4 and TNF-α On Local And Remote Injuries Following Ischaemia And Reperfusion Injury" *British Journal of Pharmacology* 134 (5): 985-994, 2001.

Abrahamsen, et al., "Cytokines and Bone Loss in a 5-Year Longitudinal Study—Hormone Replacement Therapy Suppresses Serum Soluble Interlukin-6 Receptor and Increases Interleukin-1-Receptor Antagonist: The Danish Osteoporosis Prevention Study" *Journal of Bone and Mineral Research* 15: 1545-1554, 2000.

Cain, et al., "p-38 MAPK Inhibition Decreases TNF-α Production and Enhances Postischemic Human Myocardial Function" *Journal of Surgical Research* 83: 7-12, 1999.

Koyano, et al., "Effects of FR167653 on Ischenia-reperfusion Injury: Evaluation Through Preservation and Transplantation in Canine Hearts" *J. Heart Lung Transplant* 17: 1247-54, 1998.

Souza, et al., "Effects of Inhibition of PDE4 and TNF-α On Local And Remote Injuries Following Ischaemia And Reperfusion Injury" *British Journal of Pharmacology* 134: 985-994, 2001.

International Search Report for Related International Application No. PCT/US2004/000293, Aug. 13, 2007.

Yusuf-Makagiansar et al. "Inhibition of LFA-1/ICAN-1 and VLA-4/VCAM-1 as a Therapeutic Approach to Inflammation and Autoimmune Diseases", *Med. Res. Rev.* 22(2):146-167 (2002).

Norton et al. "Expression of adhesion molecules in human intestinal graft-*versus*-host disease", *Clin. Exp. Immunol.* 87:231-236 (1992).

Brodt et al. "Liver Endothelial E-Selectin Mediates Carcinoma Cell Adhesion and Promotes Liver Metastasis", *Int. J. Cancer* 71:612-619 (1997).

Finzel et al. "ICAM-1 supports adhesion of human small-cell lung carcinoma to endothelial cells", *Clin. and Exp. Metastasis* 21:185-189 (2004).

Rosette et al. "Role of ICAM1 in invasion of human breast cancer cells", *Carcinogenesis* 26(5):943-950 (2005).

Tak et al. "NF-kB: a key role in inflammatory diseases", *J. Clin. Investigation* 107(1):7-11 (2001).

* cited by examiner

DEAZAPURINES AND USES THEREOF

RELATED APPLICATIONS

The present Application claims the benefit under 35 U.S.C. § 371 of International Application No.: PCT/US03/00366 (published PCT application No. WO 03/57696), filed Jan. 7. 2003, which claims priority to U.S. Patent Application No.: 60/346,598, filed Jan. 7, 2002, each of the above cited applications is incorporated herein by reference in its entirety.

BACKGROUND OF THE INVENTION

Inflammation is a process resulting from the dilation and increased permeability of blood vessels at site of injury or infection. Chemokines and cytokines released at the site increase the expression of cell surface proteins on endothelial cells, allowing circulating leukocytes to stick to the vessel wall and migrate to the site of injury/infection within the tissue. These cell surface proteins, termed "cell adhesion molecules" allow the interaction between the leukocytes and the endothelial cells, and mediate the migration of leukocytes into the tissue. Additionally, cell adhesion molecules are required for many of the cell-to-cell interactions in the inflammatory and immune responses. There are three classes of adhesion molecules: selectins, integrins and immunmoglobulin-related proteins which can be expressed on leukocytes and endothelial cells. Several of the adhesion molecules, including E-selectin and ICAM, are induced by cytokines such as IL-1 and TNF, and their expression is mediated by the transcriptional factor, NF-κB.

Sustained or inappropriate expression of adhesion molecules can lead to inflammatory or autoimmune disorders. Exaggerated expression of E-selectin and/or ICAM can result in chronic inflammation and has been associated with several inflammatory or autoimmune disorders. Therefore, inhibitors of cell adhesion molecules may be useful for the treatment of these diseases.

Inflammatory and autoimmune diseases are not well managed by current therapy and developments of better drugs are widely pursued. For example, rheumatoid arthritis is a state of chronic inflammation within the joint characterized by cartilage and bone destruction. Traditional therapies for inflammatory or autoimmune disease, such as rheumatoid arthritis, include nonsteroidal anti-inflammatory drugs and salicylates, gold compounds, hydroxychloroquine, sulfasalazine, corticosteroids, oral penicillamines, and cytotoxic or immunosuppressive drugs. However, many of these therapies are not always sufficiently effective and have resulted in serious side effects. More recently, injectable forms of TNFα neutralizing proteins have been successfully marketed for the treatment of rheumatoid arthritis and Crohn's Disease; however, an orally available inhibitor has not been developed for these inflammatory or autoimmune diseases.

Clearly, there remains a need to identify new classes of therapeutic agents for the treatment of inflammatory or autoimmune and proliferative diseases, preferably that are orally available, and are free of serious side effects. It would also be desirable to define new classes of therapeutic agents for the treatment of inflammatory or autoimmune and proliferative disorders in general.

SUMMARY OF THE INVENTION

As discussed above, there remains a need for the development of novel therapeutic agents useful for treating inflammatory or autoimmune and proliferative diseases. The present invention provides novel compounds of general formula (I),

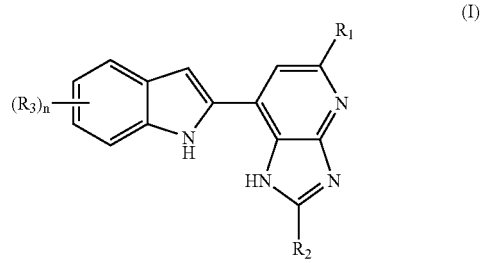

and pharmaceutical compositions thereof, as described generally and in classes and subclasses herein, as well as methods of making and using such compounds

DESCRIPTION OF CERTAIN PREFERRED EMBODIMENTS OF THE INVENTION

In recognition of the need to investigate and define new classes of therapeutic agents for the treatment of rheumatoid arthritis and other disorders (in certain embodiments, inflammatory or autoimmune and proliferative disorders), the present invention provides novel deazapurines and analogues thereof, as described in more detail herein, which are useful generally in the treatment of inflammatory or autoimmune and proliferative disorders. In certain embodiments, the compounds of the present invention can be used for the treatment of diseases and disorders including, but not limited to, rheumatoid arthritis, ulcerative colitis/Crohn's disease, central nervous system diseases (CNS) such as multiple sclerosis, systemic lupus erythematosus, asthma, allograft rejection/graft versus host disease (GVHD), psoriasis, atopic dermatitis, eczema, uticaria, allergic rhinitis, myasthenia gravis, diabetes, idiopathic thrombocytopenia purpura, glomerulonephritis, cardiovascular disease, and cancer.

1) General Description of Compounds of the Invention

The compounds of the invention include compounds of the general formula (I) (and tautomers thereof) as further defined below:

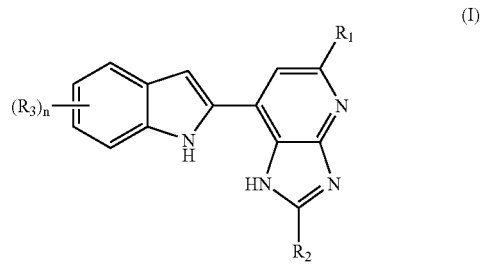

and pharmaceutically acceptable derivatives thereof;
wherein n is an integer from 0-4;
$R_1$ is hydrogen, —$NH_2$, —NHMe, —NHAc, —OH, F, —OMe, —CN, or —NH(C=O)OEt;

R$_2$ is hydrogen, —NR$_A$R$_B$, —OR$_A$, an aliphatic, heteroaliphatic, aryl, or heteroaryl moiety, wherein R$_A$ and R$_B$ are each independently hydrogen or an aliphatic, heteroaliphatic, aryl or heteroaryl moiety;

each occurrence of R$_3$ is independently hydrogen, halogen, cyano, or an aliphatic, heteroaliphatic, aryl or heteroaryl moiety, or a group -G-R$_C$, wherein G is absent or is —CH$_2$—, —NR$_D$—, —O—, or (C=O), and wherein R$_C$ is hydrogen, —NR$_F$R$_G$, —OR$_F$, —SR$_F$, or an aliphatic, heteroaliphatic, aryl, or heteroaryl moiety, wherein R$_D$, R$_F$ and R$_G$ are each independently hydrogen, —NR$_x$R$_y$, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein R$_D$ and R$_C$ or R$_F$ and R$_G$ taken together are a 3-, 4-, 5-, 6-, 7- or 8-membered substituted or unsubstituted cycloaliphatic or cycloheteroaliphatic moiety; wherein each occurrence of R$_x$ and R$_y$ is independently hydrogen, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein R$_x$ and R$_y$ taken together are a 4-, 5- or 6-membered substituted or unsubstituted, saturated or unsaturated cycloaliphatic or cycloheteroaliphatic moiety;

whereby each of the foregoing aliphatic or heteroaliphatic moieties may be independently substituted or unsubstituted, cyclic or acyclic, linear or branched, saturated or unsaturated and wherein each of the foregoing aryl or heteroaryl moieties may be independently substituted or unsubstituted.

In certain embodiments, the present invention defines certain classes of compounds which are of special interest. For example, one class of compounds of special interest includes those compounds substituted with two occurrences of R$_3$ in which the compound has the structure:

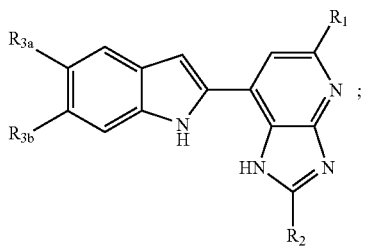

wherein R$_{3a}$ and R$_{3b}$ are each independently hydrogen, halogen, cyano, or an aliphatic, heteroaliphatic, aryl or heteroaryl moiety, or a group -G-R$_C$, wherein G is absent, —CH$_2$—, —NR$_D$—, —O—, or (C=O), and wherein R$_C$ is hydrogen, —NR$_F$R$_G$, —OR$_F$, —SR$_F$, or an aliphatic, heteroaliphatic, aryl, or heteroaryl moiety, wherein R$_D$, R$_F$ and R$_G$ are each independently hydrogen, —NR$_x$R$_y$, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein R$_D$ and R$_C$ or R$_F$ and R$_G$ taken together are a 3-, 4-, 5-, 6-, 7- or 8-membered substituted or unsubstituted cycloaliphatic or cycloheteroaliphatic moiety; wherein each occurrence of R$_x$ and R$_y$ is independently hydrogen, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein R$_x$ and R$_y$ taken together are a 4-, 5- or 6-membered substituted or unsubstituted, saturated or unsaturated cycloaliphatic or cycloheteroaliphatic moiety;

whereby each of the foregoing aliphatic or heteroaliphatic moieties may be independently substituted or unsubstituted, cyclic or acyclic, linear or branched, saturated or unsaturated; and wherein each of the foregoing aryl or heteroaryl moieties may be independently substituted or unsubstituted.

Another class of compounds of special interest comprises compounds having the structure:

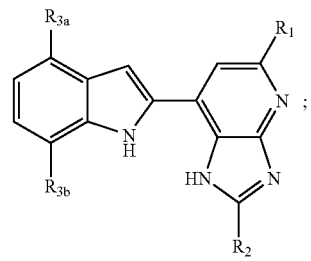

wherein R$_{3a}$ and R$_{3b}$ are each independently hydrogen, halogen, cyano, or an aliphatic, heteroaliphatic, aryl or heteroaryl moiety, or a group -G-R$_C$, wherein G is absent, —CH$_2$—, —NR$_D$—, —O—, or (C=O), and wherein R$_C$ is hydrogen, —NR$_F$R$_G$, —OR$_F$, —SR$_F$, or an aliphatic, heteroaliphatic, aryl, or heteroaryl moiety, wherein R$_D$, R$_F$ and R$_C$ are each independently hydrogen, —NR$_x$R$_y$, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein R$_D$ and R$_C$ or R$_F$ and R$_G$ taken together are a 3-, 4-, 5-, 6-, 7- or 8-membered substituted or unsubstituted cycloaliphatic or cycloheteroaliphatic moiety; wherein each occurrence of R$_x$ and R$_y$ is independently hydrogen, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein R$_x$ and R$_y$ taken together are a 4-, 5- or 6-membered substituted or unsubstituted, saturated or unsaturated cycloaliphatic or cycloheteroaliphatic moiety;

whereby each of the foregoing aliphatic or heteroaliphatic moieties may be independently substituted or unsubstituted, cyclic or acyclic, linear or branched, saturated or unsaturated; and wherein each of the foregoing aryl or heteroaryl moieties may be independently substituted or unsubstituted.

Another class of compounds of special interest comprises compounds having the structure of formula (I) in which R$_3$, is —CH$_2$NR$_F$R$_G$ and R$_{3b}$ is hydrogen and the compound has the structure:

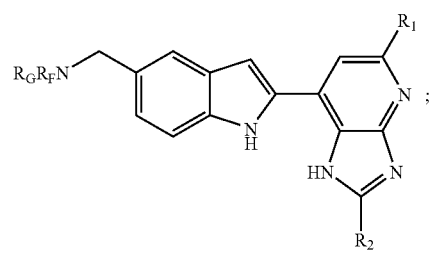

wherein R$_1$, R$_2$, R$_F$ and R$_G$ are as defined generally above and in classes and subclasses herein.

Another class of compounds of special interest comprises compounds having the structure of formula (I) in which $R_{3b}$ is —CH$_2$NR$_F$R$_G$ and $R_{3a}$ is hydrogen and the compound has the structure:

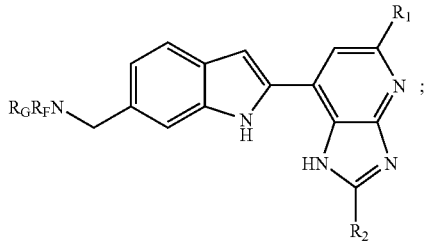

wherein $R_1$, $R_2$, $R_F$ and $R_G$ are as defined generally above and in classes and subclasses herein.

Another class of compounds of special interest comprises compounds having the structure of formula (I) in which $R_{3c}$, is —CH$_2$NR$_F$R$_G$, and $R_{3d}$ is hydrogen and the compound has the structure:

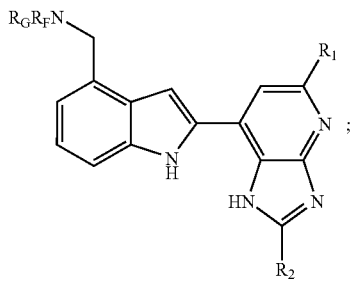

wherein $R_1$, $R_2$, $R_F$ and $R_G$ are as defined generally above and in classes and subclasses herein.

Another class of compounds of special interest comprises compounds having the structure of formula (I) in which $R_{3a}$ is —(CH=CH)$_q$CH$_2$(CH$_2$)$_r$NR$_F$R$_G$ and $R_{3b}$ is hydrogen and the compound has the structure:

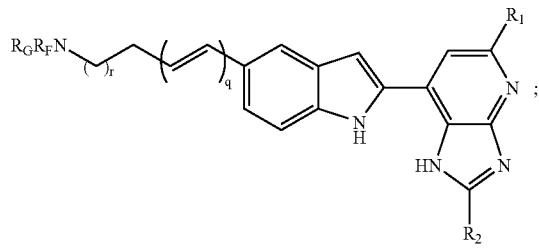

wherein q and r are each independently 0 or 1; and $R_1$, $R_2$, $R_F$ and $R_G$ are as defined generally above and in classes and subclasses herein.

Another class of compounds of special interest comprises compounds having the structure of formula (I) in which $R_{3a}$ is hydrogen and $R_{3b}$ is —(CH=CH)$_q$CH$_2$(CH$_2$)$_r$NR$_F$R$_G$ and the compound has the structure:

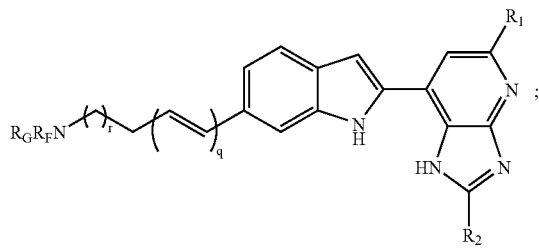

wherein q and r are each independently 0 or 1; and $R_1$, $R_2$, $R_F$ and $R_G$ are as defined generally above and in classes and subclasses herein.

Another class of compounds of special interest includes compounds having the structure of formula (I) in which $R_{3a}$ is —(C=O)NR$_F$R$_G$ and $R_{3b}$ is hydrogen and the compound has the structure:

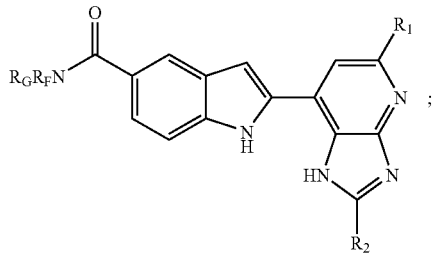

wherein $R_1$, $R_2$, $R_F$ and $R_G$ are as defined generally above and in classes and subclasses herein.

Another class of compounds of special interest includes compounds having the structure of formula (I) in which $R_{3b}$ is —(C=O)NR$_F$R$_G$ and $R_{3a}$ is hydrogen and the compound has the structure:

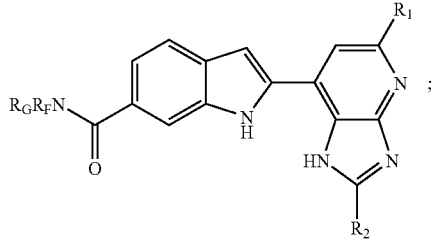

wherein $R_1$, $R_2$, $R_F$ and $R_G$ are as defined generally above and in classes and subclasses herein.

Another class of compounds of special interest comprises compounds having the structure of formula (I) in which $R_{3a}$ is —CH$_2$S(=O)$_m$NR$_F$R$_G$ and $R_{3b}$ is hydrogen and the compound has the structure:

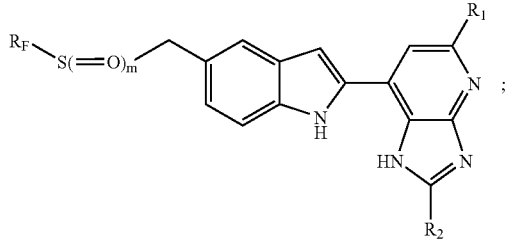

wherein $R_1$ and $R_2$ are as defined generally above and in classes and subclasses herein;

m is 0, 1 or 2; and $R_F$ is an aliphatic, cycloaliphatic, heteroaliphatic, cycloheteroaliphatic, aryl, or heteroaryl moiety;

whereby each of the foregoing aliphatic or heteroaliphatic moieties may be independently substituted or unsubstituted, cyclic or acyclic, linear or branched, saturated or unsaturated; and wherein each of the foregoing aryl or heteroaryl moieties may be independently substituted or unsubstituted.

Another class of compounds of special interest comprises compounds having the structure of formula (1) in which $R_{3a}$ is —$CH_2OR_F$ and $R_{3b}$ is hydrogen and the compound has the structure:

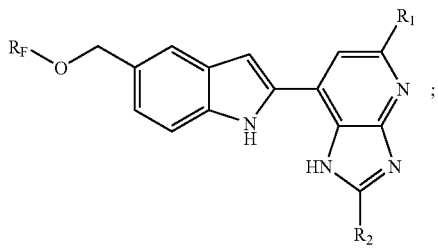

wherein $R_1$ and $R_2$ are as defined generally above and in classes and subclasses herein; and $R_F$ is hydrogen, a protective group or an aliphatic, cycloaliphatic, heteroaliphatic, cycloheteroaliphatic, aryl, or heteroaryl moiety;

whereby each of the foregoing aliphatic or heteroaliphatic moieties may be independently substituted or unsubstituted, cyclic or acyclic, linear or branched, saturated or unsaturated; and wherein each of the foregoing aryl or heteroaryl moieties may be independently substituted or unsubstituted.

A number of important subclasses of each of the foregoing classes deserve separate mention; these subclasses include subclasses of the foregoing classes in which:

i) $R_1$ is $NH_2$;
ii) $R_1$ is hydrogen;
iii) $R_1$ is NHMe;
iv) $R_1$ is NHAc;
v) $R_2$ is $NH_2$, OH, $C_1$-$C_6$ alkyl or $C_1$-$C_6$ alkenyl, said alkyl and alkenyl groups optionally substituted with halogen or hydroxyl;
vi) $R_2$ is $C_1$-$C_2$ alkyl;
vii) $R_2$ is methyl;
viii) $R_2$ is hydrogen;
ix) one of $R_F$ or $R_G$ is hydrogen or lower alkyl; and the other is an alkyl, heteroalkyl, aryl, heteroaryl, alkylaryl or alkylheteroaryl, optionally independently substituted for each occurrence with one or more of halogen, alkoxy, thioalkyl, or substituted or unsubstituted alkyl, heteroalkyl, aryl, or heteroaryl, or wherein $R_F$ and $R_G$ taken together are a 6-membered substituted or unsubstituted heterocyclic moiety;
x) one of $R_F$ or $R_G$ is hydrogen or lower alkyl; and the other is an aryl, heteroaryl, alkylaryl or alkylheteroaryl moiety, optionally independently substituted for each occurrence with one or more of halogen, alkoxy, thioalkyl, or substituted or unsubstituted alkyl, heteroalkyl, aryl, or heteroaryl, or wherein $R_F$ and $R_G$ taken together are a 6-membered substituted or unsubstituted cyclic or heterocyclic moiety;
xi) one of $R_F$ or $R_G$ is hydrogen or lower alkyl; and the other is phenyl, pyridyl, (alkyl)phenyl, or (alkyl)pyridyl, optionally substituted with one or more occurrences of halogen, trifluoromethoxy, methoxy, trifluoromethyl, methylthio, or substituted or unsubstituted lower alkyl, lower heteroalkyl, aryl or heteroaryl; and xii) one of $R_F$ or $R_G$ is hydrogen or lower alkyl; and the other is a cyclic or acyclic, linear or branched aliphatic moiety optionally substituted with one or more of substituted or unsubstituted aryl, heteroaryl, amide, alkoxy, hydroxyl, thioalkyl, thiol, acyl or amino;

xiii) $R_F$ is an alkyl, cycloalkyl, heteroalkyl, cycloheteroalkyl, aryl, heteroaryl, alkylaryl or alkylheteroaryl, optionally independently substituted for each occurrence with one or more of halogen, alkoxy, thioalkyl, or substituted or unsubstituted alkyl, heteroalkyl, aryl, or heteroaryl; and/or xiv) $R_F$ is hydrogen, a protecting group, or an alkyl, cycloalkyl, heteroalkyl, cycloheteroalkyl, aryl, heteroaryl, alkylaryl or alkylheteroaryl, optionally independently substituted for each occurrence with one or more of halogen, alkoxy, thioalkyl, or substituted or unsubstituted alkyl, heteroalkyl, aryl, or heteroaryl.

As the reader will appreciate, compounds of particular interest include, among others, those which share the attributes of one or more of the foregoing subclasses. Some of those subclasses are illustrated by the following sorts of compounds:

I) Compounds of the Formula (and Pharmaceutically Acceptable Derivatives Thereof):

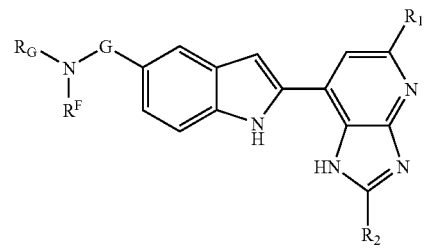

wherein $R_1$ and $R_2$ are as defined generically and in classes and subclasses herein; G is $CH_2$ or —(C=O) and one of $R_G$ or $R_F$ is hydrogen or lower allyl; and the other is an alkyl, heteroalkyl, aryl, heteroaryl, alkylaryl or alkylheteroaryl moiety, optionally independently substituted for each occurrence with one or more of halogen, alkoxy, thioalkyl, or substituted or unsubstituted alkyl, heteroalkyl, aryl, or heteroaryl, or wherein $R_F$ and $R_G$ taken together are a 3 to 8-membered substituted or unsubstituted cyclic or heterocyclic moiety.

In certain embodiments, one of $R_F$ or $R_G$, is hydrogen or lower alkyl; and the other is an aryl, heteroaryl, alkylaryl or alkylheteroaryl moiety, optionally independently substituted for each occurrence with one or more of halogen, alkoxy, thioalkyl, or substituted or unsubstituted alkyl, heteroalkyl, aryl, or heteroaryl, or wherein $R_F$ and $R_G$ taken together are a 3 to 8-membered substituted or unsubstituted cyclic or heterocyclic moiety.

In certain other embodiments, one of $R_F$ or $R_G$ is hydrogen or lower alkyl; and the other is phenyl, pyridyl, (alkyl)phenyl, or (alkyl)pyridyl, optionally substituted with one or more occurrences of halogen, trifluoromethoxy, methoxy, trifluoromethyl, methylthio, or substituted or unsubstituted lower alkyl, lower heteroalkyl, aryl or heteroaryl.

In still other embodiments, one of $R_F$ or $R_G$ is hydrogen or lower alkyl; and the other is a cyclic or acyclic, linear or branched aliphatic moiety optionally substituted with one or more of substituted or unsubstituted aryl, heteroaryl, amide, alkoxy, hydroxyl, thioalkyl, thiol, acyl or amino.

II) Compounds of the Formula (and Pharmaceutically Acceptable Derivatives Thereof):

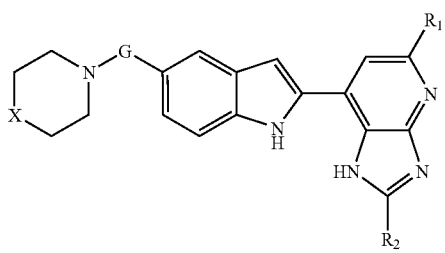

wherein $R_1$ and $R_2$ are as defined generically and in classes and subclasses herein; G is $CH_2$ or —(C=O) and X is O, S, C=O, S=O, C—$CR_4R_5$, $NR_4$, or $CR_4R_5$; wherein each occurrence of $R_4$ and $R_5$ is independently hydrogen, hydroxyl, halogen, cyano an aliphatic, heteroaliphatic, aryl, or heteroaryl moiety, or is an acyl moiety substituted with an aliphatic, heteroaliphatic, aryl or heteroaryl moiety;

whereby each of the foregoing aliphatic or heteroaliphatic moieties may be independently substituted or unsubstituted, cyclic or acyclic, linear or branched, and wherein each of the foregoing aryl or heteroaryl moieties may be independently substituted or unsubstituted.

III) Compounds of the Formula (and Pharmaceutically Acceptable Derivatives Thereof):

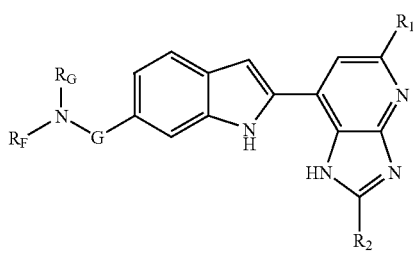

wherein $R_1$ and $R_2$ are as defined generically and in classes and subclasses herein; G is $CH_2$ or —(C=O) and one of $R_G$ or $R_F$ is hydrogen or lower all; and the other is an alkyl, heteroalkyl, aryl, heteroaryl, alkylaryl or alkylheteroaryl, optionally independently substituted for each occurrence with one or more of halogen, alkoxy, thioalkyl, or substituted or unsubstituted alkyl, heteroalkyl, aryl, or heteroaryl, or wherein $R_F$ and $R_G$ taken together are a 3 to 8-membered substituted or unsubstituted cyclic or heterocyclic moiety.

In certain embodiments, one of $R_F$ or $R_G$ is hydrogen or lower alkyl; and the other is an aryl, heteroaryl, alkylaryl or alkylheteroaryl moiety, optionally independently substituted for each occurrence with one or more of halogen, alkoxy, thioalkyl, or substituted or unsubstituted alkyl, heteroalkyl, aryl, or heteroaryl, or wherein $R_F$ and $R_G$ taken together are a 3 to 8-membered substituted or unsubstituted cyclic or heterocyclic moiety.

In certain other embodiments, one of $R_F$ or $R_G$ is hydrogen or lower alkyl; and the other is phenyl, pyridyl, (alkyl)phenyl, or (alkyl)pyridyl, optionally substituted with one or more occurrences of halogen, trifluoromethoxy, methoxy, trifluoromethyl, methylthio, or substituted or unsubstituted lower alkyl, lower heteroalkyl, aryl or heteroaryl.

In still other embodiments, one of $R_F$ or $R_G$ is hydrogen or lower alkyl; and the other is a cyclic or acyclic, linear or branched aliphatic moiety optionally substituted with one or more of substituted or unsubstituted aryl, heteroaryl, amide, alkoxy, hydroxyl, thioalkyl, thiol, acyl or amino.

IV) Compounds of the Formula (and Pharmaceutically Acceptable Derivatives Thereof):

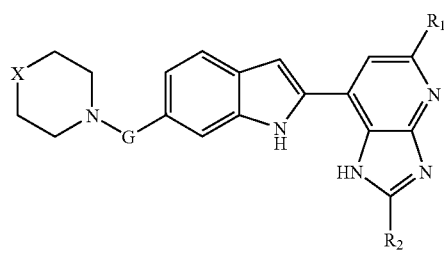

wherein $R_1$ and $R_2$ are as defined generically and in classes and subclasses herein; G is $CH_2$ or —(C=O) and X is O, S, C=O, S=O, C=$CR_4R_5$, $NR_4$, or $CR_4R_5$; wherein each occurrence of $R_4$ and $R_5$ is independently hydrogen, hydroxyl, halogen, cyano an aliphatic, heteroaliphatic, aryl, or heteroaryl moiety, or is an acyl moiety substituted with an aliphatic, heteroaliphatic, aryl or heteroaryl moiety;

whereby each of the foregoing aliphatic or heteroaliphatic moieties may be independently substituted or unsubstituted, cyclic or acyclic, linear or branched, and wherein each of the foregoing aryl or heteroaryl moieties may be independently substituted or unsubstituted.

V) Compounds of the Formula (and Pharmaceutically Acceptable Derivatives Thereof):

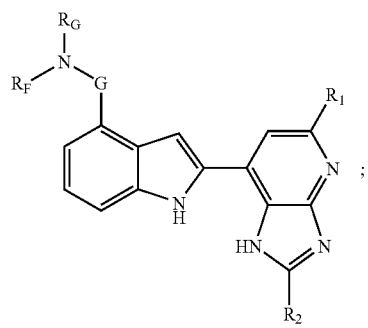

wherein $R_1$ and $R_2$ are as defined generically and in classes and subclasses herein; G is $CH_2$ or —(C=O) and one of $R_G$ or $R_F$ is hydrogen or lower alkyl; and the other is an alkyl, heteroalkyl, aryl, heteroaryl, alkylaryl or alkylheteroaryl, optionally independently substituted for each occurrence with one or more of halogen, alkoxy, thioalkyl, or substituted or unsubstituted alkyl, heteroalkyl, aryl, or heteroaryl, or wherein $R_F$ and $R_G$ taken together are a 3 to 8-membered substituted or unsubstituted cyclic or heterocyclic moiety.

In certain embodiments, one of $R_F$ or $R_G$ is hydrogen or lower alkyl; and the other is an aryl, heteroaryl, alkylaryl or alkylheteroaryl moiety, optionally independently substituted for each occurrence with one or more of halogen, alkoxy, thioalkyl, or substituted or unsubstituted alkyl, heteroalkyl, aryl, or heteroaryl, or wherein $R_F$ and $R_G$ taken together are a 3 to 8-membered substituted or unsubstituted cyclic or heterocyclic moiety.

In certain other embodiments, one of $R_F$ or $R_G$ is hydrogen or lower alkyl; and the other is phenyl, pyridyl, (alkyl) phenyl, or (alkyl)pyridyl, optionally substituted with one or more occurrences of halogen, trifluoromethoxy, methoxy, trifluoromethyl, methylthio, or substituted or unsubstituted lower alkyl, lower heteroalkyl, aryl or heteroaryl.

In still other embodiments, one of $R_F$ or $R_G$ is hydrogen or lower alkyl; and the other is a cyclic or acyclic, linear or branched aliphatic moiety optionally substituted with one or more of substituted or unsubstituted aryl, heteroaryl, amide, alkoxy, hydroxyl, thioalkyl, thiol, acyl or amino.

VI) Compounds of the Formula (and Pharmaceutically Acceptable Derivatives Thereof):

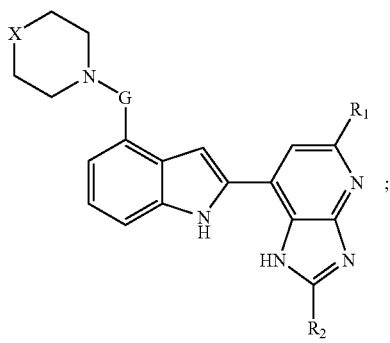

wherein $R_1$ and $R_2$ are as defined generically and in classes and subclasses herein; G is $CH_2$ or —(C=O) and X is O, S, C=O, S=O, C=$CR_4R_5$, $NR_4$, or $CR_4R_5$; wherein each occurrence of $R_4$ and $R_5$ is independently hydrogen, hydroxyl, halogen, cyano an aliphatic, heteroaliphatic, aryl, or heteroaryl moiety, or is an acyl moiety substituted with an aliphatic, heteroaliphatic, aryl or heteroaryl moiety;

whereby each of the foregoing aliphatic or heteroaliphatic moieties may be independently substituted or unsubstituted, cyclic or acyclic, linear or branched, and wherein each of the foregoing aryl or heteroaryl moieties may be independently-substituted or unsubstituted.

VII) Compounds of the Formula (and Pharmaceutically Acceptable Derivatives Thereof):

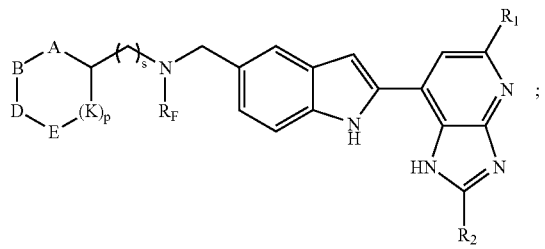

wherein $R_F$, $R_1$ and $R_2$ are as defined generically and in classes and subclasses herein; p is an integer from 0-3; s is an integer from 0-4; A, B, D, E and each occurrence of K are independently absent, O, S, C=O, S=O, C=$CR_4R_5$, $NR_4$, or $CR_4R_5$, wherein each occurrence of $R_4$ and $R_5$ is independently hydrogen, hydroxyl, halogen, cyano, —$OR_x$, —$SR_x$, —$NR_xR_y$, an aliphatic, heteroaliphatic, aryl, or heteroaryl moiety, or is an acyl moiety substituted with an aliphatic heteroaliphatic, aryl or heteroaryl moiety; and wherein A and B, B and D, D and E, E and K and any two adjacent K groups may be linked by a single or double bond as valency permits; wherein each occurrence of $R_x$ and $R_y$ is independently hydrogen, a protecting group, or an aliphatic, heteroaliphatic, aryl, heteroaryl, aliphaticaryl, heteroaliphatic aryl, aliphaticheteroaryl or heteroaliphaticheteroaryl moiety, whereby each of the foregoing aliphatic or heteroaliphatic moieties may be independently substituted or unsubstituted, cyclic or acyclic, linear or branched, saturated or unsaturated and wherein each of the foregoing aryl, heteroaryl aliphaticaryl, heteroaliphatic aryl, aliphaticheteroaryl or heteroaliphaticheteroaryl moieties may be independently substituted or unsubstituted.

In certain exemplary embodiments,

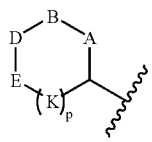

represents a substituted or unsubstituted phenyl, pyridyl or furanyl moiety. In certain other embodiments,

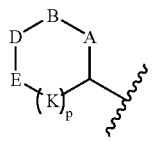

represents a substituted or unsubstituted, saturated or unsaturated 3-, 4-, 5-, 6-, 7-, or 8-membered cycloalkyl or cycloheteroalkyl moiety. In certain exemplary embodiments,

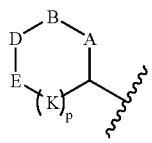

represents substituted or unsubstituted cyclopropyl, cyclobutyl, cyclopentyl, cyclohexyl, cycloheptyl or cyclooctyl. In certain exemplary embodiments,

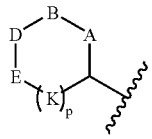

represents a substituted or unsubstituted bicyclic aliphatic moiety.

In certain exemplary embodiments, $R_F$ is hydrogen or lower alkyl. In certain embodiments, $R_F$ is hydrogen or methyl.

It will also be appreciated that for each of the subgroups I-VII described above, a variety of other subclasses are of special interest, including, but not limited to those classes described above i)-xiv) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, a mixture of stereoisomers or diastereomers are provided.

Additionally, any and all tautomers of the foregoing compounds are encompassed by the invention. The invention is not limited to the tautomeric structures depicted herein. As but one example, compounds described and depicted generally as:

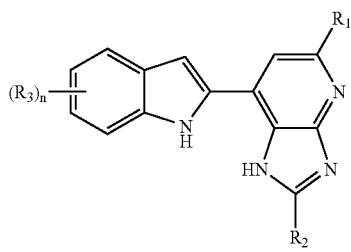

may also be described and depicted as:

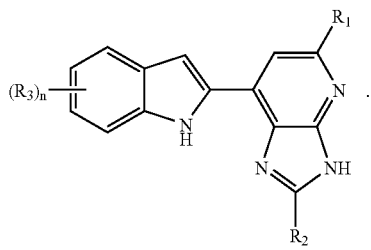

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared by using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

2) Compounds and Definitions

As discussed above, this invention provides novel compounds with a range of biological properties. Compounds of this invention have biological activities relevant for the treatment of inflammatory or autoimmune disorders and/or proliferative disorders. In certain embodiments, the compounds of the invention are useful for the treatment of rheumatoid arthritis, ulcerative colitis/Crohn's disease, central nervous system diseases (CNS) such as multiple sclerosis, systemic lupus erythematosus, asthma, allograft rejection/graft versus host disease (GVHD), psoriasis, atopic dermatitis, eczema, uticaria, allergic rhinitis, myasthenia gravis, diabetes, idiopathic thrombocytopenia purpura, glomerulonephritis, cardiovascular disease, and cancer.

Compounds of this invention include those specifically set forth above and described herein, and are illustrated in part by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety which is susceptible to removal in vivo yielding the parent molecule as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Certain compounds of the present invention, and definitions of specific functional groups are also described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", has used herein, it is meant that a particular functional moiety, e.g. O, S, or N, is temporarily blocked so that a reaction can be carried out selectively at another reactive site in a multi-functional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g. formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this: invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of inflammatory or autoimmune and proliferative disorders, including, but not limited to rheumatoid arthritis, psoriasis, asthma and cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —$CH_2$-cyclopropyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl-n, hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure NHR' wherein R' is alkyl, as defined herein. The term "aminoalkyl" refers to a group having the structure $NH_2R'$—, wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of sutstituents of the above-described aliphatic (and other) moieties of compounds of the invention include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. It will also be appreciated that aryl and heteroaryl moieties, as defined herein may be attached via an aliphatic, heteroaliphatic, alkyl or heteroalkyl moiety and thus also include -(aliphatic)aryl, -(heteroaliphatic)aryl, -(aliphatic)heteroaryl, -(heteroaliphatic) heteroaryl, alkyl)aryl, -(heteroalkyl)aryl, -(heteroalkyl)aryl, and -(heteroalkyl)heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and heteroalkyl)heteroaryl" are interchangeable. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl and the like. In certain embodiments of the present invention, the term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bycyclic aryl groups) can be unsubstituted or substituted, wherein substitution includes replacement of one, two or three of the hydrogen atoms thereon independently with any one or more of the following moieties including, but not limited to: aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted with substituents including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties which contain one or more oxygen sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN;

—$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —$C(O)R_x$; —$CO_2(R_x)$; —$CON(R_x)_2$; —$OC(O)R_x$; —$OCO_2R_x$; —$OCON(R_x)_2$; —$N(R_x)_2$; —$S(O)_2R_x$; —$NR_x(CO)R_x$ wherein each occurrence of $R_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substitutents described above and herein may be substituted or unsubstituted. Additional examples or generally applicable substituents are illustrated by the specific embodiments shown in the Examples which are described herein.

3) Research Uses, Formulation and Administration

According to the present invention, the inventive compounds may be assayed in any of the available assays known in the art for identifying compounds having a pre-determined biological activity. For example, the assay may be cellular or non-cellular, in vivo or ill vitro, high- or low-throughput format, etc. In certain exemplary embodiments, the inventive compounds are tested in assays to identify those compounds having antiproliferative/anticancer activity, inflammatory cytokine signaling pathway inhibitory activity, adhesion molecule expression inhibitory activity and/or anti-inflammatory effect.

Thus, in one aspect, compounds of this invention which are of particular interest include those which:

exhibit activity generally as inhibitors of adhesion molecule expression on the endothelial cell surface upon stimulation with inflammatory cytokines;

exhibit activity as inhibitors of inflammatory cytokine signaling pathway;

exhibit an anti-inflammatory effect on suitable cell lines maintained in vitro, or in animal studies using a scientifically acceptable model;

exhibit an antiproliferative and/or anticancer effect on suitable cell lines maintained in vitro, or in animal studies using a scientifically acceptable model; and exhibit a favorable therapeutic profile (e.g., safety, efficacy, and stability).

As discussed above, certain compounds as described herein exhibit activity generally as inhibitors cell adhesion molecules on endothelial cells (E-selectin and ICAM) and transcriptional activation induced by inflammatory cytokine signaling. More specifically, compounds of the invention demonstrate immunomodulatory activity and thus the invention further provides a method for treating an inflammatory or autoimmune disorder or a proliferative disorder. The method involves the administration of a therapeutically effective amount of the compound or a pharmaceutically acceptable derivative thereof to a subject (including, but not limited to a human or animal) in need of it. In certain embodiments, the inventive compounds as useful for the treatment of rheumatoid arthritis, ulcerative colitis/Crohn's disease, central nervous system diseases (CNS) such as multiple sclerosis, systemic lupus erythematosus, asthma, allograft rejection/graft versus host disease (GVHD), psoriasis, atopic dermatitis, eczema, uticaria, allergic rhinitis, myasthenia gravis, diabetes, idiopathic thrombocytopenia purpura, glomerulonephritis, cardiovascular disease, and cancer.

In certain embodiments, the method involves administration of a therapeutically effective amount of the compound or a pharmaceutically acceptable derivative thereof to a subject (including, but not limited to a human or animal) in need of it. In certain embodiments, a pharmaceutical composition comprising an inventive compound (or pharmaceutically acceptable derivative thereof), a carrier or diluent and optionally an additional therapeutic agent is provided.

Pharmaceutical Compositions

As discussed above this invention provides novel compounds that have biological properties useful for the treatment of inflammatory and proliferative disorders, including, but not limited to rheumatoid arthritis, ulcerative colitis/Crohn's disease, central nervous system diseases (CNS) such as multiple sclerosis, systemic lupus erythematosus, asthma, allograft rejection/graft versus host disease (GVHD), psoriasis, atopic dermatitis, eczema, uticaria, allergic rhinitis, myasthenia gravis, diabetes, idiopathic thrombocytopenia purpura, glomerulonephritis, cardiovascular disease, and cancer.

Accordingly, in another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier. In certain embodiments, these compositions optionally further comprise one or more additional therapeutic agents. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an anti-inflammatory agent (e.g., an agent for the treatment of rheumatoid arthritis or psoriasis) or cytotoxic agent or anticancer agent approved for the treatment of cancer, as discussed in more detail herein, or it may be any one of a number of agents undergoing approval in the Food and Drug Administration that ultimately obtain approval for the treatment of an immune disorder or cancer. It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared ill situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses and Formulations of Compounds of the Invention

As described in more detail herein, in general, the present invention provides compounds useful for the treatment of inflammatory or autoimmune disorders and the treatment of proliferative disorders. Without wishing to be bound by any particular theory, more generally, the compounds of the invention have been shown to inhibit adhesion molecule expression such as E-selectin and ICAM-1 on the endothelial cell surface induced by stimulation with inflammatory cytokines. Such cell surface molecules play a critical role for inflammatory cell infiltration and cell-cell interactions within inflammatory and immune responses. The compounds also reduce activation of the transcriptional factor NF-κB and inhibit the transcriptional activation in inflammatory cytokine signaling pathways, which regulates many genes such as IL-1α and TNF α involved in the pathology of several inflamatory diseases. More generally, the identification of NF-κB as a key player in the pathogenesis of inflammation suggest that NF-κB targeted therapeutics may be effective in inflammatory and immune disorders (Lee, generally, NF-κB in Defense and Disease, *J. Clin. Investig.* 2001, 107, 7).

As detailed in the exemplification herein in assays to determine the ability of compounds to inhibit cytokine-induced adhesion molecule expression by endothelial cells, certain inventive compounds, (generally where one occurrence of $R_3$ is hydrogen, and the other occurrence of $R_3$ is a moiety as described generally herein) exhibited $IC_{50}$ values (E-Selectin and ICAM-1) less than 1 μM. In other embodiments, exemplary compounds exhibited $IC_{50}$ values less than 10 μM.

As discussed above, compounds of the invention exhibit immunomodulatory activity and exhibit activity for the inhibition of tumor cell growth. As such, compounds of the invention are particularly useful for the treatment of diseases and disorders including, but not limited to, rheumatoid arthritis, ulcerative colitis/Crohn's disease, central nervous system diseases (CNS) such as multiple sclerosis, systemic lupus erythematosus, asthma, allograft rejection/graft versus host disease (GVHD), psoriasis, atopic dermatitis, eczema, uticaria, allergic rhinitis, myasthenia gravis, diabetes, idiopathic thrombocytopenia purpura, glomerulonephritis, cardiovascular disease, and cancer.

Thus, as described above, in another aspect of the invention, methods for the treatment of inflammatory or autoimmune and proliferative disorders are provided comprising administering a therapeutically effective amount of a compound of formula (I), as described herein, to a subject in need thereof. In certain embodiments, the inventive compounds are useful for the treatment of rheumatoid arthritis, ulcerative colitis/Crohn's disease, central nervous system diseases (CNS) such as multiple sclerosis, systemic lupus erythematosus, asthma, allograft rejection/graft versus host disease (GVHD), psoriasis, atopic dermatitis, eczema, uticaria, allergic rhinitis, myasthenia gravis, diabetes, idiopathic thrombocytopenia purpura, glomerulonephritis, cardiovascular disease, and cancer.

It will be appreciated that the compounds and compositions, according to the method of the present invention, may be administered using any amount and any route of administration effective for the treatment of inflammatory or autoimmune and proliferative disorders. Thus, the expression "effective amount" as used herein, refers to a sufficient amount of agent to kill or inhibit the growth of tumor cells, or refers to a sufficient amount to reduce the effects of an inflammatory or autoimmune response or disorder. The exact amount required will vary from subject to subject, depending on the species, age, and general condition of the subject, the severity of the infection, the particular therapeutic agent, its mode of administration, and the like.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that tie total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Furthermore, after formulation with an appropriate pharmaceutically acceptable carrier in a desired dosage, the pharmaceutical compositions of this invention can be administered to humans and other animals orally, rectally, parenterally, intracistemally, intravaginally, intraperitoneally, topically (as by powders, ointments, or drops), bucally, as an oral or nasal spray, or the like, depending on the severity of the infection being treated. In certain embodiments, the compounds of the invention may be administered at dosage levels of about 0.001 mg/kg to about 50 mg/kg, from about 0.01 mg/kg to about 25 mg/kg, or from about 0.1 mg/kg to about 10 mg/kg of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anti-inflammatory agent or anticancer agent), or they may achieve different effects (e.g., control of any adverse effects).

For example, other therapies or anticancer agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In certain embodiments, the pharmaceutical compositions of the present invention further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g. for shrinking tumors and reducing pressure, bleeding, pain and other symptoms of cancer).

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1989, "Comprehensive Organic Transformations", VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

1) Exemplary Compounds

Certain exemplary compounds of the invention are listed below and are referred to by compound number as indicated.

| | ER-# | Structure |
|---|---|---|
| 1 | 805600 (IC375) | 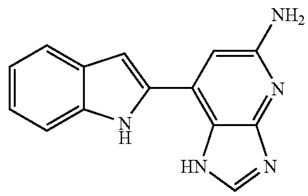 |
| 2 | 805894 (IC400) | 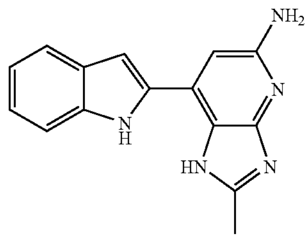 |
| 3 | 806006 | 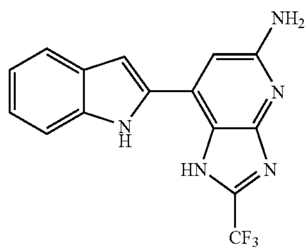 |
| 4 | 805985 (IC403) | 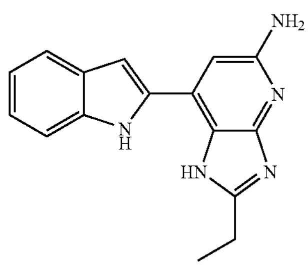 |
| 5 | 805984 | 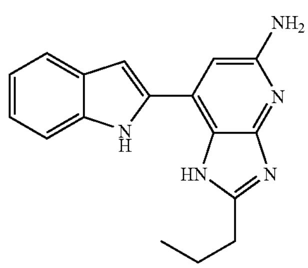 |
| 6 | 806002 | 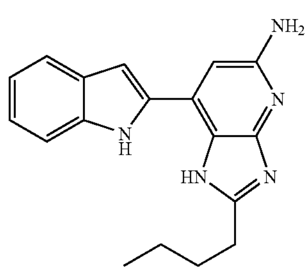 |

-continued
| ER-# | Structure |
|---|---|
| 7 | 805969 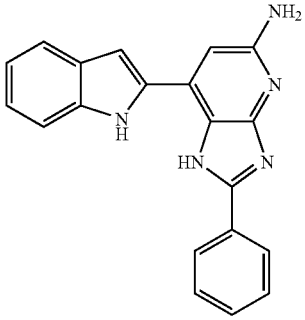 |
| 8 | 805971 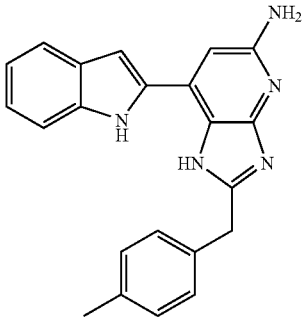 |
| 9 | 805996 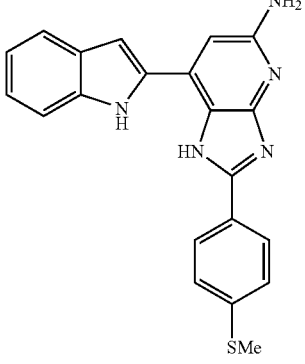 |
| 10 | 805639 (IC397) 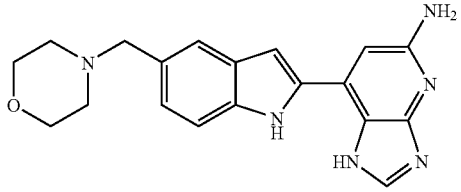 |
| 11 | 805895 (IC405) 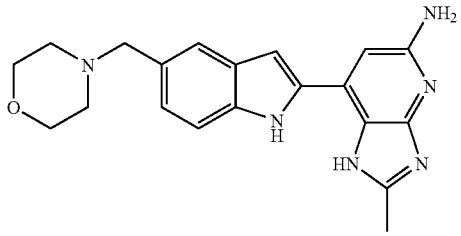 |

-continued
| ER-# | Structure |
|---|---|
| 12 806007 | 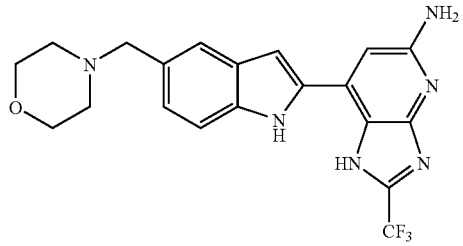 |
| 13 805976 | 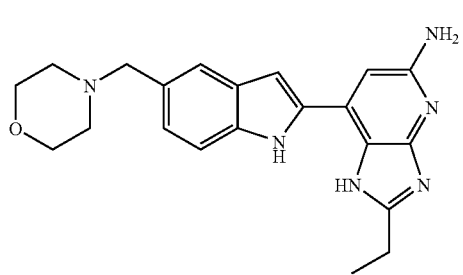 |
| 14 805975 | 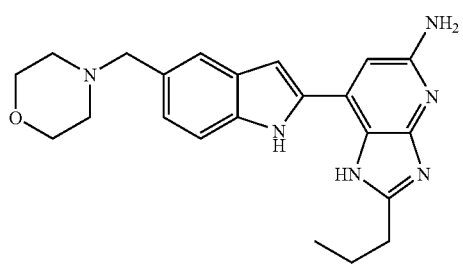 |
| 15 805999 | 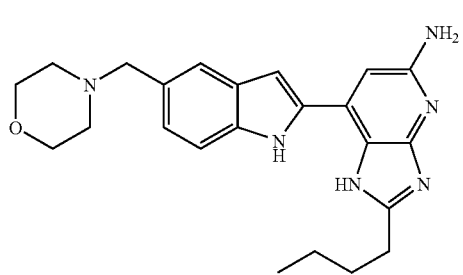 |
| 16 806011 | 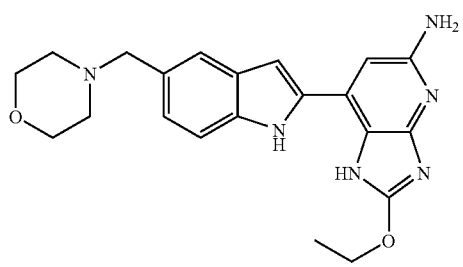 |

-continued

| ER-# | Structure |
|---|---|
| 17 805970 | |
| 18 805972 | |
| 19 805997 | |
| 20 806010 | |

-continued

| ER-# | Structure |
|---|---|
| 21 806014 | |
| 22 806094 | |
| 23 806095 | |
| 24 806097 | |
| 25 806107 | |
| 26 806123 | |

| | ER-# | Structure |
|---|---|---|
| 27 | 806136 | 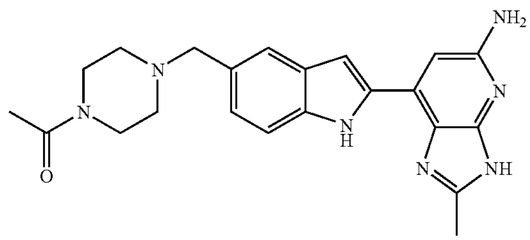 |
| 28 | 806181 | 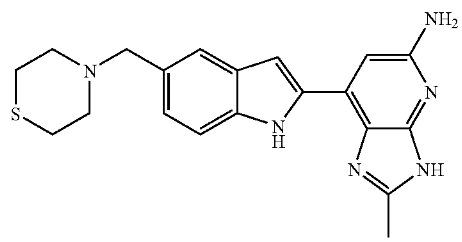 |
| 29 | 806221 | 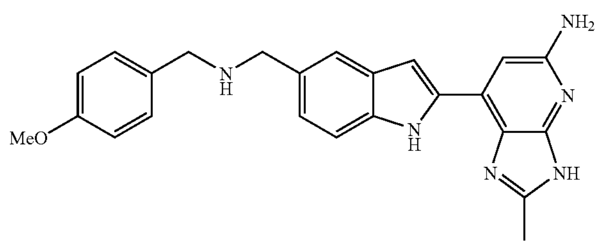 |
| 30 | 806220 | 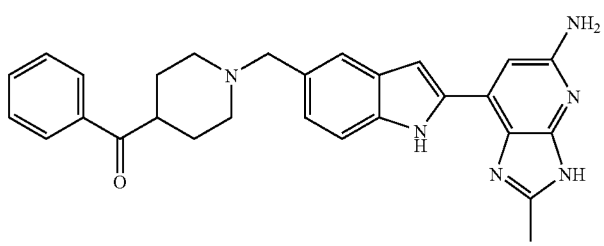 |
| 31 | 806224 | 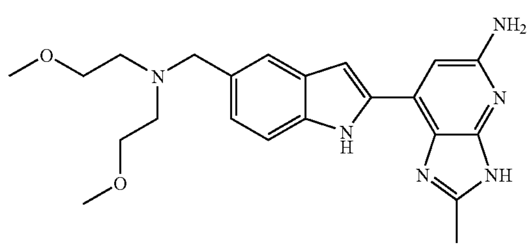 |
| 32 | 806228 | 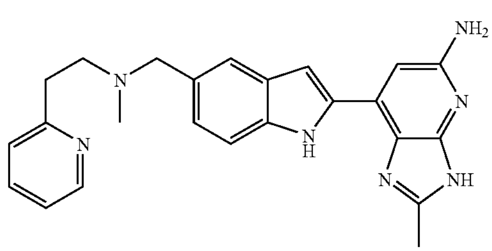 |

-continued
| ER-# | Structure |
|---|---|
| 33 806276 | 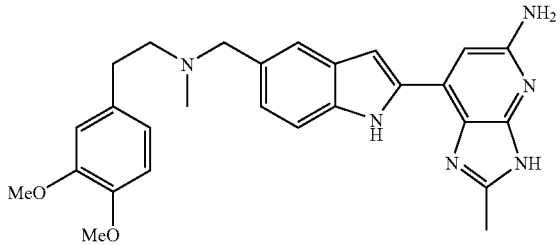 |
| 34 806275 | 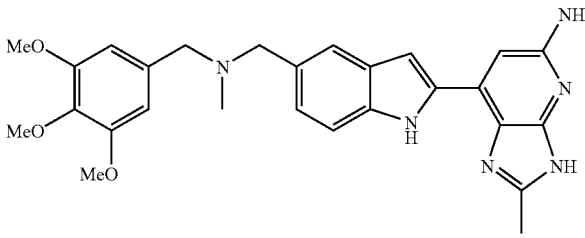 |
| 35 806274 | 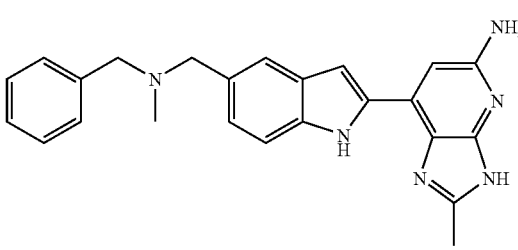 |
| 36 806273 | 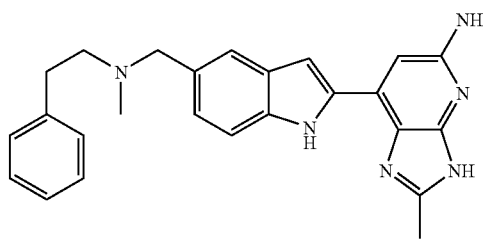 |
| 37 806286 | 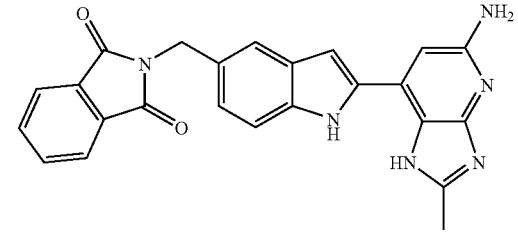 |
| 38 806287 | 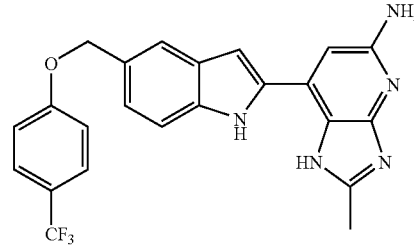 |

-continued

| ER-# | Structure |
|---|---|
| 39 | 806311 |
| 40 | 806317 |
| 41 | 806320 |
| 42 | 806329 |
| 43 | 806333 |
| 45 | 806336 |

| ER-# | Structure |
|---|---|
| 46 | 806355 |
| 47 | 806358 |
| 48 | 806359 |
| 49 | 806363 |
| 50 | 806362 |
| 51 | 806361 |

-continued

| ER-# | Structure |
|---|---|
| 52 806368 | |
| 53 806372 | |
| 54 806373 | |
| 55 806374 | |
| 56 806375 | |
| 57 806383 | |

-continued
| ER-# | Structure |
|---|---|
| 58 806393 | 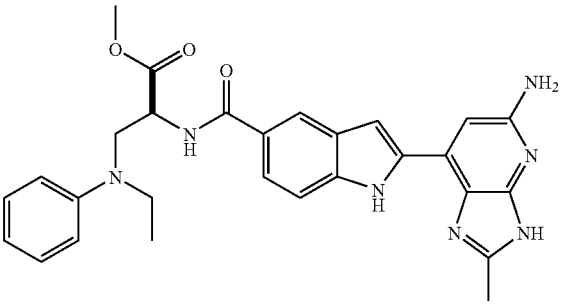 |
| 59 806401 | 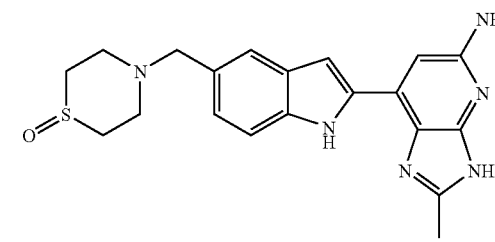 |
| 60 806402 | 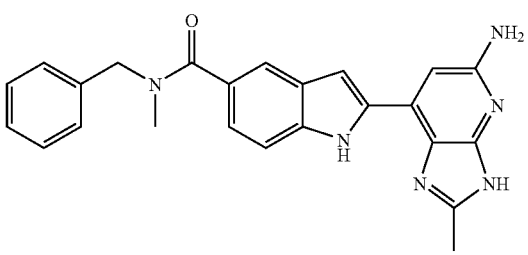 |
| 61 806404 | 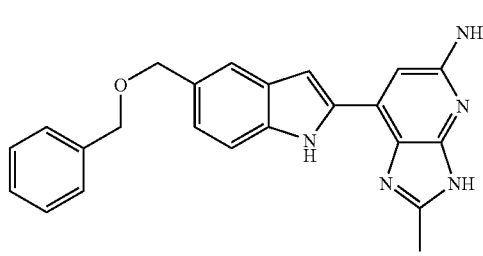 |
| 62 806417 | 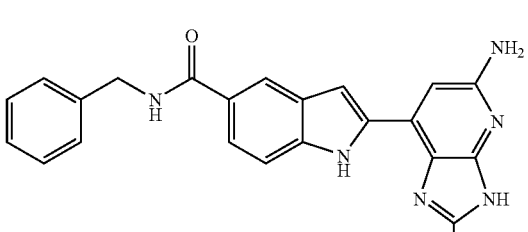 |
| 63 806419 | 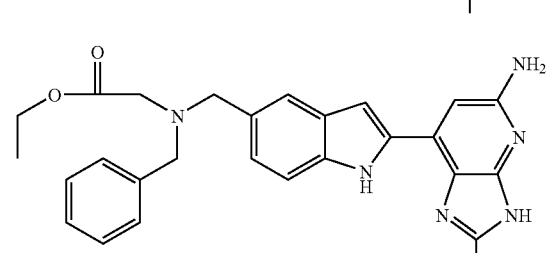 |

-continued

| ER-# | | Structure |
|---|---|---|
| 64 | 806420 | 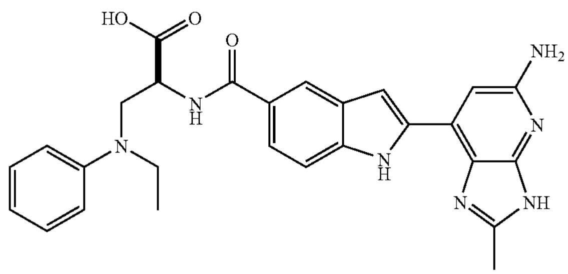 |
| 65 | 806421 | 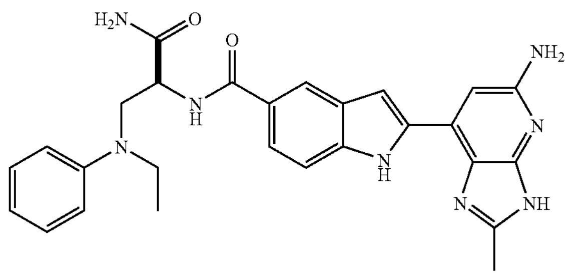 |
| 66 | 806432 | 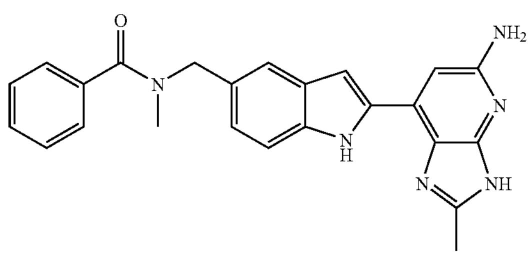 |
| 67 | 806435 | 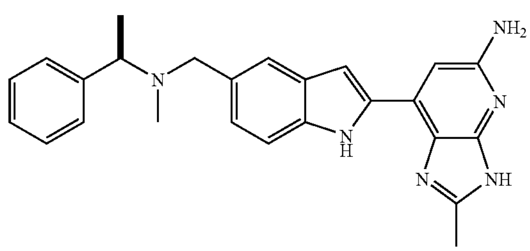 |
| 68 | 806437 | 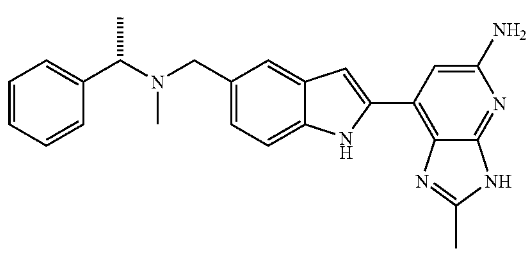 |
| 69 | 806569 | 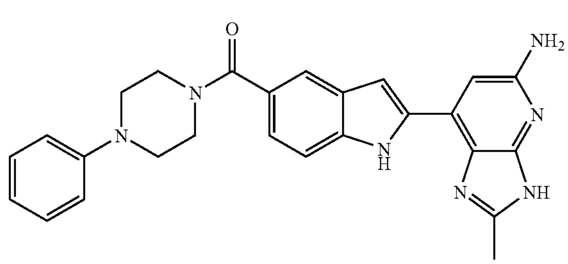 |

| ER-# | Structure |
|---|---|
| 70 806609 | |
| 71 806610 | |
| 72 806644 | |
| 73 806645 | |
| 74 806646 | |
| 75 806647 | |

-continued
| ER-# | Structure |
|---|---|
| 76 806653 | 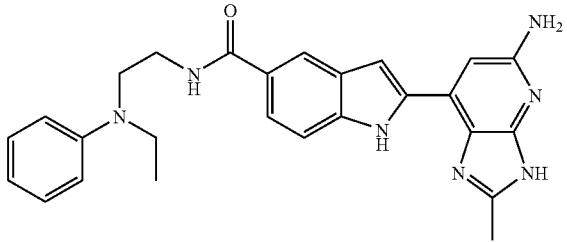 |
| 77 806671 | 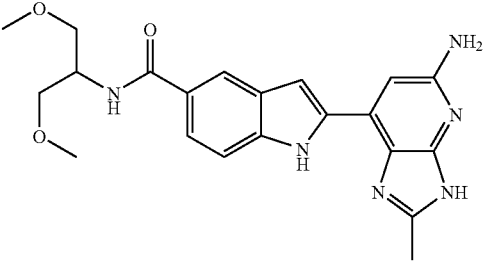 |
| 78 806781 | 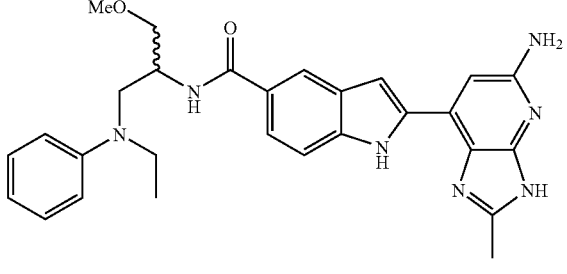 |
| 79 806790 | 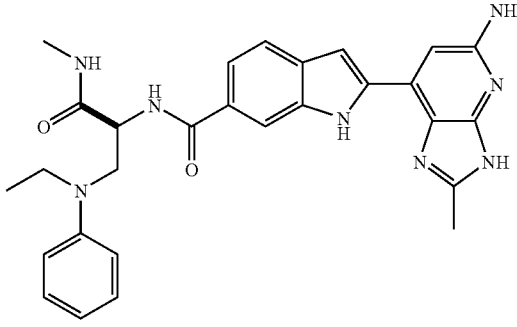 |
| 80 806796 | 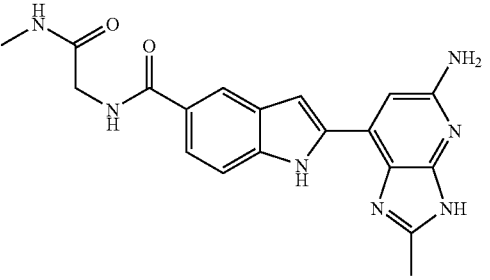 |

-continued
| ER-# | | Structure |
|---|---|---|
| 81 | 806820 | 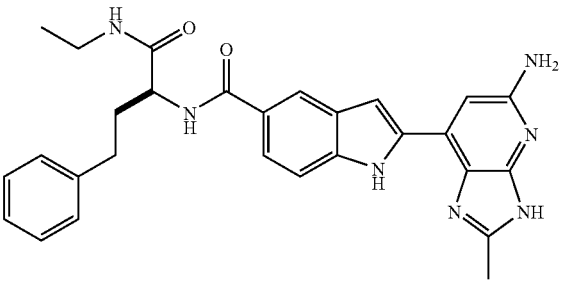 |
| 82 | 806839 | 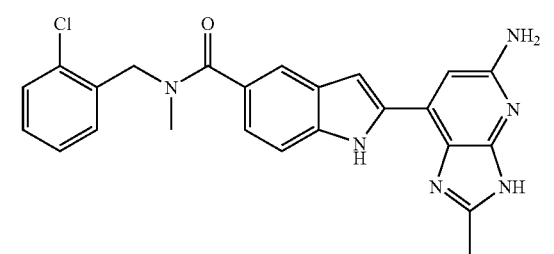 |
| 83 | 806840 | 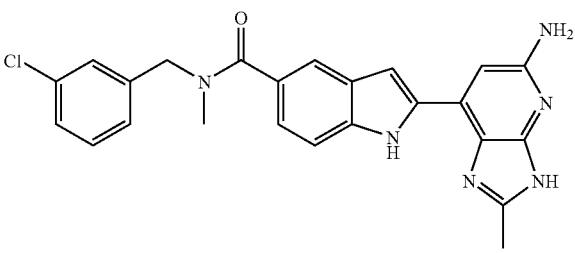 |
| 84 | 806841 | 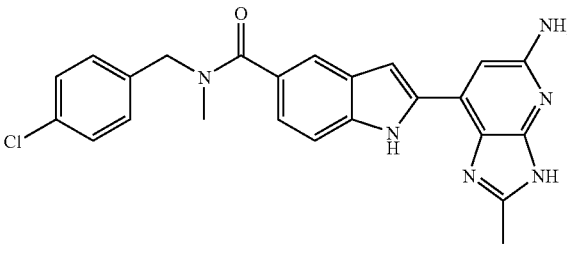 |
| 85 | 806842 | 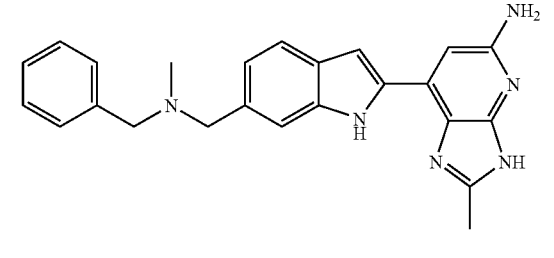 |
| 86 | 806843 | 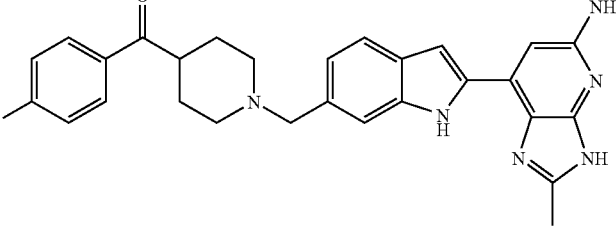 |

-continued
| ER-# | Structure |
|---|---|
| 87 806844 | 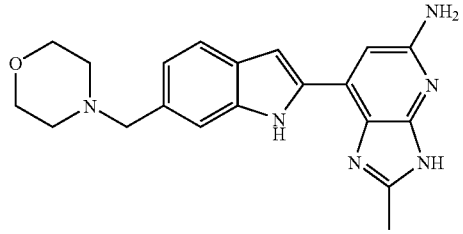 |
| 88 806860 | 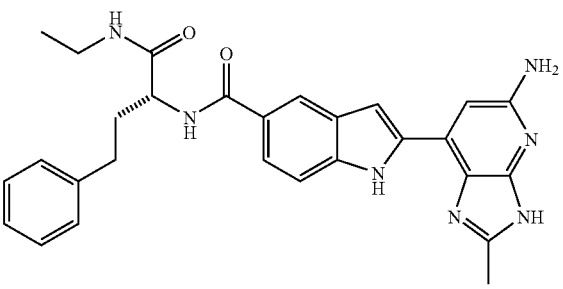 |
| 89 806874 | 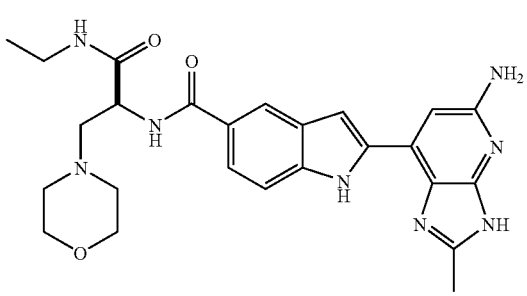 |
| 90 806875 | 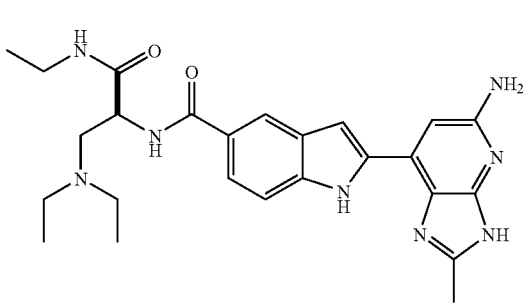 |
| 91 806878 | 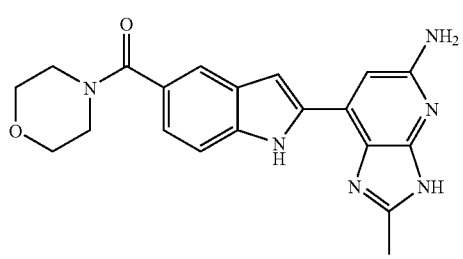 |

-continued
| ER-# | Structure |
|---|---|
| 92 | 806899 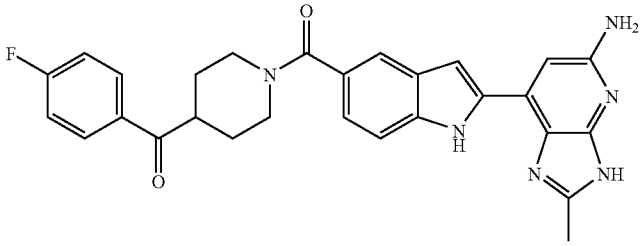 |
| 93 | 806900 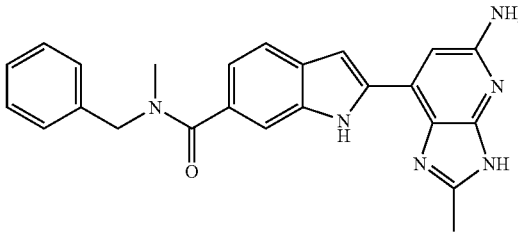 |
| 94 | 806901 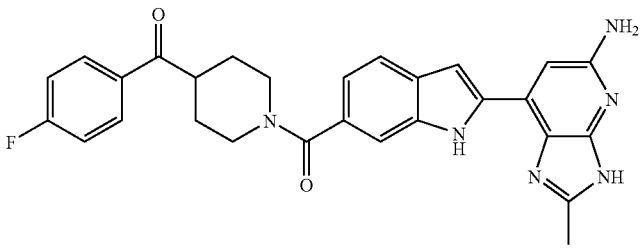 |
| 95 | 806902 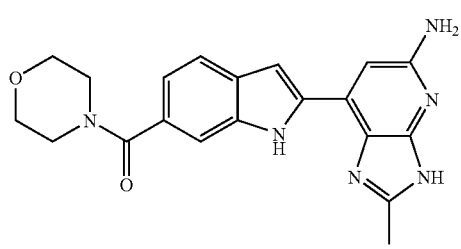 |
| 96 | 806903 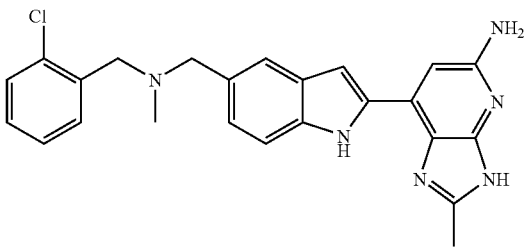 |
| 97 | 806904 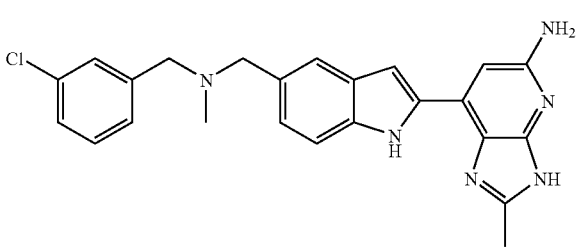 |

-continued

| ER-# | Structure |
|---|---|
| 98 806905 | |
| 99 806987 | |
| 100 807014 | |
| 101 807015 | |
| 102 807139 | |
| 103 807140 | |

| ER-# | Structure |
|---|---|
| 104 | 807183 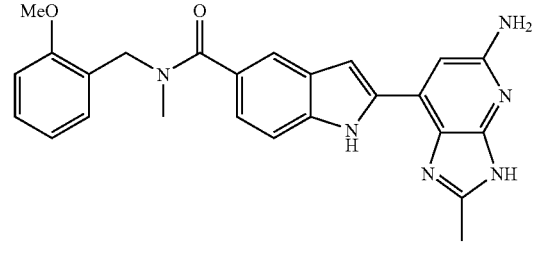 |
| 105 | 807240 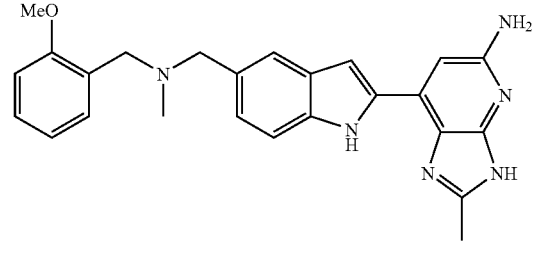 |
| 106 | 807313 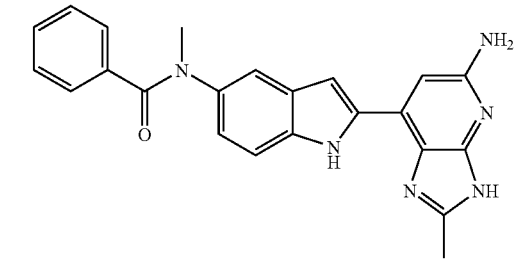 |
| 107 | 807377 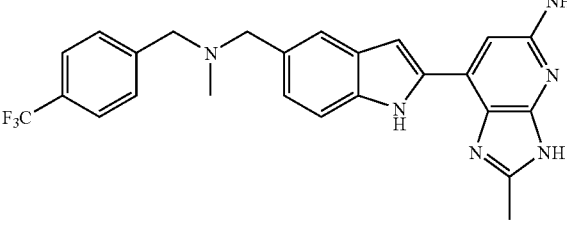 |
| 108 | 807392 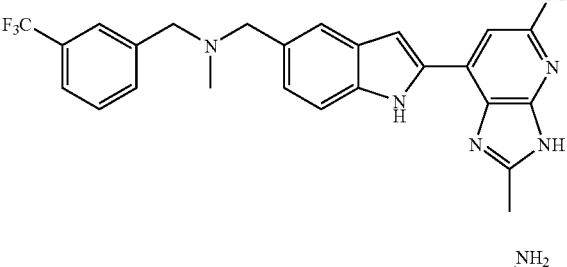 |
| 109 | 807400 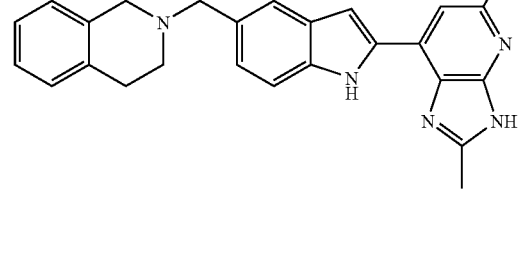 |

-continued
| ER-# | Structure |
|---|---|
| 110 | 807401 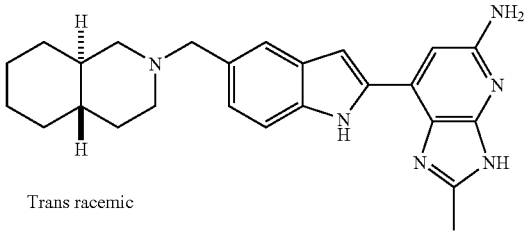  Trans racemic |
| 111 | 807399 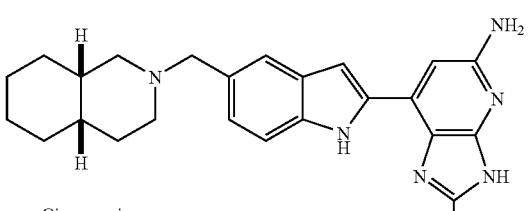  Cis racemic |
| 112 | 807447 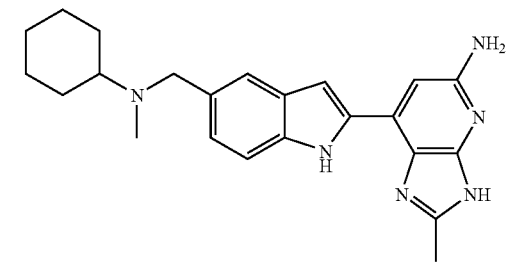 |
| 113 | 807448 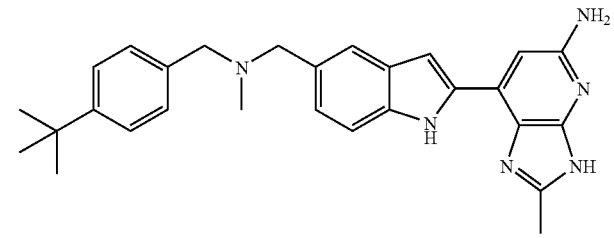 |
| 114 | 807449 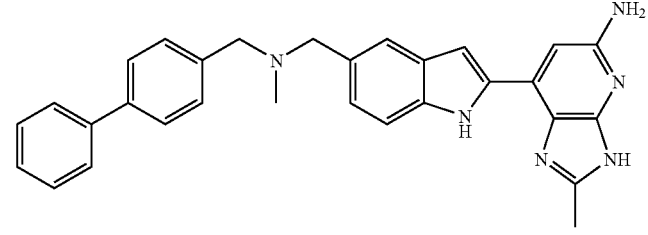 |
| 115 | 807450 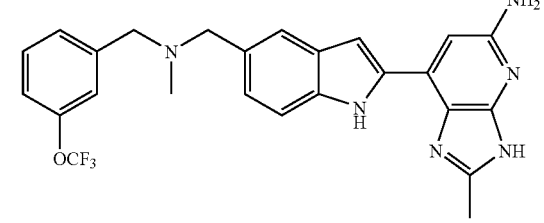 |

-continued

| ER-# | Structure |
|---|---|
| 116 | 807451 |
| 117 | 807452 |
| 118 | 807453 |
| 119 | 807454 |
| 120 | 807457 |
| 121 | 807458 |

| ER-# | Structure |
|---|---|
| 122 807459 | |
| 123 807460 | |
| 124 807462 | |
| 125 807463 | |
| 126 807464 | |
| 127 807465 | |

-continued

| ER-# | Structure |
|---|---|
| 128 | 807466 |
| 129 | 807467 |
| 130 | 807469 |
| 131 | 807496 |
| 132 | 807497 |
| 133 | 807498 |

| ER-# | Structure |
|---|---|
| 134 | 807505 |
| 135 | 807506 |
| 136 | 807528 |
| 137 | 807531 |
| 138 | 807532 |
| 139 | 807543 |

-continued

| | ER-# | Structure |
|---|---|---|
| 140 | 807544 | 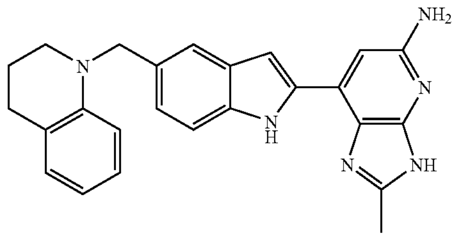 |
| 141 | 807546 | 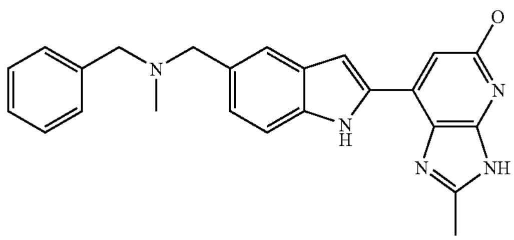 |
| 142 | 807548 | 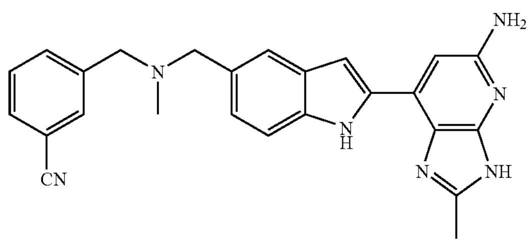 |
| 143 | 807549 | 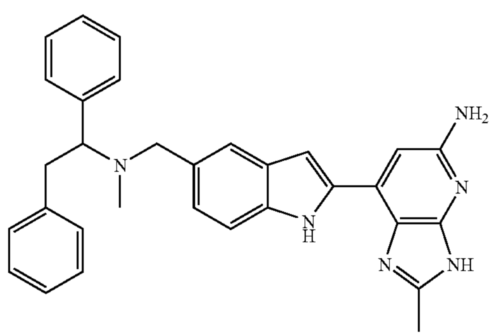 |
| 144 | 807550 | 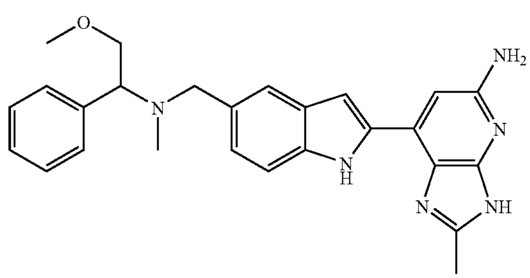 |

-continued
| ER-# | Structure |
|---|---|
| 145 807562 | 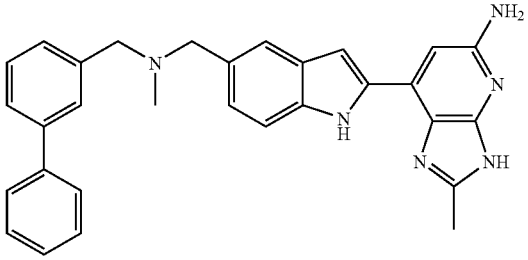 |
| 146 807571 | 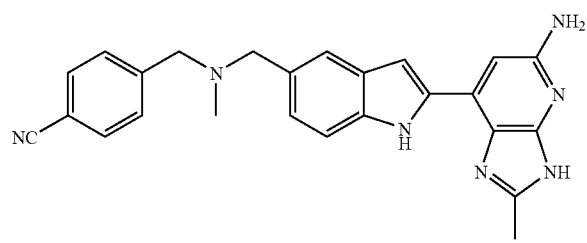 |
| 147 807573 | 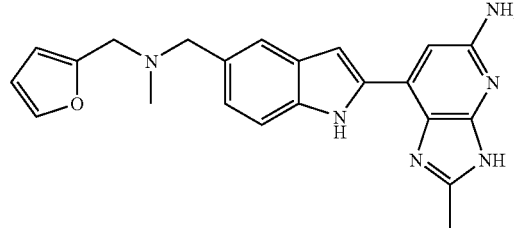 |
| 148 807584 | 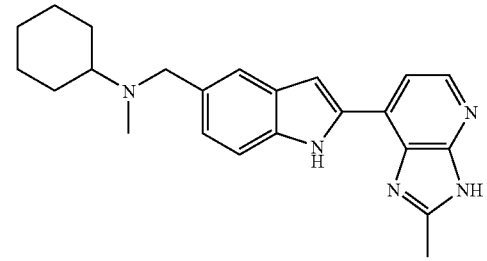 |
| 149 807585 | 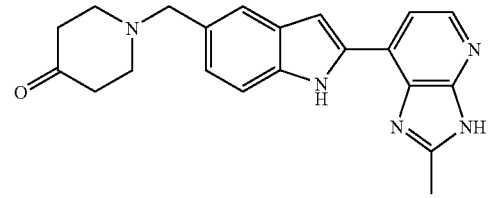 |
| 150 807586 | 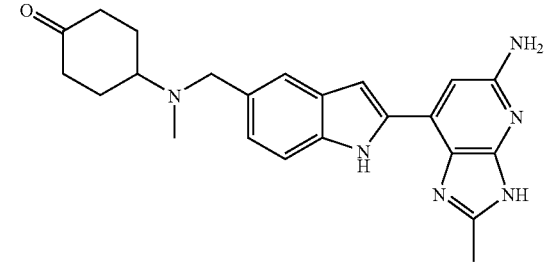 |

-continued
| ER-# | Structure |
|---|---|
| 151 807587 | 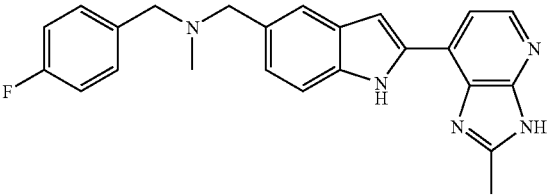 |
| 152 807636 | 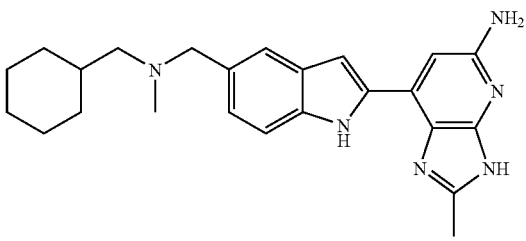 |
| 153 807649 | 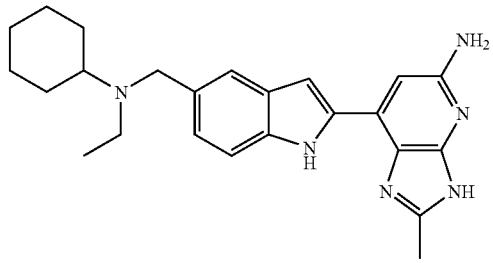 |
| 154 807660 | 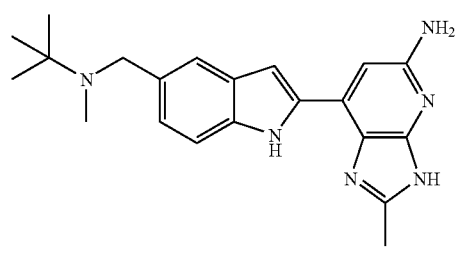 |
| 155 807662 | 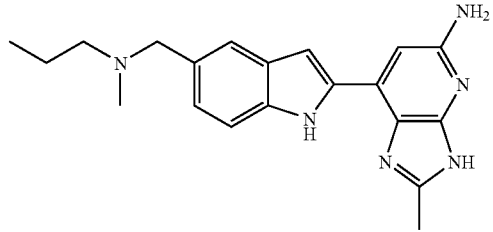 |
| 156 807663 | 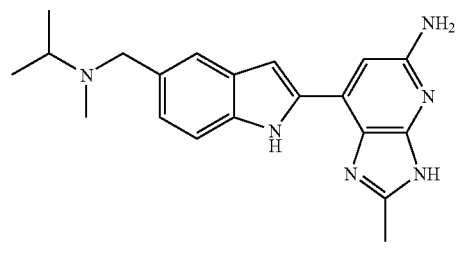 |

| ER-# | Structure |
|---|---|
| 157 807703 | |
| 158 807704 | |
| 159 807748 | |
| 160 807749 | |
| 161 807750 | |
| 162 807751 | |

| ER-# | Structure |
|---|---|
| 163 807754 | |
| 164 807758 | |
| 165 807759 | |
| 166 807762 | |
| 167 807779 | |

-continued
| ER-# | | Structure |
|---|---|---|
| 168 | 807787 | 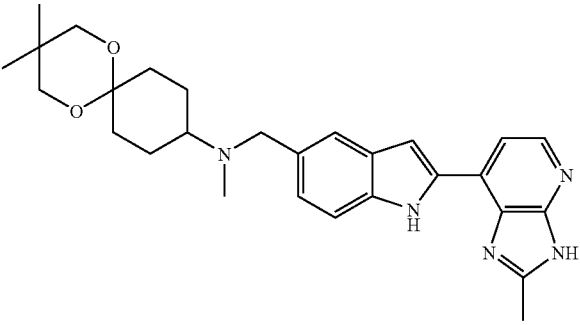 |
| 169 | 807788 | 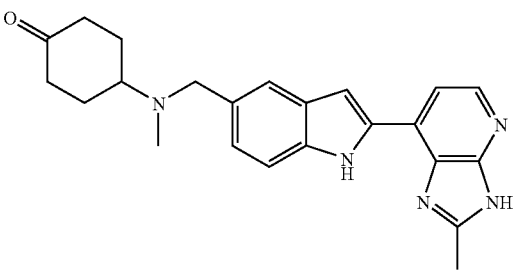 |
| 170 | 807789 | 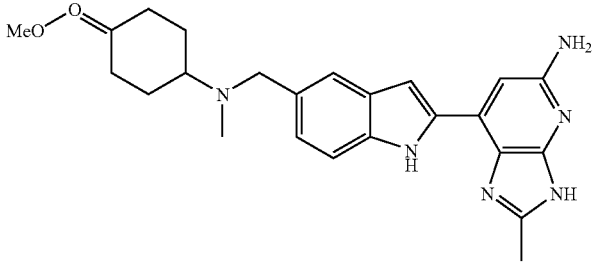 |
| 171 | 807790 | 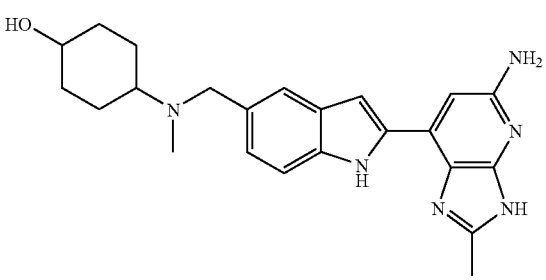 |
| 172 | 807794 | 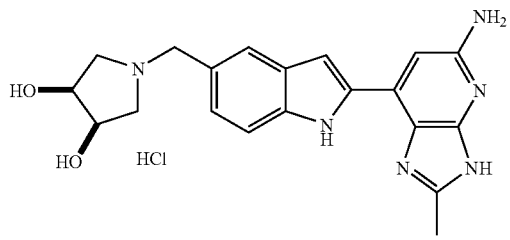 |

-continued

| ER-# | | Structure |
|---|---|---|
| 173 | 807835 | 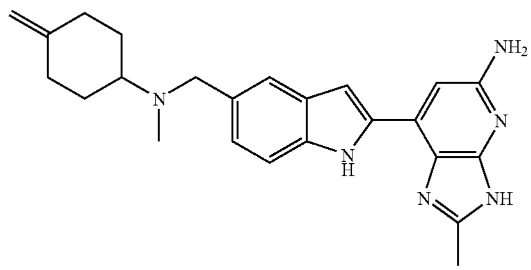 |
| 174 | 807836 | 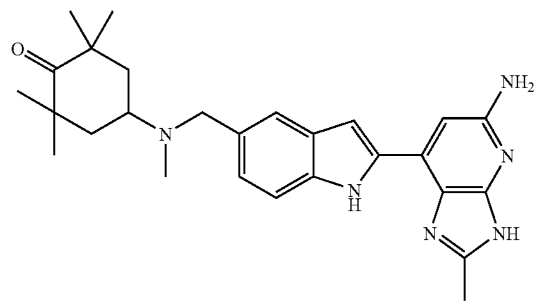 |
| 175 | 807837 | 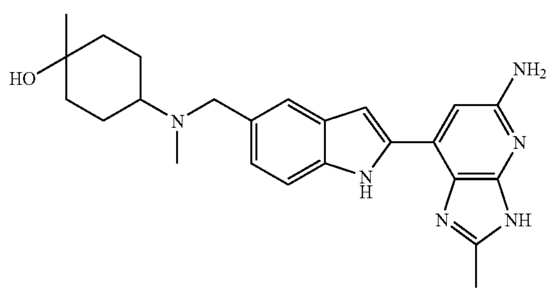 |
| 176 | 807862 | 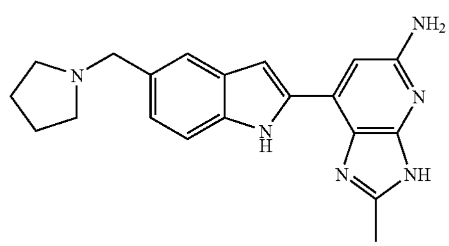 |
| 177 | 807865 | 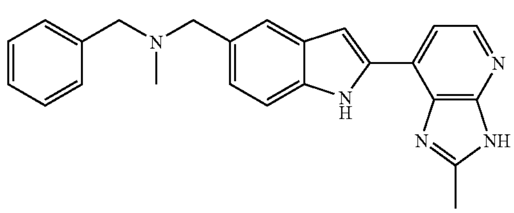 |
| 178 | 807876 | 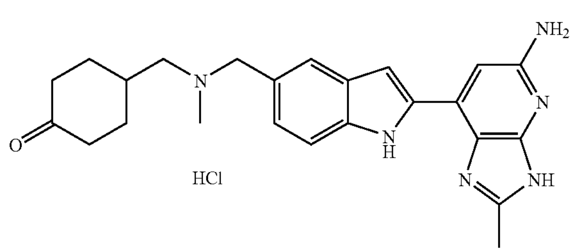 |

| ER-# | Structure |
|---|---|
| 179 | 807892 |
| 180 | 807920 |
| 181 | 807930 |
| 182 | 807931 |
| 183 | 807952 |

-continued

| ER-# | | Structure |
|---|---|---|
| 184 | 807956 | 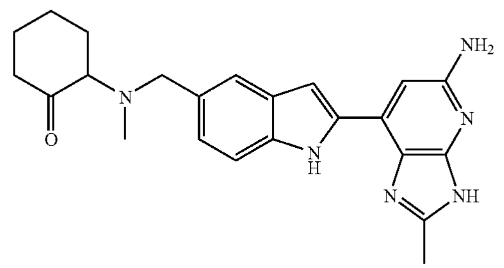 |
| 185 | 807962 | 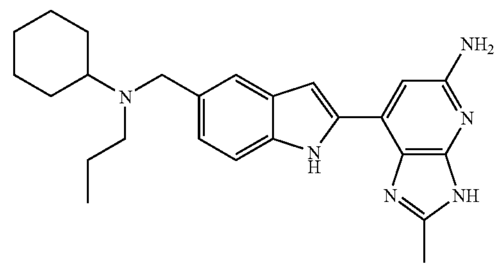 |
| 186 | 807976 | 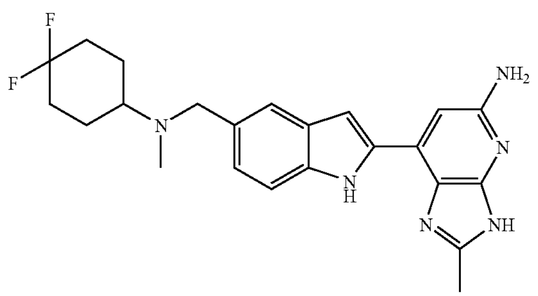 |
| 187 | 807977 | 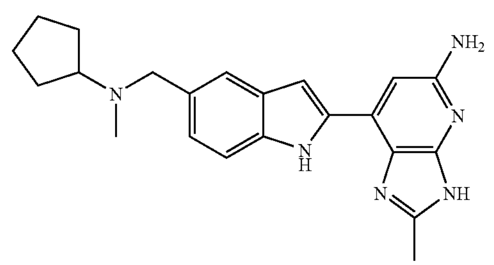 |
| 188 | 807978 | 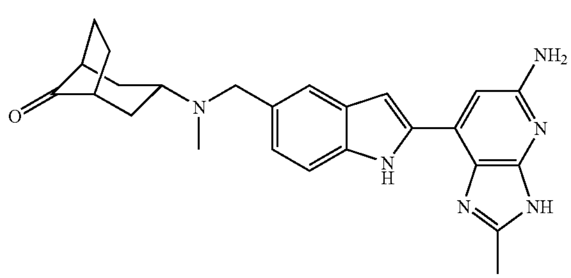 |

-continued

| ER-# | | Structure |
|---|---|---|
| 189 | 807980 | 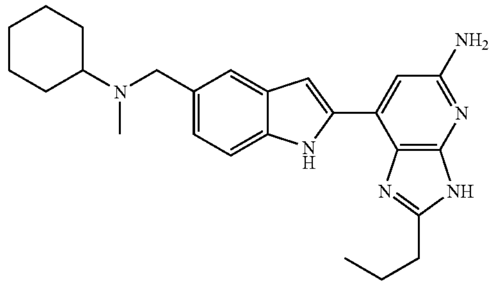 |
| 190 | 808009 | 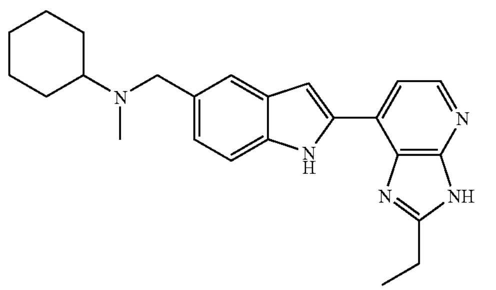 |
| 191 | 808028 | 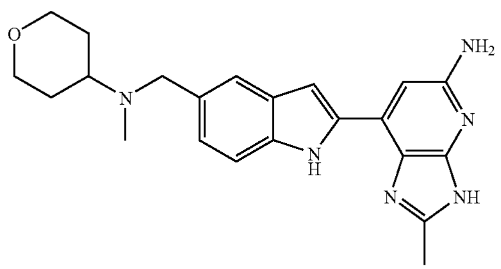 |
| 192 | 808036 | 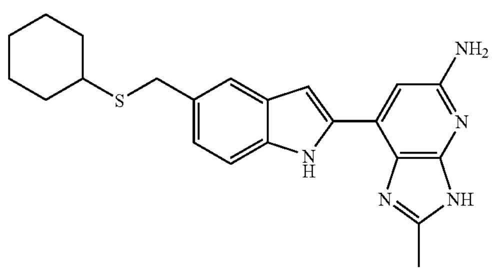 |
| 193 | 808039 | 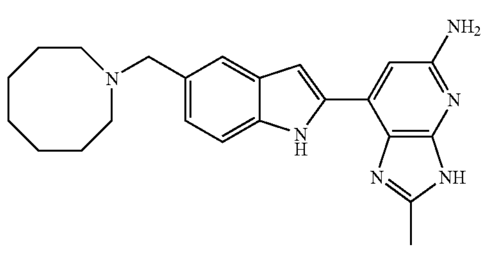 |

-continued
| ER-# | | Structure |
|---|---|---|
| 194 | 808040 | 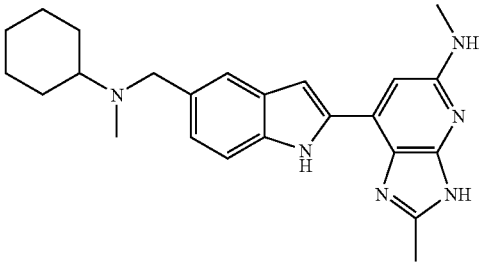 |
| 195 | 808041 | 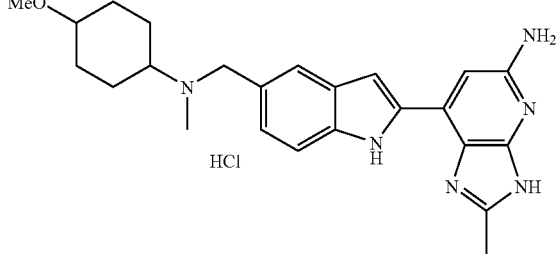 |
| 196 | 808069 | 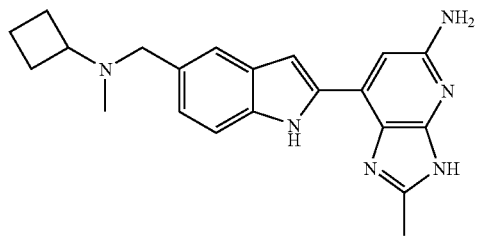 |
| 197 | 808078 | 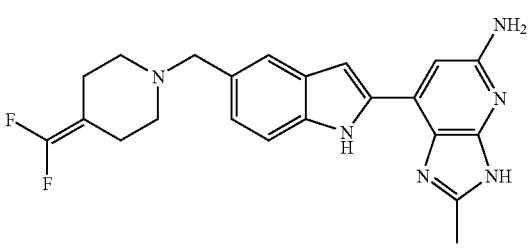 |
| 198 | 808079 | 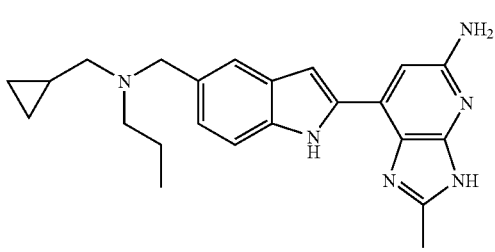 |
| 199 | 808080 | 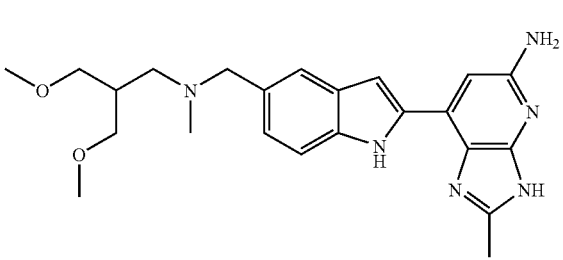 |

-continued
| ER-# | | Structure |
|---|---|---|
| 200 | 808081 | 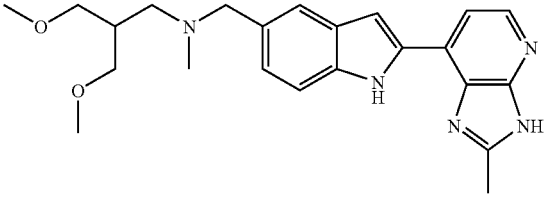 |
| 201 | 808082 | 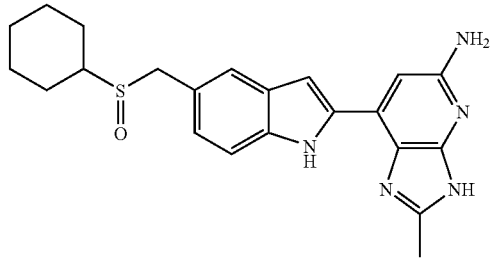 |
| 202 | 808083 | 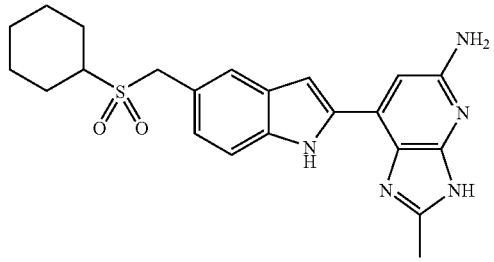 |
| 203 | 808084 | 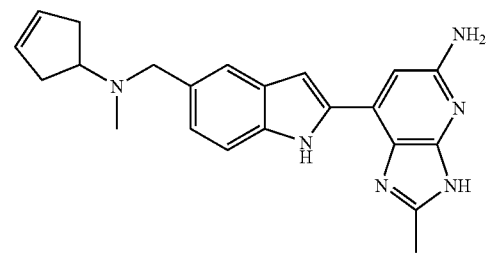 |
| 204 | 808085 | 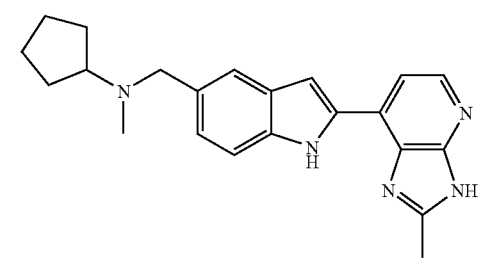 |

-continued
| ER-# | | Structure |
|---|---|---|
| 205 | 808086 | 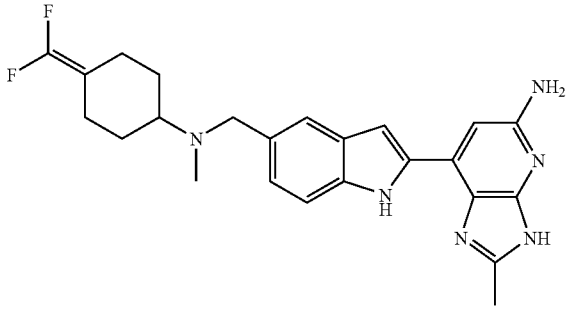 |
| 206 | 808101 | 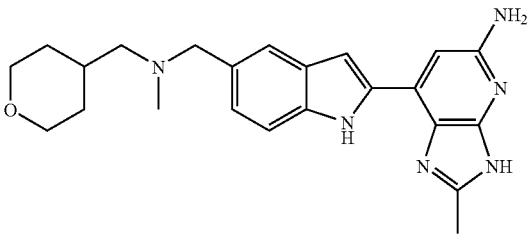 |
| 207 | 808102 | 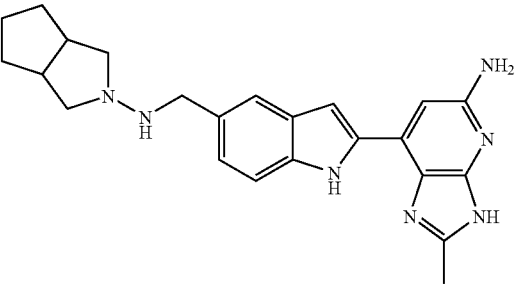 |
| 208 | 808103 | 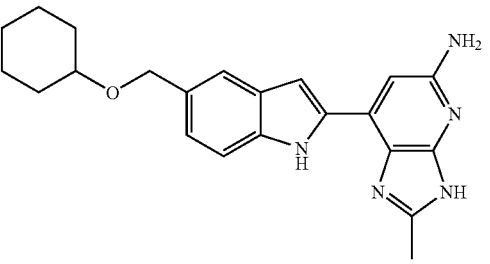 |
| 209 | 808107 | 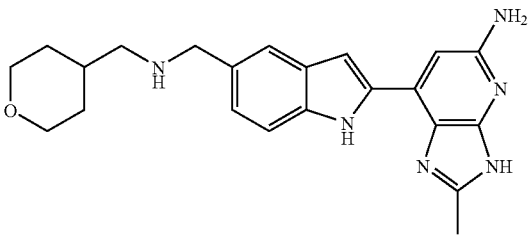 |

| | | |
|---|---|---|
| 210 | 808128 | 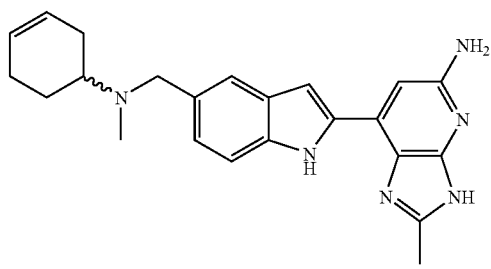 |
| 211 | 808151 | 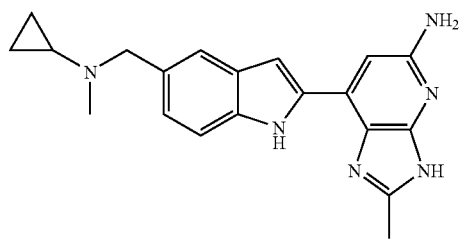 |
| 212 | 808152 | 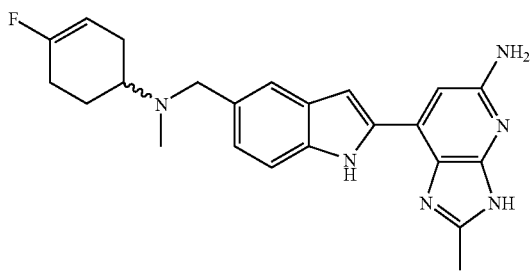 |
| 213 | 808153 | 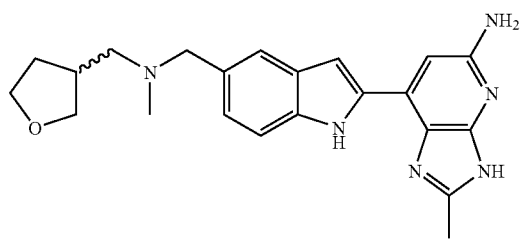 |
| 214 | 808160 | 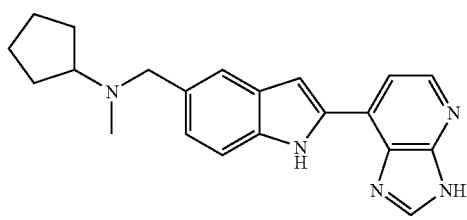 |
| 215 | 808164 | 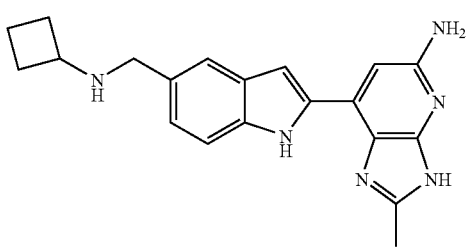 |

-continued
| | | |
|---|---|---|
| 216 | 808247 | 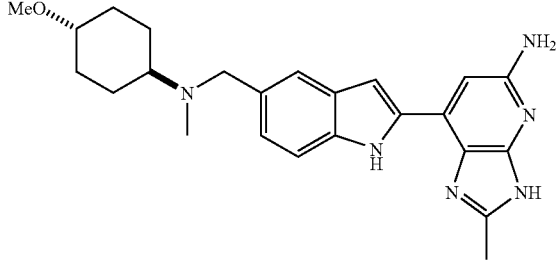 |
| 217 | 808254 | 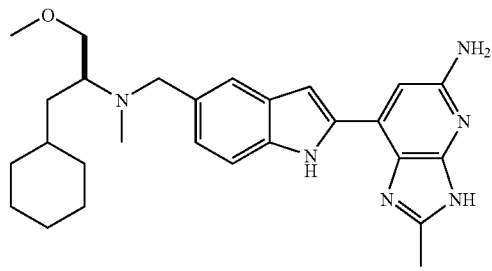 |
| 218 | 808255 | 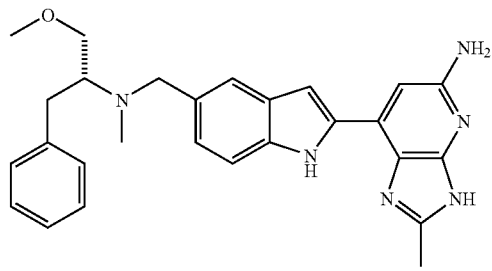 |
| 219 | 808256 | 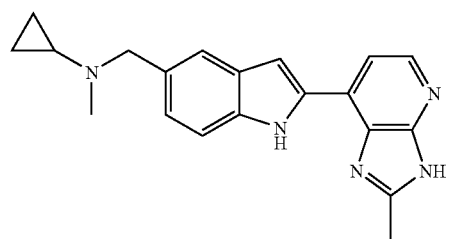 |
| 220 | 808257 | 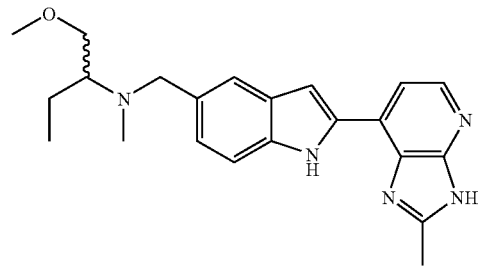 |
| 221 | 808259 | 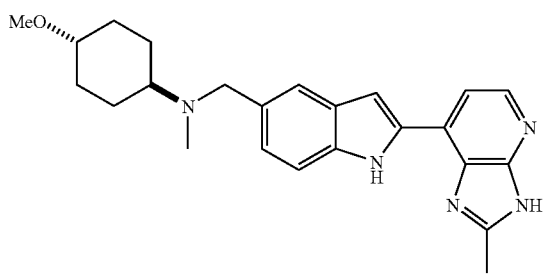 |

-continued
| | | |
|---|---|---|
| 222 | 808260 | 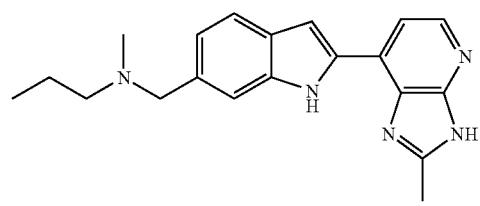 |
| 223 | 808261 | 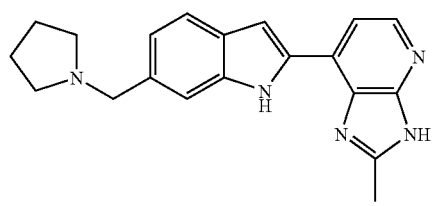 |
| 224 | 808262 | 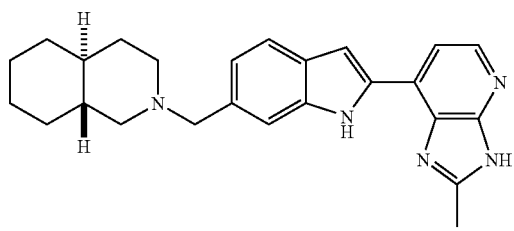 |
| 225 | 808266 | 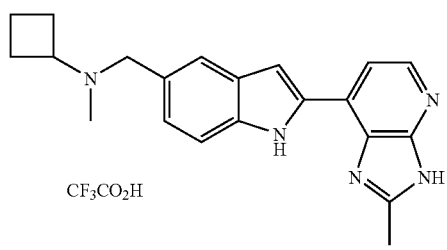<br>$CF_3CO_2H$ |
| 226 | 808268 | 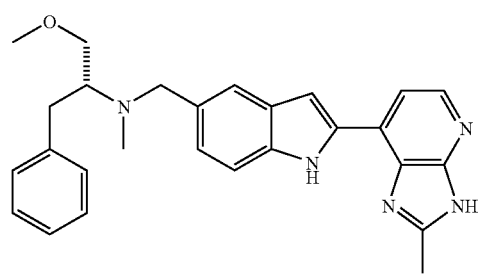 |
| 227 | 808269 | 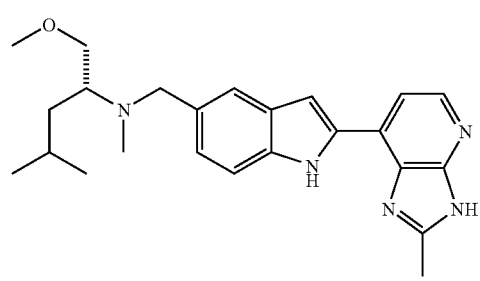 |

-continued
| 228 | 808281 | 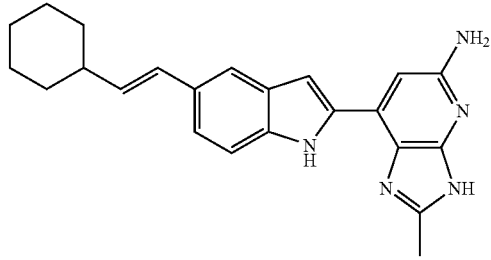 |
| 229 | 808283 | 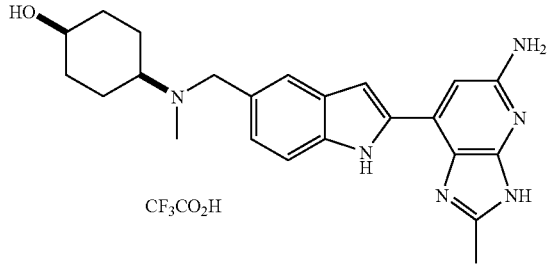 |
| 230 | 808284 | 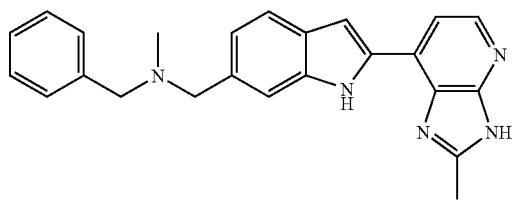 |
| 231 | 808285 | 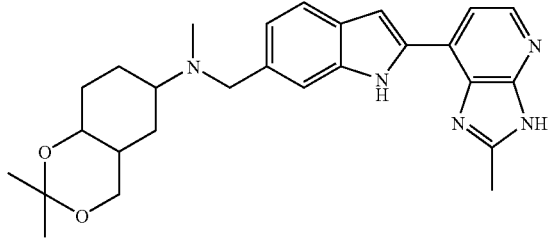 |
| 232 | 808286 | 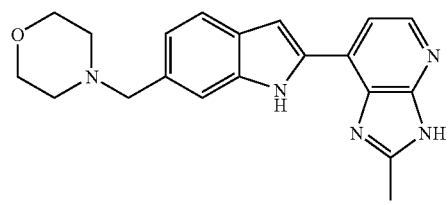 |
| 233 | 808287 | 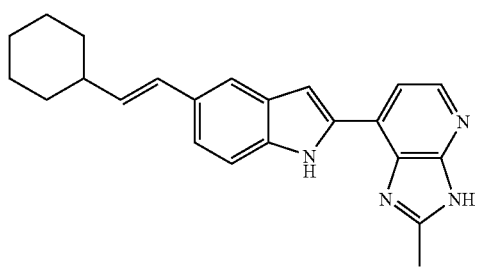 |

-continued
| | | |
|---|---|---|
| 234 | 808288 | 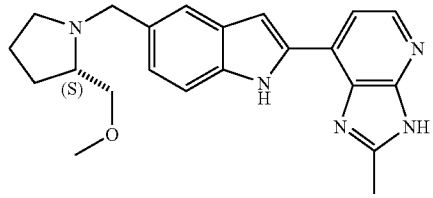 |
| 235 | 808289 | 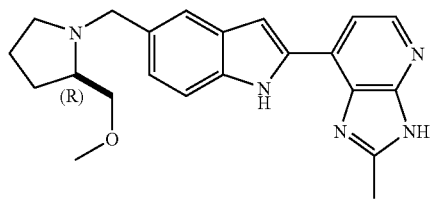 |
| 236 | 808290 | 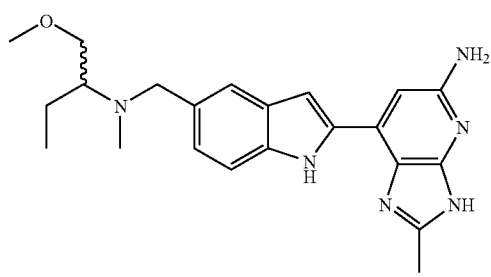 |
| 237 | 808291 | 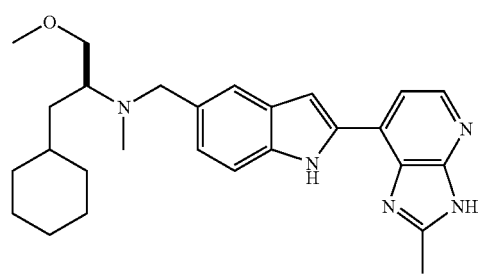 |
| 238 | 808310 | 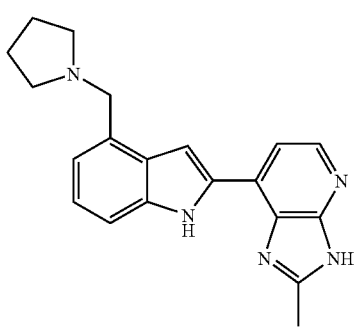 |
| 239 | 808311 | 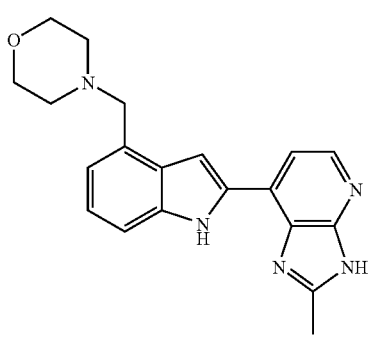 |

| 240 | 808312 | 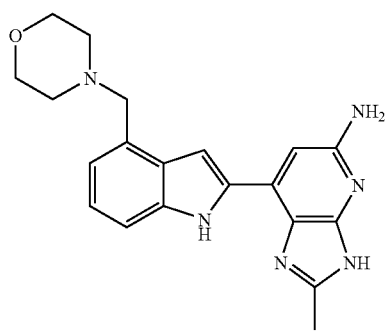 |
| 241 | 808313 | 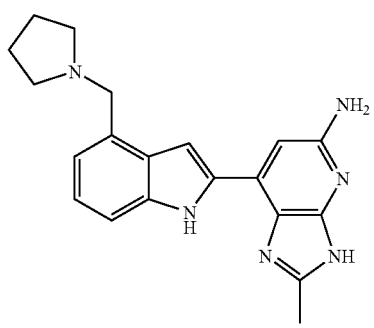 |
| 242 | 808319 | 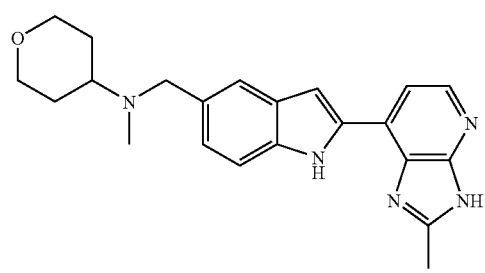 |
| 243 | 808322 | 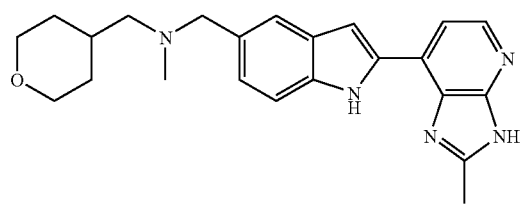 |
| 244 | 808346 | 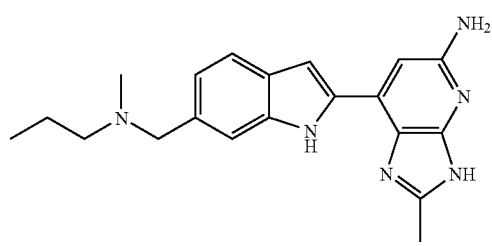 |

| | | |
|---|---|---|
| 245 | 808347 | 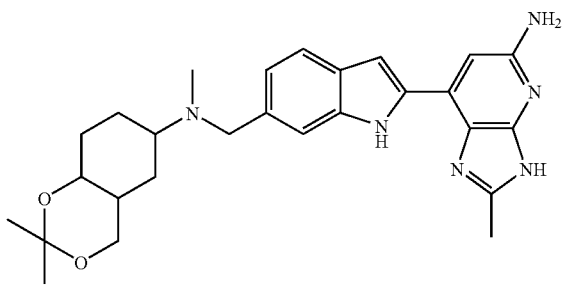 |
| 246 | 808355 | 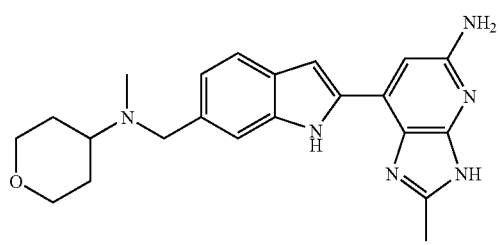 |
| 247 | 808356 | 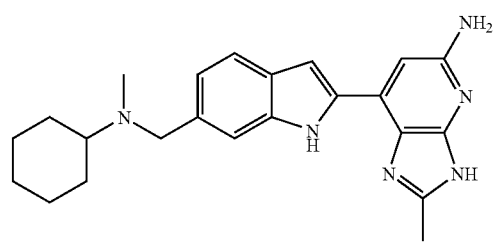 |
| 248 | 808361 | 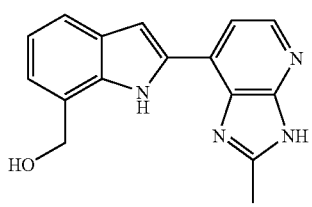 |
| 249 | 808362 | 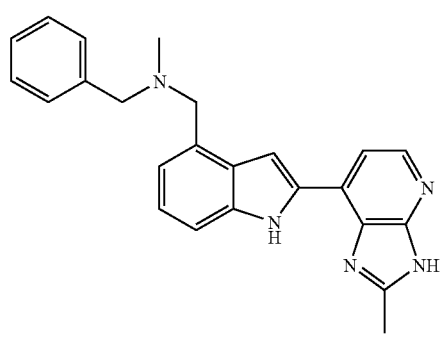 |

-continued
| 250 | 808363 | 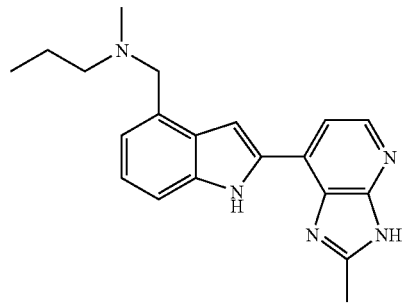 |
| 251 | 808364 | 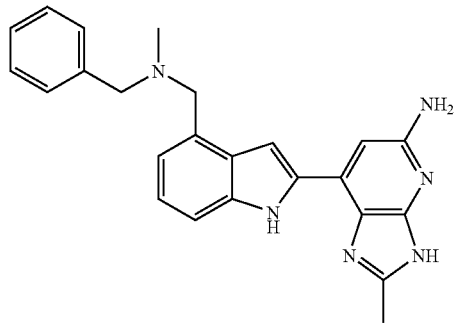 |
| 252 | 808365 | 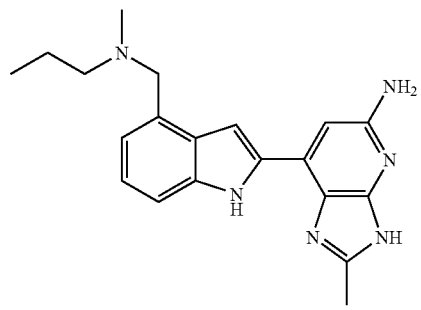 |
| 253 | 808370 | 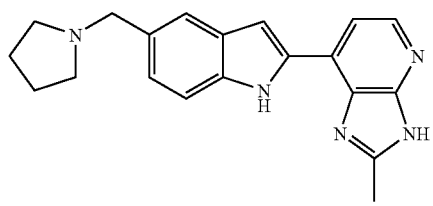 |
| 254 | 808371 | 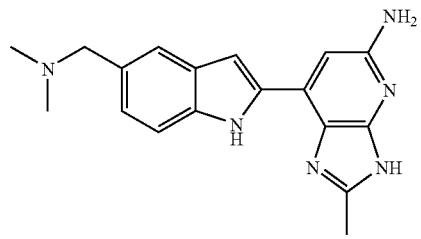 |
| 255 | 808372 | 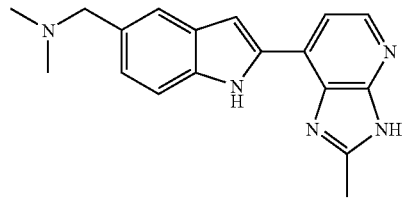 |

-continued
| 256 | 808385 | 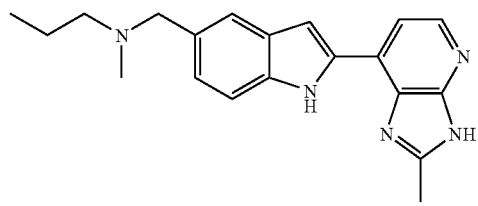 |
| 257 | 808386 | 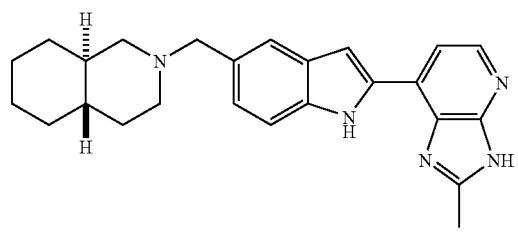 |
| 258 | 808387 | 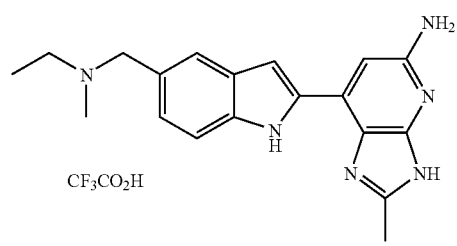 |
| 259 | 808388 | 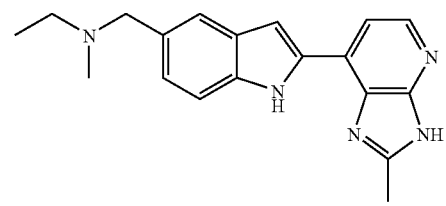 |
| 260 | 808469 | 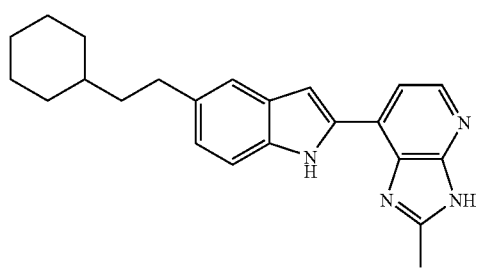 |
| 261 | 808470 | 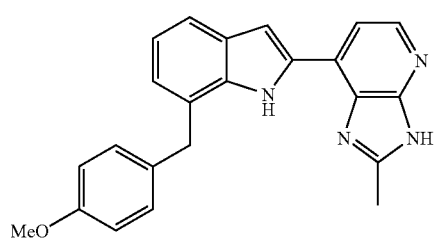 |

-continued
| | | |
|---|---|---|
| 262 | 808473 | 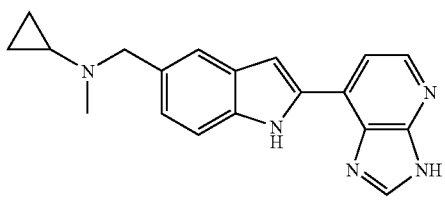 |
| 263 | 808496 | 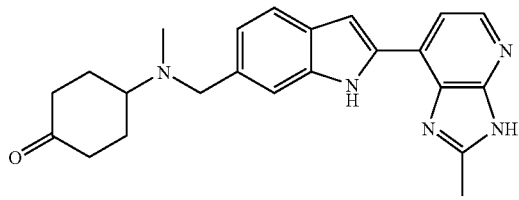 |
| 264 | 808497 | 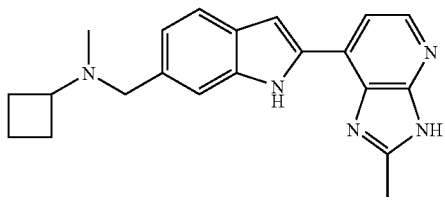 |
| 265 | 808498 | 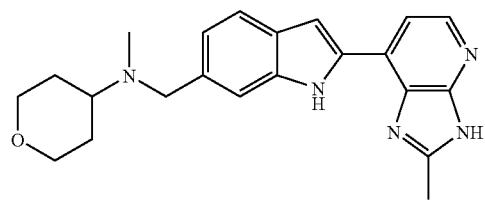 |
| 266 | 808499 | 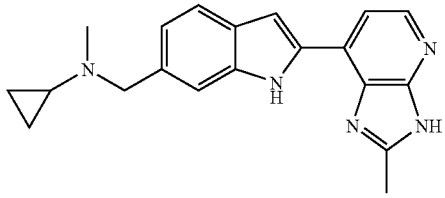 |
| 267 | 808500 | 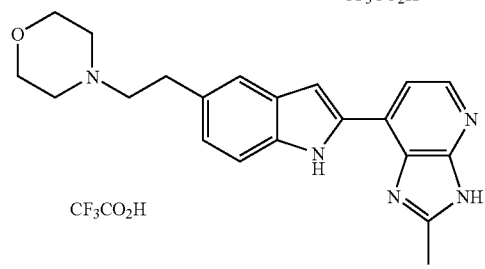 |
| 268 | 808501 | 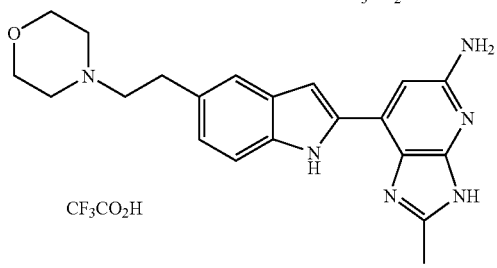 |

| | | | |
|---|---|---|---|
| 269 | 808513 | 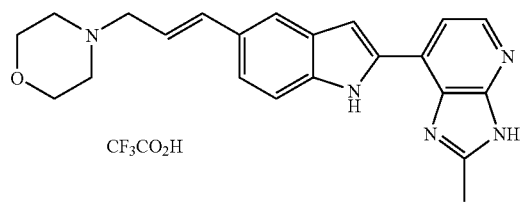 | CF₃CO₂H |
| 270 | 808514 | 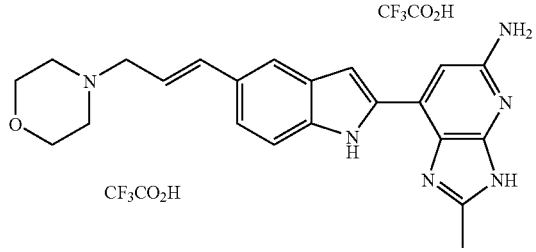 | |
| 271 | 808541 | | |
| 272 | 808542 | 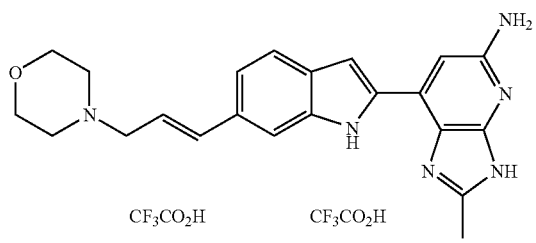 | |
| 273 | 808543 | | |
| 274 | 808544 | 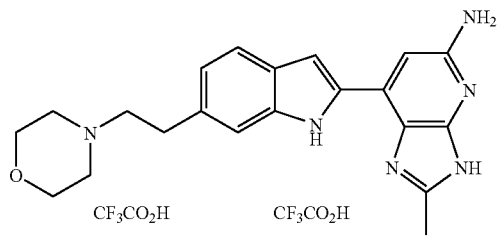 | |

-continued
| | | |
|---|---|---|
| 275 | 808548 | 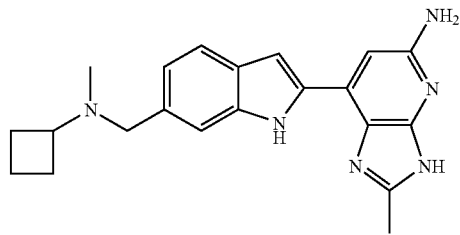 |
| 276 | 808571 | 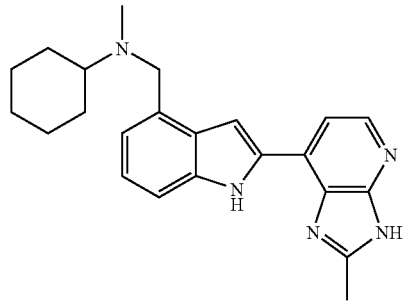 |
| 277 | 808576 | 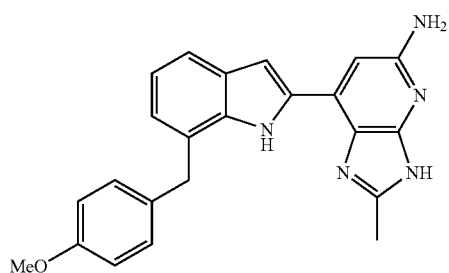 |
| 278 | 808600 | 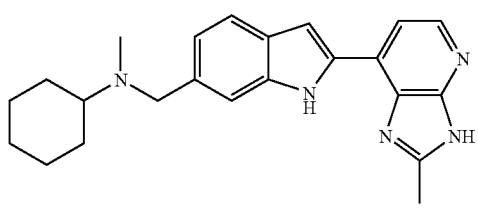 |
| 278 | 808617 | 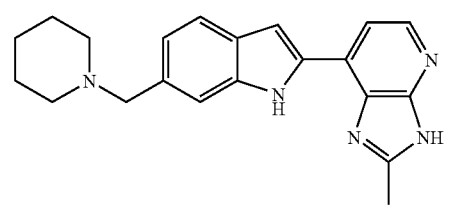 |
| 279 | 808620 | 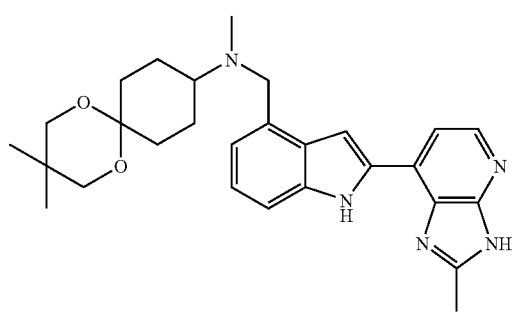 |

| | | -continued |
|---|---|---|
| 280 | 808622 | 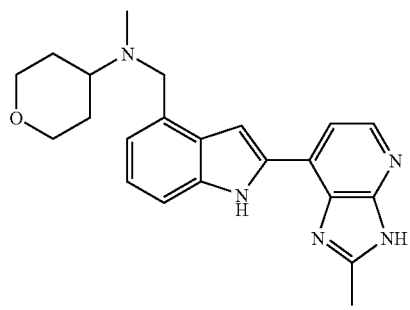 |
| 281 | 808623 | 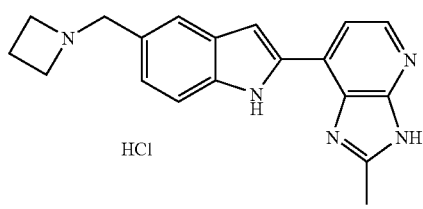 |
| 282 | 808624 | 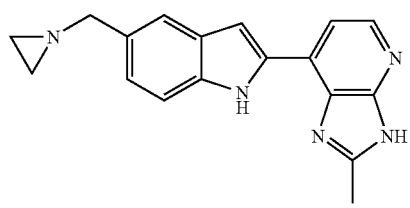 |
| 283 | 808627 | 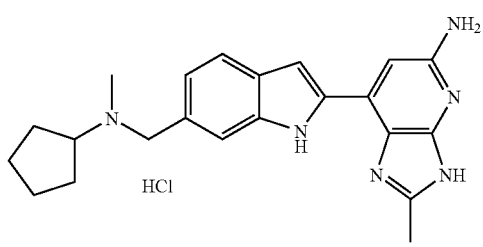 |
| 284 | 808628 | 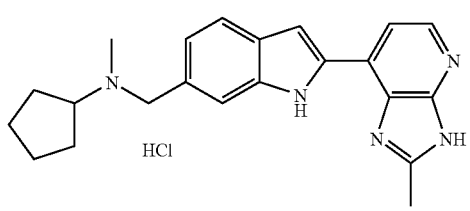 |
| 285 | 808629 | 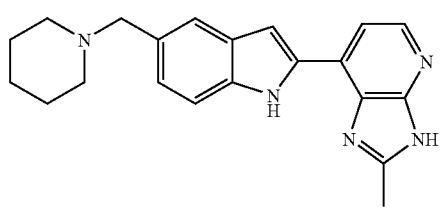 |

-continued
| | | |
|---|---|---|
| 286 | 808631 | 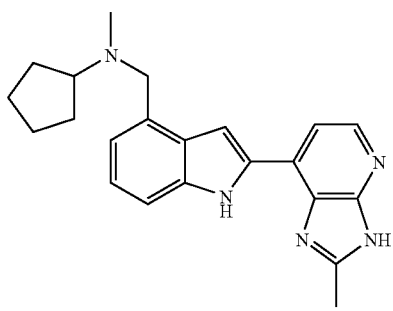 |
| 287 | 808635 | 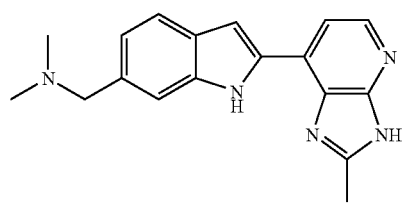 |
| 288 | 808636 | 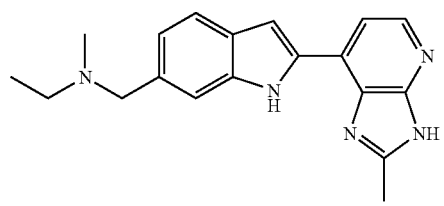 |
| 289 | 808637 | 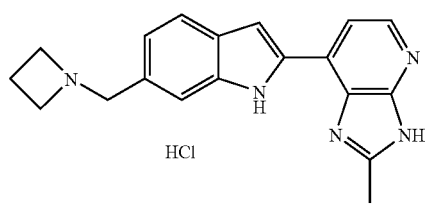 HCl |
| 290 | 808658 | 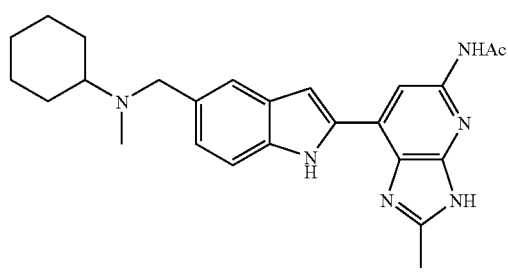 |
| 291 | 808660 | 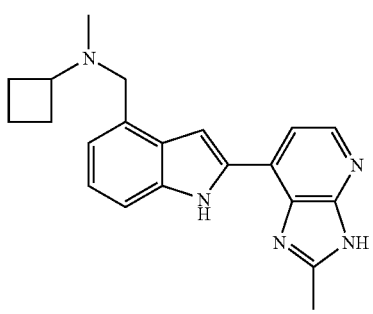 |

-continued
| | | |
|---|---|---|
| 292 | 808661 | 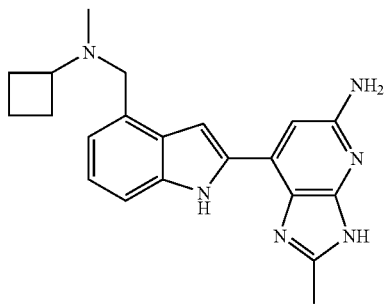 |
| 293 | 808663 | 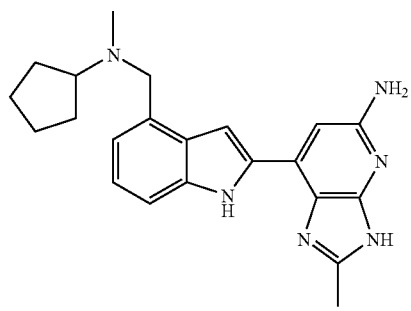 |
| 294 | 808665 | 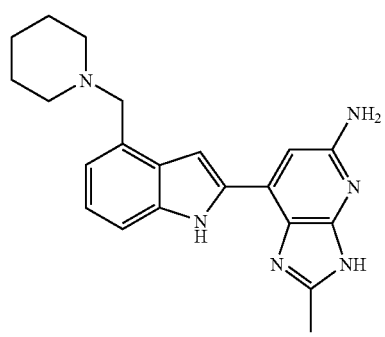 |
| 295 | 808672 | 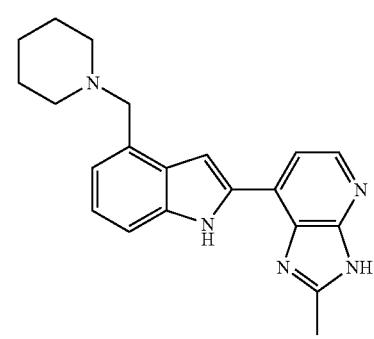 |
| 296 | 808673 | 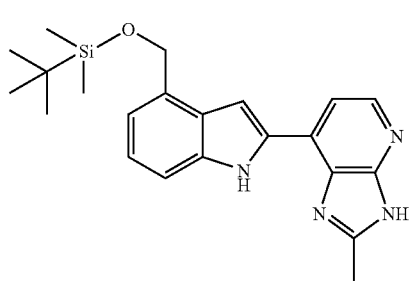 |

-continued
| 297 | 808675 | 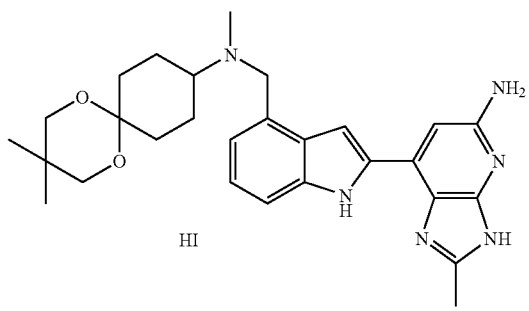 |
| | | HI |
| 298 | 808691 | 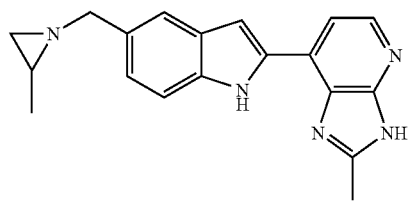 |
| 299 | 808692 | 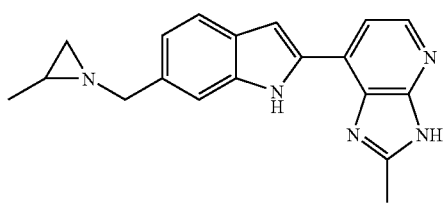 |
| 300 | 808702 | 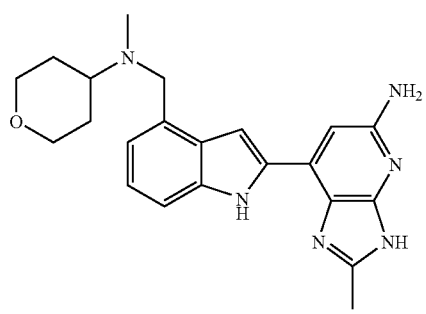 |
| 301 | 808703 | 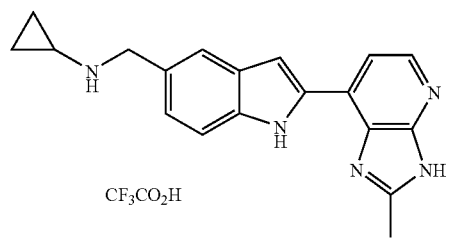 |
| | | CF$_3$CO$_2$H |
| 302 | 808704 | 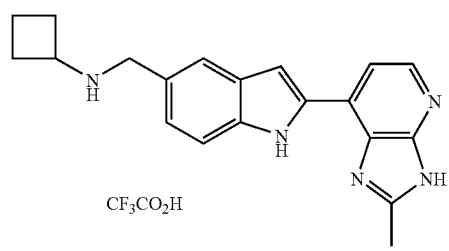 |
| | | CF$_3$CO$_2$H |

-continued
| | | | |
|---|---|---|---|
| 303 | 808705 | 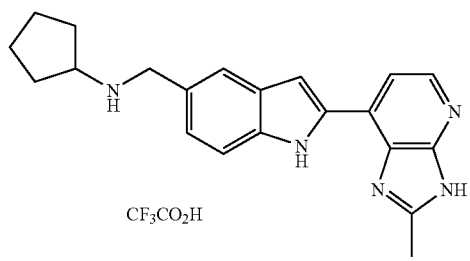 CF₃CO₂H | |
| 304 | 808711 | 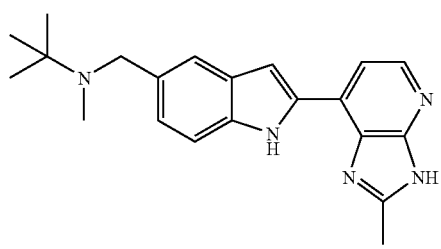 | |
| 305 | 808712 | 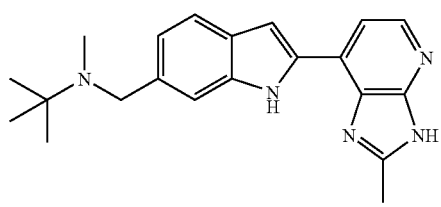 | |
| 306 | 808713 | 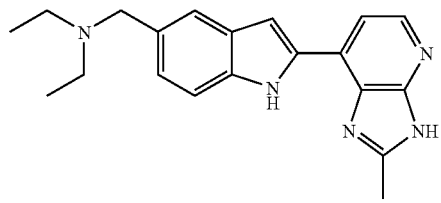 | |
| 307 | 808714 | 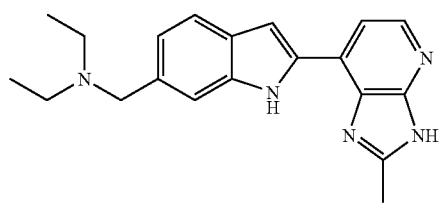 | |
| 308 | 808717 | 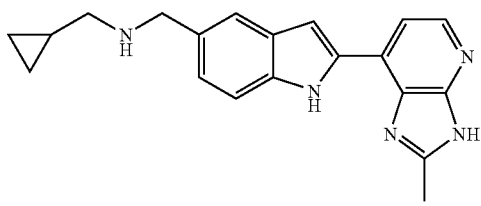 | |
| 309 | 808719 | 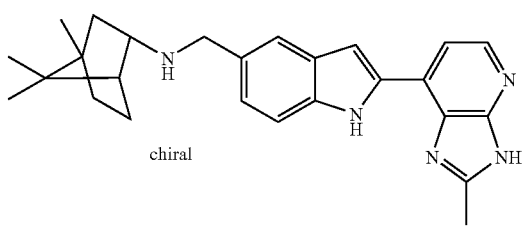 chiral | |

-continued
| | | |
|---|---|---|
| 310 | 808720 | 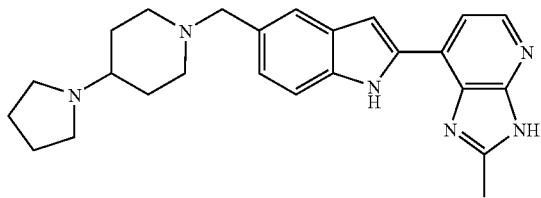 |
| 311 | 808833 | 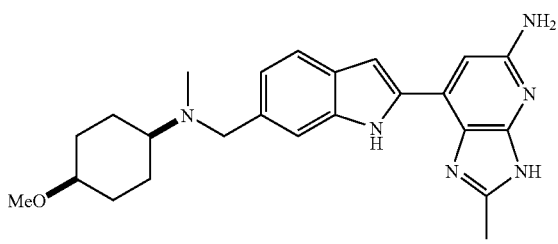 |
| 312 | 808834 | 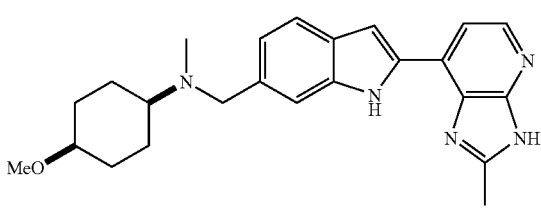 |
| 313 | 808835 | 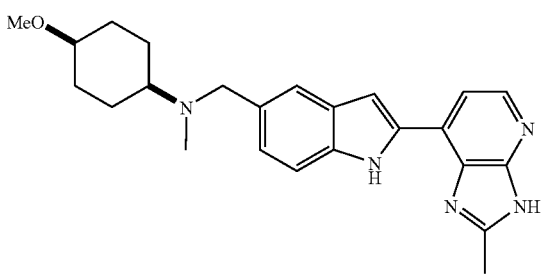 |
| 314 | 808836 | 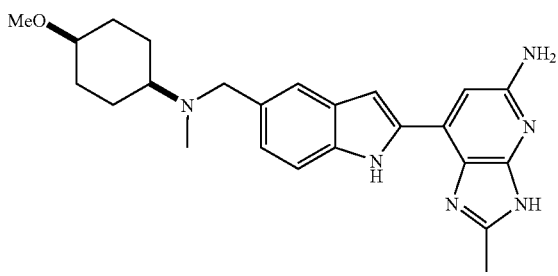 |
| 315 | 808849 |  |

-continued
| | | |
|---|---|---|
| 316 | 808983 | 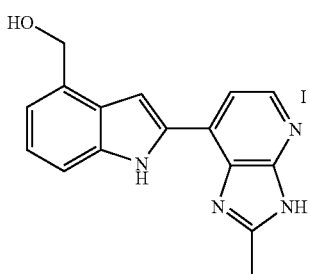 |
| 317 | 808984 | 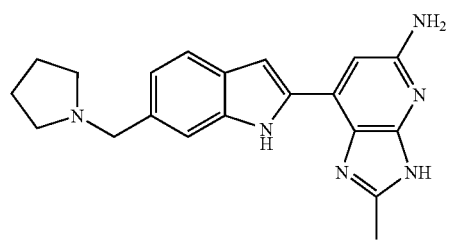 |
| 318 | 809047 | 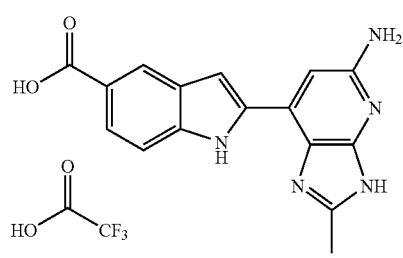 |
| 319 | 809187 | 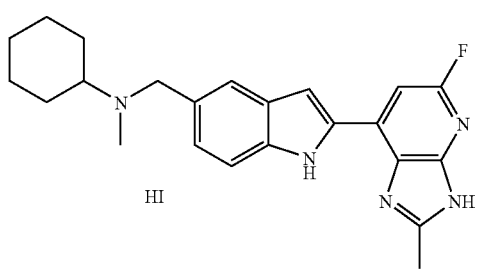 |
| 320 | 809189 | 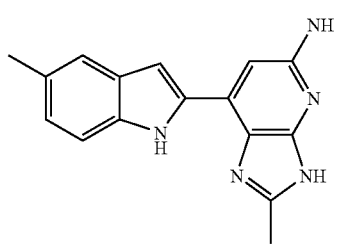 |
| 321 | 809190 | 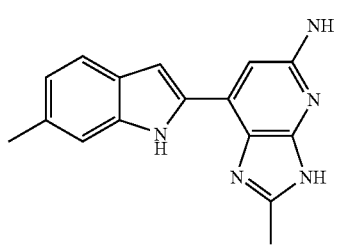 |

-continued
| | | |
|---|---|---|
| 322 | 809191 | 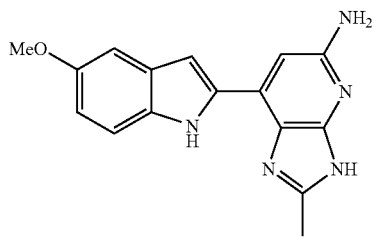 |
| 323 | 809192 | 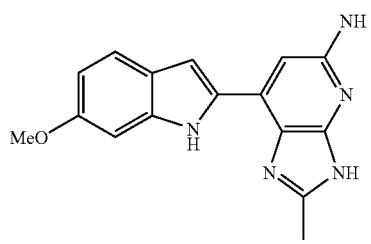 |
| 324 | 809193 | 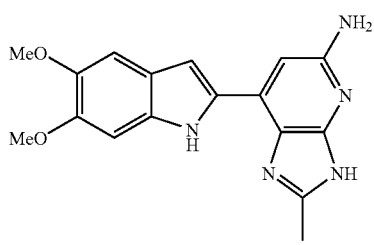 |
| 325 | 809196 | 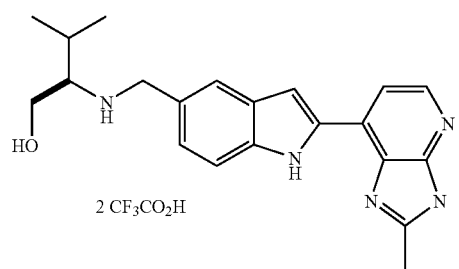 |
| 326 | 809197 | 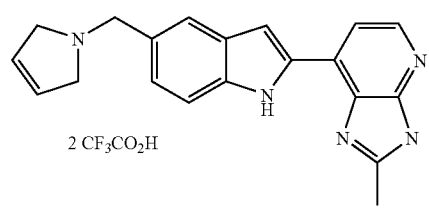 |
| 327 | 809198 | 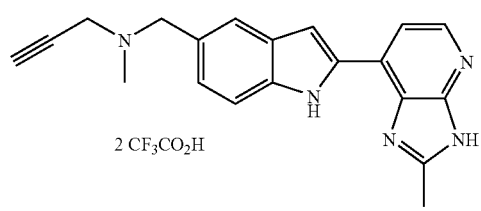 |

-continued
| | | | |
|---|---|---|---|
| 328 | 809199 | 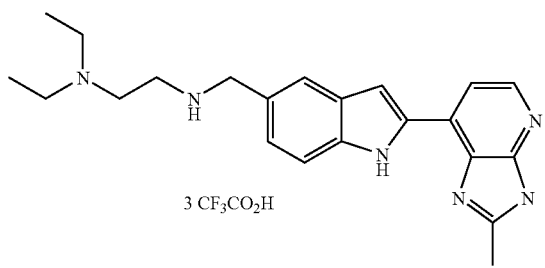 3 CF₃CO₂H | |
| 329 | 809200 | 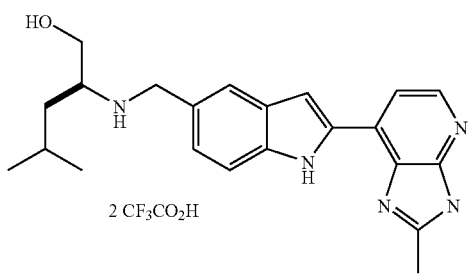 2 CF₃CO₂H | |
| 330 | 809201 | 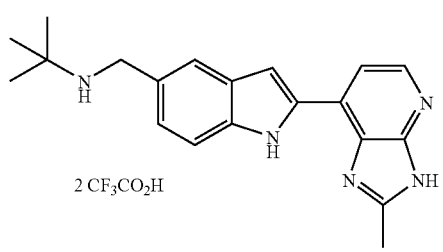 2 CF₃CO₂H | |
| 331 | 809202 | 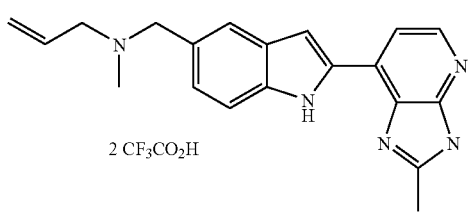 2 CF₃CO₂H | |
| 332 | 809203 | 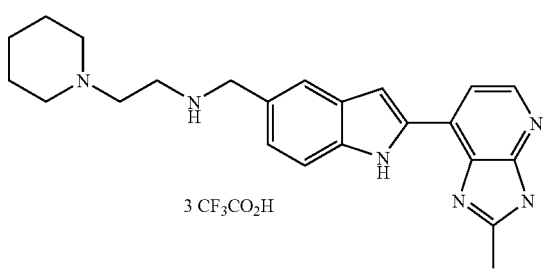 3 CF₃CO₂H | |
| 333 | 809204 | 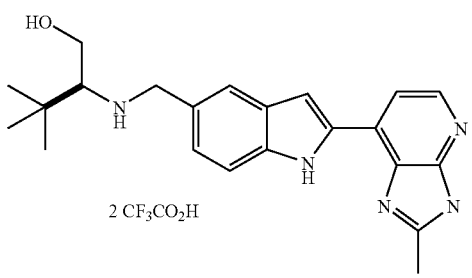 2 CF₃CO₂H | |

-continued
| 334 | 809205 | 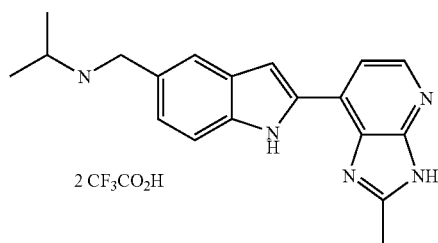 2 CF₃CO₂H |
| 335 | 809206 | 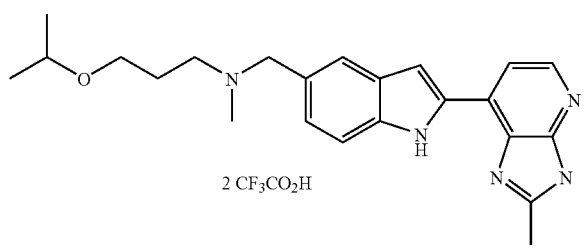 2 CF₃CO₂H |
| 336 | 809207 | 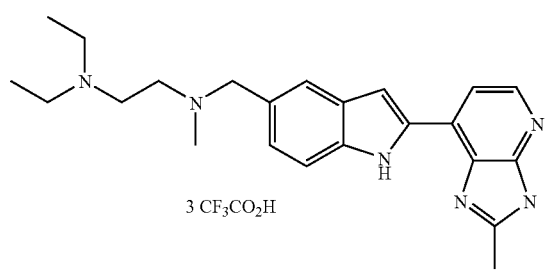 3 CF₃CO₂H |
| 337 | 809208 | 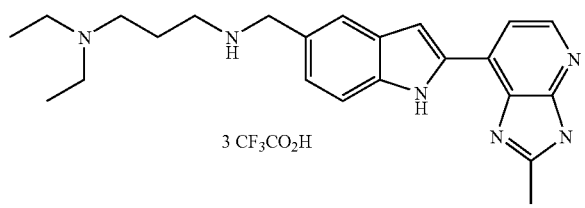 3 CF₃CO₂H |
| 338 | 809209 | 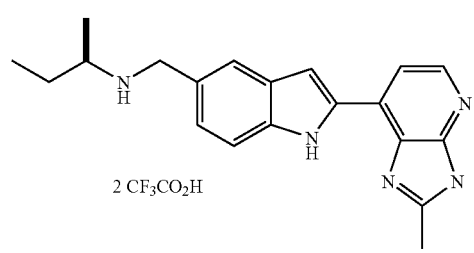 2 CF₃CO₂H |
| 339 | 809210 | 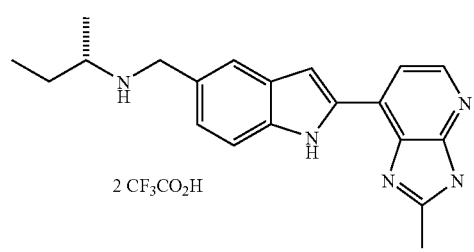 2 CF₃CO₂H |

-continued
| 340 | 809211 | 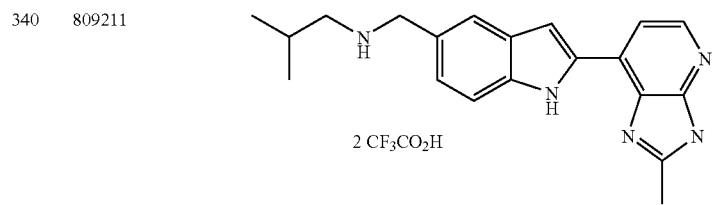 2 CF₃CO₂H |
| 341 | 809212 | 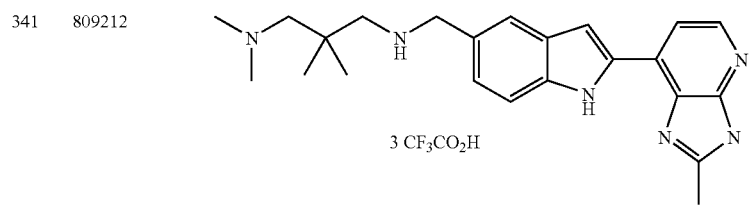 3 CF₃CO₂H |
| 342 | 809213 | 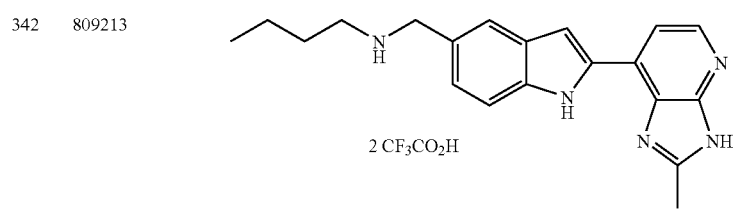 2 CF₃CO₂H |
| 343 | 809214 | 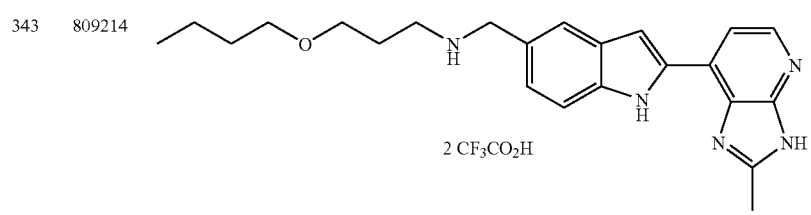 2 CF₃CO₂H |
| 344 | 809215 | 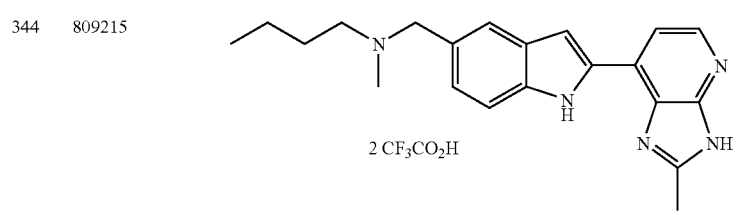 2 CF₃CO₂H |
| 345 | 809216 | 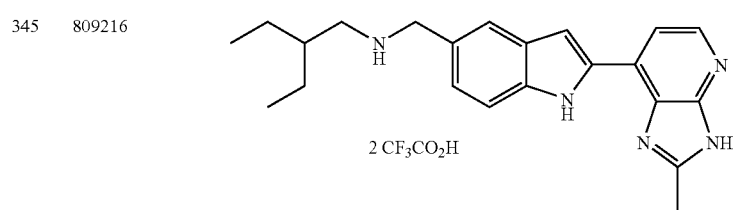 2 CF₃CO₂H |
| 346 | 809217 | 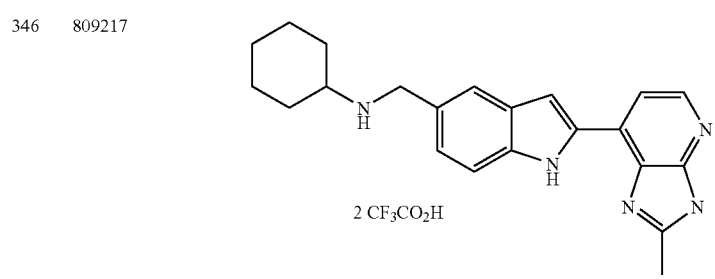 2 CF₃CO₂H |

-continued
| | | | |
|---|---|---|---|
| 347 | 809218 | 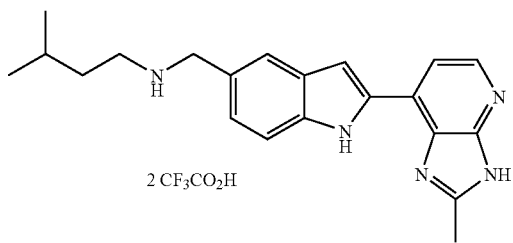 2 CF₃CO₂H | |
| 348 | 809219 | 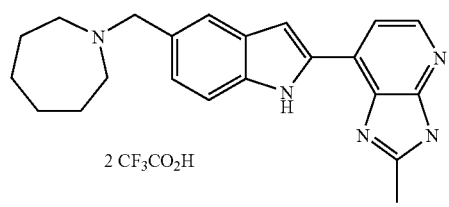 2 CF₃CO₂H | |
| 349 | 809220 | 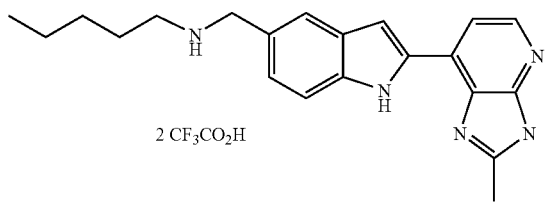 2 CF₃CO₂H | |
| 350 | 809221 | 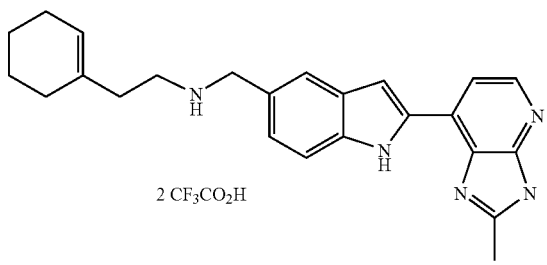 2 CF₃CO₂H | |
| 351 | 809222 | 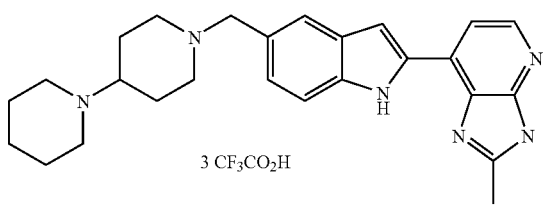 3 CF₃CO₂H | |
| 352 | 809223 | 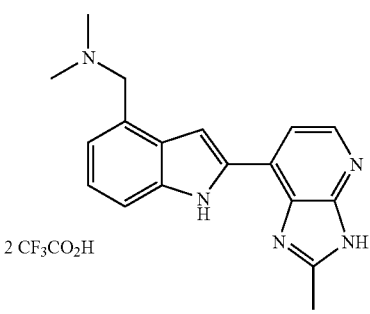 2 CF₃CO₂H | |

-continued
| | | |
|---|---|---|
| 353 | 809224 | 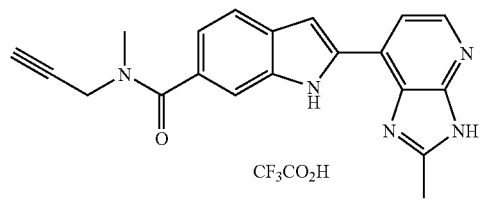 CF₃CO₂H |
| 354 | 809225 | 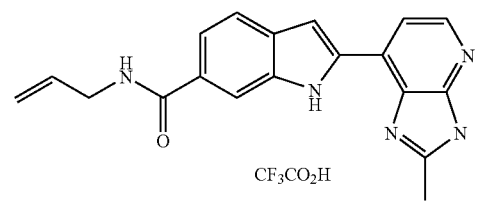 CF₃CO₂H |
| 355 | 809226 | 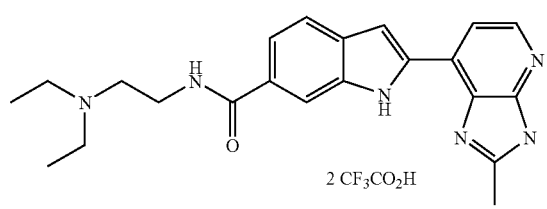 2 CF₃CO₂H |
| 356 | 809227 | 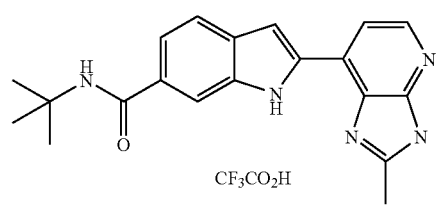 CF₃CO₂H |
| 357 | 809228 | 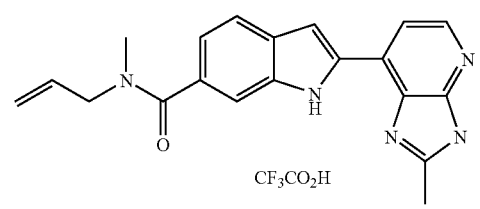 CF₃CO₂H |
| 358 | 809229 | 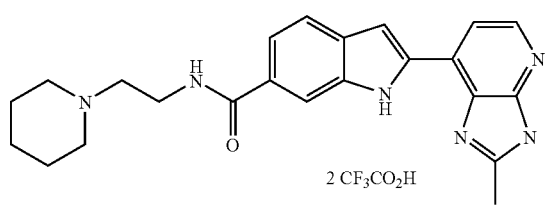 2 CF₃CO₂H |
| 359 | 809230 | 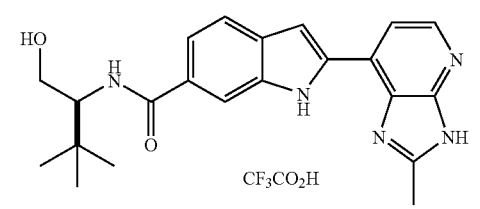 CF₃CO₂H |

-continued
| 360 | 809231 | 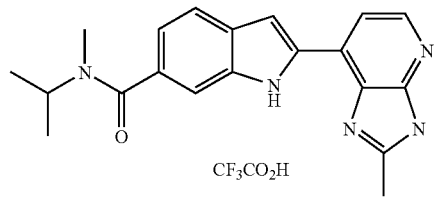<br>CF₃CO₂H |
| 361 | 809232 | 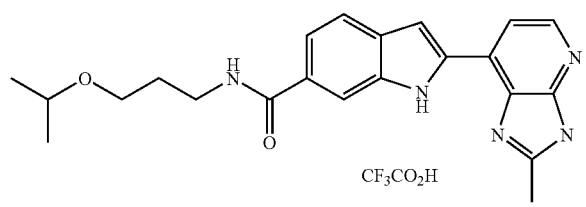<br>CF₃CO₂H |
| 362 | 809233 | 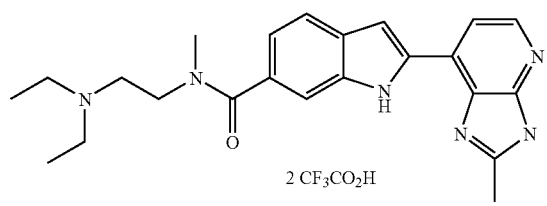<br>2 CF₃CO₂H |
| 363 | 809234 | 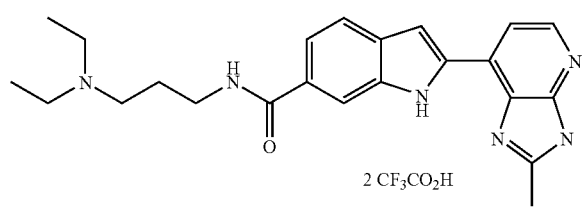<br>2 CF₃CO₂H |
| 364 | 809235 | 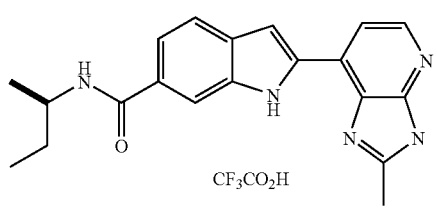<br>CF₃CO₂H |
| 365 | 809236 | 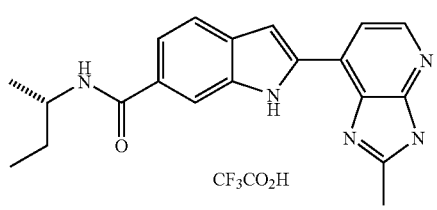<br>CF₃CO₂H |
| 366 | 809237 | 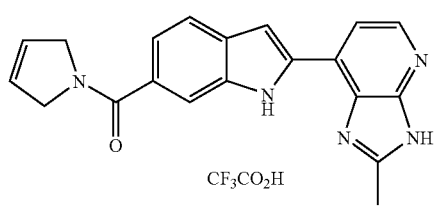<br>CF₃CO₂H |

| | | |
|---|---|---|
| 367 | 809238 | 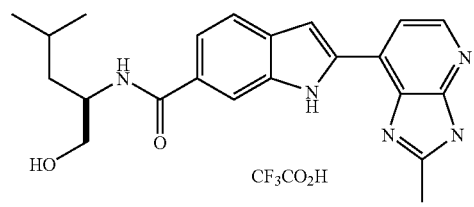 |
| 368 | 809251 | 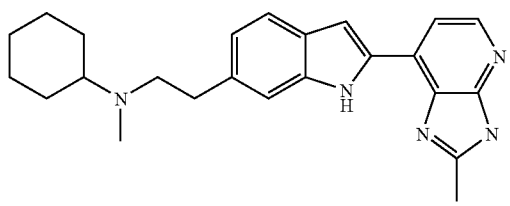 |
| 369 | 809252 | 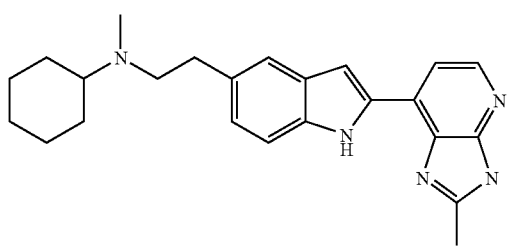 |
| 370 | IC261 | 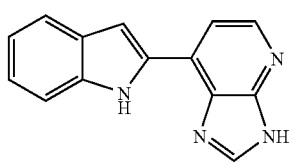 |
| 371 | IC375 | 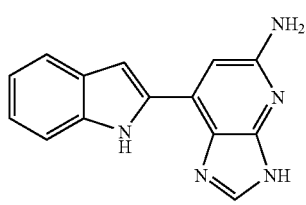 |
| 372 | IC380 | 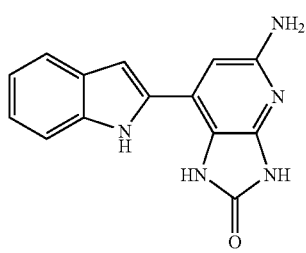 |
| 373 | IC395 | 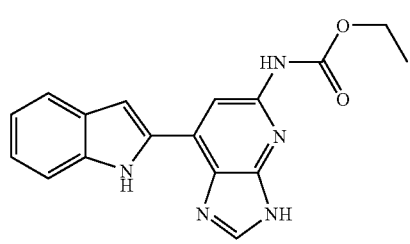 |

-continued
| 374 | IC396 | 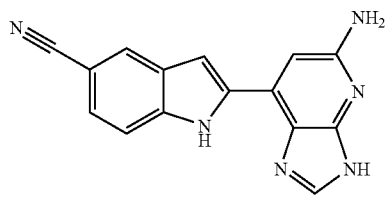 |
| 375 | IC400 | 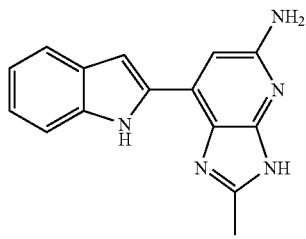 |
| 376 | IC401 | 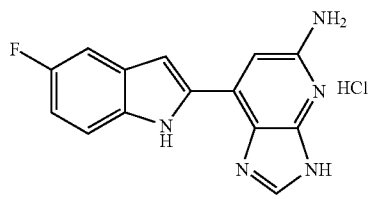 |
| 377 | IC402 | 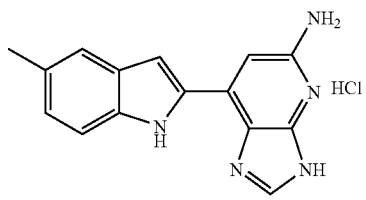 |
| 378 | IC403 | 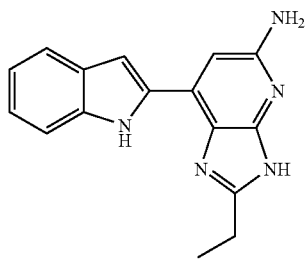 |
| 379 | IC404 | 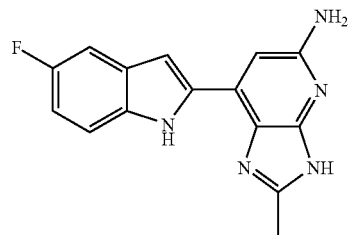 |
| 380 | IC415 | 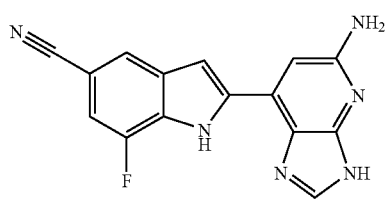 |

| 381 | IC416 | 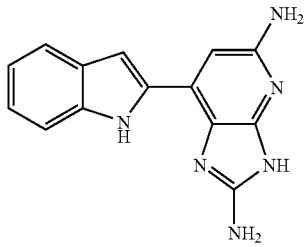 |

2) Experimental Procedures:

As described above, the present invention provides novel deazapurines having formula (I) as described above and in certain classes and subclasses herein. The synthesis of several exemplary compounds is described in detail below. It will be appreciated that the methods as described herein can be applied to each of the compound as disclosed herein and equivalents thereof. Additionally, certain reagents and starting materials are well known to those skilled in the art. Although the following examples describe certain exemplary compounds, it will be appreciated that the use of alternate starting materials will readily yield other analogues encompassed by the invention.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, or by proton nuclear magnetic resonance, of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride or sodium bicarbonate. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous sodium or magnesium sulphate, then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica gel, using a single solvent or mixed solvent as eluent. Suitably purified desired product containing elutes were combined and concentrated under reduced pressure at an appropriate temperature (generally less than 45° C.) to constant mass.

Experimentals for Certain Exemplary Compounds:

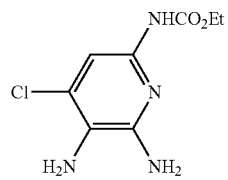

1

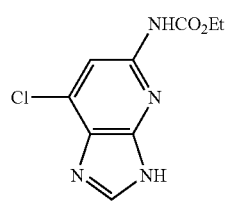

2

In certain embodiments, compounds 1 and 2 were prepared according to the procedure of Temple, C.; Smithy, B. H.; Montgomery, J. A.; *J Org Chem.* 1973, 38, 613-5.

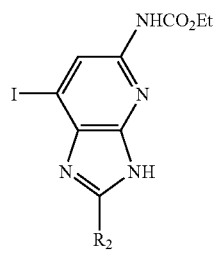

3

Dry HCl (gas) was bubbled through a 2 M solution of nitrile $R_2$—CN) in ethyl ether containing 1 mole equivalent of ethanol at −10° C. for 1-2 hours. After stirring from additional an hour to overnight at room temperature, nitrogen was bubbled through to purge excess HCl gas and ether. The remaining slurry or suspension was filtered, washed with ether three times and then dried under vacuum to give the corresponding ethyl imidate hydrogen chloride.

A mixture of 1 (1 mmol) and the ethyl imidate hydrogen chloride (1.1 mmol) in 5 mL of ethanol was heated at 65-70° C. until reaction was completed (1.5 h to overnight). The mixture was cooled to room temperature, diluted with 20 mL of water, stirred for 30 min., filtered and washed with water. The cake was collected and dried under vacuum to give the desired product 3.

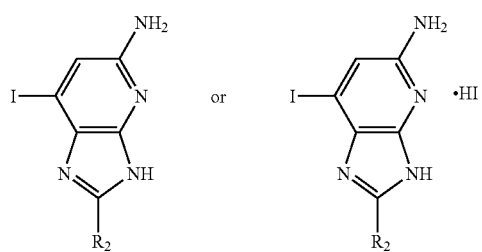

4 or 5

A solution of 3 (1 mmol) in 2.8 mL of 57% HI (aq., 20 mmol) was heated at reflux until reaction was completed (12-20 h). The mixture was cooled to 0° C., slowly diluted with 5 N NaOH solution (19 mmol) and then with 1 mL of sat. NaHCO₃ to pH~9. The resulting mixture was extracted with either ethyl acetate or ethyl acetate/THF mixture until extraction was completed. The combined extracts was dried over Na₂SO₄, filtered and concentrated to give the desired product 4 as free form. Washing the product with ethyl acetate resulted in a better purity if necessary in certain cases. The HI mono-salt form of 4 was obtained after cooling the reaction mixture to room temperature, filtration, washing with water and drying the collected yellow solid in high vacuumn.

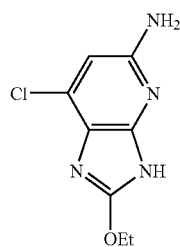

5

A mixture of 1 (300 mg, 1.3 mmol) and tetraethyl orthocarbonate (2.6 mmol) in 10 mL of acetic acid was stirred at room temperature overnight and reaction was completed. The reaction mixture was concentrated under reduced vacuum and the residue was diluted with sat NaHCO₃, extracted with EtOAc, dried over Na₂SO₄, filtered, concentrated to give a brownish solid. This solid was dissolved in 24 mL of H₂O-MeOH (1:1) solution containing 1.2 g of KOH and heated at reflux for 2.5 h. After cooling to room temperature, the mixture was extracted with EtOAc. The extracts was washed with water, dried over Na₂SO₄, filtered, concentrated and the product was purified by chromatography (10% MeOH-EtOAc) to give 5 (45 mg, 16%).

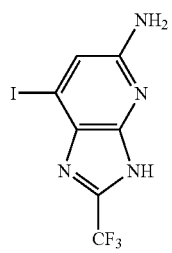

6

A solution of 1 (203 mg, 0.88 mmol) in trifluoroacetic acid (2 mL) was heated at 70° C. for 12 h, cooled to room temperature, concentrated and the residue was diluted with sat. NaHCO₃ (10 ml) and EtOAc (10 mL). The separated aqueous phase was extracted with 4×10 mL of EtOAc and the combined organic layer was dried over Na₂SO₄, filtered and concentrated to give a yellow solid. This yellow solid was mixed with 3 mL of polyphosphoric acid, heated at 200° C. for 3 h and cooled to room temperature. The reaction mixture was carefully quenched with sat. NaHCO₃ (80 ml) and extracted with 4×20 mL of EtOAc. The combined organic layer was dried over Na₂SO₄, filtered and concentrated to give a brownish yellow solid. This solid was dissolved in 5 mL of 57% HI solution and heated at 110° C. for 12 h. After cooling to room temperature, the reaction mixture was carefully poured into sat. NaHCO₃ (60 ml) containing 3 mL of 1 N NaOH and extracted with 4×20 mL of EtOAc. The combined organic layer was dried over Na₂SO₄, filtered and concentrated and the product was purified by chromatography (50 to 100% EtOAc-hexanes) to give the desired product 6 (132 mg, 46% for 3 steps).

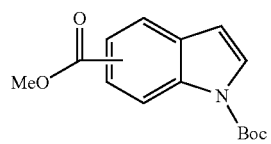

7

A mixture of methyl indole-5-carboxylate (27 g, 155 mmol) (or the corresponding 4-, 6- and 7-carboxylate), di-t-butyl dicarbonate (40 g, 1.2 eq.), Et₃N (26 mL, 1.2 eq.) and DMAP (0.1 g, 0.005 eq.) in THF (165 mL) was stirred at room temperature overnight. The reaction mixture was quenched by addition of sat. NaHCO₃ (350 mL). The separated aqueous layer was extracted once with EtOAc. The combined organic phase was concentrated and the product was purified by chromatography (5% and 10% EtOAc-hexanes) to provide 7 (42 g, 100%).

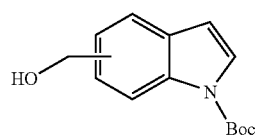

8

To a solution of 7 (42 g, 152 mmol) in dichloromethane (400 mL) at −78° C. was added a 1 M solution of DIBAL-H in toluene (460 mL, 3.0 eq.) during 30 min of period. The cooling bath was replaced with −40° C., the reaction mixture was stirred and warmed to −30° C. and TLC showed reaction was completed. The reaction was quenched with careful addition of MeOH (57 mL, 9.0 eq.) and water (19 mL, 9.0 eq.), diluted with EtOAc (150 mL) and then warmed to rt. The resulting suspension mixture was filtered through celite washing with EtOAc until the product was no longer detected. The filtrate was concentrated and the product was purified by chromatography (15% and 30% EtOAc-hexanes) to provide 8 (29 g, 75%).

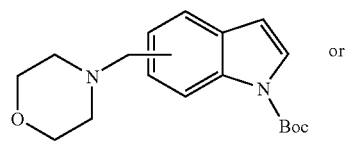

9

-continued

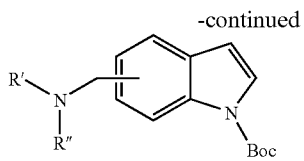

Methanesulfonyl chloride (10.1 mL, 1.2 eq.) was added to a solution of 8 (27.0 g, 109 mmol, 1.0 eq.) and diisopropylethylamine (57 mL, 3.0 eq.) in dichloromethane (250 mL) at 0° C. during 5 min. After stirring additional 15 min, morpholine (14.3 mL, 1.5 eq. or cyclic or acyclic R'R"NH) was added to the reaction mixture and stirred at room temperature overnight. The mixture was poured into sat. NaHCO₃ (100 mL) and water (20 mL), the separated aqueous phase was extracted with 4×50 mL of EtOAc. The combined organic phase was dried over Na₂SO₄, filtered, concentrated and the product was purified by chromatography (15% to 40% EtOAc-hexanes) to provide 9 (34.0 g, 99%).

10

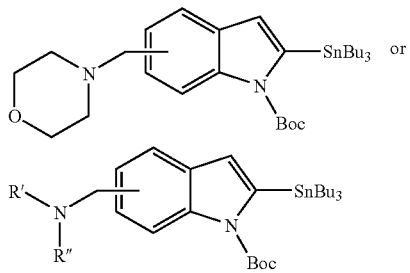

Method A: To a solution of diisopropylamine (17.0 mL, 1.2 eq.) in THF (350 mL) at −78° C. was added nBuLi (2.5 M in hexanes, 48.6 mL, 1.2 eq.) over a 15 min period and the reaction mixture was stirred and warmed to room temperature after removing the cooling bath. The reaction mixture was cooled back to −78° C. and a solution of 9 (32 g, 101 mmol) in THF (120 mL) was introduced by cannulation during 15 min. The resulting mixture was stirred and warmed to −20° C. during 15 min and then Bu₃SnCl (31.5 mL, 1.15 eq.) was introduced. The mixture was stirred and warmed to room temperature and poured into a sat NH₄Cl (300 mL). The separated aqueous phase was extracted with 3×100 mL of EtOAc. The combined organic phase was dried over Na₂SO₄, filtered, concentrated and the product was purified by vacuum chromatography (5% to 50% EtOAc-hexanes) to provide 10 (55 g, 89%).

Method B: This reaction was also carried out by following the same protocol as that used for the preparation of 15 from 14.

11

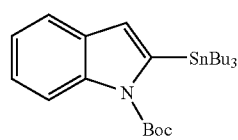

Compound 11 was prepared from indole-1-carboxylic acid tert-butyl ester in 86% following the same procedure for the preparation of 10 from 9.

12

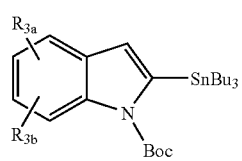

Compound 12 was prepared from mono- or di-substituted indole following similar procedures for the preparation of 7 and 10.

13

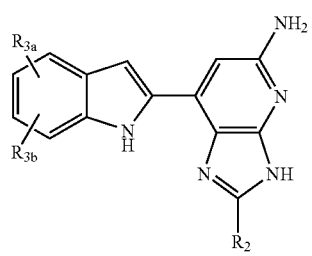

A mixture of 4 (0.4 mmol, 1.0 eq., or 2 or 5 or 6), 10 (1.6 eq., or 11 or 12) and [(C₆H₅)₃P]₄Pd (0.1 eq.) in degassed DMF (1 mL) under nitrogen with or without K₂CO₃ (1.0 eq.) was heated at 110° C. for 18-28 h, cooled to room temperature and concentrated under high vacuum. The residue was diluted with sat. NaHCO₃ (10 mL) and EtOAc. The separated aqueous phase was extracted with EtOAc multiple times until there was no product detected. The combined organic phase was dried over Na₂SO₄, filtered and concentrated. The product was purified by chromatography (5% or 10% MeOH-EtOAc) to give the desired product 13.

| Compound # (ER # or IC #) | Structure of 13 | MS (ES) or/and ¹H NMR |
|---|---|---|
| IC 400 | 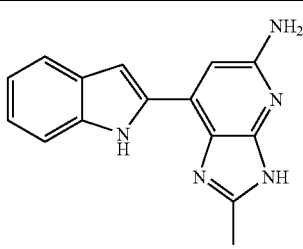 | ¹H NMR |

| Compound # (ER # or IC #) | Structure of 13 | MS (ES) or/and $^1$H NMR |
|---|---|---|
| 806014 | | 287.3 (M − H)⁻ |
| 806006 | | 316.3 (M − H)⁻ |
| 805985 | | 278.3 (M + H)⁺ |
| 805984 | | 292.3 (M + H)⁺ |
| 806002 | | 306.3 (M + H)⁺ |

| Compound # (ER # or IC #) | Structure of 13 | MS (ES) or/and ¹H NMR |
|---|---|---|
| 805969 | | 326.3 (M + H)⁺ |
| 805971 | | 354.3 (M + H)⁺ |
| 805996 | | ¹H NMR |
| 805639 (IC 379) | | ¹H NMR |
| 805895 (IC 405) | | ¹H NMR |

-continued

| Compound # (ER # or IC #) | Structure of 13 | MS (ES) or/and $^1$H NMR |
|---|---|---|
| 806007 | | 425.2 (M − H)$^-$ |
| 805976 | | $^1$H NMR |
| 805975 | | $^1$H NMR |
| 805999 | | $^1$H NMR |
| 806011 | | 393.3 (M + H)$^+$ |

-continued

| Compound # (ER # or IC #) | Structure of 13 | MS (ES) or/and $^1$H NMR |
|---|---|---|
| 805970 | | $^1$H NMR |
| 805972 | | 453.3 (M + H)$^+$ |
| 805997 | | 469.2 (M − H)$^−$ |
| 806010 | | 455.3 (M + H)$^+$ |

-continued

| Compound # (ER # or IC #) | Structure of 13 | MS (ES) or/and $^1$H NMR |
|---|---|---|
| 809189 | | $^1$H NMR |
| 809190 | | $^1$H NMR |
| 809191 | | $^1$H NMR |
| 809192 | | $^1$H NMR |
| 809193 | | $^1$H NMR |

14

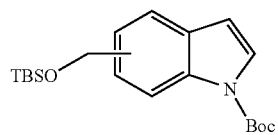

To a mixture of 8 (5-hydroxymethyl-indole-1-carboxylic acid tert-butylester as an example, 24.4 g, 98.8 mmol), Et$_3$N (41 mL, 3 eq.) and DMAP (1.2 g, 0.1 eq.) in dichloromethane (185 mL) was added TBSCl (23.1 g, 1.5 eq.) at room temperature and the resulting mixture was stirred overnight. The reaction was quenched with the addition of sat NaHCO$_3$ (200 mL) and the separated aqueous layer was extracted with 3×50 mL dichloromethane. The combined organic phase was dried over Na$_2$SO$_4$, filtered, concentrated and the product was purified by vacuum chromatography (3% EtOAc-hexanes) to provide 14 (5-tert-butyl-dimethyl-silanyloxymethyl)-indole-1-carboxylic acid tert-butyl ester) as a colorless oil (33.9 g, 95%).

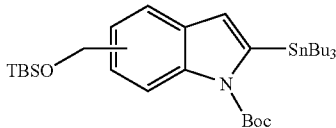

15

To a solution of 14 (5-tert-butyl-dimethyl-silanyloxymethyl-indole-1-carboxylic acid tert-butyl ester as an example, 33.5 g, 92.7 mmol) in THF (650 mL) below −72° C. was added tBuLi (63 mL, 1.7 M in pentane, 1.2 eq.) dropwise over a period of 45 min and stirring was continued for an additional 40 min. The resulting brown solution was briefly warmed to −60° C. and then cooled back to below −72° C. Bu₃SnCl (31.6 mL, 1.3 eq.) was then introduced to the reaction mixture and stirred at −40° C. for 15 min. The reaction was quenched at −35° C. with sat. NaHCO₃ (250 mL) and the separated aqueous layer was extracted with 3×150 mL EtOAc. The combined organic phase was dried over Na₂SO₄, filtered, concentrated and the product was purified by vacuum chromatography (hexanes) to provide 15 (5-(tert-butyl-dimethyl-silanyloxymethyl)-2-tributylstannyl-indole-1-carboxylic acid tert-butyl ester) as a colorless oil (60.6 g, 100%).

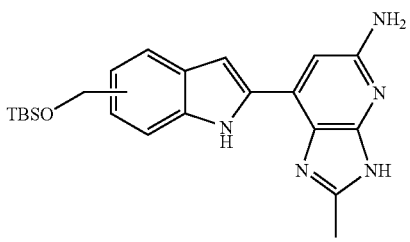

16

A solution of 15 (5-(tert-butyl-dimethyl-silanyloxymethyl)-2-tributylstannyl-indole-1-carboxylic acid tert-butyl ester as an example, 60.6 g, 3.0 eq.) in DMF (100 mL) was added in four portions during 24 h period to a solution of 4 (R₂=Me, 8.51 g, 31.0 mmol), Pd(Ph₃P)₄ (3.2 g, 0.09 eq.) and Et₃N (26 mL, 3.0 eq.) in DMF (100 mL) with or without K₂CO₃ (1.0 eq.) at 110° C. under nitrogen atmosphere. The resulting mixture was stirred for 20 h, cooled to room temperature and concentrated. The residue was diluted with sat. NaHCO₃ (300 mL) and EtOAc (300 mL), filtered and washed with EtOAc to get rid of dark gray sludge. The separated aqueous phase from the filtrate was extracted with 6×200 mL EtOAc until no desired product detected by TLC. The combined organic phase was dried over Na₂SO₄, filtered and concentrated. The residue was diluted with EtOAc and the resulting suspension was filtered, washed with EtOAc and 2×MeOH to give 16 (4.27 g). The filtrate was concentrated and the residual product was purified by chromatography (0 to 5% MeOH-EtOAc) to give additional 16 (2.59 g). The products were combined to give 16 (7-[5-(tert-butyl-dimethyl-silanyloxymethyl)-1H-indol-2-yl]-2-methyl-3H-imidazo[4,5-b]pyridin-5-ylamine) as a greenish gray solid (6.86 g, 54%).

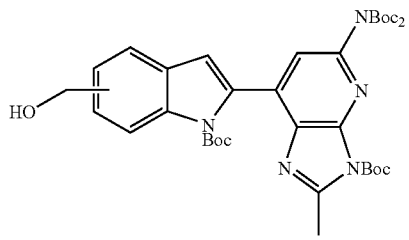

17

A solution of tBuOK in THF (1.66 M, 96.3 mL, 9.5 eq.) was added to a mixture of 16 (7-[5-(tert-butyl-dimethyl-silanyloxymethyl)-1H-indol-2-yl]-2-methyl-3H-imidazo[4,5-b]pyridin-5-ylamine as an example, 6.86 g, 16.8 mmol) and di-tert-butyl dicarbonate (39 mL, 10 eq.) in THF (1.1 L) at below −28° C. during 40 min period. After stirring for 10 min, the reaction was quenched by addition of sat. NaHCO₃ (300 mL) and warmed to room temperature. The separated aqueous layer was extracted by 3×150 mL of EtOAc. The combined organic phase was dried over Na₂SO₄, filtered, concentrated and the product was purified by vacuum chromatography (10 to 20% EtOAc/hexanes) to provide a di-Boc-protected intermediate.

The di-Boc-protected intermediate was then dissolved in 55 mL THF containing Et₃N (55 mL), DIBOC (22.5 g, 6.0 eq.) and DMAP (0.21 g, 0.1 eq.) and heated at 65° C. for 5 h. After cooling to room temperature, the mixture was concentrated and the product was purified by vacuum chromatography (10% EtOAc-hexanes) to provide tetra-Boc-protected intermediate.

The tetra-Boc-protected intermediate was then dissolved in a solution of HF/pyridine in THF (0.89 M, 5.3 eq., HF/pyridine solution was prepared by mixing of 10 g of 70% R_F/pyridine, 52.5 mL of pyridine and 330 mL of THF) and stirred at room temperature for 40 h. The reaction mixture was then carefully quenched with sat NaHCO₃ (250 mL) and the separated aqueous layer was extracted by 3×50 mL of EtOAc. The combined organic phase was washed with brine (50 mL), dried over Na₂SO₄, filtered, concentrated and the product was purified by vacuum chromatography (10 to 50% EtOAc-hexanes) to provide 17 (5-di-(tert-butoxycarbonyl)amino-7-(1-tert-butoxycarbonyl-5-hydroxylmethyl-1H-indol-2-yl)-2-methyl-imidazo[4,5-b]pyridine-3-carboxylic acid ter-1-butyl ester, 5.64 g, 48% for three steps) as a light yellow solid.

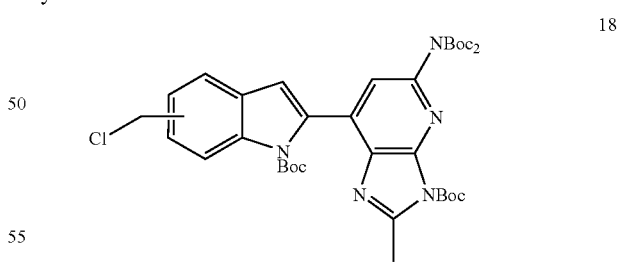

18

Methylsulfonylchloride (0.14 mL, 1.5 eq.) was added to a mixture of 17 (5-di-(tert-butoxycarbonyl)amino-7-(1-tert-butoxycarbonyl-5-hydroxylmethyl-1H-indol-2-yl)-2-methyl-imidazo[4,5-b]pyridine-3-carboxylic acid tert-butyl ester as an example, 830 mg, 1.2 mmol) and diisopropylethylamine (2.08 mL, 10 eq.) in dichloromethane (10 mL) at 0° C. and the resulting mixture was stirred and warmed to room temperature. After stirring for 7 h at room temperature, the mixture was kept at 0° C. for two days, warmed to room temperature and concentrated to half of its volume. The product was then purified by chromatography (20% to 30%

EtOAc/hexanes) to give 18 (5-di-(tert-butoxycarbonyl)amino-7-(1-tert-butoxycarbonyl-5-chloromethyl-1H-indol-2-yl)-2-methyl-imidazo[4,5-b]pyridine-3-carboxylic acid tert-butyl ester, 770 mg, 90%).

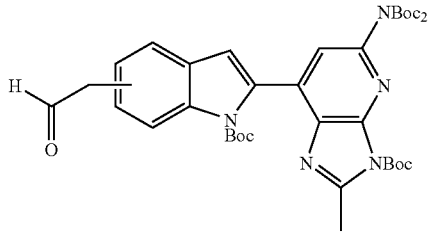

19

A mixture of 17 (5-di-(tert-butoxycarbonyl)amino-7-(1-tert-butoxycarbonyl-5-hydroxylmethyl-1H-indol-2-yl)-2-methyl-imidazo[4,5-b]pyridine-3-carboxylic acid tert-butyl ester as an example, 122 mg, 0.18 mmol) and Dess-Martin periodinane (223 mg, 3.0 eq.) in dichloromethane (4 mL) was stirred at room temperature for 1 h. The resulting mixture was diluted with diethyl ether (60 mL), stirred for 20 min and filtered through celite washing with diethyl ether. The filtrate was washed with sat. NaHCO$_3$ (20 mL) containing Na$_2$S$_2$O$_3$ (500 mg) and the aqueous phase was back extracted with 2×25 mL diethyl ether. The combined organic layer was dried over Na$_2$SO$_4$, filtered, concentrated and the product was purified by chromatography (10 to 30% EtOAc-hexanes) to provide 19 (5-di-(tert-butoxycarbonyl)amino-7-(1-tert-butoxycarbonyl-5-formyl-1H-indol-2-yl)-2-methyl-imidazo[4,5-b]pyridine-3-carboxylic acid tert-butyl ester, 117 mg, 96%).

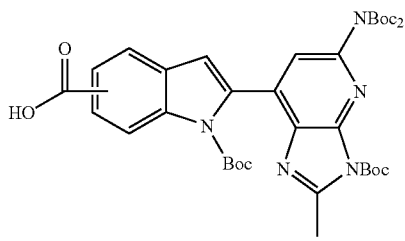

20

A solution of KMnO$_4$ (436 mg, 2 eq.) and KH$_2$PO$_4$ (563 mg, 3 eq.) in water (15 mL) was added to a solution of 19 (5-di-(tert-butoxycarbonyl)amino-7-(1-tert-butoxycarbonyl-5-formyl-1H-indol-2-yl)-2-methyl-imidazo[4,5-b]pyridine-3-carboxylic acid tert-butyl ester as an example, 958 mg, 1.38 mmol) in tBuOH (10 mL) at room temperature during 3 min and the resulting mixture was stirred for 30 min. The mixture was then diluted with EtOAc. (20 mL), filtered through celite washing with EtOAc. The filtrate was diluted with brine (60 mL), water (40 mL) and EtOAc (200 mL). The separated aqueous phase was extracted with 3×30 mL of EtOAc. The combined organic layer was dried over Na$_2$SO$_4$, filtered, concentrated and the product was purified by chromatography (30 to 100% EtOAc/hexanes) to provide 20 (2-(3-tert-butylcarbonyl-5-di-(tert-butylcarbonyl)amino-2-methyl-3H-imidazo[4,5-b]pyridin-7-yl)-indole-1,5-carboxylic acid 1-tert-butyl ester, 678 mg, 69%).

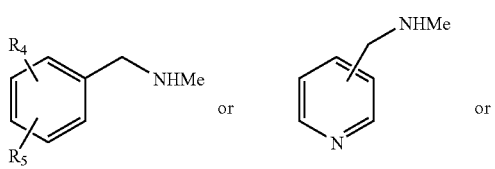

21

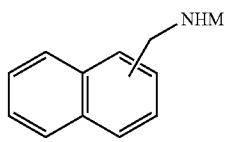

-continued

A mixture of (mono- or di-)substituted benzyl chloride (or bromide) or bromomethylnaphthalene or chloromethylpyridine hydrochloride (20 mmol) and methylamine (22 mL, 40% in water, 10 eq.) in MeOH (18 mL) was stirred at room temperature for 1-5 days until reaction was completed. After concentration, the reaction mixture was diluted with sat. NaHCO$_3$ (50 mL), extracted with EtAOc until there was no product detected. The combine extracts were dried over Na$_2$SO$_4$, filtered, concentrated to give the product 21.

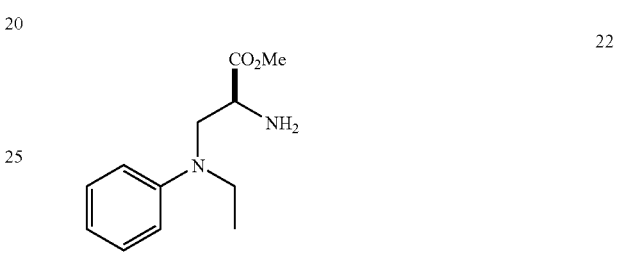

22

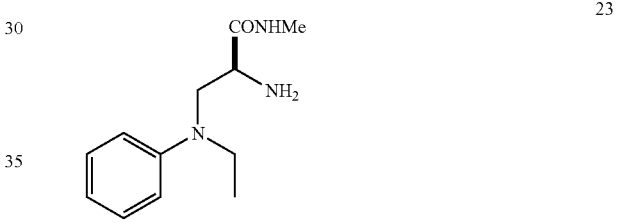

23

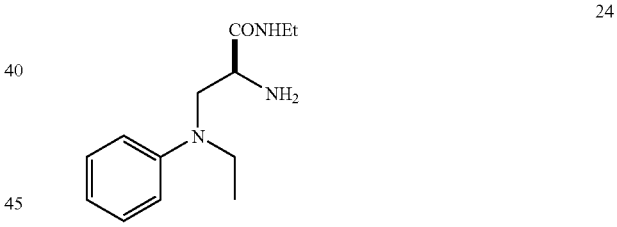

24

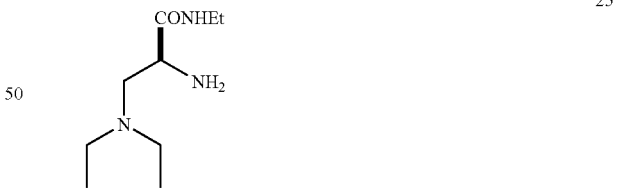

25

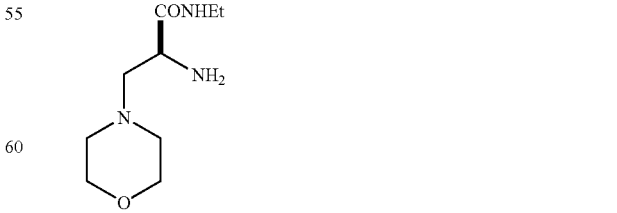

26

Amines 22-26 were prepared following a modified procedure disclosed in published PCT application number WO 01/00610 A1.

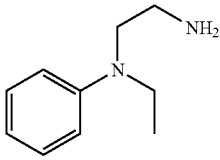

27

Methanesulfonyl chloride (0.80 mL, 1.2 eq.) was added to a solution of 2-(ethyl-phenyl-amino)-ethanol (1.43 g, 8.65 mmol) and diisopropylethylamine (3.0 mL, 2.0 eq.) in dichloromethane (10 mL) at 0° C. and the resulting mixture was stirred for 15 min. A solution of ammonia (20 mL, 2 M in MeOH) was then introduced and the resulting mixture was stirred at room temperature for five days and concentrated. The residue was diluted with a solution of HCl (7 mL, 1 N) and washed with 3×EtOAc. The aqueous phase was treated with a solution of NaOH (15 mL, 1 N) and extracted once with EtOAc. The extract was dried over $Na_2SO_4$, filtered, concentrated to give the product 27.

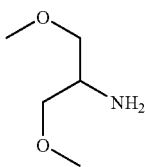

28

To a solution of 2-benzyloxy-propane-1,3-diol (5.0 g, 27.4 mmol) in 5:1 THF-DMF (200 mL) at 0° C. was added NaH (1.5 g, 2.3 eq.) followed by methyl iodide (5.1 mL, 3.0 eq.). The resulting white slurry mixture was stirred at room temperature over weekend. The reaction mixture was quenched with sat. $NH_4Cl$, extracted with EtOAc, dried over $Na_2SO_4$, filtered, concentrated and the product was purified by chromatography (50% EtOAc/hexanes) to give (2-methoxy-1-methoxymethyl-2-ethoxymethyl)-benzene (5.6 g, 97%).

A mixture of (2-methoxy-1-methoxymethyl-2-ethoxymethyl)-benzene (5.5 g) and $Pd(OH)_2$ (0.4 g) in MeOH (150 mL) was stirred at room temperature under hydrogen gas until reaction was completed. The reaction mixture was filtered and concentrated to give 1,3-dimethoxy-propan-2-ol (3.0 g, 96%).

Methanesulfonyl chloride (0.61 mL, 2.0 eq.) was added to a solution of 1,3-dimethoxy-propan-2-ol (0.50 g, 4.14 mmol) and triethylamine (2.3 mL, 4.0 eq.) in dichloromethane (2 mL) at 0° C. and the resulting mixture was stirred for 15 min. The reaction was quenched by sat. $NaHCO_3$ and the mixture was extracted with EtOAc. The combined extracts were dried over $Na_2SO_4$, filtered and concentrated. The residue and $NaN_3$ (0.80 g, 3.0 eq.) was dissolved in DMSO (10 mL) and heated at 90° C. over weekend. After cooling to room temperature, the mixture was diluted with sat. $NaHCO_3$ and extracted with diethyl ether. The combined extracts were dried over $Na_2SO_4$, filtered and concentrated to give azide intermediate (320 mg, 48%).

A mixture of the azide intermediate (320 mg) and $Pd(OH)_2$ in MeOH (15 mL) was stirred at room temperature under hydrogen gas for 1 h. The reaction mixture was filtered and concentrated to give 28 (150 mg, 63%).

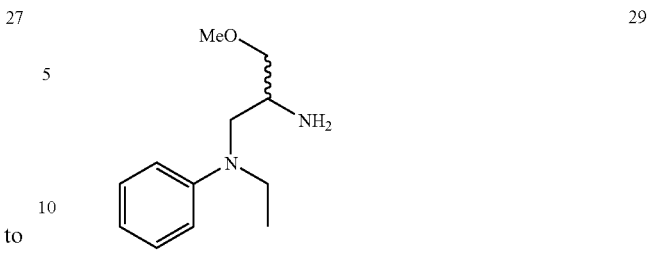

29

A mixture of ethyl-phenyl-amine (4.15 mL, 33 mmol), allyl bromide (4.3 mL, 1.5 eq.) and $K_2CO_3$ (9.1 g, 2.0 eq.) in acetone (50 mL) was heated at reflux for overnight. After cooling to room temperature, the reaction mixture was diluted with water (50 mL) and EtOAc (100 m). The separated organic phase was dried over $Na_2SO_4$, filtered and concentrated and the product was purified by chromatography (10% EtOAc/hexanes) to give allyl-ethyl-phenyl-amine (5.32 g, 100%).

A solution of $OsO_4$ (7.8 mL, 0.1 M in water, 0.03 eq.) was added to a mixture of allyl-ethyl-phenyl-amine (4.10 g, 25.3 mmol) and NMO (5.92 g, 2.0 eq.) in 9:1 acetone-water (40 mL) at room temperature and the resulting mixture was stirred overnight. The mixture was diluted with sat. Na $HCO_3$ (80 mL), sat $Na_2S_2O_3$ (20 mL) and 1:1 $Et_2O$-hexanes (100 mL). The separated aqueous phase was extracted with 2×30 mL of EtOAc and the combined organic phase was dried over $Na_2SO_4$, filtered and concentrated and the product was purified by chromatography (30% EtOAc-hexanes) to give 3-(ethyl-phenyl-amino)-propane-1,2-diol (4.25 g, 86%). Methanesulfonyl chloride (2.5 mL, 1.5 eq.) was added to a solution 3-(ethyl-phenyl-amino)-propane-1,2-diol (4.22 g, 21.6 mmol) and triethylamine (9.03 mL, 3.0 eq.) in dichloromethane (20 mL) at −30 to −35° C. and the resulting mixture was stirred and warmed to 0° C. The reaction was quenched by sat. $NaHCO_3$ (30 mL) and the separated aqueous phase was extracted with 2×20 mL $CH_2Cl_2$ and 20 mL EtOAc. The combined extracts were dried over $Na_2SO_4$, filtered and concentrated. The residue was dissolved in MeOH (30 mL) and treated with NaOMe (2.3 g, 2.0 eq.) at 65-70° C. for 3 h. After cooling to room temperature, the mixture was diluted with sat. $NaHCO_3$ (50 mL) and extracted with 3×30 mL of EtOAc. The combined extracts were dried over $Na_2SO_4$, filtered and concentrated and the product was purified by chromatography (10% EtOAc/hexanes) to give ethyl-oxiranylmethyl-phenyl-amine (1.72 g, 45%).

A solution of ethyl-oxiranylmethyl-phenyl-amine (1.72 g, 9.65 mmol) and NaOMe (1.04 g, 2.0 eq.) in MeOH(8 mL) was heated at reflux for over weekend. After cooling to room temperature, the mixture was diluted with sat. $NaHCO_3$ (20 mL) and extracted with 3×20 mL of EtOAc. The combined extracts were dried over $Na_2SO_4$, filtered and concentrated and the product was purified by chromatography (30% EtOAc-hexanes) to give 1-(ethyl-phenyl-amino)-3-methoxy-propan-2-ol (1.95 g, 97%).

A solution of 1-(ethyl-phenyl-amino)-3-methoxy-propan-2-ol (1.95 g, 9.32 mmol) and NMO (2.18 g, 2.0 eq.) in dichloromethane (15 mL) was treated with TPAP (150 mg, 0.05 eq.) at room temperature until reaction was completed. The reaction mixture was diluted with sat. $NaHCO_3$ (50 mL) and extracted with 3×30 mL EtOAc. The combined extracts were dried over $Na_2SO_4$, filtered and concentrated and the product was purified by chromatography (10 to 15% EtOAc-hexanes) to give 1-(ethyl-phenyl-amino)-3-methoxy-propan-2-one (0.98 mg, 51%).

A mixture of 1-(ethyl-phenyl-amino)-3-methoxy-propan-2-one (17 mg, 0.08 mmol), hydroxylamine hydrochloride (30 mg) and pyridine (0.3 mL) in MeOH (0.4 mL) was stirred at room temperature for 1.5 h. The reaction mixture was diluted with sat NaHCO₃ and extracted with 3×EtOAc. The combined extracts were dried over Na₂SO₄, filtered and concentrated. The residue was dissolved in THF (0.8 mL) and treated with lithium aluminum hydride (0.3 mL, 1 M in THF) at room temperature for overnight. Work-up and purification by chromatography (5:95 ratio of 2 M NH₃ in MeOH:CH₂Cl₂) gave 29 as light yellow oil.

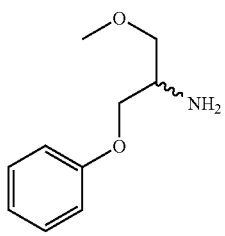

30

Compound 30 was prepared from 3-phenoxy-propane-1,2-diol in 21% overall yield following the same procedures for the preparation of 29 from 3-(ethyl-phenyl-amino)-propane-1,2-diol.

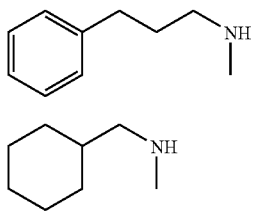

31

32

A mixture of 3-(bromo-propyl)-benzene or bromomethyl-cyclohexane (1 M, 1.0 eq.) in MeOH and 40% MeNH₂ in water (60 eq.) was stirred at room temperature or at 45° C. until reaction was completed. After cooling to room temperature, the mixture was concentrated and the residue was diluted with saturated NaHCO₃ and extracted with 3×CH₂Cl₂ (or/and 3×EtOAc). The combined extracts were dried over Na₂SO₄, filtered and concentrated to give 31 or 32.

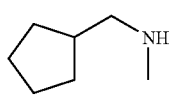

33

Methanesulfonylchloride (0.8 mL, 1.0 eq.) was added to a mixture of cyclopentyl-methanol (1.1 mL, 1.0 eq.) and ethyldiiosopropylamine (3.9 mL, 10 eq.) in CH₂Cl₂ (5 mL) at 0° C. and the resulting mixture was stirred and warmed to room temperature. After addition of saturated NaHCO₃, the separated aqueous phase was extracted with CH₂Cl₂ and the combined organic layer was concentrated to give crude mesylate intermediate. This mesylate was then treated with MeNH₂ following the same procedure for the preparation of 31/32 to give 33.

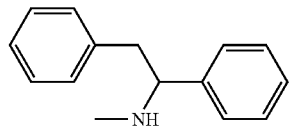

34

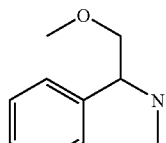

35

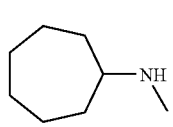

36

A solution of TiCl₄ in CH₂Cl₂ (1 M, 1.56 mmol) was added to a mixture of 1,2-diphenyl-ethanone (307 mg, 1.56 mmol), Et₃N (655 µL) and methylamine (1.02 mL) in THF (5 mL) at 0° C. After stirring 1.5 h, a solution of NaBH₄ (280 mg, 37.8 mmol) in MeOH (8 mL) was added and the resulting mixture was stirred for 2 h. A saturated Na₂CO₃ was then added and the reaction mixture was stored in freezer overnight. After thawing, the organic layer was removed and the aqueous phase was extracted with 3×CH₂Cl₂. The combined organic phases were dried over Na₂SO₄, filtered and concentrated. Purification by preparative thin layer chromatography (80% EtOAc/hexanes) afforded 34 (195 mg, 59%).

Compounds 35 and 36 were prepared in a similar manner from 2-methoxy-1-phenyl-ethanone and cycloheptanone, respectively.

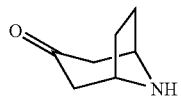

39

To a solution of Boc-nortropinone (0.5 g, 2.2 mmol, 1.0 equiv) in CH₂Cl₂ (10 mL) was added TFA (10 mL). The reaction mixture was stirred for 2 hours and then was concentrated. After addition of EtOAc and saturated NaHCO₃, the reaction mixture was extracted with 3×EtOAc. The combined organic layers were dried over Na₂SO₄, filtered and concentrated to give 37 (0.25 g).

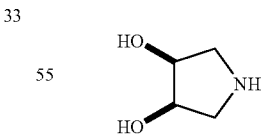

38

To a solution of 2,5-dihydro-pyrrole-1-carboxylic acid phenyl ester (2 g, 10 mmol, 1.0 eq.) in Acetone/water (9:1, 20 mL) was added OsO₄ (4% in water, 1 mL) and NMO (2.3 g, 20 mmol, 2 eq.). The mixture was stirred at room temperature overnight, concentrated to remove most of the Acetone, poured into saturated NaHCO₃ and extracted with 3×EtOAc. The combined organic layers were dried over Na₂SO₄, filtered and concentrated. The crude mixture was purified by silica chromatography (70% to 90% EtOAc- Hexanes) to give 3,4-dihydroxy-pyrrolidine-1-carboxylic acid phenyl ester (2.04 g, 88%).

To a solution of 3,4-dihydroxy-pyrrolidine-1-carboxylic acid phenyl ester (1.93 g, 8.1 mmol, 1.0 eq.) in MeOH (20 mL) was added Palladium hydroxide and placed under $H_2$ for 4 h. The catalyst was filtered off through celite and rinsed with MeOH. The filtrate was concentrated (25° C.) to give 38 as reddish oil (840 mg, 100%).

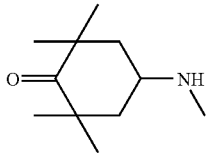

39

To a suspension of NaH (8.99 g, 0.225 mol, 4.6 eq.) in DME (70 mL) at 0° C. was slowly added a solution of 1,4-dioxa-spiro[4.5]decan-8-one (7.56 g, 0.048 mol, 1.0 eq.) in DME (24 mL). After stirring for 30 minutes, a solution of MeI (14 mL, 0.225 mol, 4.6 eq.) in DME (70 ml) was slowly introduced over 7 h and the resulting mixture was lowly warmed to room temperature and stirred overnight. The reaction was quenched by slow addition of water until no more bubbling observed. The reaction mixture was poured over iced water and extracted with 3× hexanes. The organic layers were combined, dried over $MgSO_4$, filtered and concentrated. The crude mixture was purified by chromatography (100% hexanes to remove oil, then 5:1 Hexanes-EtOAc) to give 7,7,9,9-tetramethyl-1,4-dioxa-spiro[4.5]decan-8-one (4.16 g, 40%).

To a solution of 7,7,9,9-tetramethyl-1,4-dioxa-spiro[4.5] decan-8-one (4.15 g, 0.019 mol, 1.0 eq.) in THF (60 mL) was added 1 N HCl (30 mL) and the resulting mixture was stirred at room temperature overnight, concentrated to remove most of the THF, extracted with 3×EtOAc. The organic layers were combined, dried over $MgSO_4$, filtered and concentrated to give 2,2,6,6-tetramethyl-cyclohexane-1,4-dione as a white solid (3.43 g, >100%).

To a solution of 2,2,6,6-tetramethyl-cyclohexane-1,4-dione (0.40 g, 2.4 mmol, 1.0 eq.) in THF (8 mL) was added molecular sieves (4 Å, 80 mg), 2 M solution of $MeNH_2$ in THF (1.3 mL, 2.6 mmol, 1.1 eq.), and AcOH (0.17 mL, 3.0 mmol, 1,2 eq.). After 5 minutes of stirring, $NaBH(OAc)_3$ (0.71 g, 3.33 mmol, 1.4 eq.) was added and the resulting mixture was stirred at room temperature overnight. The reaction was quenched with the addition of saturated $NaHCO_3$. The mixture was then concentrated and the aqueous layer was extracted with 3×EtOAc. The combined organic layers were washed once with saturated $NaHCO_3$, dried over $MgSO_4$, filtered and concentrated to give a crude pale yellow oil that was crystallized to give 39 as a white crystals (0.40 g, >100%).

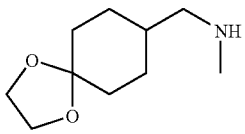

40

To solution of methyltriphenylphosphonium bromide (17 g, 1.5 eq.) in THF (100 mL) at 0° C. was added dropwise n-butyllithium (2.5 M in hexanes, 18 mL, 1.4 eq.) and the resulting mixture was stirred for 1 h. A solution of 1,4-dioxa-spiro[4.5]decan-8-one (5.0 g, 32 mmol, 1.0 eq.) in THF (10 mL) was then introduced dropwise and the resulting mixture was warmed to room temperature and stirred overnight. The reaction was quenched by addition of sat. $NaHCO_3$ and the separated aqueous layer was extracted with 4×EtOAc. The combined organic phase was dried over $Na_2SO_4$, filtered and concentrated. The residue was purified by chromatography (5% to 10% EtOAc/hexanes) to give 8-methyene-1,4-dioxa-spiro[4.5]decane (3.92 g, 79%).

To a solution of 8-methyene-1,4-dioxa-spiro[4.5]decane (2.0 g, 13 mmol, 1.0 eq.) in THF (10 mL) at 0° C. was added dropwise 9-BBN (0.5 M in THF, 104 mL, 4.0 eq.) and the resulting mixture was stirred for 15 min and then warmed to room temperature and stirred overnight. Then $NaBO_4 \cdot 4H_2O$ (32 g, 16 eq.) was introduced at 0° C. portionwise and the resulting mixture was warmed to room temperature and stirred overnight, diluted with hexanes (30 mL) and the separated aqueous phase was extracted with EtOAc. The combined organic phase was dried over over $Na_2SO_4$, filtered and concentrated. The residue was purified by silica gel chromatography (50% to 100% EtOAc-hexanes) to give (1,4-dioxa-spiro[4.5]dec-8-yl)-methanol (1.5 g, 67%).

To a solution of (1,4-dioxa-spiro[4.5]dec-8-yl)-methanol (1.0 g, 5.8 mmol, 1.0 eq.) and ethyldiisopropylamine (17 mL, 3.0 eq.) in methylene chloride (4 mL) at 0° C. was added dropwise MsCl (0.46 mL, 1.0 eq.) and the resulting mixture was warmed to room temperature and stirred for 2 h. The reaction was quenched by addition of sat. $NaHCO_3$ and the separated aqueous phase was extracted with 3× methylene chloride and 4×EtOAc. The combined organic phase was dried over over $Na_2SO_4$, filtered and concentrated to give a crude methanesulfonic acid 1,4-dioxa-spiro[4.5] dec-8-ylmethyl ester.

A mixture of the crude methanesulfonic acid 1,4-dioxa-spiro[4.5]dec-8-ylmethyl ester (400 mg) in MeOH (2 mL) and aqueous $MeNH_2$ (40% w/w, 5 mL) was heated at reflux (60° C. oil both) for overnight. The reaction was quenched by addition of sat $NaHCO_3$ and the separated aqueous phase was extracted with 4× methylene chloride and 4×EtOAc. The combined organic phase was dried over over $Na_2SO_4$, filtered and concentrated to give crude 40 as brown oil.

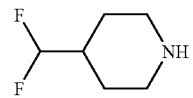

41

To a solution of 4-oxo-piperidine-1-carboxylic acid benzyl ester (0.50 g, 2.14 mmol, 1.0 eq.) in THF (20 mL) was added dibromodifluoromethane (0.90 mL, 4.5 eq.) at −30° C. followed by HMPA (1.75 mL, 4.5 eq.). The cooling bath was removed and the reaction mixture was swirled periodically. After 30 min, zinc dust (0.63 g, 4.5 eq.) and HMPA (80 µL 0.4 eq.) was added and the mixture was heated at reflux for 18 h. Upon cooling to room temperature, the residue was washed with diethyl ether several times. The combined ether washings were washed successively with saturated aqueous copper (II) sulphate, brine, dried over $Na_2SO_4$ and concentrated. The residue was purification by chromatography (20% EtOAc-hexanes) to afford 4-difluoromethylene-piperidine-1-carboxylic acid benzyl ester (0.32 g, 56%) as a colorless oil.

A mixture of 4-difluoromethylene-piperidine-1-carboxylic acid benzyl ester (269 mg) and Pearlman's catalyst in methanol (2.5 mL) was stirred under hydrogen atmosphere (using hydrogen filled balloon) for 4 h at room temperature. The reaction mixture was filtered through celite and the filtrate was concentrated to give 41 (138 mg) as pale yellow oil.

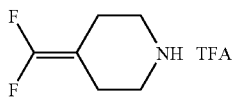

42

Following the same procedure to prepare 41, 4-difluoromethylene-piperidine-1-carboxylic acid 2,2-dimethyl-propyl ester (368 mg) was prepared using 4-oxo-piperidine-1-carboxylic acid 2,2-dimethyl-propyl ester (500 mg). The 4-difluoromethylene-piperidine-1-carboxylic acid 2,2-dimethyl-propyl ester (368 mg) in methylene chloride (1.0 mL) at room temperature was treated with trifluoroacetic acid (TFA, 0.5 mL) for 1.5 h. After concentration of of the reaction mixture, the crude 42 was used directly without further purification.

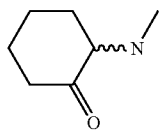

43

To a solution of 2-amino-cyclohexanol (3.50 g 23.0 mmol, 1.0 eq.) in CH$_2$Cl$_2$ (100 mL) was added ethylchloroformate (2.65 mL, 1.2 eq.) followed by an aqueous solution of K$_2$CO$_3$ (16.0 g in 200 mL of H$_2$O). The mixture was stirred vigorously for 1 h. The separated aqueous layer was extracted twice with CH$_2$Cl$_2$. The combined organic layers were dried over MgSO$_4$, filtered and concentrated to give (2-hydroxy-cyclohexyl)-carbamic acid ethyl ester (4.36 g, >100%).

To a solution of (2-hydroxy-cyclohexyl)-carbamic acid ethyl ester (2.06 g, 11.0 mmol, 1.0 eq.) in THF (80 mL) was added LiAlH$_4$ (1.09 g, 28.7 mmol, 2.6 eq.) and the resulting mixture was heated at 65° C. for 2 h. The reaction mixture was cooled to 0° C., quenched with water, and the separated aqueous phase was extracted with 3×EtOAc. The combined organic phase was dried over MgSO$_4$, filtered and concentrated to give 2-methylamino-cyclohexanol (1.19 g, 84%).

To a solution of 2-methylamino-cyclohexanol (0.204 g, 1.58 mmol, 1.0 eq.) and di-tert-butyl dicarbonate (0.422 g, 1.2 eq.) in CH$_2$Cl$_2$ (7.0 mL) was added was added a solution of K$_2$CO$_3$ in water (1.09 g in 14.0 mL of H$_2$O) and the resulting mixture was stirred vigorously for 1 h. The separated aqueous layer was extracted twice with CH$_2$Cl$_2$. The combined organic phase was dried over MgSO$_4$, filtered and concentrated to give (2-hydroxy-cyclohexyl)-methyl-carbamic acid tert-butyl ester (0.332 g, 92%).

To a solution of (2-hydroxy-cyclohexyl)-methyl-carbamic acid tert-butyl ester (0.237 g, 1.03 mmol, 1.0 eq.) in CH$_2$Cl$_2$ (7.0 mL) at 0° C. was added molecular sieves (4 Å, 3 mL). The reaction was stirred for 5 minutes and then NMO (0.422 g, 3.5 eq.) and TPAP (0.025 g, 0.07 eq.) were introduced. The reaction mixture was stirred at 0° C. for 5 minutes, and then 40 minutes at room temperature. After diluted with hexanes, the reaction mixture was passed through a silica gel pad, using hexanes at the beginning to remove CH$_2$Cl$_2$, and then using a 1:1 mixture of hexanes-EtOAc to get the desired product. After concentration of the hexanes-EtOAc filtrate, methyl-(2-oxo-cyclohexyl)-carbamic acid tert-butyl ester was obtained as a white solid (0.235 g, 100%).

To a solution of methyl-(2-oxo-cyclohexyl)-carbamic acid tert-butyl ester (0.202 g, 0.89 mmol, 1.0 eq.) in CH$_2$Cl$_2$ (3.0 mL) was added TEA (1.0 mL) and the reaction mixture was stirred at room temperature for 3 h. The reaction mixture was then concentrated to give 43 (0.285 g, >100%).

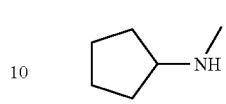

44

To a solution of cyclopentylamine (5.8 mL, 59 mmol, 1.0 eq.) in CH$_2$Cl$_2$ (250 mL) at room temperature was added ethylchloroformate (7.3 mL, 1.3 eq.) followed by an aqueous solution of K$_2$CO$_3$ (37 g in 500 mL of H$_2$O). The mixture was stirred vigorously for 1 h. The separated aqueous layer was extracted twice with CH$_2$Cl$_2$. The combined organic layers were dried over MgSO$_4$, filtered and concentrated to give cyclopentyl-carbamic acid ethyl ester (9.6 g, 88%).

To a solution of the cyclopentyl-carbamic acid ethyl ester (6.00 g, 32.4 mmol, 1.0 eq.) in THF (250 mL) was added LiAlH$_4$ (3.08 g, 2.5 eq.) and the resulting mixture was heated at 65° C. for 2 h. The reaction was then cooled to 0° C. and quenched by addition of water. The separated aqueous layer was extracted with 3×EtOAc. The combined organic phase was dried over MgSO$_4$, filtered and concentrated to give 44 (2.01 g, 62%).

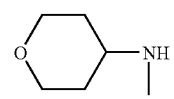

45

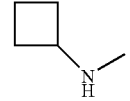

46

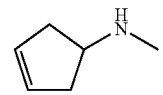

47

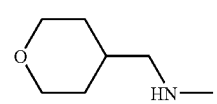

48

Compounds 45-58 were prepared following the same procedures for the preparation of 44 from the corresponding primary amines.

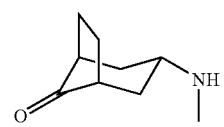

49

To a solution of cyclopentanone (25.0 mL, 0.28 mol, 1.0 eq.) in toluene (100 mL), was added pyrrolidine (27.5 mL, 1.2 eq.). The reaction was equipped with a Dean-Stark and heated at reflux overnight. The reaction mixture was cooled to room temperature and concentrated to give the crude 1-cyclopent-1-enyl-pyrrolidine (45.8 g, >100%).

To a solution of Pd(OAc)$_2$ (0.06 g, 0.06 eq.), PPh$_3$ (0.32 g, 0.24 eq.) and carbonic acid 2-ethoxycarbonyloxymethyl-allyl ester ethyl ester (1.23 g, 5.30 mmol, 1.0 eq., prepared following Tetrahedron 1998, 54(49), 14885-14904) in CH$_3$CN (30 ml) was added 1-cyclopent-1-enyl-pyrrolidine (1.01 g, 1.4 eq.) and the resulting mixture was heated at 45° C. for 35 minutes. Then water (15 mL) was introduced and the reaction mixture was heated at 50° C. for 1 h, cooled to room temperature and diluted with EtOAc (30 mL). The separated aqueous phase was extracted twice with EtOAc. The combined organic phase was dried over MgSO$_4$, filtered and concentrated. The residue was purified by silica gel chromatography (10% to 15% EtOAc-hexanes) to give 3-methylene-bicyclo[3,2,1]octan-8-one (0.14 g, 70%) as a pale yellow liquid.

To a solution of 3-methylene bicyclo[3,2,1]octan-8-one (0.14 g, 1.04 mmol, 1.0 eq.) in benzene (10 mL) was added ethylene glycol (0.65 g, 16 eq.) and PTSA (0.01 g, 0.06 eq.). The reaction was equipped with a Dean-Stark and heated at reflux overnight. After cooling to room temperature, Et$_3$N (0.15 mL) was introduced and the resulting mixture was passed through a cake of SiO$_2$ and MgSO$_4$. The cake was washed with CH$_2$Cl$_2$ and the combined filtrates were concentrated to give 3-methylene bicyclo[3,2,1]octan-8-one ethylene ketal (0.21 g, >100%).

To a solution of 3-methylenyl bicyclo[3,2,1]octan-8-one ethylene ketal (0.21 g, 1.15 mmol, 1.0 eq.) in CH$_2$Cl$_2$ (2 mL) at −78° C. was bubbled O3 until the reaction stayed blue (about 3 min). The O3 bubbling was stopped and the reaction mixture was stirred for 5 min at −78° C. The reaction was quenched by addition of triphenylphosphine (0.43 g, 1.4 eq.) and stirring at −78° C. for 10 minutes. The reaction mixture was allowed to warm at room temperature, stirred for 40 minutes and concentrated. The residue was ppurified by silica gel chromatography (10% to 15% EtOAc-hexanes) to give bicyclo[3,2,1]octane-3,8-dione 8-ethylene ketal as a colorless oil (0.08 g, 40%).

To a solution of bicyclo[3,2,1]octane-3,8-dione 8-ethylene ketal (53.1 mg, 0.27 mmol, 1.0 eq.) in THF (1.0 mL) at 0° C. was added Et$_3$N (0.11 mL, 2.9 eq.) followed by MeNH$_2$ (2.0 M in THF, 0.21 mL, 1.5 eq.). After stirring at room temperature for 5 minutes, TiCl$_4$ (0.30 mL, 10.0 eq.) was introduced dropwise and the resulting mixture was stirred at 0° C. for 45 minutes. A solution of NaBH$_4$ (53.1 mg, 5.1 eq.) in MeOH (2.0 mL) was then introduced and the resulting mixture was stirred at 0° C. for 1 h. The reaction was quenched with saturated NaHCO$_3$ and the separated aqueous layer was extracted with 3×EtOAc. The combined organic phase was dried over MgSO$_4$, filtered and concentrated to give the crude product, 3-methylamino-bicyclo[3,2,1]octan-8-one ethylene ketal (24.1 mg).

To a solution of 3-methylamino-bicyclo[3,2,1]octan-8-one ethylene ketal (94.5, 0.48 mmol, 1.0 eq.) in acetone (2.0 mL) was added 1N HCl (1.5 mL) and the reaction was stirred overnight at room temperature. The reaction mixture was neutralized with saturated NaHCO$_3$ until pH was higher than 7, extracted with 3×EtOAc. The combined organic phase was dried over MgSO$_4$, filtered and concentrated to give 49 (40.0 mg, 54%).

50

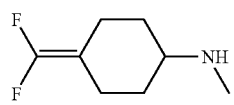

To a solution of (3,3-dimethyl-1,5-dioxa-spiro[5,5]undec-9-yl)-methyl-amine hydrochloride (1.0 g, 4 mmol, 1.0 eq.) in THF (12 mL) was added di-tert-butyl dicarbonate (1.1 mL, 1.2 eq.), triethylamine (2 mL) and DMAP (catalytical amount). The resulting mixture was heated at 90° C. for 6, cooled to room temperature, poured in saturated NaHCO$_3$, and the separated aqueous layer was extracted with 3×EtOAc. The combined organic layers were dried over Na$_2$SO$_4$, filtered and concentrated. The residue was purified by silica gel chromatography (10% EtOAc/hexanes) to give (3,3-dimethyl-1,5-dioxa-spiro[5,5]undec-9-yl)-methyl-carbamic acid tert-butyl ester (1.4 g, 91%) as a white solid.

To a solution of (3,3-dimethyl-1,5-dioxa-spiro[5,5]undec-9-yl)-methyl-carbamic acid tert-butyl ester (1.27 g, 3.63 mmol, 1.0 eq.) in acetone (40 mL) and water (20 mL) was added PPTS (228 mg, 0.25 eq.) and the resulting reaction was heated to reflux overnight, cooled to room temperature, concentrated to 20 mL, poured in saturated NaHCO$_3$ and extracted with 3×EtOAc. The combined organic layers were dried over Na$_2$SO$_4$, filtered and concentrated. The residue was purified by silica gel chromatography (hexanes to 20% EtOAc/hexanes) to give methyl-(4-oxo-cyclohexyl)-carbamic acid tert-butyl ester (735 mg, 88%) as a white solid.

To a solution of methyl-(4-oxo-cyclohexyl)-carbamic acid tert-1-butyl ester (0.69 g, 3.04 mmol, 1.0 eq.) in THF (25 mL) at −30° C. was added CBr$_2$F$_2$ (1.25 mL, 4.5 eq.) followed slow addition of by P(N(CH$_3$)$_2$)$_3$. The resulting mixture was warmed to room temperature over 0.5 h and Zn was introduced. The resulting mixture was stirred at reflux for 16 h, cooled to room temperature and diluted with Et$_2$O. The organic phase was decanted and the aqueous phase extracted with 2×Et$_2$O. The combined organic phase was washed with saturated CuSO$_4$ solution until it stayed blue, dried over Na$_2$SO$_4$, filtered and concentrated. The residue was purified by chromatography (20% EtOAc-Hexanes) to give (4-difluoromethylene-cyclohexyl)-methyl-carbamic acid tert-butyl ester (475 mg, 60%) as a white solid.

To a solution of (4-difluoromethylene-cyclohexyl)-methyl-carbamic acid tert-butyl ester (150 mg, 0.57 mmol, 1.0 eq.) in CH$_2$Cl$_2$ (1.5 mL) was added TFA (1.5 mL). The reaction mixture was stirred for 4 h and then was concentrated to give 50 (85 mg). The crude compound was taken to the next step without further purification.

51

To a solution of cyclopropylamine (5.0 g, 87.5 mmol) and triethylamine (30 mL) in dichloromethane (100 mL) at 0° C. was added dropwise benzyl chloroformate (15.0 ml, 10.5 mmol) and the resulting mixture was stirred for 2 h. Additional benzyl chloroformate (1 mL) was added and the resulting reaction mixture was stirred overnight. The reaction was then quenched by addition of a saturated NaHCO$_3$ and the separated aqueous phase was extracted several times with dichloromethane. The combined dichloromethane extracts were dried over Na$_2$SO$_4$, filtered and concentrated. The residue was purified by chromatography (15% EtOAc to 5% MeOH/EtOAc) to give cyclopropyl-carbamic acid benzyl ester (11.8 g, 71%).

To a solution of cyclopropyl-carbamic acid benzyl ester (11.8 g) and methyl iodide (excess) in THF (80 mL) and DMF (20 mL) at 0° C. was added NaH (2.20 g, 91.6 mmol) and the resulting mixture was warmed to room temperature and stirred overnight. The reaction was then quenched at 0° C. by sat. NaHCO$_3$. The separated aqueous phase was extracted several times with EtOAc. The combined extracts were dried over Na$_2$SO$_4$, filtered and concentrated. The residue was purified by chromatography (5% to 20% EtOAc/hexanes) to give cyclopropyl-methyl-carbamic acid benzyl ester (11.32 g, 91%).

A mixture of cyclopropyl-methyl-carbamic acid benzyl ester (10.7 g) and Pd(OH)₂ in MeOH (100 mL) was stirred at room temperature under H₂ balloon for 17 h, diluted with concentrated HCl (4.8 mL), filtered through celite and concentrated. The residue was azeotroped with toluene several times to give cyclopropyl-methyl-amine hydrochloride (51, 5.75 g). The crude material was used without further purification.

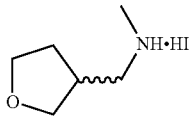

52

To a solution of (tetrahydro-furan-3-yl)-methanol (1.00 g, 9.79 mmol, 1.0 eq.), PPh₃ (3.85 g, 1.5 eq.) and imidazole (1.33 g, 2.0 eq.) in CH₂Cl₂ (15 mL) at 0° C. was added I₂ (3.73 g, 1.5 eq.) and the resulting mixture was stirred at 0° C. for 30 min and then at room temperature for 30 min. The reaction mixture was diluted with sat. Na₂S₂O₃ solution and the separated aqueous layer was extracted by 3×EtOAc and 4×CH₂Cl₂. The combined extracts were dried over Na₂SO₄, filtered and concentrated. The residue was purified by chromatography (15% EtOAc/hexanes) to give 3-iodomethyl-tetrahydro-furan as yellow oil (1.59 g, 76%).

A mixture of 3-iodomethyl-tetrahydro-furan (500 mg, 2.36 mmol, 1.0 eq.) and MeNH₂ (40% in H₂O, 1.62 mL, 8.0 eq.) in MeOH (1 mL) was heated at 60° C. for 3 h. After cooling to room temperature, the reaction mixture was diluted with excess Et₃N and concentrated. This process was repeated until no MeNH₂ was detected by ¹HNMR. The residual yellow oil (52) was used directly without further purification.

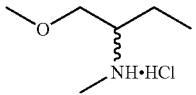

53

To a solution of 1-methoxymethyl-propylamine (2.50 g, 24.3 mmol, 1.0 eq.) in dioxane (15 mL) was added an aqueous solution of K₂CO₃ (15 g in 15 mL of H₂O) and the mixture was cooled to 0° C. CBZ-Cl (4.16 mL, 1.2 eq.) was then introduced and the resulting mixture was warmed to room temperature and stirred for 3 h, extracted with EtOAc. The combined organicphase was dried over Na₂SO₄, filtered and concentrated. The residue was purified by chromatography (hexanes to 40% EtOAc/hexanes) to give (1-methoxymethyl-propyl)-carbamic acid benzyl ester (4.4 g, 76%) as a white solid.

To a solution of (1-methoxymethyl-propyl)-carbamic acid benzyl ester (4.4 g, 18.5 mmol, 1.0 eq.) and MeI (6.9 mL, 111 mmol, 6 eq.) in THF/DMF (4:1, 50 mL) at 0° C. was slowly added NaH (1.35 g, 55.5 mmol, 3 eq.). The resulting mixture was warmed to room temperature and stirred over night. The reaction was quenched carefully by slow addition of water until no bubbling (H₂) was observed. The reaction mixture was poured over ice water and extracted with 3×EtOAc. The combined organic phase was dried over Na₂SO₄, filtered and concentrated. The residue was purified by silica gel chromatography (30% to 50% EtOAc-hexanes) to give (1-methoxymethyl-propyl)-methyl-carbamic acid benzyl ester (4.4 g, 94%).

To a solution of (1-methoxymethyl-propyl)-methyl-carbamic acid benzyl ester (4.4 g, 17.5 mmol, 1.0 eq.) in MeOH (30 mL) was added Palladium hydroxide and the resulting mixture was stirred at room temperature under H₂ for 1.5 h. The mixture was then filtered through celite and washed with MeOH. The filtrate was treated with concentrated HCl (1.6 mL, 1 eq.) and concentrated to give 53 (2.67 g, 100%). ¹H NMR confirmed the compound. The crude compound was used to the next step without further purification.

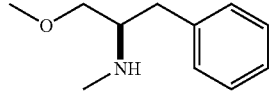

54

Compound 54 was prepared from (1-benzyl-2-hydroxy-ethyl)-carbamic acid benzyl ester following the same procedures of step 2 and 3 for the parparation of 53.

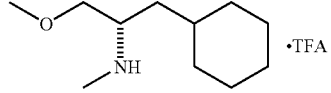

55

(1-cyclohexylmethyl-2-hydroxy-ethyl)-methyl-carbamic acid benzyl ester was prepared from (1-cyclohexylmethyl-2-hydroxy-ethyl)-carbamic acid benzyl ester following the same procedure of step 2 for the preparation of 53. (1-Cyclohexylmethyl-2-hydroxy-ethyl)-methyl-carbamic acid benzyl ester was then treated with TFA-CH₂Cl₂ (1:1) at room temperature for 4 h. The mixture was then concentrated to give 55.

56

To a solution of (R)-(−)-leucinol (2.0 g, 17 mmol, 1.0 eq.), Et₃N (3.6 mL, 1.5 eq.) and DMAP (10 mg) in THF (2 mL) was added Boc₂O (4.5 g, 1.2 eq.) at room temperature. After stirring for 5 h, the reaction was quenched by water and the separated aqueous phase was extracted with 4× ether. The combined organic phase was dried over Na₂SO₄, filtered and concentrated. The residue was purified by chromatography (20% to 30% EtOAc/hexanes) to give (1-hydroxymethyl-3-methyl-butyl)-carbamic acid tert-butyl ester (1.9 g, 53%). ¹H NMR confirmed the compound.

Compound 56 was prepared from (1-hydroxymethyl-3-methyl-butyl)-carbamic acid tert-butyl ester following the same procedures for the preparation of 55.

57

Methyllithium (1M in THF) (120 mL, 3.5 eq.) was added to a solution of 4-hydroxy-cyclohexanecarboxylic acid (cis/trans mixture) (5.00 g, 1 eq.) in THF (350 mL) at −78° C. After stirring at −78° C. for 45 min, the cooling bath was removed and the resulting mixture was warmed to room temperature and stirred overnight. After total 24 h, the resulting reaction mixture was poured into ice/water (800 mL). This mixture was vigorously stirred. The separated aqueous phase was extracted with MeOH/EtOAc (~1/20). The combined organic layer was dried over Na₂SO₄, filtered and concentrated. The crude product was purified by chromatography (50% to 100% EtOAc/hexanes) to give 1-(4-hydroxy-cyclohexyl)-ethanone (2.08 g, 42%).

A mixture of 1-(4-hydroxy-cyclohexyl)-ethanone (2.24 g, 1 eq.), toluene (160 mL), neopentylglycol (1.96 g, 1.2 eq.) and pTsOH (150 mg, 0.05 eq.) in a flask equipped with Dean-Stark apparatus was heated to reflux overnight. The mixture was cooled down to room temperature and contentrated. The crude product was purified by silic gel column chromatography (25% to 50% EtOAc/hexanes) to give 4-(2,5,5-trimethyl-[1,3]dioxan-2-yl)-cyclohexanol (2.23 g, 62%).

TPAP (161 mg, 0.05 eq.) was added to a solution of 4-(2,5,5-trimethyl-[1,3]dioxan-2-yl)-cyclohexanol (2.22 g, 1 eq.) and NMO (2.28 g, 2 eq.) in MeCN (65 mL). The reaction mixture was stirred at room temperature overnight. Saturated aqueous solution of $Na_2S_2O_3$ was added to the mixture and the resulting mixture was stirred vigorously for 15 minutes. The separated aqueous phase was extracted with $CH_2Cl_2$. The combined organic layer was dried over $Na_2SO_4$, filtered through Celite and concentrated. The crude product was purified by silica gel column chromatography (25% to 50% EtOAc/hexanes) to give 4-(2,5,5-trimethyl-[1,3]dioxan-2-yl)-cyclohexanone (1.87 g, 85%).

Compound 57 was prepared from 4-(2,5,5-trimethyl-[1,3]dioxan-2-yl)-cyclohexanone following the procedure for the preparation of 34 from 1,2-diphenyl-ethanone.

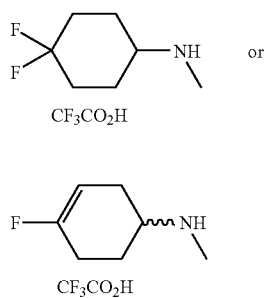

58 or

59

To a suspension of (3,3-dimethyl-1,5-dioxa-spiro[5,5]undec-9-yl)-methyl-amine hydrochloride (6.9 g, 27.6 mmol, 1.0 eq.), Et3N (15 mL, 4.0 eq.) and DMAP (catalytic amount) in THF-MDF (1:1, 100 mL) was added di-t-butyl dicarbonate (7.6 mL, 1.2 eq.) and the resulting mixture was heated at 90° C. for 6 h. After cooling to room temperature, he reaction mixture was diluted with sat. $NaHCO_3$ and the separated aqueous layer was extracted with 2×EtOAc. The combined organic layer was dried over $Na_2SO_4$, filtered and concentrated. The crude product was purified by chromatography (10% to 20% EtOAc/hexanes) to give (3,3-dimethyl-1,5-dioxa-spiro[5,5]undec-9-yl)-methyl-carbamic acid tert-butyl ester as a white solid (9.53 g, 99%).

A solution of (3,3-dimethyl-1,5-dioxa-spiro[5,5]undec-9-yl)-methyl-carbamic acid tert-butyl ester (9.53 g, 27.2 mmol, 1.0 eq.) and PPTS (2.1 g, 0.3 eq.) in acetone-water (2:1, 500 mL) was heated at 80° C. for 18 h, cooled to room temperature and concentrated to remove acetone. The residual aqueous solution was diluted with $NaHCO_3$ and extracted with 2×EtOAc. The combined organic layer was dried over $Na_2SO_4$, filtered and concentrated. The crude product was purified by chromatography (20% to 50% EtOAc/hexanes) to give methyl-(4-oxo-cyclohexyl)-carbamic acid tert-butyl ester as a white solid (5.38 g, 87%).

To a solution of methyl-(4-oxo-cyclohexyl)-carbamic acid tert-butyl ester (134 mg, 0.59 mmol, 1.0 eq.) in $CH_2Cl_2$ (0.5 mL) at room temperature was added $(MeOCH_2CH_2)_2NSF_3$ (217 µL, 2.0 eq.) followed by ethanol (10 µL, 0.3 eq.). After stirring for 1 h, the reaction was quenched carefully by addition of sat $NaHCO_3$ and stirred until gas evolution ceased. The separated aqueous phase was extracted with $CH_2Cl_2$. The combined organic extracts were dried over $Na_2SO_4$, filtered and concentrated. The crude mixture was purified by chromatography (5% to 10% EtOAc/hexanes) to give mixture of (4,4-difluoro-cyclohexyl)-methyl-carbamic acid tert-butyl ester and (4-difluoro-cyclohex-3-enyl)-methyl-carbamic acid tert-butyl ester. To a solution of the mixture products in $CH_2Cl_2$ (1.5 mL) at room temperature was added trifluoroacetic acid (1.5 mL) at room temperature and the resulting mixture was stirred for 2.5 h and concentrated to give a mixture of 53 and 59 (2:1 ratio by $H^1$-NMR).

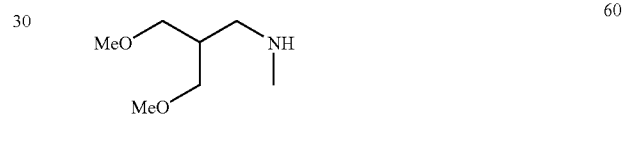

60

To a solution of 3-chloro-2-chloromethy-1-propene (20.0 g, 160 mmol, 1.0 eq.) in THF (40 mL) at 0° C. was added NaOMe (100 mL of 25% solution in methanol, 2.8 eq.). After cooling bath was removed, the reaction mixture was stirred at room temperature for 20 h and at 35° C. for 20 h. The reaction was quenched with sat. $NH_4Cl$ (10 mL) and the mixture was diluted with ether (200 mL) and filtered washing with ether. The filtrate was concentrated by distillation of ether, THF and EtOH at atmospheric pressure to give light yellow liquid residue. Fractional distillation of the residue gave 3-methoxy-2-methoxymethy-1-propene (8.9 g, 43%). b.p.=120-130° C.

To a solution of the 3-methoxy-2-methoxymethy-1-propene (3.5 g, 30 mmol, 1.0 eq.) in THF (10 mL) at 0° C. was added $BH_3$.THF (1M in THF, 18 mL, 0.6 eq.) and the resulting mixture was stirred for 40 min. The reaction was quenched with water followed by sodium perborate (10.6 g, 2.3 eq.), warmed to room temperature, stirred overnight, diluted with $CH_2Cl_2$ and filtered through celite. The filtrate was diluted with brine and the separated aqueous layer was extracted with $CH_2Cl_2$. The combined extracts were dried over $Na_2SO_4$ and filtered. The filtrate was didstilled at atmospheric pressure to give light yellow liquid residue. Fractional distillation of the residue at 40 milliTorr gave 3-methoxy-2-methoxymethypropan-1-ol (1.93 g, 48%). b.p.=90-110° C.

To a solution of alcohol 3-methoxy-2-methoxymethypropan-1-ol (0.90 g, 6.7 mmol, 1.0 eq.) in $CH_2Cl_2$ (10 mL) at 0° C. was added Et₃N (1.9 mL, 2.0 eq.) followed by MsCl (0.63 mL, 1.2 eq.). After stirring for 40 min, the reaction was quenched with methylamine (40% in water). After concentration of the reaction mixture at room temperature, the residue was diluted with methanol (2 mL) and methylamine (3 mL, 40% in water), heated at 50° C. for 18 h cooled to room temperature, saturated with Na₂CO₃ and extracted with ether. The combined extracts were dried over Na₂SO₄ and filtered. The filtrate was didstilled at atmospheric pressure to give crude product 60 (0.78 g, 80%) as a light yellow liquid.

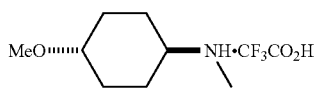

61

To a solution of trans-4-amino-cyclohexanol hydrochloride (5.0 g, 32.9 mmol, 1.0 eq.) in water (80 mL) and THF (60 mL) at room temperature was added NaHCO₃ (6.4 g, 2.3 eq.) and (Boc)₂O (14.8 mL, 2.0 eq.). After stirring for 48 h, most of THF from reaction mixture was removed by concentration and the aqueous residue was extracted with EtOAc. The combined organic extracts were dried over Na₂SO₄, filtered and concentrated. The crude product was crystallized from EtOAc-hexanes (9:1) to give (4-trans-hydroxy-cyclohexyl)-carbamic acid tert-butyl ester (5.2 g, 75%).

To a solution of (4-trans-hydroxy-cyclohexyl)-carbamic acid tert-butyl ester (3.0 g, 13.9 mmol, 1.0 eq.) and methyl iodide (4.3 mL, 5.0 eq.) in N-methyl-2-pyrrolidinone (NMP) (50 mL) at 0° C. was added 60% NaH in mineral oil (1.67 g, 3.0 eq.) in a controlled portion wise manner and the resulting mixture was stirred for 3 h at room temperature. The reaction mixture was quenched with methanol (3.0 mL), stirred for 30 min, diluted with sat. NH₄Cl and the mixture was extracted three times with EtOAc. The combined organic extracts were dried over Na₂SO₄, filtered and concentrated. The crude mixture was purified by silica gel chromatography (20% EtOAc/hexanes) to give (4-trans-methoxy-cyclohexyl)-methyl-carbamic acid tert-butyl ester (3.25 g, 96%).

To a solution of trans-(4-methoxy-cyclohexyl)-methyl-carbamic acid tert-butyl ester (445 mg, 1.83 mmol, 1.0 eq.) in CH₂Cl₂ (2 mL) at room temperature was added trifluoroacetic acid (2 mL). After stirring for 2 h, the reaction mixture was concentrated to give 61 (685 mg, 145%, contains residual TFA). ¹H NMR confirmed the structure and the product was used without further purification.

Alternatively, compound 61 may be prepared according to the following scheme:

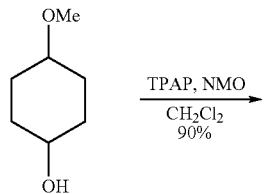

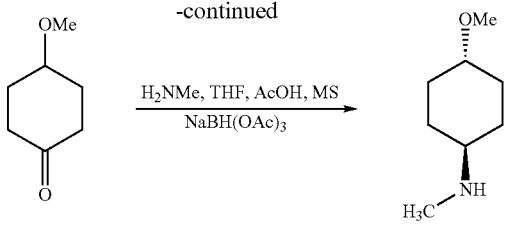

Thus, oxidation of 4-methoxy cyclohexanol under suitable conditions (e.g., TPAP, NMO) in a suitable solvent (e.g., methylene chloride) gives the corresponding ketone. Reductive amination of 4-methoxy cyclohexanone under suitable conditions (e.g., dimethylamine, NaBH(OAc)₃, AcOH in THF) gives access to the corresponding amine 61 with good stereoselectivity (i.e., trans).

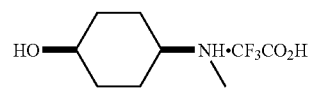

62

To a suspension of methyl-(4-oxo-cyclohexyl)-carbamic acid tert-butyl ester (an intermediate for the preparation of 58 and 59, 580 mg, 2.56 mmol, 1.0 eq.) in THF (8 mL) at −78° C. was added LS-selectride (1 M solution in THF, 5.7 mL, 2.2 eq.). After stirring for 2.5 h, the reaction mixture was warmed to 0° C. and stirred for 30 min. The reaction was quenched with sat. NH₄Cl and the separated aqueous layer was extracted with EtOAc-hexanes (1:1). The combined organic extracts were dried over Na₂SO₄, filtered and concentrated. The crude mixture was purified by silica gel chromatography (33% to 50% EtOAc/hexanes) to give (4-cis-hydroxy-cyclohexyl)-methyl-carbamic acid tert-butyl ester (391 mg, 67%).

Compound 62 was prepared from (4-cis-hydroxy-cyclohexyl)-methyl-carbamic acid tert-butyl ester following the same procedure for the preparation of 61 from (4-trans-hydroxy-cyclohexyl)-carbamic acid tert-butyl ester.

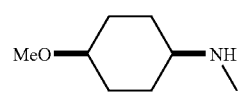

63

To a solution of (4-cis-hydroxy-cyclohexyl)-methyl-carbamic acid tert-butyl ester (1.95 g, 8.52 mmol, 1.0 eq.) in DMF (20 mL) at 0° C. was added NaH (559 mg, 2.5 eq.). After stirring for 10 min, methyl iodide (3.9 mL, 7.6 eq.) was introduced and the cooling bath was removed. After stirring for 5 h atr room temperature, the reaction was quenched with methanol (1.5 mL), stirred for 15 min and diluted with sat. NH₄Cl. The mixture was extracted with EtOAc-hexanes (1:1). The combined organic extracts were dried over Na₂SO₄, filtered and concentrated. The crude mixture was purified by silica gel chromatography (10% to 25% EtOAc/hexanes) to give (4-cis-methoxy-cyclohexyl)-methyl-carbamic acid tert-butyl ester (1.73 g, 84%).

To a solution of (4-cis-methoxy-cyclohexyl)-methyl-carbamic acid tert-butyl ester (1.73 g, 7.12 mmol, 1.0 eq.) in CH$_2$Cl$_2$ (4 mL) at room temperature was added trifluoroacetic acid (4 mL). After stirring for 3.5 h, the reaction mixture was concentrated to give a crude product. This product was dissolved in CH$_2$Cl$_2$ (50 mL) and washed with sat. Na$_2$CO$_3$ (40 mL). The aqueos layer was back extracted with 5×CH$_2$Cl$_2$. The combined organic extracts were dried over Na$_2$SO$_4$, filtered and concentrated to give free amine 63 (1.12 g, 109%, contains residual CH$_2$Cl$_2$).

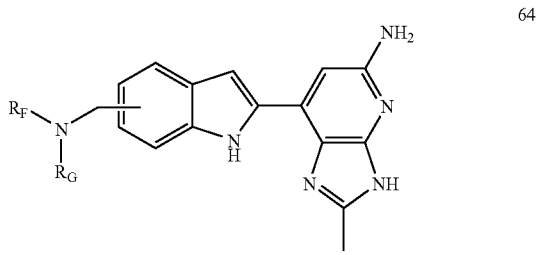

64

A mixture of 18 (0.01-0.1 M, 1.0 eq.), diisopropylethylamine (5.0 eq.) and any one of amine from 21-63 or other commercially available primary or secondary alkylamine (3-10 eq.) in dichloromethane was stirred at room temperature or at 40° C. for several hours to five days until reaction was completed. The reaction mixture was concentrated and the intermediate product, either with or without purification by chromatography (EtOAc/hexanes), was dissolved in 1:1 mixture of dichloromethane and trifluoroacetic acid (0.05 M) and stirred at room temperature with or without anisole (5-10 eq.) for 3-4 h until reaction was completed. The reaction was then carefully quenched with sat. NaHCO$_3$, extracted with EtOAc until there was no product detected. The combined extracts were dried over Na$_2$SO$_4$, filtered, concentrated and the product 64 was purified by reverse phase HPLC (MeOH-water).

The following procedure has been used for aromatic amines (R$_F$ and/or R$_G$=Ar). To a solution of N-ethylaniline (47 µL, 6 eq.) in THF (1 mL) at −78° C. was added nBuLi (148 µL, 2.5 M in hexanes, 6 eq.) followed by HMPA (200 µL) and stirred for 10 min. A solution of 18 (44 mg, 0.062 mmol) in THF (0.7 mL) was introduced by rinsing with THF (0.3 mL). After 10 min stirring, the reaction mixture was quenched with sat. NaHCO$_3$ (15 mL), extracted with 3×EtOAc. The combine extracts were dried over Na$_2$SO$_4$, filtered, concentrated and the product was purified by chromatography (EtOAc) to give an intermediate. This intermediate and anisole (100 µL) was dissolved in 1:1 mixture of dichloromethane and trifluoroacetic acid (2 mL) and stirred at room temperature 3 h. The reaction was then carefully quenched with sat. NaHCO$_3$, extracted with 4×EtOAc. The combine extracts were dried over Na$_2$SO$_4$, filtered, concentrated and the product 64 was purified by reverse phase HPLC (MeOH-water).

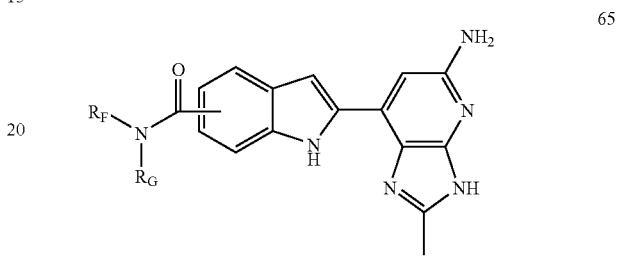

65

Diisopropylethylamine (1.6 eq.) was added to a solution of 20 (0.03-0.05 M, 1.0 eq.) and TOTU (1.5 eq.) in DMF at room temperature and stirred for 15 min. To the resulting mixture was added any one amine from 21-63 or other commercially available primary or secondary amine (1.5 eq.). The reaction mixture was stirred for several hours to overnight until reaction completed. The reaction mixture was concentrated and the intermediate product, either with or without purification by chromatography (EtOAc/hexanes), was dissolved in 1:1 mixture of dichloromethane and trifluoroacetic acid (0.01-0.05M) and stirred at room temperature with or without anisole (5-10 eq.) for 3-4 h until reaction was completed. The reaction was then carefully quenched with sat. NaHCO$_3$, extracted with EtOAc until there was no product detected. The combine extracts were dried over Na$_2$SO$_4$, filtered, concentrated and the product 65 was purified by reverse phase HPLC (MeOH-water).

Compounds in the following table were prepared either following the preparation of 13 or 64 or 65.

| Compound # (ER # or IC #) | Structure of 64 or 65 | MS (ES) or/and $^1$HNMR |
|---|---|---|
| 806094 | | $^1$H NMR |

-continued

| Compound # (ER # or IC #) | Structure of 64 or 65 | MS (ES) or/and $^1$HNMR |
|---|---|---|
| 806095 | | $^1$H NMR |
| 806123 | | 361.4 (M + H)$^+$ |
| 806136 | | 404.3 (M + H)$^+$ |
| 806181 | | $^1$H NMR |
| 806221 | | 413.3 (M + H)$^+$ |
| 806220 | | 465.3 (M + H)$^+$ |

| Compound # (ER # or IC #) | Structure of 64 or 65 | MS (ES) or/and ¹HNMR |
|---|---|---|
| 806224 | | 409.3 (M + H)+ |
| 806228 | | 412.3 (M + H)+ |
| 806276 | | 471.3 (M + H)+ |
| 806275 | | 487.3 (M + H)+ |
| 806274 | | 397.3 (M + H)+ |
| 806273 | | 411.3 (M + H)+ |

-continued
| Compound # (ER # or IC #) | Structure of 64 or 65 | MS (ES) or/and ¹HNMR |
|---|---|---|
| 806317 | 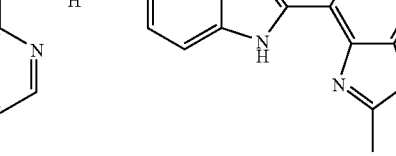 | 398.2 (M + H)⁺ |
| 806320 | 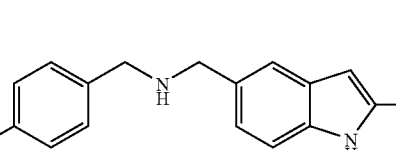 | 417.2 (M + H)⁺ |
| 806329 | 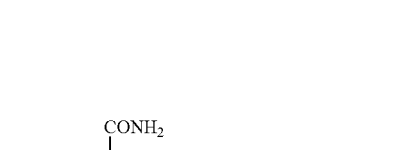 | 424.3 (M + H)⁺ |
| 806333 | 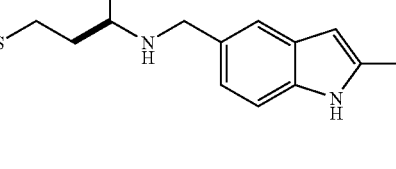 | 497.3 (M + H)⁺<br>520.2 (M + Na)⁺ |
| 806336 | 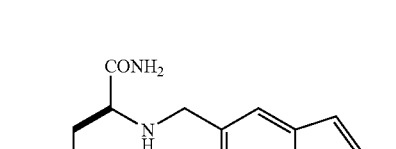 | 411.3 (M + H)⁺ |
| 806358 | 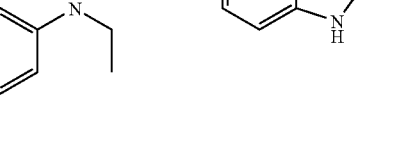 | 397.2 (M + H)⁺ |

-continued

| Compound # (ER # or IC #) | Structure of 64 or 65 | MS (ES) or/and ¹HNMR |
|---|---|---|
| 806359 | | 383.3 (M + H)⁺ |
| 806363 | | 462.2 (M + H)⁺ |
| 806362 | | 440.3 (M + H)⁺ |
| 806361 | | 479.2 (M + H)⁺ |
| 806368 | | 369.2 (M + H)⁺ |
| 806372 | | 495.2 (M + H)⁺ |

| Compound # (ER # or IC #) | Structure of 64 or 65 | MS (ES) or/and ¹HNMR |
|---|---|---|
| 806373 | 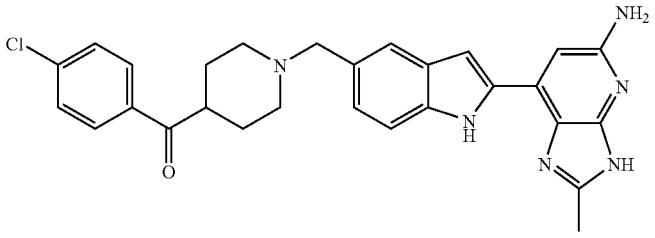 | 499.2 (M + H)⁺ |
| 806374 | 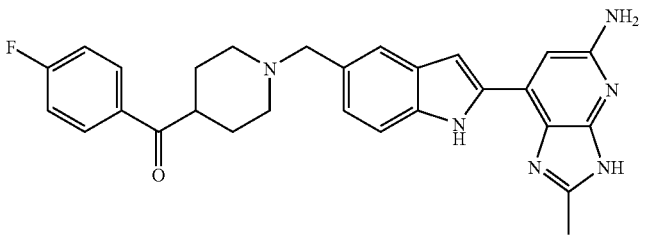 | 483.2 (M + H)⁺ |
| 806375 | 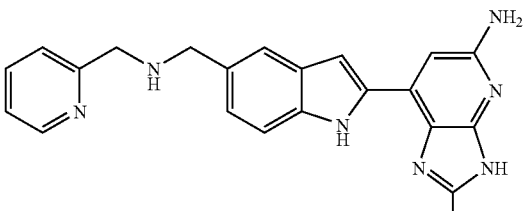 | 384.3 (M + H)⁺ |
| 806383 | 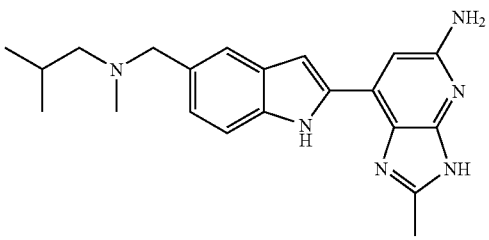 | 363.3 (M + H)⁺ |
| 806393 | 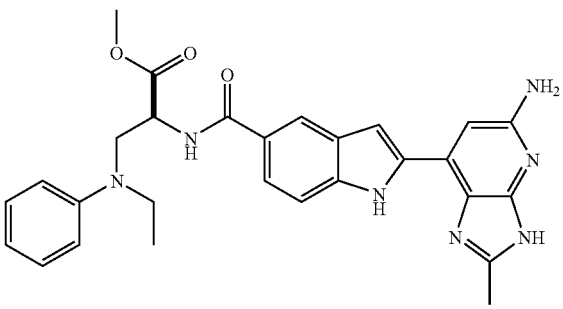 | 512.2 (M + H)⁺ |

-continued

| Compound # (ER # or IC #) | Structure of 64 or 65 | MS (ES) or/and ¹HNMR |
|---|---|---|
| 806402 | | 411.2 (M + H)⁺ 433.2 (M + Na)⁺ |
| 806417 | | 397.2 (M + H)⁺ |
| 806419 | | 469.2 (M + H)⁺ |
| 806421 | | 511.2 (M + H)⁺ |
| 806435 | | 411.3 (M + H)⁺ |
| 806437 | | 411.3 (M + H)⁺ |

-continued
| Compound # (ER # or IC #) | Structure of 64 or 65 | MS (ES) or/and ¹HNMR |
|---|---|---|
| 806569 | 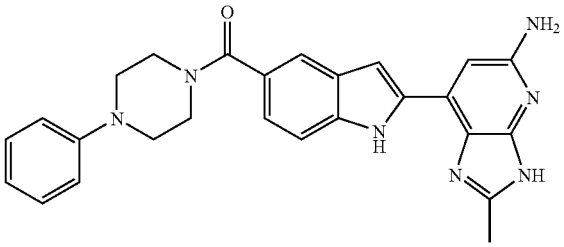 | 452.3 (M + H)⁺ |
| 806609 | 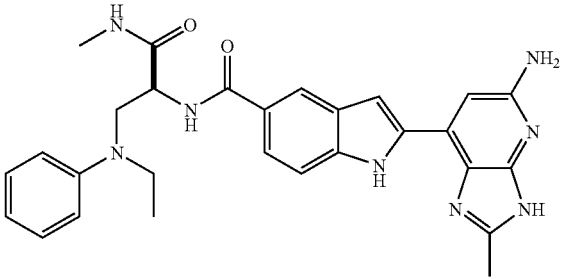 | 495.3 (M − H)⁻ |
| 806610 | 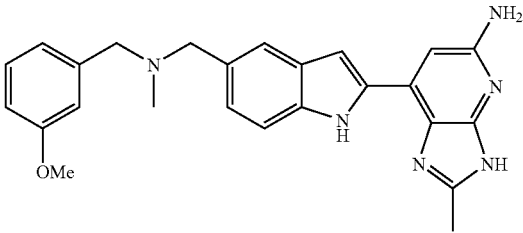 | 425.4 (M − H)⁻ |
| 806647 | 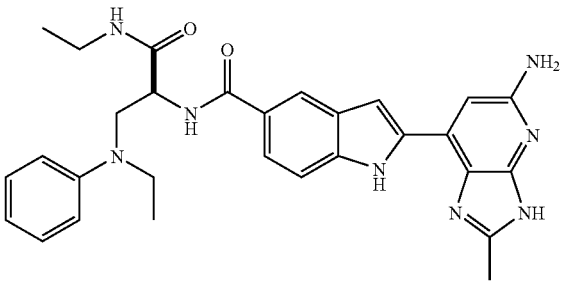 | 496.3 (M + H)⁺ |
| 806653 | 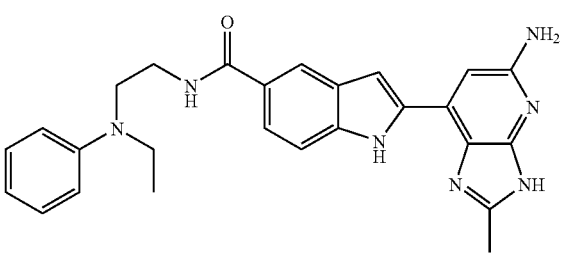 | 454.3 (M + H)⁺ |

-continued

| Compound # (ER # or IC #) | Structure of 64 or 65 | MS (ES) or/and ¹HNMR |
|---|---|---|
| 806671 | | 409.3 (M + H)+ |
| 806781 | | ¹H NMR |
| 806790 | | 509.3 (M − H)− |
| 806796 | | ¹H NMR |
| 806820 | | 496.3 (M + H)+ |

| Compound # (ER # or IC #) | Structure of 64 or 65 | MS (ES) or/and ¹HNMR |
|---|---|---|
| 806839 | | 467.2 (M + Na)+ |
| 806840 | | 467.2 (M + Na)+ |
| 806841 | | 445.3 (M + H)+ |
| 806842 | | 397.3 (M + H)+ |
| 806843 | | 483.3 (M + H)+<br>505.3 (M + Na)+ |
| 806844 | | 363.3 (M + H)+<br>385.3 (M + Na)+ |

| Compound # (ER # or IC #) | Structure of 64 or 65 | MS (ES) or/and $^1$HNMR |
|---|---|---|
| 806860 | | 496.3 (M + H)$^+$ |
| 806874 | | $^1$H NMR |
| 806875 | | $^1$H NMR |
| 806878 | | $^1$H NMR |
| 806899 | | $^1$H NMR |

| Compound # (ER # or IC #) | Structure of 64 or 65 | MS (ES) or/and ¹HNMR |
|---|---|---|
| 806900 | | ¹H NMR |
| 806901 | | 497.1 (M + H)⁺ |
| 806902 | | 377.3 (M + H)⁺ |
| 806903 | | 431.1 (M + H)⁺ |
| 806904 | | 431.2 (M + H)⁺ |
| 806905 | | 431.2 (M + H)⁺ |

-continued

| Compound # (ER # or IC #) | Structure of 64 or 65 | MS (ES) or/and ¹HNMR |
|---|---|---|
| 806987 | | 441.3 (M + H)⁺<br>463.2 (M + Na)⁺ |
| 807014 | | 343.3 (M + Na)⁺ |
| 807139 | | ¹H NMR |
| 807140 | | 427.3 (M + H)⁺ |
| 807183 | | 463.3 (M + Na)⁺<br>441.3 (M + H)⁺ |
| 807240 | | 427.2 (M + H)⁺ |

| Compound # (ER # or IC #) | Structure of 64 or 65 | MS (ES) or/and $^1$HNMR |
|---|---|---|
| 807377 | | $^1$H NMR |
| 807392 | | $^1$H NMR |
| 807400 | | $^1$H NMR |
| 807401 | Trans racemic | $^1$H NMR |
| 807399 | Cis racemic | $^1$H NMR |
| 807447 | | $^1$H NMR |

| Compound # (ER # or IC #) | Structure of 64 or 65 | MS (ES) or/and $^1$HNMR |
|---|---|---|
| 807448 | | $^1$H NMR |
| 807449 | | $^1$H NMR |
| 807450 | | 481.1 (M + H)$^+$ |
| 807451 | | 481.1 (M + H)$^+$ |
| 807452 | | 465.1 (M + H)$^+$ |
| 807453 | | $^1$H NMR |

-continued

| Compound # (ER # or IC #) | Structure of 64 or 65 | MS (ES) or/and ¹HNMR |
|---|---|---|
| 807454 | | ¹H NMR |
| 807457 | | ¹H NMR |
| 807458 | | ¹H NMR |
| 807459 | | ¹H NMR |
| 807460 | | 481.1 (M + H)⁺ |
| 807460 | | ¹H NMR |

-continued

| Compound # (ER # or IC #) | Structure of 64 or 65 | MS (ES) or/and ¹HNMR |
|---|---|---|
| 807463 | | ¹H NMR |
| 807464 | | ¹H NMR |
| 807465 | | ¹H NMR |
| 807466 | | ¹H NMR |
| 807467 | | ¹H NMR |
| 807469 | | ¹H NMR |

-continued
| Compound # (ER # or IC #) | Structure of 64 or 65 | MS (ES) or/and $^1$HNMR |
|---|---|---|
| 807497 | 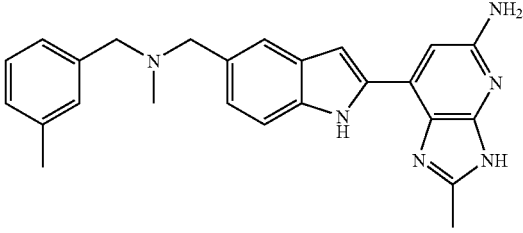 | $^1$H NMR |
| 807498 | 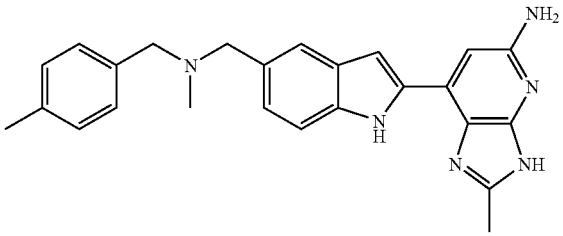 | $^1$H NMR |
| 807505 | 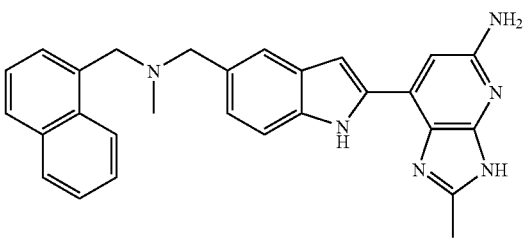 | $^1$H NMR |
| 807506 | 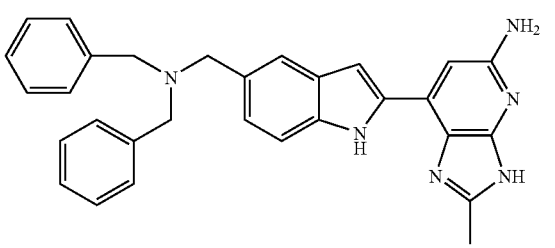 | $^1$H NMR |
| 807528 | 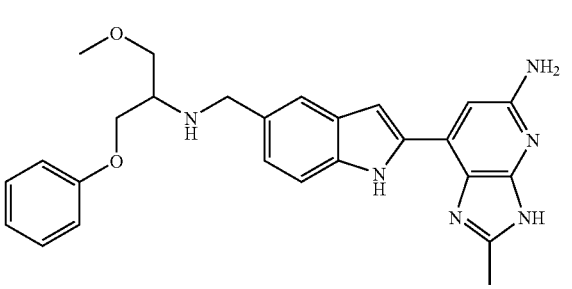 | $^1$H NMR |
| 807531 | 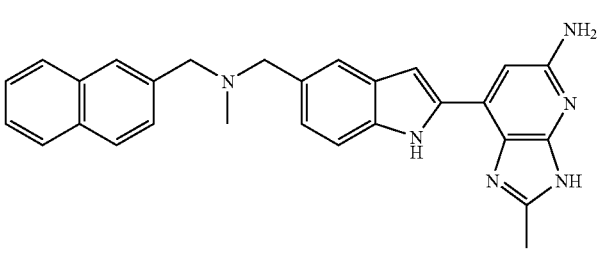 | $^1$H NMR |

| Compound # (ER # or IC #) | Structure of 64 or 65 | MS (ES) or/and $^1$HNMR |
|---|---|---|
| 807532 | | $^1$H NMR |
| 807543 | | $^1$H NMR |
| 807544 | | $^1$H NMR |
| 807548 | | $^1$H NMR |
| 807549 | | $^1$H NMR |

| Compound # (ER # or IC #) | Structure of 64 or 65 | MS (ES) or/and ¹HNMR |
|---|---|---|
| 807550 | 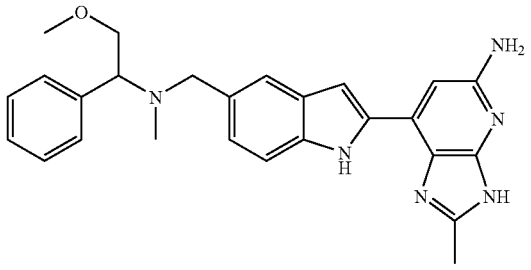 | ¹H NMR |
| 807562 | 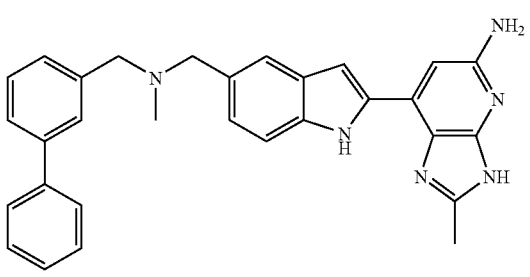 | ¹H NMR |
| 807571 | 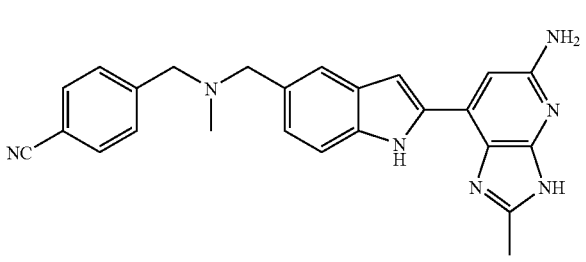 | ¹H NMR |
| 807573 | 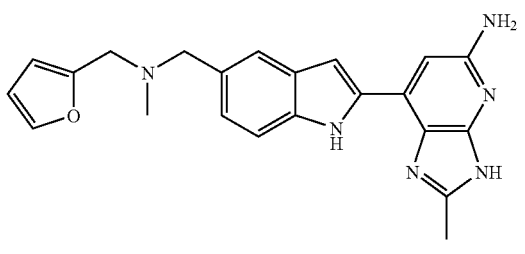 | 387.3 (M + H)⁺ |
| 807586 | 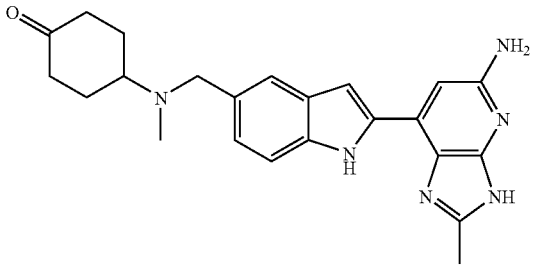 | ¹H NMR |

-continued

| Compound # (ER # or IC #) | Structure of 64 or 65 | MS (ES) or/and ¹HNMR |
|---|---|---|
| 807636 | | ¹H NMR |
| 807649 | | ¹H NMR |
| 807660 | | ¹H NMR |
| 807662 | | ¹H NMR |
| 807663 | | ¹H NMR |
| 807703 | | ¹H NMR |

-continued

| Compound # (ER # or IC #) | Structure of 64 or 65 | MS (ES) or/and ¹HNMR |
|---|---|---|
| 807704 | | ¹H NMR |
| 807748 | | ¹H NMR |
| 807749 | | ¹H NMR |
| 807751 | | ¹H NMR |
| 807754 | | ¹H NMR |
| 807758 | | ¹H NMR |

| Compound # (ER # or IC #) | Structure of 64 or 65 | MS (ES) or/and ¹HNMR |
|---|---|---|
| 807762 | | ¹H NMR |
| 807779 | | ¹H NMR |
| 807794 | | ¹H NMR |
| 807836 | | ¹H NMR |
| 807862 | | ¹H NMR |

-continued

| Compound # (ER # or IC #) | Structure of 64 or 65 | MS (ES) or/and ¹HNMR |
|---|---|---|
| 807876 | | ¹H NMR |
| 807892 | | ¹H NMR |
| 807920 | | ¹H NMR |
| 807930 | | ¹H NMR |
| 807931 | | ¹H NMR |

| Compound # (ER # or IC #) | Structure of 64 or 65 | MS (ES) or/and ¹HNMR |
|---|---|---|
| 807952 | 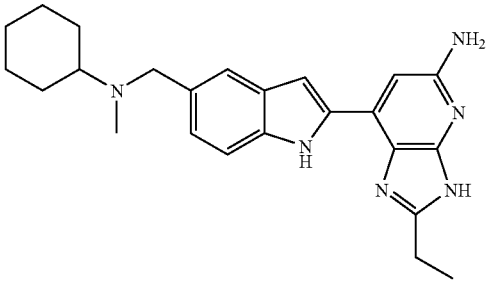 | ¹H NMR |
| 807956 | 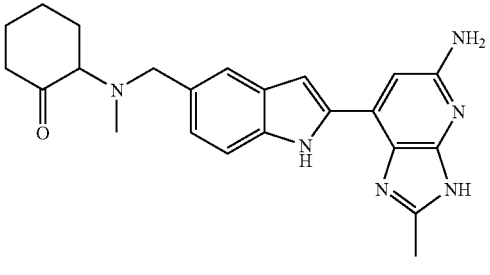 | ¹H NMR |
| 807962 | 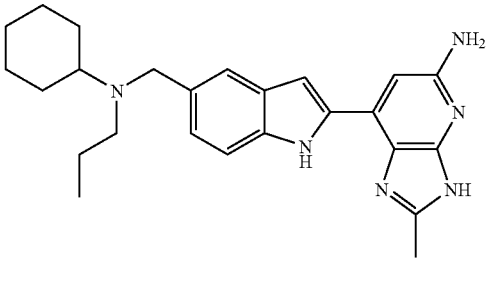 | ¹H NMR |
| 807977 | 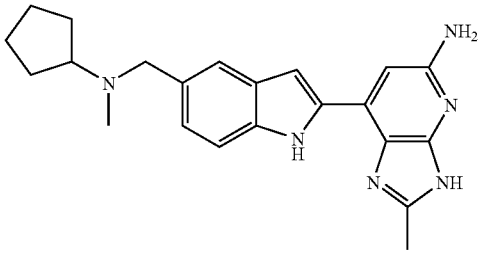 | ¹H NMR |
| 807978 | 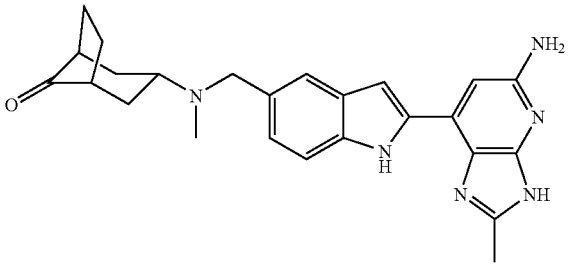 | ¹H NMR |

| Compound # (ER # or IC #) | Structure of 64 or 65 | MS (ES) or/and ¹HNMR |
|---|---|---|
| 807980 | | ¹H NMR |
| 808028 | | ¹H NMR |
| 808039 | | ¹H NMR |
| 808069 | | ¹H NMR |
| 808078 | | ¹H NMR |
| 808079 | | ¹H NMR |

| Compound # (ER # or IC #) | Structure of 64 or 65 | MS (ES) or/and ¹HNMR |
|---|---|---|
| 808084 | 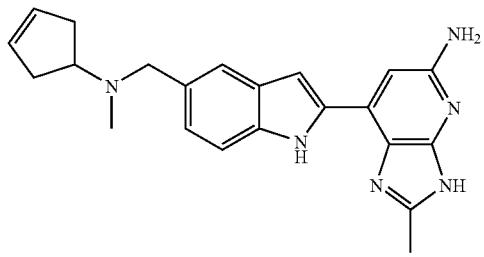 | ¹H NMR |
| 808086 | 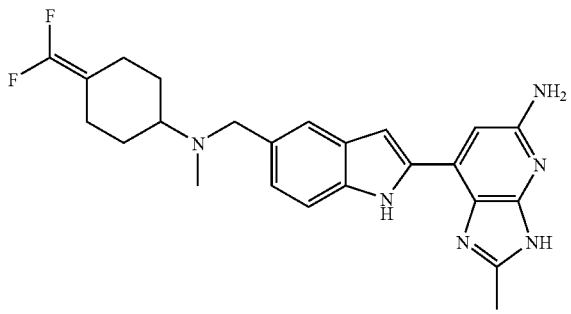 | ¹H NMR |
| 808101 | 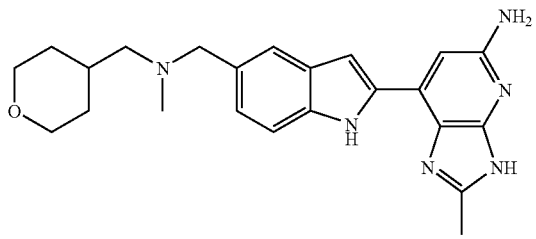 | ¹H NMR |
| 808102 | 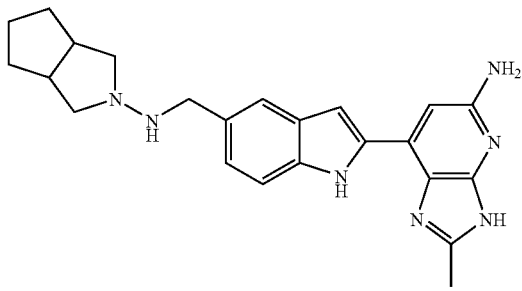 | ¹H NMR |
| 808107 | 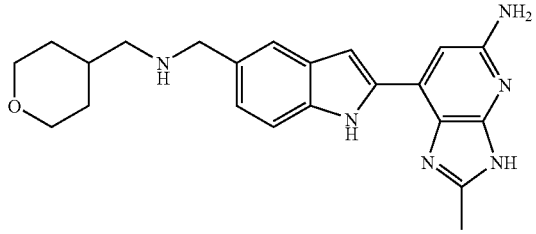 | ¹H NMR |

| Compound # (ER # or IC #) | Structure of 64 or 65 | MS (ES) or/and ¹HNMR |
|---|---|---|
| 808151 | | ¹H NMR |
| 808153 | | ¹H NMR |
| 808164 | | ¹H NMR |
| 808247 | | ¹H NMR |
| 808254 | | ¹H NMR |

| Compound # (ER # or IC #) | Structure of 64 or 65 | MS (ES) or/and $^1$HNMR |
|---|---|---|
| 808255 | | $^1$H NMR |
| 808283 | | $^1$H NMR |
| 808290 | | $^1$H NMR |
| 808312 | | $^1$H NMR |
| 808313 | | $^1$H NMR |

| Compound # (ER # or IC #) | Structure of 64 or 65 | MS (ES) or/and ¹HNMR |
|---|---|---|
| 808346 | | ¹H NMR |
| 808347 | | ¹H NMR |
| 808355 | | ¹H NMR |
| 808356 | | ¹H NMR |
| 808364 | | ¹H NMR |

| Compound # (ER # or IC #) | Structure of 64 or 65 | MS (ES) or/and ¹HNMR |
|---|---|---|
| 808365 | | ¹H NMR |
| 808371 | | ¹H NMR |
| 808387 | | ¹H NMR |
| 808548 | | ¹H NMR |
| 808661 | | ¹H NMR |

-continued

| Compound # (ER # or IC #) | Structure of 64 or 65 | MS (ES) or/and ¹HNMR |
|---|---|---|
| 808663 | | ¹H NMR |
| 808665 | | ¹H NMR |
| 808675 | HI | ¹H NMR |
| 808702 | | ¹H NMR |
| 808833 | | ¹H NMR |

| Compound # (ER # or IC #) | Structure of 64 or 65 | MS (ES) or/and $^1$HNMR |
|---|---|---|
| 808836 | *[Structure: MeO-cyclohexyl-N(Me)-CH2-indole-2-(6-amino-2-methyl-imidazopyridine)]* | $^1$H NMR |
| 808984 | *[Structure: pyrrolidinyl-CH2-indole-2-(6-amino-2-methyl-imidazopyridine)]* | $^1$H NMR |

*[Structure ER-806286: phthalimide-CH2-indole-2-(6-amino-2-methyl-imidazopyridine)]*

*[Structure ER-806287: 4-CF3-phenoxy-CH2-indole-2-(6-amino-2-methyl-imidazopyridine)]*

Diethyl azodicarboxylate (9.1 μL, 2.0 eq.) was added to a solution of 17 (20 mg, 0.03 mmol, 1.0 eq.), triphenylphosphine (15 mg, 2.0 eq.) and phthalimide (8.5 mg, 2.0 eq.) in toluene (2 mL) at room temperature and the resulting mixture was stirred for 19 h. The reaction mixture was concentrated and the intermediate was purified by chromatography (30% EtOAc-hexanes) to give 19.3 mg (81%). This intermediate was dissolved in 1:1 mixture of dichloromethane and trifluoroacetic acid (2 mL) and stirred at room temperature for 2 h until reaction was completed. The reaction was then carefully quenched with sat. NaHCO$_3$ (15 mL), extracted with 7×10 mL of EtOAc. The combine extracts were dried over Na$_2$SO$_4$, filtered, concentrated and the product was purified by reverse phase HPLC (MeOH-water) to give ER-806286 (2.4 mg, 24%). MS (ES) 423.2 (M+H)$^+$.

Compound ER-806287 was prepared from 4-trifluoromethylphenol following the same procedure for the preparation of ER-806286. MS (ES) 438.2 (M+H)$^+$.

*[Structure ER-806311: phenyl-S-CH2-indole-2-(6-amino-2-methyl-imidazopyridine)]*

A mixture of 18 (12.5 mg, 0.018 mmol), diisopropylethylamine (0.2 mL, 65 eq.) and thiophenol (10 μL, 5.5 eq.) in DMF (0.5 mL) at room temperature was stirred for two days. The reaction mixture was concentrated and purified by chromatography (30% EtOAc-hexanes) to give an intermediate 12.7 mg (92%). This intermediate and anisole (100 μL) were dissolved in 1:1 mixture of dichloromethane and trifluoroacetic acid (2 mL) and stirred at room temperature for 40 min. The reaction was then carefully quenched with sat. NaHCO$_3$ (15 mL), extracted with 7×EtOAc. The combine extracts were dried over Na$_2$SO$_4$, filtered, concentrated and the product was purified by chromatography (5% MeOH-EtOAc) to give ER-806311 (4.5 mg, 65%). MS (ES) 386.2 (M+H)$^+$.

ER-806355

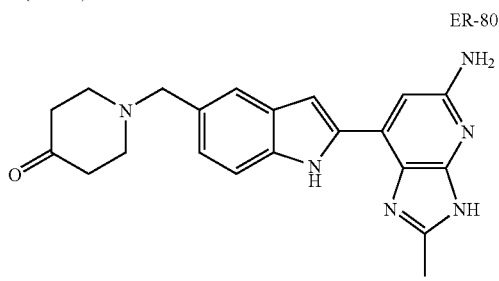

Methylsulfonyl chloride (9 μL, 2 eq.) was added to a solution of 17 (40.5 mg, 0.058 mmol) and diisopropylethylamine (100 μL, 10 eq.) in dichloromethane (1 mL) at 0° C. and stirred for 30 min. 4-hydroxypiperidine (30 mg, 5.0 eq.) and DMF (0.5 mL) were introduced and the reaction mixture was warmed to room temperature and stirred for 2.5 days. The reaction was quenched with sat. NaHCO$_3$ (10 mL) and the separated aqueous phase was extracted with 4×EtOAc. The combine organic extracts were dried over Na$_2$SO$_4$, filtered and concentrated and the product was purified by reverse HPLC (MeOH-water) to give an intermediate (25 mg, 65%). This intermediate was dissolved in dichloromethane (0.5 mL) and treated with TPAP (5 mg) and NMO (20 mg) at room temperature for 10 min. The reaction was quenched by addition of water and Na$_2$S$_2$O$_3$ extracted with 4×EtOAc. The combine organic extracts were dried over Na$_2$SO$_4$, filtered and concentrated and the product was purified by chromatography (15% EtOAc-hexanes) to give an intermediate (13.7 mg). This intermediate and anisole (100 μL) were dissolved in dichloromethane (1 mL) and treated with trifluoroacetic acid (1 mL) at room temperature for 4 h. The reaction was then carefully quenched with sat. NaHCO$_3$ (15 mL), extracted with 4×EtOAc. The combine extracts were dried over Na$_2$SO$_4$, filtered, concentrated and the product was purified by reverse phase HPLC (MeOH-water) to give ER-806355 (3.4 mg, 16% for three steps). $^1$H NMR (DMSO-d$_6$) δ 2.35 (t, J=6 Hz, 4H), 2.49 (s, 3H), 2.70 (t, J=6 Hz, 4H), 3.67 (s, 2H), 5.74 (s, 2H), 6.73 (s, 1H), 7.16 (dd, J=8.2 and 1.2 Hz, 1H), 7.28 (d, J=1.2 Hz, 1H), 7.53 (d, J=8.2, 1H), 7.55 (s, 1H).

ER-806401

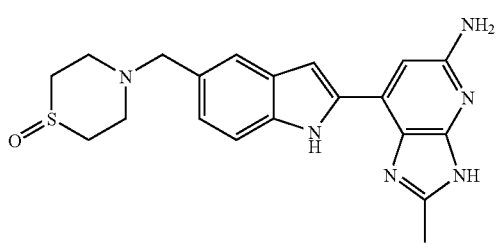

Hydrogen peroxide (4 mL, 30% in water, 3.6 eq.) was added to a solution of thiomorpholine (1.0 g, 9.7 mmol) in acetic acid (12 mL) at room temperature. The resulting mixture was stirred at 100° C. overnight, cooled to room temperature and concentrated. Thiomorpholine sulfoxide from the residue was crystallized from ethanol as a deep colored solid. Following the general procedure for the preparation of 64, compound ER-806401 was prepared from 18 and Thiomorpholine sulfoxide. MS (ES) 417.2 (M+Na)$^+$.

ER-806404

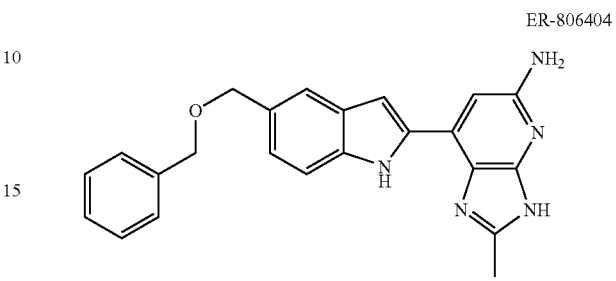

A mixture of 18 (5 mg) and benzyl alcohol (100 μL) was treated with tBuOK (1 mL, 1.66 M in THF) at room temperature overnight. The reaction mixture was quenched with sat. NaHCO$_3$ and extracted with 3×EtOAc. The combine extracts were dried over Na$_2$SO$_4$, filtered, concentrated and the crude intermediate and anisole (50 μL) were dissolved in dichloromethane (0.5 mL) and treated with trifluoroacetic acid (0.5 mL) at room temperature for 3 h. The reaction was then carefully quenched with sat. NaHCO$_3$, extracted with 4×EtOAc. The combine extracts were dried over Na$_2$SO$_4$, filtered, concentrated and the product was purified by thin layer chromatograph (10% MeOH/EtOAc) to give ER-806404 (1.0 mg, 37%). MS (ES) 384.2 (M+H)$^+$.

ER-806644

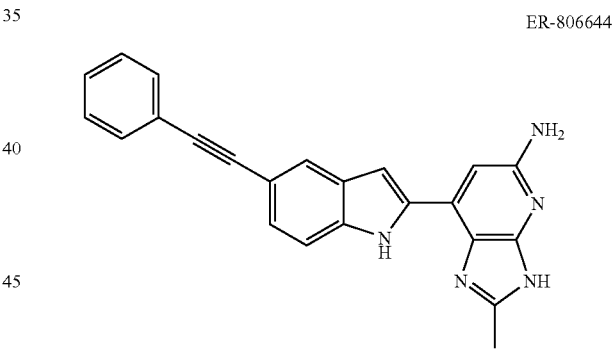

To a solution of 5-iodoindole (5.0 g, 20.6 mmol), phenylacetylene (3.4 mL, 1.5 eq.) and diethylamine (10 mL) in DMF (2 mL) was added Pd(Ph$_3$P)$_4$ (120 mg, 0.005 eq.) and CuI (39 mg, 0.01 eq.) under nitrogen atmosphere at cooling water both temperature and the resulting mixture was stirred for 3 h at room temperature. The reaction was diluted with sat. NaHCO$_3$ (50 mL), extracted with 4×30 mL of EtOAc. The combined extracts were dried over Na$_2$SO$_4$, filtered, concentrated and the product was purified by chromatograph (15 to 20% EtOAc/hexanes) to give 5-phenylethynyl-1H-lindole (4.41 g, 98%).

Compound 5-phenylethynyl-lindole-1-carboxylic acid tert-butyl ester was prepared from 5-phenylethynyl-1H-lindole following the procedure for the preparation of 7 (indole-1,5-dicarboxylic acid 1-tert-butyl ester 5-methyl ester as an example) from methyl indole-5-carboxylate.

Compound 5-phenylethynyl-2-tributylstannanyl-indole-1-carboxylic acid tert-butyl ester was prepared from 5-phenylethynyl-1indole-1-carboxylic acid tert-butyl ester following the procedure for the preparation of 10 from 9.

Compound ER-806644 was prepared from 5-phenylethynyl-2-tributylstannanyl-indole-1-carboxylic acid tert-butyl ester and 4 ($R_1$=Me) following the procedure for the preparation of 13. MS (ES) 364.2 (M+H)$^+$.

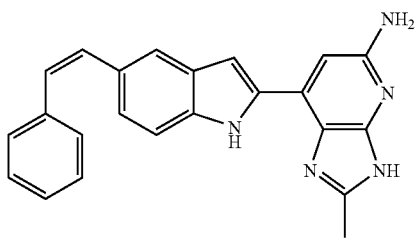

ER-806645

A solution of ER-806644 (6.5 mg) and Lindlar catalyst (50 mg) in THF (2 mL) was stirred at room temperature under hydrogen gas for 1 h. The resulting mixture was filtered through celite and the filtrate was concentrated. The residual solid was washed several times with EtOAc to give ER-806645 as a light yellow solid (2.0 mg, 31%). MS (ES) 366.3 (M+H)$^+$.

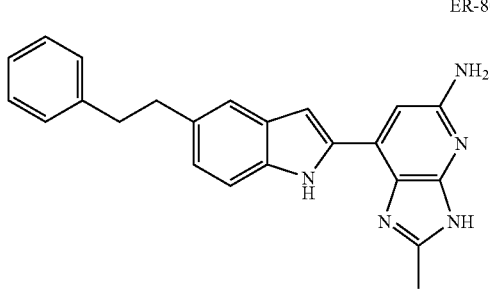

ER-806646

A solution of ER-806644 (5 mg) and Pd(OH)$_2$ (10 mg) in THF (2 mL) was stirred at room temperature under hydrogen gas for overnight. The resulting mixture was filtered through celite and the filtrate was concentrated and the product was purified by reverse phase HPLC (MeOH-water) to give ER-806646 (1.3 mg, 26%). MS (ES) 368.3 (M+H)$^+$.

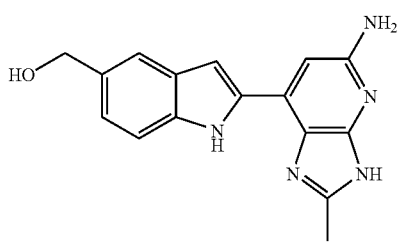

ER-806095

A solution of 16 (20 mg) in 1:1 THF-MeOH (3 mL) at room temperature was treated with a solution of 1 N HCl (0.5 mL) for 30 min. The reaction mixture was diluted with sat. NaHCO$_3$ and extracted with EtOAc. The combined extracts were dried over Na$_2$SO$_4$, filtered, concentrated and the product was purified by reverse phase HPLC (MeOH-water) to give ER-806095 (2.6 mg, 18%). $^1$H NMR.

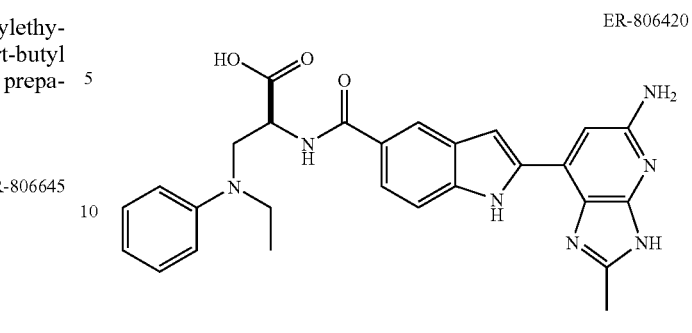

ER-806420

A solution of ER-806393 (1.3 mg) in MeOH (0.5 mL) was treated at room temperature with a solution of 1 N LiOH (0.1 mL) for overnight. The reaction mixture was then neutralized with a solution of 1 N HCl (0.1 mL) to pH=5 and concentrated. The residue was taken up in 1:1 MeOH-EtOAc and filtered. The filtrate was concentrated and purified by reverse phase HPLC (MeOH-water) to give ER-806420 (0.5 mg, 40%). MS (ES) 496.3 (M–H)$^{31}$.

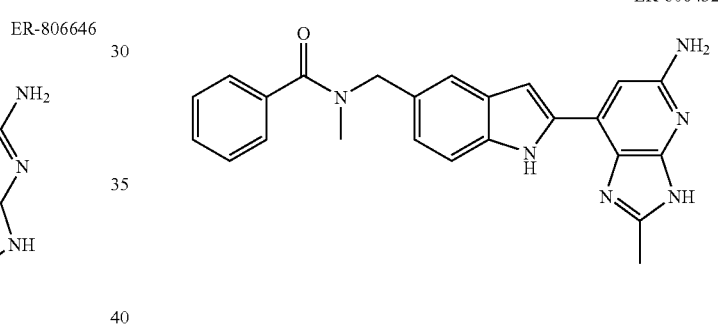

ER-806432

A mixture of 18 (15.5 mg, 0.02 mmol) and methylamine (0.11 mL, 2.0 M in THF, 1.0 eq.) in dichloromethane (0.5 mL) was stirred at room temperature overnight, diluted with sat.NaHCO$_3$ and extracted with 3×EtOAc. The combined extracts were dried over Na$_2$SO$_4$, filtered and concentrated. The residue was dissolved in DMF (0.5 mL) as a solution A.

Diisopropylethylamine (5.3 μL, 1.4 eq.) was added to a solution of benzoic acid (3.4 mg, 1.3 eq.) and TOTU (10 mg, 1.4 eq.) in DMF (0.3 mL) at room temperature and stirred for 15 min. Solution A was then introduced by rinsing with 3×0.5 mL of DMF and the resulting mixture was stirred overnight, concentrated, diluted with sat.NaHCO$_3$ and extracted with 3×EtOAc. The combined extracts were dried over Na$_2$SO$_4$, filtered and concentrated. The residue and anisole (50 μL) was dissolved in dichloromethane (0.5 mL) and treated with trifluoroacetic acid (0.5 mL) at room temperature for 3 h. The reaction mixture was carefully quenched with sat.NaHCO$_3$ and EtOAc and the separated aqueous phase was extracted with 3×EtAOc. The combined extracts were dried over Na$_2$SO$_4$, filtered, concentrated and the product was purified by reverse phase HPLC (MeOH-water) to give ER-806432 (1.4 mg, 16% for three steps). MS (ES) 411.2 (M+H)$^+$.

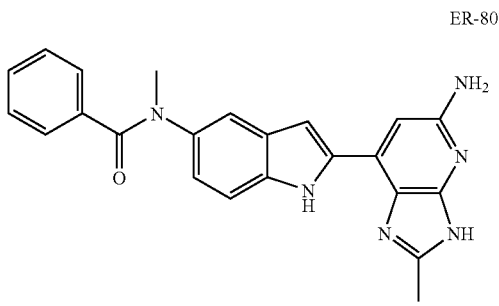

ER-807313

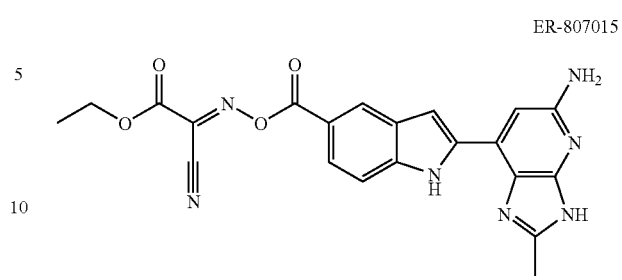

ER-807015

5-nitro-indole-1-carboxylic acid tert-butyl ester was prepared from 5-nitroindole following the same procedure for the preparation of 7 from methyl indole-5-carboxylate.

A solution of 5-nitro-indole-1-carboxylic acid tert-butyl ester (0.50 g) and catalytic amount of Pd(OH)$_2$ in a mixture of MeOH-EtOAc was stirred at room temperature under hydrogen for 1 h. The reaction mixture was filtered through celite and the filtrate was concentrated to provide 5-amino-2,3-dihydro-indole-1-carboxylic acid tert-butyl ester (0.44 g, 98%).

Benzoyl chloride (305 μL, 1.5 eq.) was added to a solution of 5-amino-2,3-dihydro-indole-1-carboxylic acid tert-butyl ester (407 mg, 1.74 mmol) and triethylamine (1.2 mL, 5.0 eq.) in dichloromethane (5 mL) at 0° C. and the resulting mixture was stirred for 15 min. The reaction was then quenched by addition of sat. NaHCO$_3$ and the mixture was extracted with 3×EtOAc. The combined extracts were dried over Na$_2$SO$_4$, filtered, concentrated and the product was purified by chromatography (20 to 100% EtOAc-hexanes) to give 5-benzoylamino-2,3-dihydro-indole-1-carboxylic acid tert-butyl ester (588 mg, 100%).

Sodium hydride (60 mg, 1.5 eq.) was added to a mixture of 5-benzoylamino-2,3-dihydro-indole-1-carboxylic acid tert-butyl ester (570 mg, 1.68 mmol) and methyl iodide (0.42 mL, 4.0 eq.) in DMF (10 mL) at 0° C. and the resulting mixture was stirred for 20 min. After concentration, the residue from reaction mixture was diluted with sat. NaHCO$_3$ and extracted with 3×EtOAc. The combined extracts were dried over Na$_2$SO$_4$, filtered, concentrated and the product was purified by chromatography (30% EtOAc-hexanes) to give 5-(benzoyl-methyl-amino)-2,3-dihydro-indole-1-carboxylic acid tert-butyl ester (547 mg, 93%).

A mixture of 5-(benzoyl-methyl-amino)-2,3-dihydro-indole-1-carboxylic acid tert-butyl ester (500 mg) and MnO$_2$ (5 g) in toluene (20 mL) was heated at 80° C. for 1 h. Additional MnO$_2$ (5 g) was introduced and the resulting mixture was stirred at 80° C. for 1 h. After cooling to room temperature, the mixture was filtered through celite and the filtrate was concentrated. The product was purified by chromatography (30% EtOAc-hexanes) to give 5-(benzoyl-methyl-amino)-indole-1-carboxylic acid tert-butyl ester (372 mg, 75%).

5-(benzoyl-methyl-amino)-2-tributylstrannanyl-indole-1-carboxylic acid tert-butyl ester was prepared from 5-(benzoyl-methyl-amino)-indole-1-carboxylic acid tert-butyl ester following the procedure for the preparation of 10 from 9.

Compound ER-807313 was prepared from 5-(benzoyl-methyl-amino)-2-tributylstrannanyl-indole-1-carboxylic acid tert-butyl ester and 4 (R$_1$=Me) following the procedure for the preparation of 13. MS (ES) 397.2 (M+H)$^+$ and 419.1 (M+Na)$^+$.

Compound ER-807015 was prepared as a by-product during preparation of 65 from statically hindered amines and yielded a satisfactory $^1$H NMR spectrum.

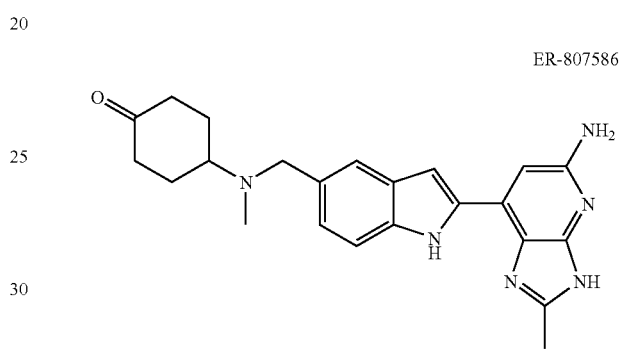

ER-807586

A mixture of 18 (51 mg, 1.0 eq.), (3,3-dimethyl-1,5-dioxa-spiro[5.5]undec-9-yl)-methyl-amine hydrochloride (71 mg, 4.0 eq.), ethyldiisopropylamine (0.25 mL, 20 eq.) and DMF (0.3 mL) in CH$_2$Cl$_2$ (2.5 mL) was stirred at room temperature for 23 μl. After concentration, the residue was dissolved in 1 N HCl (0.6 mL) and acetone (0.6 mL) and heated at reflux for 16 h. After cooling to room temperature, the reaction was then carefully quenched with sat. NaHCO$_3$, extracted with EtOAc until there was no product detected. The combine extracts were dried over Na$_2$SO$_4$, filtered, concentrated and the product was purified by reverse phase HPLC (MeOH-water) to give ER-807586 (6.4 mg, 22%). $^1$HNMR and MS (ES) 403.5 (M+H)$^+$.

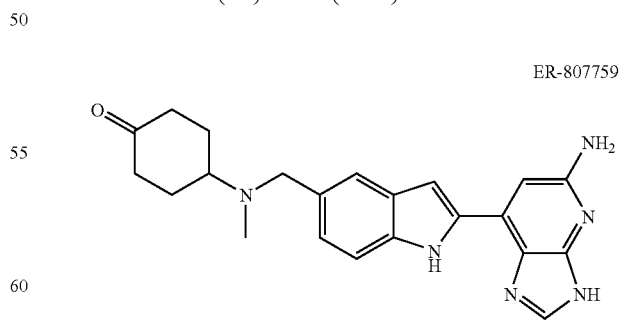

ER-807759

ER-807759 was prepared following the same procedure for 13 (ER-805639 as an example) in Stille coupling reaction and for ER-807586 in ketal hydrolysis reaction. $^1$HNMR and MS (ES) 389 (M+H)$^+$.

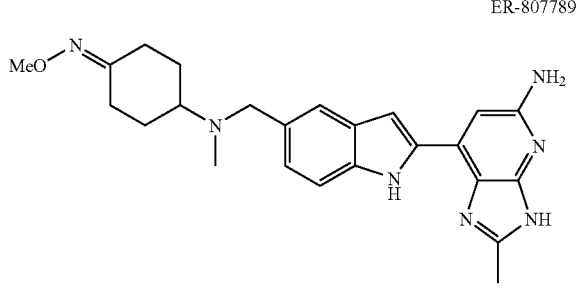

ER-807789

To a suspension of ER-807586 (5 mg, 0.0124 mmol, 1.0 eq.) in water (0.5 mL) was added $NH_2OMe·HCl$ (5.2 mg, 0.623 mmol, 50 eq.). The solid became soluble and saturated $NaHCO_3$ (0.3 mL) was slowly added and the resulting mixture was stirred overnight. The reaction mixture was diluted with EtOAc and saturated $NaHCO_3$, and extracted with 4×EtOAc. The organic layers were combined, dried over $MgSO_4$, filtered and concentrated. The crude mixture was purified by silica gel chromatography (10% MeOH-EtOAc) to give ER-807789 as a white solid (5.3 mg, 100%). $^1$HNMR and MS (ES) 432 (M+H)$^+$.

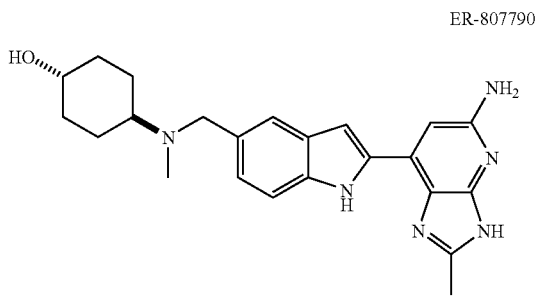

ER-807790

To a solution of ER-807586 (15 mg) in MeOH-THF (1:1, 1 mL) was added $NaBH_4$ (20 mg) and the mixture was stirred for 30 min, diluted with saturated $NaHCO_3$ and extracted with 4×EtOAc. The organic layers were combined, dried over $MgSO_4$, filtered and concentrated. The crude mixture was purified by reverse HPLC (MeOH—$H_2O$) to give ER-807790. $^1$HNMR and MS (ES) 405.5 (M+H)$^+$.

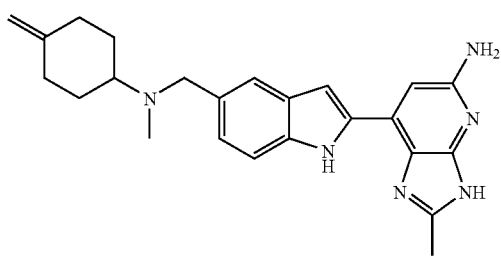

ER-807835

To a solution of n-BuLi (1.6 M in hexanes, 0.35 mL, 0.56 mmol, 31.3 eq.) in THF (2.0 mL) at 0° C. was added methyl triphenylphosphonium bromide (0.20 g, 0.56 mmol, 31 eq.). The reaction was wormed to room temperature and stirred for 40 minutes. A portion of the solution (0.6 mL) was transferred to another flask and ER-807586 (7.2 mg, 0.0179 mmol, 1.0 eq.) was added. The resulting mixture was stirred at room temperature for 18 hours and water was added and the mixture was extracted with 3×EtOAc. The organic layers were combined, dried over $MgSO_4$, filtered and concentrated. The crude mixture was purified by reverse HPLC (MeOH—$H_2O$) to give ER-807835 (0.8 mg, 12%) $^1$H NMR and MS (ES) 401.5 (M+$^1$H).

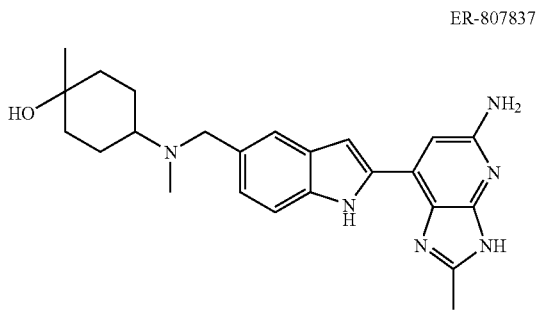

ER-807837

To a solution of ER-807586 (11.5 mg, 0.0286 mmol, 1.0 eq.) in THF (2.0 mL) at 0° C. was added MeMgCl (3.0 M in THF, 0.25 mL, 0.75 mmol, 26.3 eq.). The reaction was warmed and stirred at room temperature for 18 hours. The reaction was quenched with saturated $NaHCO_3$, and then was extracted with 3×EtOAc. The organic layers were combined, dried over $MgSO_4$, filtered and concentrated. The resulting mixture was purified by silica gel chromatography (100% EtOAc, then 10% to 30% MeOH-EtOAc) to give ER-807837 (0.8 mg, 7%). $^1$H NMR and MS (ES) 419.4 (M+$^1$H).

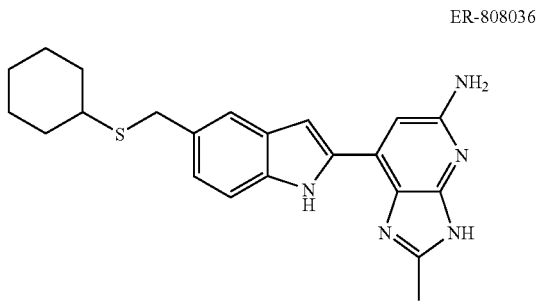

ER-808036

5-chloromethyl-indole-1-carboxylic acid tert-butyl ester was prepared from 8 following the procedure for the preparation of 9 but without the addition of morpholine.

A mixture of 5-chloromethyl-indole-1-carboxylic acid tert-butyl ester (0.82 g, 3.10 mmol, 1.0 eq.), cyclohexyl mercaptan (0.53 mL, 1.4 eq.) and $K_2CO_3$ (0.90 g, 2.0 eq.) in DMF (6 mL) was heated at 40° C. until reaction completed. The reaction mixture was cooled to room temperature, diluted with sat. $NH_4Cl$ and extracted with diethyl ether. The organic extracts were dried over $MgSO_4$, filtered and concentrated. The resulting mixture was purified by chromatography (5% EtOAc/hexanes) to give 5-cyclohexylsulfanylmethyl-indole-1-carboxylic acid tert-butyl ester (0.79 g, 74%).

ER-808036 was prepared from 5-cyclohexylsulfanylmethyl-indole-1-carboxylic acid tert-butyl ester following the procedures for the preparation of 16 from 14.

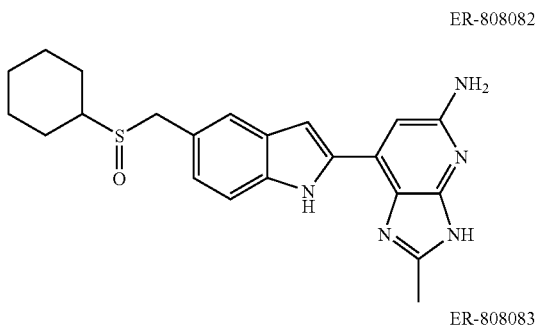

ER-808082

ER-808083

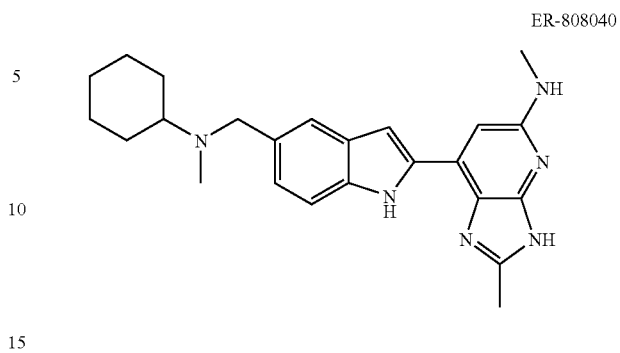

ER-808040

To a solution of ER-808036 (60 mg, 0.15 mmol, 1.0 eq.) in THF (2.5 mL) and MeOH (1.5 mL) at −78° C. was added a solution of mCPBA (60 mg, ~70%, 1.6 eq.) in THF. After stirring for 2 h, the reaction was quenched by addition of sat. $Na_2S_2O_3$ and sat $NaHCO_3$. The separated aqueous layer was extracted with 5×EtOAc, and the combined organic phase was dried over $Na_2SO_4$, filtered and concentrated. The crude mixture was purified by chromatography (5% to 10% MeOH/EtOAc) to give semipure products (18 mg and 32 mg each). After further purification by reverse phase HPLC (MeOH-water), ER-808082 (3.2 mg) and ER-808083 (3.2 mg) were obtained. $^1$NMR confirmed both of the products.

To a suspension of compound 3 (R=Me, 300 mg, 1.03 μmol, 1.0 eq.) in THF (5 mL) at room temperature was added dropwise $LiAH_4$ (1.0 M in THF, 2.56 mL, 2.5 eq.) and the resulting mixture was then heated at 65° C. for 30 min. Afetr cooling to 0° C., the reaction was quenched by addition of MeOH (1.2 mL, 30 eq.) and water (30 eq.), stirred and warmed to room temperature and filtered through celite washing with EtOAc. The filtrate was concentrated and the residue was purified by silica gel chromatography (EtOAc then 10% MeOH-EtOAc) to give 7-chloro-2-methyl-5-methylamino-3H-imidazo[4,5-b]pyridine as a white solid (190 mg, 94%).

ER-808040 was prepared from 7-chloro-2-methyl-5-methylamino-3H-imidazo[4,5-b]pyridine and 5-[(cyclohexyl-methyl-amino)-methyl]-2-tributylstannanyl-indole-1-carboxylic acid tert-butyl ester (prepared from 8 and cyclohexyl-methyl-amine following the procedures for the preparation of 10) following the procedure for the preparation of 13. $^1$HNMR confirmed the compound.

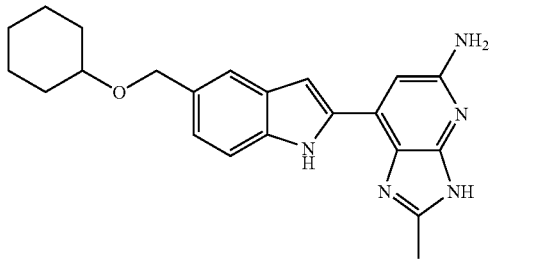

ER-808103

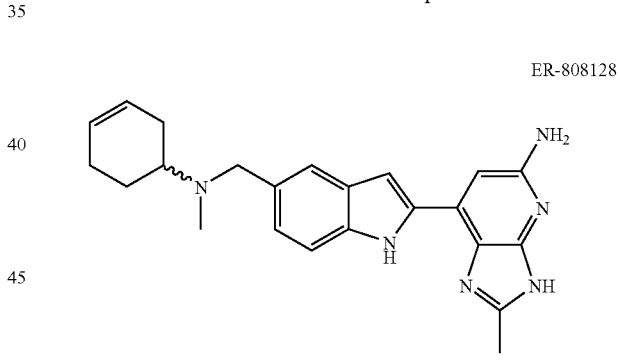

ER-808128

A mixture of 5-chloromethyl-indole-1-carboxylic acid tert-butyl ester (0.41 g, 1.55 mmol, 1.0 eq.), cyclohexanol (0.82 mL, 5.0 eq.) and $Ag_2O$ (1.80 g, 5.0 eq.) in diethyl ether (5 mL) was stirred at 35° C. over weekend. After cooling to room temperature, the reaction mixture was filtered through celite washing with ether. The filtrate was concentrated and the residue was purified by chromatography (3% EtOAc/hexanes) to give N-Boc-5-cyclohexyloxymethylindole (160 mg, 28%) as colorless oil. $^1$HNMR comfirmed the compound.

ER-808103 was prepared from 5-cyclohexyloxymethyl-indole-1-carboxylic acid tert-butyl ester following the procedures for the preparation of 16 from 14. Both MS (ES) and $^1$HNMR comfirmed the compound.

To a solution of ER-807790 (17 mg, 0.042 mmol, 1.0 eq.) in $CH_2Cl_2$ (1 mL) at 0° C. was added $(MeOCH_2CH_2)_2NSF_3$ (14 mL, 1.8 eq.) and the resulting mixture was stirred for 1 h at 0° C. and 1 h at room temperature. The reaction was quenched with sat. $NaHCO_3$ and the separated aqueous layer was extractred with $CH_2Cl_2$ followed by EtOAc-THF (1:1). The combined organic extracts were dried over $Na_2SO_4$, filtered and concentrated. The residue was purified by reverse HPLC (MeOH-water) to give ER-808128 (2 mg, 13%). $^1$H NMR and MS confirmed the structure.

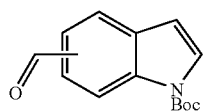

5-formyl-indole-1-carboxylic acid tert-butyl ester or
6-formyl-indole-1-carboxylic acid tert-butyl ester To a solution of the 8 (8.0 g, 32.4 mmol, 1 eq.) in CH$_2$Cl$_2$ (24 mL) was added portionwise Dess-Martin reagent (17.9 g, 1.3 eq.) at 0° C. and the resulting mixture was warmed slowly to room temperature and stirred for 30 min. The reaction mixture was diluted with Et$_2$O (100 mL), filtered through celite rinsing with Et$_2$O (50 m). The filtrate was washed with sat. NaHCO$_3$, dried over Na$_2$SO$_4$, filtered and concentrated. The crude product was azeotroped with tolune to give 5-formyl-indole-1-carboxylic acid tert-butyl ester (7.3 g, 95%) or similarly 6-formyl-indole-1-carboxylic acid tert-butyl ester

ER-808281

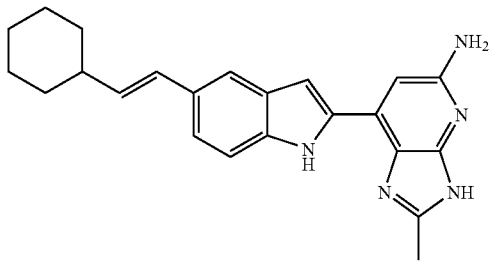

Mg (turnings) was activated by washing with 1N HCl and Et$_2$O, and dried on high vacuum overnight Bromomethyl-cyclohexane (0.8 mL, 1 eq.) in Et$_2$O (4 mL) was added to the activated Mg (418 mg, 3 eq.) in Et$_2$O (10 mL) slowly to keep the internal temperature at 30-33° C. The resulting reaction mixture was heated at 34° C. for 1 h and cooled to 0° C. A solution of 5-formyl-indole-1-carboxylic acid tert-butyl ester (900 mg) in Et$_2$O (15 mL) was then introduced and the resulting mixture was warmed to room temperature, heated at 30-32° C. for 4 h, cooled to room temperature and then quenched with the addition of sat. NH$_4$Cl. The separated aqueous phase was extracted with EtOAc, the combined organic layer was dried over MgSO$_4$, filtered and concentrated. The crude product was purified by chromatography (10% to 25% EtOAc/hexanes) to give the corresponding alcohol (949 mg, 85%).

To a mixture of the alcohol (513 mg, 1 eq.) and Et$_3$N (625 µL, 3 eq.) in CH$_2$Cl$_2$ (15 mL) at 0° C. was added methanesulfonic anhydride (390 mg, 1.5 eq.). The cooling bath was removed and the resulting mixture was stirred for 2.5 h and diluted with sat. NaHCO$_3$. The separated aqueous layer was extracted with CH$_2$Cl$_2$. The combined organic layer was dried over Na$_2$SO$_4$, filtered and concentrated. The crude product was purified by chromatography (hexanes to 10% EtOAc/hexanes) to give 5-(2-cyclohexyl-vinyl)-indole-1-carboxylic acid tert-butyl ester (380 mg, 78%).

ER-808281 was prepared from 5-(2-cyclohexyl-vinyl)-indole-1-carboxylic acid tert-butyl ester following the procedures for the preparation of 16 from 14. MS (ES) and $^1$HNMR confirmed the compound.

ER-808469

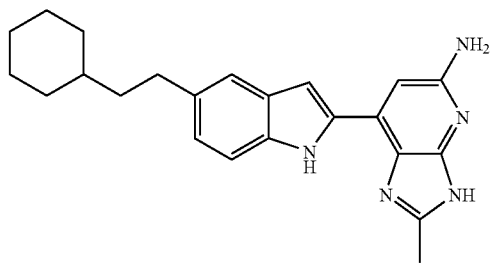

A solution of ER-808281 (~10 mg, 1 eq.) in MeOH (5 mL) with 10% Pd/C (catalytic) was kept under positive H$_2$ atmosphere overnight at room temperature. The mixture was then loaded onto silica gel eluting with EtOAc to 20% MeOH/EtOAc to give ER-808469 (7.5 mg). MS (ES) and $^1$HNMR confirmed the compound.

5-vinyl-indole-1-carboxylic acid tert-butyl ester or
6-vinyl-indole-1-carboxylic acid tert-butyl ester T a suspension of methyltriphenylphosphonium bromide (8.1 g, 22.7 mmol) in THF (140 mL) at 0° C. was added nBuLi (1.6 M in hexanes, 14.2 mL, 22.7 mmol) dropwise over 10 min. After 10 min of stirring, a solution of the 5-formyl-indole-1-carboxylic acid tert-butyl ester (4.63 g, 14.8 mmol) in THF (20 mL) was introduced slowly over 20 min. The reaction was warmed slowly to room temperature, stirred 30 min. The reaction mixture was poured into saturated ammonium chloride and the separated aqueous phase was extracted with ethylacetate (3×100 mL). The combined organic phase was dried over sodium sulfate, filtered and concentrated. The residue was purified by chromatography (methylene chloride to 1% acetone-methylene chloride) to give 5-vinyl-indole-1-carboxylic acid tert-butyl ester (4.7 g, 100%) or similarly 6-vinyl-indole-1-carboxylic acid tert-butyl ester.

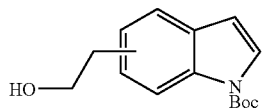

5-(2-hydroxy-ethyl)-indole-1-carboxylic acid tert-butyl ester or 6-(2-hydroxy-ethyl)-indole-1-carboxylic acid tert-butyl ester To a solution of 5-vinyl-indole-1-carboxylic acid tert-butyl ester (4.5 g, 18.5 mmol, 1.0 eq.) in THF (46 mL) at 0° C. was added 9-BBN (0.5 M in THF, 87 mL, 2.4 eq.) over 10 min. The resulting reaction mixture was stirred for 2.5 h and diluted with THF (150 mL) and water (150 mL) while keeping the temperature at 0° C. Then NaBO$_3$. 4H$_2$O (44 g)

was introduced and resulting reaction mixture was stirred and warmed to room temperature and stirred. The reaction mixture was diluted with methylene chloride (100 mL) and the separated aqueous layer was extracted 3×100 mL methylene chloride. The combined organic layers were dried over sodium sulfate, filtered and concentrated. The residue was purified by chromatography (methylene chloride to 5% acetone/methylene chloride) to give 5-(2-hydroxy-ethyl)-indole-1-carboxylic acid tert-butyl ester (3.82 g, 76%) or similarly 6-(2-hydroxy-ethyl)-indole-1-carboxylic acid tert-butyl ester.

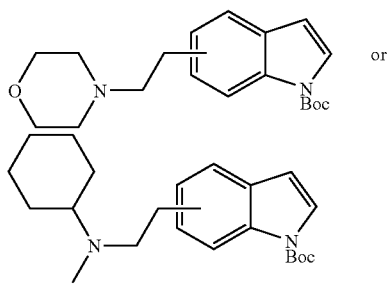

5-(2-morpholin-4-yl-ethyl)-indole-1-carboxylic acid tert-butyl ester or 5-[2-(cyclohexyl-methyl-amino)-ethyl]-indole-1-carboxylic acid tert-butyl ester or 6-(2-morpholin-4-yl-ethyl)-indole-1-carboxylic acid tert-butyl ester or 6-[2-(cyclohexyl-methyl-amino)-ethyl]-indole-1-carboxylic acid tert-butyl ester To a solution of 5-(2-hydroxy-ethyl)-indole-1-carboxylic acid tert-butyl ester (260 mg, 1 mmol, 1.0 eq.), triphenyl phosphine (391 mg, 1.5 eq.) and Imidazole (136 mg, 2 eq.) in methylene chloride (5 mL) was added iodine (328 mg, 1.3 eq.) in small portions over 20 min at room temperature. The reaction mixture was poured into water and extracted with 4×100 mL of methylene chloride. The combined organic phase was dried over sodium sulfate, filtered and concentrated. The residue was purified by silica gel chromatography (20% EtOAc/hexanes) to give a semipure iodide (600 mg). This iodide was then dissolved in MeOH (10 mL) and treated with morphoiline (1.73 mL, 20 eq.) at 60° C. for overnight. The reaction mixture was cooled to room temperature, poured into water and extracted with methylene chloride. The combined organic layers were dried over sodium sulfate, filtered and concentrated. The residue was purified by silica gel column chromatography (methylene chloride to 15% acetone/methylene chloride) to give 5-(2-morpholin-4-yl-ethyl)-indole-1-carboxylic acid tert-butyl ester (290 mg, 88%) or similarly or 5-[2-(cyclohexyl-methyl-amino)-ethyl]-indole-1-carboxylic acid tert-butyl ester or 6-(2-morpholin-4-yl-ethyl)-indole-1-carboxylic acid tert-butyl ester or 6-[2-(cyclohexyl-methyl-amino)-ethyl]-indole-1-carboxylic acid tert-butyl ester.

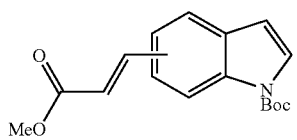

5-(2-methoxycarbonyl-vinyl)-indole-1-carboxylic acid tert-butyl ester or 6-(2-methoxycarbonyl-vinyl)-indole-1-carboxylic acid tert-butyl ester To a solution of the 5-formyl-indole-1-carboxylic acid tert-butyl ester (3.4 g, 13.8 mmol, 1.0 eq.) in toluene (35 mL) was added Ph$_3$P=CHCO$_2$Me (5.5 g, 1.2 eq.) at room temperature and the resulting mixture was stirred overnight. After concentration, the crude product purified by silica gel column chromatography (methylene chloride to 1% acetone-methylene chloride) to give 5-(2-methoxycarbonyl-vinyl)-indole-1-carboxylic acid tert-butyl ester (5.03 g, 90%) or similarly 6-(2-methoxycarbonyl-vinyl)-indole-1-carboxylic acid tert-butyl ester.

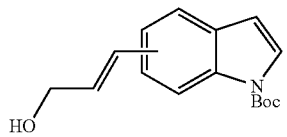

5-(3-hydroxy-propenyl)-indole-1-carboxylic acid tert-butyl ester or 6-(3-hydroxy-propenyl)-indole-1-carboxylic acid tert-butyl ester To a solution of methyl 5-(2-methoxycarbonyl-vinyl)-indole-1-carboxylic acid tert-butyl ester (4.64 g, 15.3 mmol, 1.0 eq.) in THF (87 mL) at −30° C. was added LiAlH$_4$ (1 N in THF, 18.6 mL, 1.2 eq.) by syringe pump over 20 min and the resulting mixture was stirred and warmed to −5° C. After cooling back to −30° C., the reaction was then quenched by slow addition of acetone (10 mL) keeping temperature below −15° C., poured into Rochelle salt at 0° C., stirred for 1 h and the separated aqueous layer was extracted with EtOAc. The combunede organic phase was dried over sodium sulfate, filtered and concentrated. The residue was purification by column chromatography (methylene chloride to 2% acetone/methylene chloride) to give 5-(3-hydroxy-propenyl)-indole-1-carboxylic acid tert-butyl ester (2.89 g, 70%) or or similarly 6-(3-hydroxy-propenyl)-indole-1-carboxylic acid tert-butyl ester.

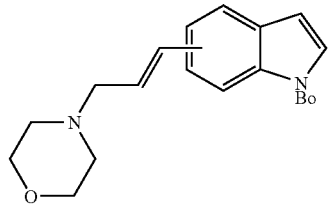

5-(3-morpholin-4-yl-propenyl)-indole-1-carboxylic acid tert-butyl ester or 6-(3-morpholin-4-yl-propenyl)-indole-1-carboxylic acid tert-butyl ester To a solution 5-(3-hydroxy-propenyl)-indole-1-carboxylic acid tert-butyl ester (0.95 mg, 3.48 mmol, 1.0 eq.) and Et$_3$N (1.8 mL, 3.0 eq.) in methylene chloride (10 mL) at 0° C. was added MsCl (0.40 mL, 1.5 eq.). The resulting mixture was stirred for 30 min and wormed to room temperature and stirred for additional 1 h. Then cyclohexyl-methyl-amine (8.3 mL, 18 eq.) was introduced and the resulting mixture was stirred over weekend, diluted with sat. NaHCO$_3$ and the separated aqueous phase was extracted with 3×EtOAc. The combined organic phase was dried over Na$_2$SO$_4$, filtered and concentrated. The residue was purified by silica gel chromatography (50% EtOAc/hexanes) to give 5-(3-morpholin-4-3,1-propenyl)-indole-1-carboxylic acid tert-butyl ester or similarly 6-(3-morpholin-4-yl-propenyl)-indole-1-carboxylic acid tert-butyl ester.

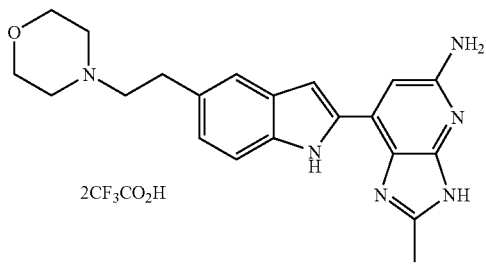

ER-808501

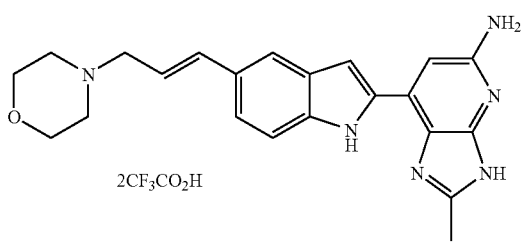

ER-808514

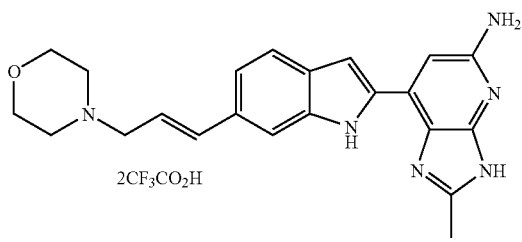

ER-8085042

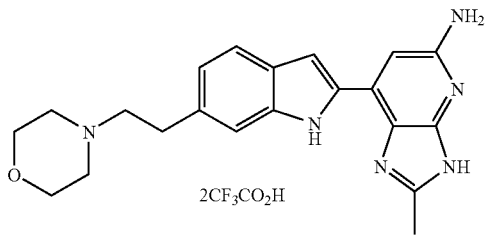

ER-808544

Analogs ER-808501, ER-808514, ER-8085042 and ER-808544 are prepared from 5-(2-morpholin-4-yl-ethyl)-indole-1-carboxylic acid tert-butyl ester, 5-(3-morpholin-4-yl-propenyl)-indole-1-carboxylic acid tert-butyl ester, 6-(3-morpholin-4-yl-propenyl)-indole-1-carboxylic acid tert-butyl ester and 6-(2-morpholin-4-yl-ethyl)-indole-1-carboxylic acid tert-butyl ester following the same procedures for the preparation of 16 from 14.

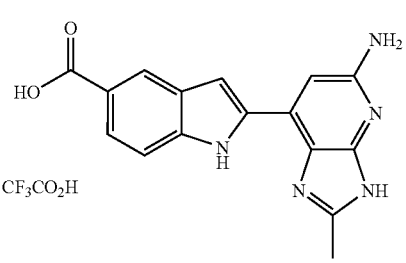

ER-809047

A solution of 20 (51 mg) in methylene chloride (1 mL) was treated at room temperature with trifluoroacetic acid (1 mL) for 3 h and concentrated. The solid residue was washed with Et$_2$O and MeOH to give crude product (18.2 mg). The crude product was then purified by reverse phase HPLC (MeOH-water) to give ER-809047 (9.6 mg, 44%). MS (ES), $^{19}$F and $^1$HNMR confirmed the structure.

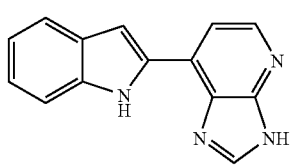

IC-261

A mixture of 7-chloro-3H-imidazo[4,5-b]pyridine (J. Heterocyclic. Chem. 198', 19, 513) (250 mg, contain 25% of 5-chloro-3H-imidazo[4,5-b]pyridine), 2-tributylstannanyl-indole-1-carboxylic acid tert-butyl ester (11, 822 mg) and tetrakis(triphenyphosphine)palladium(0) (188 mg) in DMF (10 mL) was heated at 120° C. for 6 h. The reaction mixture was extracted with AcOEt, and washed with water and brine. Organic layer was dried over MgSO$_4$ and evaporated. The residue was purified by chromatography (AcOEt/hexane) to give 7-(1H-indol-2-yl)-3H-imidazo[4,5-b]pyridine IC-261 (28 mg) as a pale brown solid. $^1$H NMR confirmed the structure.

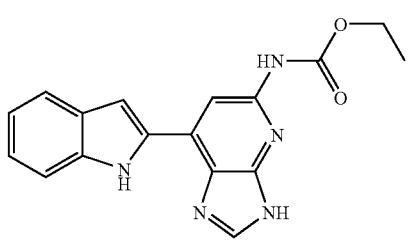

IC-395

A mixture of 2 (1.66 g, 6 mmol), 2-tributylstannanyl-indole-1-carboxylic acid tert-butyl ester (11, 3.6 g, 7 mmol), triethylamine (0.83 ml, 6 mmol), and tetrakis(triphenylphosphine)palladium(0) (600 mg, 10 mol %) in DMF (10 mL) was heated at 130° C. for 6 h. During the reaction, 11 was added in two portions (1.01 g×2). The reaction mixture was extracted with ethyl acetate and washed with water, and dried over anhydrous magnesium sulfate. After filtration, silica gel (400 mesh) was added to the residue and concentrated. The residue was purified by chromatography (AcOEt/

MeOH) to give IC-395 (240 mg) and IC-375 (80 mg). $^1$H NMR confirmed the structure.

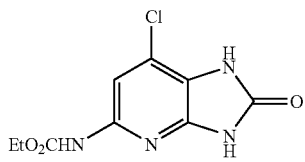

(7-chloro-2-oxo-2,3-dihydro-1H-imidazo[4,5-b]pyridin-5-yl)-carbamic acid ethyl ester To a solution of diethyl 4-chloro-5-nitro-2,6-pyridinedicarbamate (intermediate for the preparation of 1) (500 mg) in EtOH (50 mL) was added Raney Ni (1 g) and stirred for 12 h under hydrogen atmosphere at room temperature. Reaction mixture was filtered on celite and filtrate was concentrated under reduced pressure. Residue was dissolved in 2-propanol (10 mL) and stirred for 60 h under reflux. The reaction mixture was cooled to room temperature and precipitate was filtered. The filtrate was concentrated to give 250 mg of (7-chloro-2-oxo-2,3-dihydro-1H-imidazo[4,5-b]pyridin-5-yl)-carbamic acid ethyl ester as a gray solid. $^1$H NMR confirmed the structure.

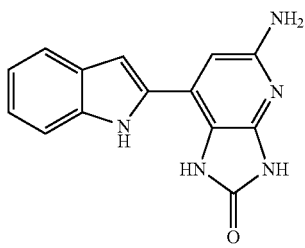

IC-380

A mixture of (7-chloro-2-oxo-2,3-dihydro-1H-imidazo[4,5-b]pyridin-5-yl)-carbamic acid ethyl ester (240 mg), 2-tributylstannanyl-indole-1-carboxylic acid tert-butyl ester (11, 472 mg) and tetrakis(triphenylphosphine)palladium(0) (54 mg) in DMF (10 mL) was heated at 120° C. for 4 h. Additional 2-tributylstannanyl-indole-1-carboxylic acid tert-butyl ester (11, 472 mg) and tetrakis(triphenylphosphine) palladium(0) (54 mg) was introduced and the resulting mixture was heated at 120° C. for an additional 12 h. The reaction mixture was concentrated under reduced pressure and purified by chromatography (AcOEt/MeOH) to give IC-380 (20 mg) as a pale gray solid. $^1$H NMR confirmed the structure.

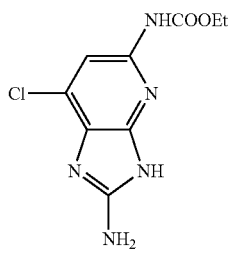

(2-amino-7-chloro-3H-imidazo[4,5-b]pyridin-5-yl)-carbamic acid ethyl ester

Cyanogen bromide (0.55 g, 5.2 mmol) was added to a stirred solution of ethyl 5,6-diamino-4-chloro-2-pyridinecarbamate (intermediate for the preparation of 1, 1.00 g, 4.3 mmol) in 20 mL of ethanol at room temperature. The solution was stirred for 3 h and then at 60° C. for 3 h. The precipitate was filtered and washed with diethyl ether to give (2-amino-7-chloro-3H-imidazo[4,5-b]pyridin-5-yl)-carbamic acid ethyl ester (0.55 g, 38%) as a yellow powder. $^1$H NMR confirmed the structure.

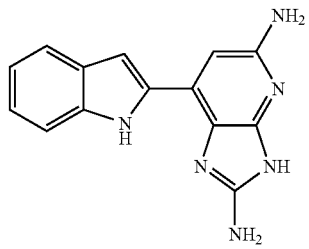

IC-416

IC-416 was obtained from (2-amino-7-chloro-3H-imidazo[4,5-b]pyridin-5-yl)-carbamic acid ethyl ester and 11 by using the typical procedure described for IC-380. $^1$H NMR confirmed the structure.

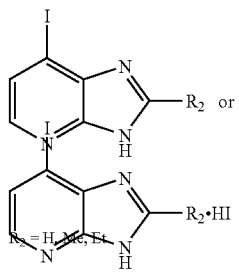

7-iodo-2-alkyl-3H-imidazo[4,5-b]pyridine

Compound 7-iodo-2-alkyl-3H-imidazo[4,5-b]pyridine (7-iodo-3H-imidazo[4,5-b]pyridine, 7-iodo-2-methyl-3H-imidazo[4,5-b]pyridine, 7-iodo-2-ethyl-3H-imidazo[4,5-b]pyridine) and/or its HI salt was prepared from 4-chloro-pyridine-2,3-diamine (Recueil, 1969, 88, 1263-1274) following the same procedure for the preparation of 2 and 4 from 1.

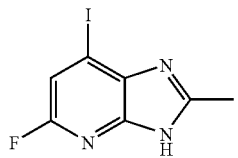

5-fluoro-7-iodo-2-methyl-3H-imidazo[4,5-b]pyridine

To a solution of 4 ($R_2$=Me, HI mono-salt, 300 mg, 0.75 mmol, 1.0 eq.) in $HBF_4$ (48-51% in water, 3 mL) at 0° C. was added NaNO2 (1.0 g, 19 eq.) portionwise over 1 h period keeing the reaction temperature under 4° C. The resulting mixture was stirred at 0° C. for 40 min and at room temperature for 30 min. The reaction was then quenched with sat $NaHCO_3$ and the resulting mixture was extracted with 5×$Et_2O$. The combined organic phase was dried over $Na_2SO_4$, filtered and concentrated to give 5-fluoro-7-iodo-2-methyl-3H-imidazo[4,5-b]pyridine as a light brown solid (170 mg, 86%). $^{19}$FNMR, $^1$HNMR and MS confirmed the structure.

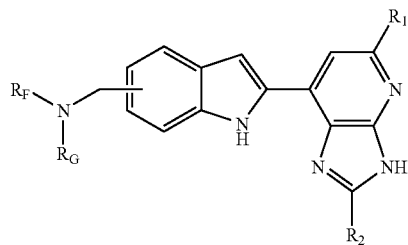

66

R₁ = H, F
R₂ = H, Me, Et

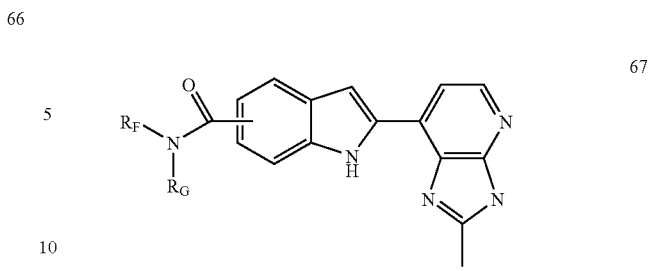

67

Compound 66 was prepared from 7-iodo-2-alkyl-3H-imidazo[4,5-b]pyridine (or its HI mono-salt) or 5-fluoro-7-iodo-2-methyl-3H-imidazo[4,5-b]pyridine and 15 following the same procedure for the preparation of 13 or 64.

Compound 67 was prepared from 7-iodo-2-methyl-3H-imidazo[4,5-b]pyridine and 15 following the same procedure for the preparation of 65.

| ER-# | 1. Structure of 66 or 67 | ¹H NMR and/or MS |
|---|---|---|
| 807496 | | ¹H NMR |
| 807584 | | ¹H NMR |
| 807585 | | ¹H NMR |
| 807587 | | ¹H NMR |
| 807750 | | ¹H NMR |

-continued

| ER-# | 1. Structure of 66 or 67 | ¹H NMR and/or MS |
|---|---|---|
| 807787 | | ¹H NMR |
| 807788 | | ¹H NMR |
| 807865 | | ¹H NMR |
| 808009 | | ¹H NMR |
| 808081 | | ¹H NMR |
| 808085 | | ¹H NMR |

| ER-# | 1. Structure of 66 or 67 | ¹H NMR and/or MS |
|---|---|---|
| 808160 | 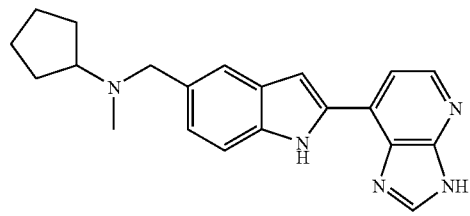 | ¹H NMR |
| 808256 | 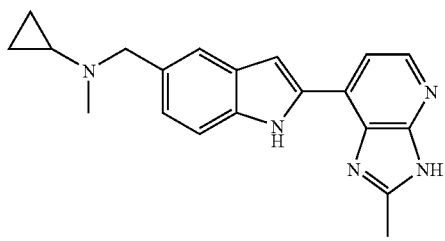 | ¹H NMR |
| 808257 | 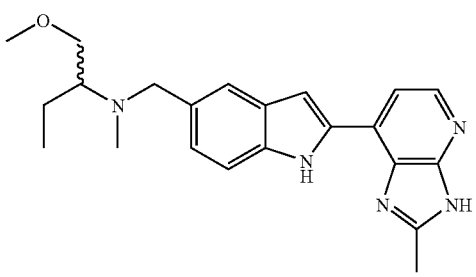 | ¹H NMR |
| 808259 | 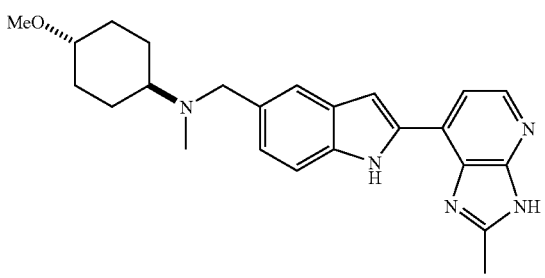 | ¹H NMR |
| 808260 | 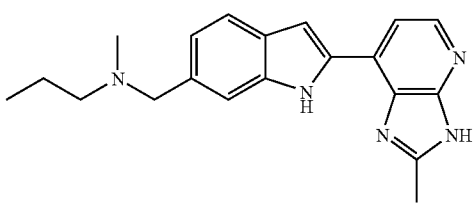 | ¹H NMR |
| 808261 | 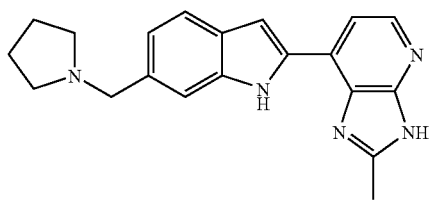 | ¹H NMR |

| ER-# | 1. Structure of 66 or 67 | ¹H NMR and/or MS |
|---|---|---|
| 808262 | 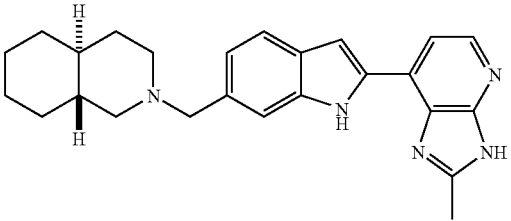 | ¹H NMR |
| 808266 | 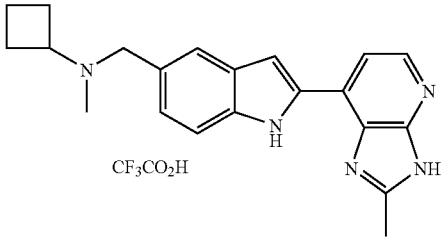 | ¹H NMR |
| 808268 | 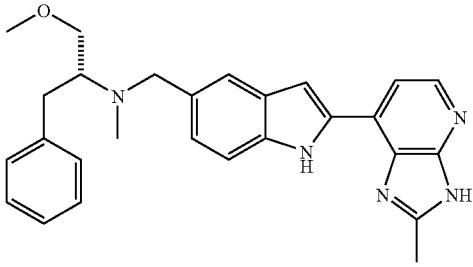 | ¹H NMR |
| 808269 | 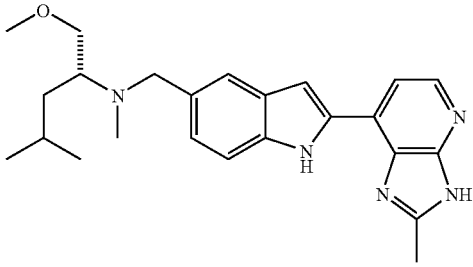 | ¹H NMR |
| 808284 | 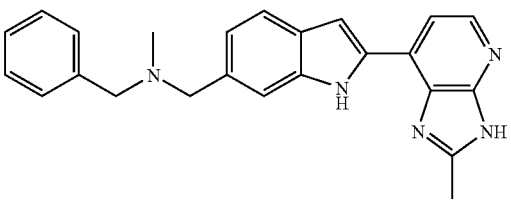 | ¹H NMR |
| 808285 | 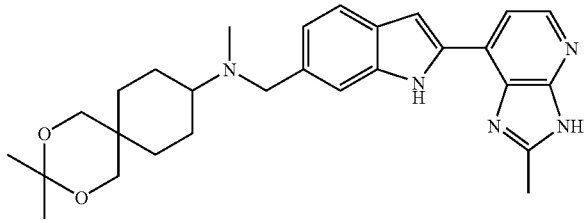 | ¹H NMR |

| ER-# | 1. Structure of 66 or 67 | ¹H NMR and/or MS |
|---|---|---|
| 808286 | | ¹H NMR |
| 808287 | | ¹H NMR |
| 808288 | | ¹H NMR |
| 808289 | | ¹H NMR |
| 808291 | | ¹H NMR |
| 808310 | | ¹H NMR |

| ER-# | 1. Structure of 66 or 67 | ¹H NMR and/or MS |
|---|---|---|
| 808311 | 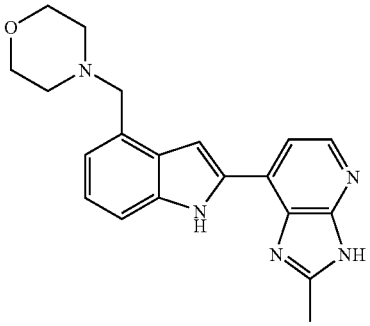 | ¹H NMR |
| 808319 | 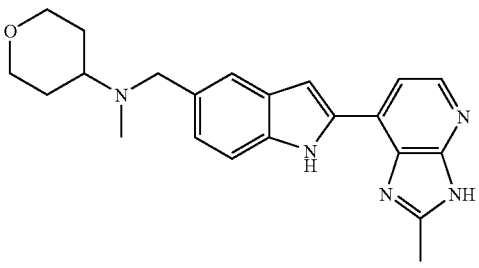 | ¹H NMR |
| 808322 | 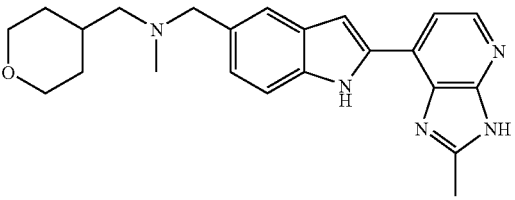 | ¹H NMR |
| 808361 | 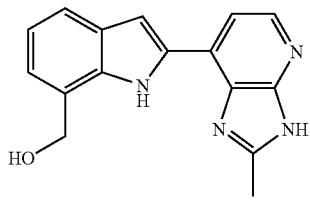 | ¹H NMR |
| 808362 | 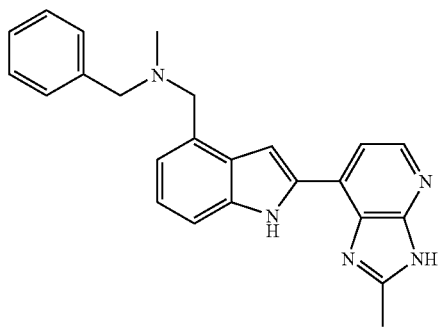 | ¹H NMR |

-continued

| ER-# | 1. Structure of 66 or 67 | ¹H NMR and/or MS |
|---|---|---|
| 808363 | | ¹H NMR |
| 808370 | | ¹H NMR |
| 808372 | | ¹H NMR |
| 808385 | | ¹H NMR |
| 808386 | | ¹H NMR |
| 808388 | | ¹H NMR |

-continued
| ER-# | 1. Structure of 66 or 67 | ¹H NMR and/or MS |
|---|---|---|
| 808469 | 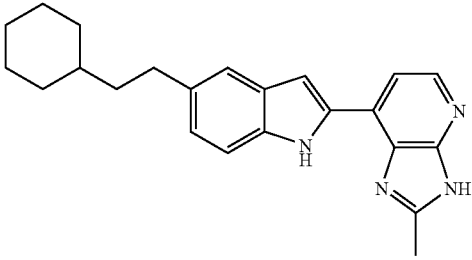 | ¹H NMR |
| 808470 | 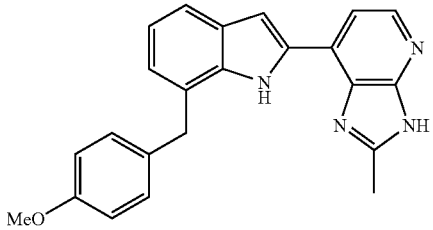 | ¹H NMR |
| 808473 | 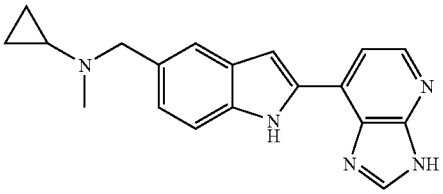 | ¹H NMR |
| 808496 | 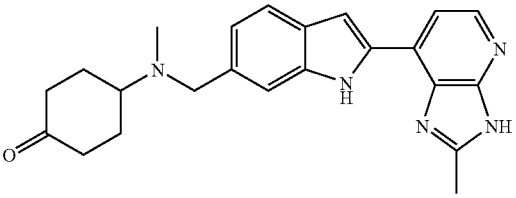 | ¹H NMR |
| 808497 | 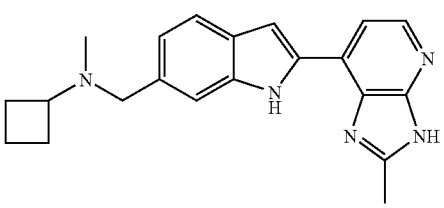 | ¹H NMR |
| 808498 | 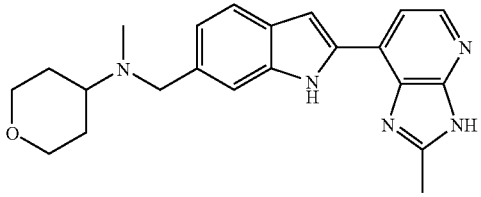 | ¹H NMR |
| 808499 | 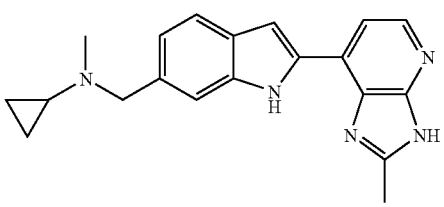 | ¹H NMR |

-continued
| ER-# | 1. Structure of 66 or 67 | 1H NMR and/or MS |
|---|---|---|
| 808500 | 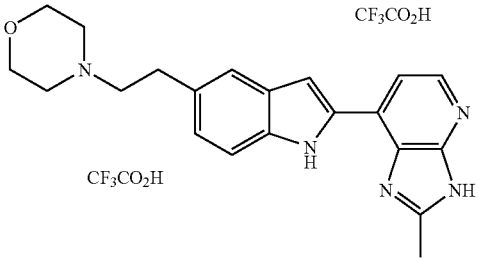 CF$_3$CO$_2$H  CF$_3$CO$_2$H | 1H NMR |
| 808513 | 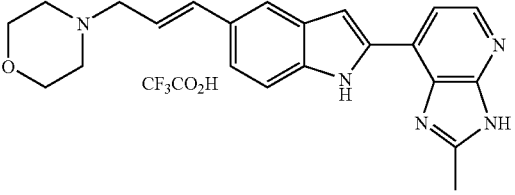 CF$_3$CO$_2$H  CF$_3$CO$_2$H | 1H NMR |
| 808541 | 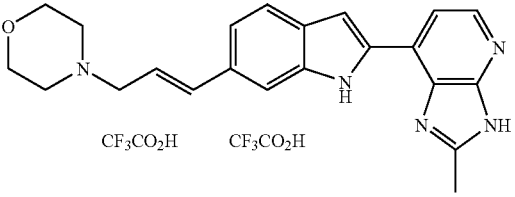 CF$_3$CO$_2$H  CF$_3$CO$_2$H | 1H NMR |
| 808543 | 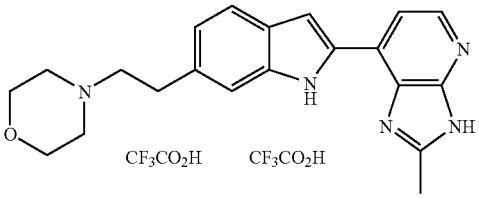 CF$_3$CO$_2$H  CF$_3$CO$_2$H | 1H NMR |
| 808571 | 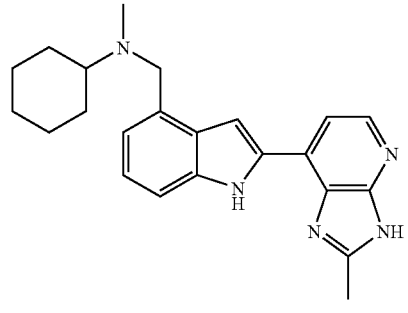 | 1H NMR |
| 808600 | 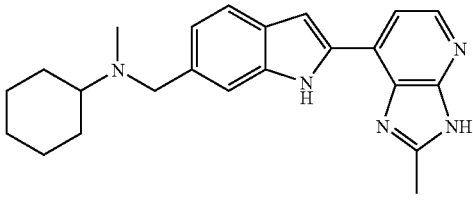 | 1H NMR |

| ER-# | 1. Structure of 66 or 67 | ¹H NMR and/or MS |
|---|---|---|
| 808617 | | ¹H NMR |
| 808620 | | ¹H NMR |
| 808622 | | ¹H NMR |
| 808623 | | ¹H NMR |
| 808624 | | ¹H NMR |
| 808628 | | ¹H NMR |

| ER-# | 1. Structure of 66 or 67 | ¹H NMR and/or MS |
|---|---|---|
| 808629 | | ¹H NMR |
| 808631 | | ¹H NMR |
| 808635 | | ¹H NMR |
| 808636 | | ¹H NMR |
| 808637 | | ¹H NMR |
| 808660 | | ¹H NMR |

| ER-# | 1. Structure of 66 or 67 | ¹H NMR and/or MS |
|---|---|---|
| 808672 | | ¹H NMR |
| 808673 | | ¹H NMR |
| 808691 | | ¹H NMR |
| 808692 | | ¹H NMR |
| 808703 | (CF₃CO₂H) | ¹H NMR |
| 808704 | (CF₃CO₂H) | ¹H NMR |

-continued

| ER-# | 1. Structure of 66 or 67 | ¹H NMR and/or MS |
|---|---|---|
| 808705 | | ¹H NMR |
| 808711 | | ¹H NMR |
| 808712 | | ¹H NMR |
| 808713 | | ¹H NMR |
| 808714 | | ¹H NMR |
| 808717 | | ¹H NMR |
| 808719 | | ¹H NMR |

-continued

| ER-# | 1. Structure of 66 or 67 | ¹H NMR and/or MS |
| --- | --- | --- |
| 808720 | | ¹H NMR |
| 808834 | | ¹H NMR |
| 808835 | | ¹H NMR |
| 808849 | | ¹H NMR |
| 809187 | | ¹H NMR |
| 809196 | | MS |

| ER-# | 1. Structure of 66 or 67 | ¹H NMR and/or MS |
|---|---|---|
| 809197 | (structure) 2 CF₃CO₂H | MS |
| 809198 | (structure) 2 CF₃CO₂H | MS |
| 809199 | (structure) 3 CF₃CO₂H | MS |
| 809200 | (structure) 2 CF₃CO₂H | MS |
| 809201 | (structure) 2 CF₃CO₂H | MS |
| 809202 | (structure) 2 CF₃CO₂H | MS |

-continued

| ER-# | 1. Structure of 66 or 67 | ¹H NMR and/or MS |
|---|---|---|
| 809203 | 3 CF₃CO₂H | MS |
| 809204 | 2 CF₃CO₂H | MS |
| 809205 | 2 CF₃CO₂H | MS |
| 809206 | 2 CF₃CO₂H | MS |
| 809207 | 3 CF₃CO₂H | MS |
| 809208 | 3 CF₃CO₂H | MS |

| ER-# | 1. Structure of 66 or 67 | ¹H NMR and/or MS |
|---|---|---|
| 809209 | 2 CF₃CO₂H | MS |
| 809210 | 2 CF₃CO₂H | MS |
| 809211 | 2 CF₃CO₂H | MS |
| 809212 | 3 CF₃CO₂H | MS |
| 809213 | 2 CF₃CO₂H | MS |
| 809214 | 2 CF₃CO₂H | MS |
| 809215 | 2 CF₃CO₂H | MS |

-continued
| ER-# | 1. Structure of 66 or 67 | ¹H NMR and/or MS |
|---|---|---|
| 809216 | 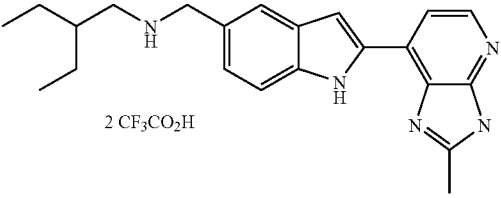<br>2 CF$_3$CO$_2$H | MS |
| 809217 | 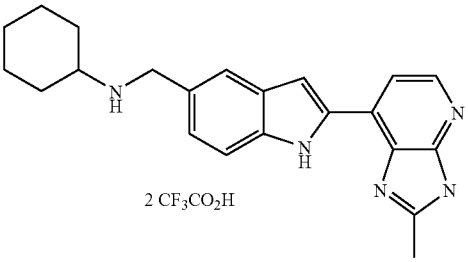<br>2 CF$_3$CO$_2$H | MS |
| 809218 | 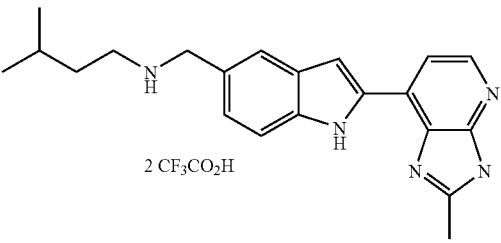<br>2 CF$_3$CO$_2$H | MS |
| 809219 | 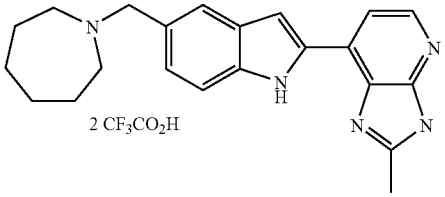<br>2 CF$_3$CO$_2$H | MS |
| 809220 | 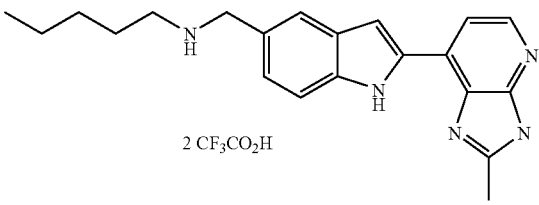<br>2 CF$_3$CO$_2$H | MS |
| 809221 | 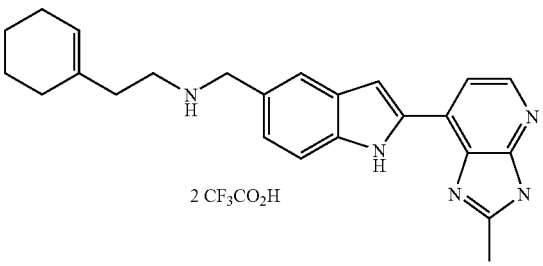<br>2 CF$_3$CO$_2$H | MS |

-continued
| ER-# | 1. Structure of 66 or 67 | $^1$H NMR and/or MS |
|---|---|---|
| 809222 | 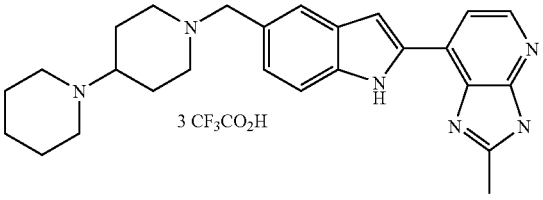 3 CF$_3$CO$_2$H | MS |
| 809223 | 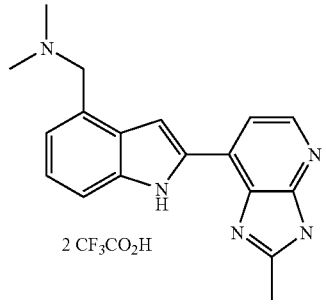 2 CF$_3$CO$_2$H | MS |
| 809224 | 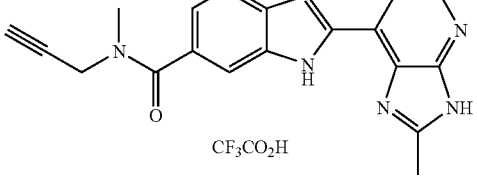 CF$_3$CO$_2$H | MS |
| 809225 | 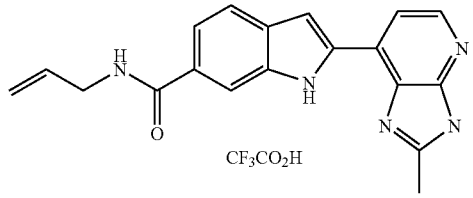 CF$_3$CO$_2$H | MS |
| 809226 | 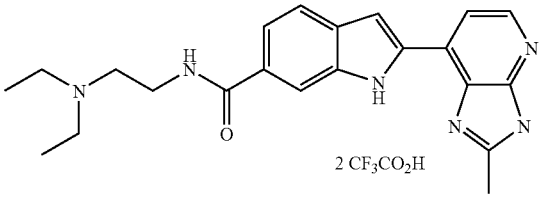 2 CF$_3$CO$_2$H | MS |
| 809227 | 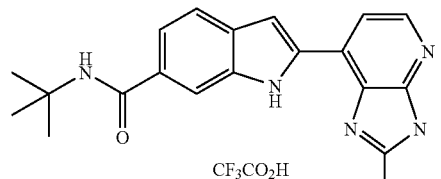 CF$_3$CO$_2$H | MS |
| 809228 | 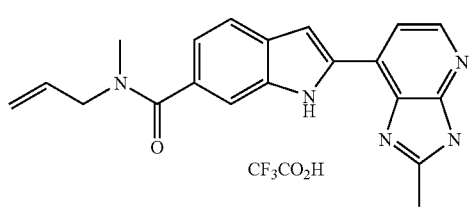 CF$_3$CO$_2$H | MS |

| ER-# | 1. Structure of 66 or 67 | ¹H NMR and/or MS |
|---|---|---|
| 809229 | (piperidinylethyl-NH-C(O)-indole-2-(methyl-imidazo-pyridine)) · 2 CF₃CO₂H | MS |
| 809230 | (HO-CH₂-C(tBu)H-NH-C(O)-indole-2-(methyl-imidazo-pyridine)) · CF₃CO₂H | MS |
| 809231 | (N-methyl-N-isopropyl-C(O)-indole-2-(methyl-imidazo-pyridine)) · CF₃CO₂H | MS |
| 809232 | (isopropoxypropyl-NH-C(O)-indole-2-(methyl-imidazo-pyridine)) · CF₃CO₂H | MS |
| 809233 | (diethylaminoethyl-N(Me)-C(O)-indole-2-(methyl-imidazo-pyridine)) · 2 CF₃CO₂H | MS |
| 809234 | (diethylaminopropyl-NH-C(O)-indole-2-(methyl-imidazo-pyridine)) · 2 CF₃CO₂H | MS |
| 809235 | (sec-butyl-NH-C(O)-indole-2-(methyl-imidazo-pyridine)) · CF₃CO₂H | MS |

-continued

| ER-# | 1. Structure of 66 or 67 | ¹H NMR and/or MS |
|---|---|---|
| 809236 | 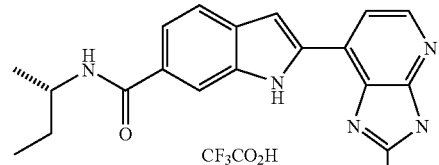 | MS |
| 809237 | 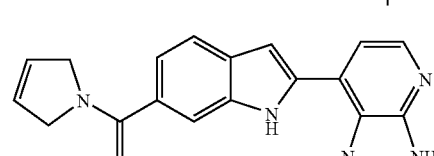 | MS |
| 809238 | 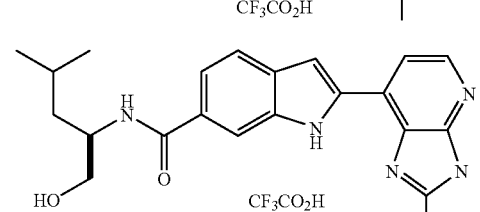 | MS |

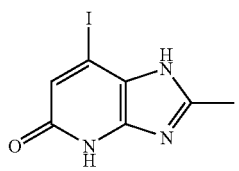

7-iodo-2-methyl-1,4-dihydro-imidazo[4,5-b]pyridin-5-one

To a solution of compound 4 (R=Me, 160 mg, 0.59 mmol) in 10 mL of 20% aqueous $H_2SO_4$ at 0° C. was added sodium nitrite (1.54 mmol) in small portions and the resulting mixture was stirred at room temperature overnight. The reaction mixture was neutralized with sat. aqueous $NH_3$ to pH 7-8, and the resulting precipitate was collected to give a yellow solid. This solid was then crystallized in water to give 140 mg of product 7-iodo-2-methyl-1,4-dihydro-imidazo[4,5-b]pyridin-5-one (87%) with satisfactory MS and ¹H NMR.

ER-807546

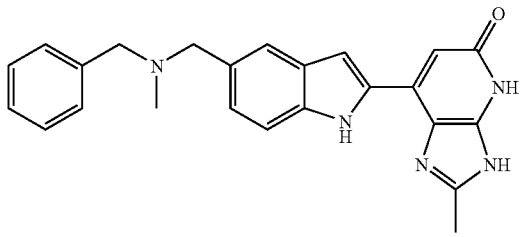

ER-807546 was prepared from 7-iodo-2-methyl-1,4-dihydro-imidazo[4,5-b]pyridin-5-one and 10 (R'=PhCH$_2$, R''=Me) following the same procedure for the preparation of 13. Satisfactory MS and ¹H NMR were obtained for ER-807546.

ER-809251

ER-809252

Analogs ER-809251 and ER-809252 are prepared from 7-iodo-2-methyl-3H-imidazo[4,5-b]pyridine and 6-[2-(cyclohexyl-methyl-amino)-ethyl]-indole-1-carboxylic acid tert-butyl ester and 5-[2-(cyclohexyl-methyl-amino)-ethyl]-indole-1-carboxylic acid tert-butyl ester respectively following the same procedures for the preparation of 16 from 14.

3) Biological Assays

HUVEC Assay Protocol:

Pooled human umbilical vein endothelial cells (HUVEC, Clonetics, Inc) were seeded in 96 well plates at $5\times10^4$ cell/ml and incubated at 37° C. The following day, 20 μl of the each compound dilution was added to the cells and incubated for 30 minutes followed by stimulation with TNFα (1 ng/ml) for four hours at 37° C. After TNF stimulation, the plates were washed with PBS containing 0.5% BSA, fixed with 0.025% glutaraldehyde, and stained with primary and secondary antibodies for detection of E-selectin and ICAM expression. The plates were incubated with 100 µl of the primary murine anti-human E-selectin and anti-human ICAM antibody (R&D Systems, Minneapolis, Minn.) diluted 1:500 in PBS containing 0.5% BSA and 5% FBS for one hour after which the plates were washed and incubated with 100 µl of a secondary peroxidase conjugated goat anti-mouse IgG antibody (Pierce, Rockford, Ill.) diluted 1:10,000 in PBS/0.5% BSA/5% FBS for 30 minutes. The plates were then washed and 100 µl of TMB substrate was added and the color reaction was allowed to develop for 15-20 minutes. The reaction was stopped by the addition of 50 µl of 1 N $H_2SO_4$ and the optical density (OD) was read on microplate spectrophotometer at 450 nm. $IC_{50}$ values were determined based on percent inhibition as calculated by the following formula:

$$\% \text{ Inhibition} = \left(1 - \left(\frac{(\text{avg. compound } OD - \text{avg. blank } OD)}{(\text{avg. } TNF\ OD - \text{avg. blank } OD)}\right)\right) * 100$$

The invention claimed is:
1. A compound having the structure (I):

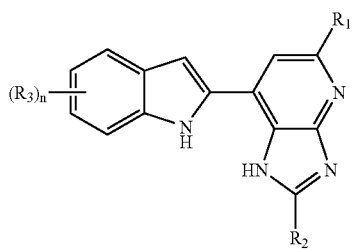

(I)

or pharmaceutically acceptable salt, ester or salt of such ester thereof;
wherein n is an integer from 0-4;
$R_1$ is hydrogen, —$NH_2$, —NHMe, —NHAc, —OH, F, —OMe, —CN, or —NH(C=O)OEt;
$R_2$ is hydrogen, —$NR_AR_B$, —$OR_A$, an aliphatic, heteroaliphatic, aryl, or heteroaryl moiety, wherein $R_A$ and $R_B$ are each independently hydrogen or an aliphatic, heteroaliphatic, aryl or heteroaryl moiety;
each occurrence of $R_3$ is independently hydrogen, halogen, cyano, or an aliphatic, heteroaliphatic, aryl or heteroaryl moiety, or a group -G-$R_C$, wherein G is absent or is —$CH_2$—, —$NR_D$—, —O—, or (C=O), and wherein $R_C$ is hydrogen, —$NR_FR_G$, —$OR_F$, —$SR_F$, or an aliphatic, heteroaliphatic, aryl, or heteroaryl moiety, wherein $R_D$, $R_F$ and $R_G$ are each independently hydrogen, —$NR_xR_y$, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein $R_D$ and $R_C$ or $R_F$ and $R_G$ taken together are a 3-, 4-, 5-, 6-, 7- or 8-membered substituted or unsubstituted cycloaliphatic or cycloheteroaliphatic moiety; wherein each occurrence of $R_x$ and $R_y$ is independently hydrogen, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein $R_x$ and $R_y$ taken together are a 4-, 5- or 6-membered substituted or unsubstituted, saturated or unsaturated cycloaliphatic or cycloheteroaliphatic moiety;
whereby each of the foregoing aliphatic or heteroaliphatic moieties may be independently substituted or unsubstituted, cyclic or acyclic, linear or branched, saturated or unsaturated and wherein each of the foregoing aryl or heteroaryl moieties may be independently substituted or unsubstituted.

2. The compound of claim 1, wherein the compound has the structure:

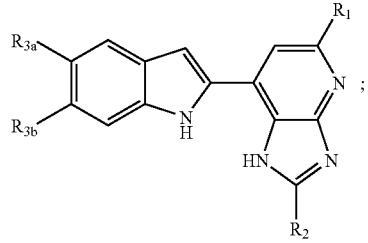

wherein $R_{3a}$ and $R_{3b}$ are each independently hydrogen, halogen, cyano, or an aliphatic, heteroaliphatic, aryl or heteroaryl moiety, or a group -G-$R_C$, wherein G is absent, —$CH_2$—, —$NR_D$—, —O—, or (C=O), and wherein $R_C$ is hydrogen, —$NR_FR_G$, —$OR_F$, —$SR_F$, or an aliphatic, heteroaliphatic, aryl, or heteroaryl moiety, wherein $R_D$, $R_F$ and $R_G$ are each independently hydrogen, —$NR_xR_y$, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein $R_D$ and $R_C$ or $R_F$ and $R_G$ taken together are a 3-, 4-, 5-, 6-, 7- or 8-membered substituted or unsubstituted cycloaliphatic or cycloheteroaliphatic moiety; wherein each occurrence of $R_x$ and $R_y$ is independently hydrogen, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein $R_x$ and $R_y$ taken together are a 4-, 5- or 6-membered substituted or unsubstituted, saturated or unsaturated cycloaliphatic or cycloheteroaliphatic moiety;
whereby each of the foregoing aliphatic or heteroaliphatic moieties may be independently substituted or unsubstituted, cyclic or acyclic, linear or branched, saturated or unsaturated; and wherein each of the foregoing aryl or heteroaryl moieties may be independently substituted or unsubstituted.

3. The compound of claim 1, wherein the compound has the structure:

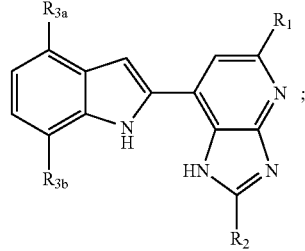

wherein $R_{3a}$ and $R_{3b}$ are each independently hydrogen, halogen, cyano, or an aliphatic, heteroaliphatic, aryl or heteroaryl moiety, or a group -G-$R_C$, wherein G is absent, —$CH_2$—, —$NR_D$—, —O—, or (C=O), and wherein $R_C$ is hydrogen, —$NR_FR_G$, —$OR_F$, —$SR_F$, or an aliphatic, heteroaliphatic, aryl, or heteroaryl moiety, wherein $R_D$, $R_F$ and $R_G$ are each independently hydrogen, —$NR_xR_y$, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein $R_D$ and $R_C$ or $R_F$ and $R_G$ taken together are a 3-, 4-, 5-, 6-, 7- or 8-membered substituted or unsubstituted cycloaliphatic or cycloheteroaliphatic moiety; wherein each occurrence of $R_x$ and $R_y$ is independently hydrogen, an aliphatic, cycloaliphatic, heteroaliphatic, cycloheteroaliphatic, aryl, or heteroaryl moiety, an acyl moiety substituted with an aliphatic, heteroaliphatic, aryl or heteroaryl moiety, or wherein $R_x$ and $R_y$ taken together are a 4-, 5- or 6-membered substituted or unsubstituted, saturated or unsaturated cycloaliphatic or cycloheteroaliphatic moiety;

whereby each of the foregoing aliphatic or heteroaliphatic moieties may be independently substituted or unsubstituted, cyclic or acyclic, linear or branched, saturated or unsaturated; and wherein each of the foregoing aryl or heteroaryl moieties may be independently substituted or unsubstituted.

4. The compound of claim 1, wherein the compound has the structure:

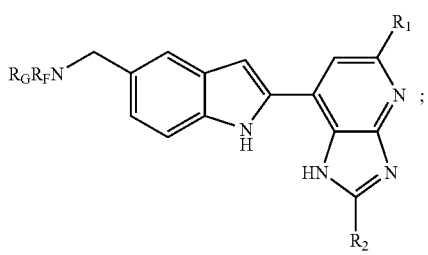

wherein $R_1$, $R_2$, $R_F$ and $R_G$ are as defined in claim 1.

5. The compound of claim 1, wherein the compound has the structure:

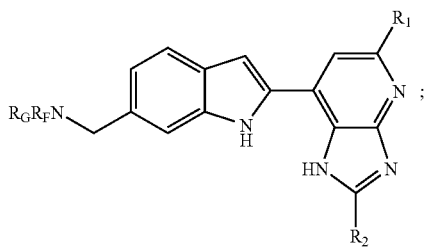

wherein $R_1$, $R_2$, $R_F$ and $R_G$ are as defined in claim 1.

6. The compound of claim 1, wherein the compound has the structure:

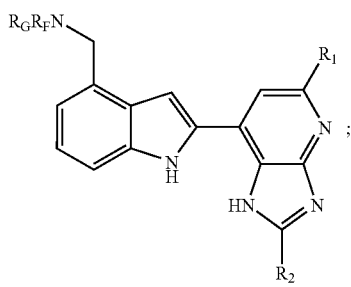

wherein $R_1$, $R_2$, $R_F$ and $R_G$ are as defined in claim 1.

7. The compound of claim 1, wherein the compound has the structure:

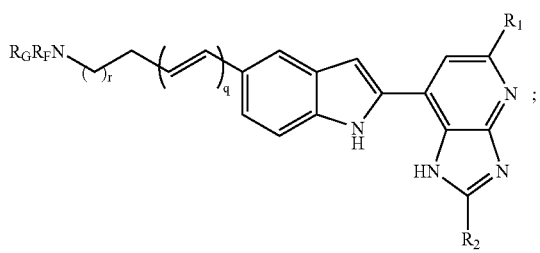

wherein q and r are each independently 0 or 1; and $R_1$, $R_2$, $R_F$ and $R_G$ are as defined in claim 1.

8. The compound of claim 1, wherein the compound has the structure:

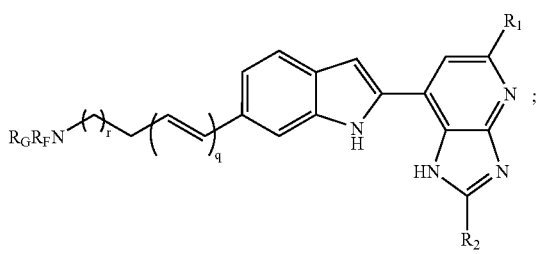

wherein q and r are each independently 0 or 1; and $R_1$, $R_2$, $R_F$ and $R_G$ are as defined in claim 1.

9. The compound of claim 1, wherein the compound has the structure:

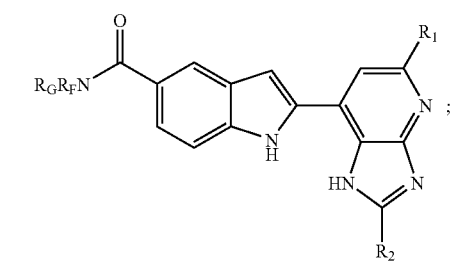

wherein $R_1$, $R_2$, $R_F$ and $R_G$ are as defined in claim 1.

10. The compound of claim 1, wherein the compound has the structure:

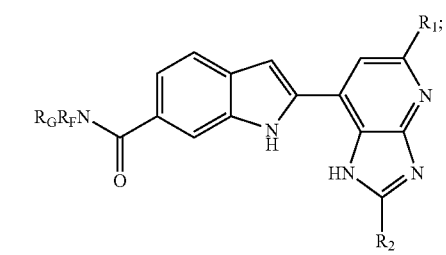

wherein $R_1$, $R_2$, $R_F$ and $R_G$ are as defined in claim 1.

11. The compound of claim 1, wherein the compound has the structure:

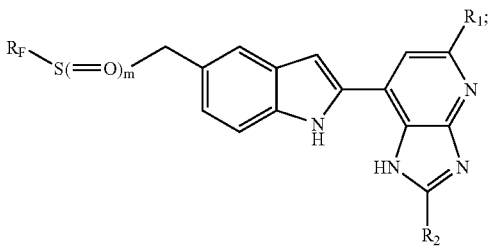

wherein $R_1$ and $R_2$ are as defined in claim 1;
m is 0, 1 or 2; and
$R^F$ is an aliphatic, cycloaliphatic, heteroaliphatic, cycloheteroaliphatic, aryl, or heteroaryl moiety;
whereby each of the foregoing aliphatic or heteroaliphatic moieties may be independently substituted or unsubstituted, cyclic or acyclic, linear or branched, saturated or unsaturated; and wherein each of the foregoing aryl or heteroaryl moieties may be independently substituted or unsubstituted.

12. The compound of claim 1, wherein the compound has the structure:

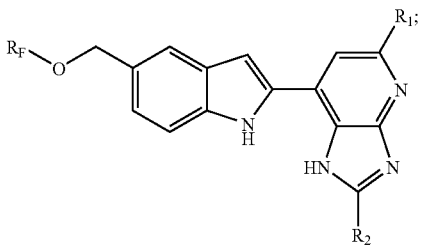

wherein $R_1$ and $R_2$ are as defined in claim 1; and
$R_F$ is hydrogen, a protective group or an aliphatic, cycloaliphatic, heteroaliphatic, cycloheteroaliphatic, aryl, or heteroaryl moiety;
whereby each of the foregoing aliphatic or heteroaliphatic moieties may be independently substituted or unsubstituted, cyclic or acyclic, linear or branched, saturated or unsaturated; and wherein each of the foregoing aryl or heteroaryl moieties may be independently substituted or unsubstituted.

13. The compound of claim 1, wherein the compound has the structure:

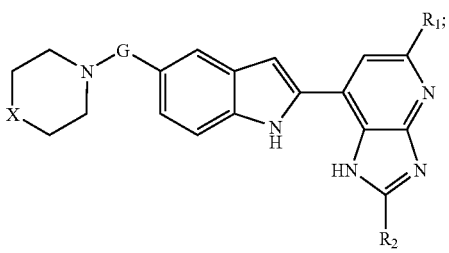

wherein $R_1$ and $R_2$ are as defined in claim 1;
G is $CH_2$ or —(C=O); and
X is O, S, C=O, S=O, C=$CR_4R_5$, $NR_4$, or $CR_4R_5$; wherein each occurrence of $R_4$ and $R_5$ is independently hydrogen, hydroxyl, halogen, cyano an aliphatic, heteroaliphatic, aryl, or heteroaryl moiety, or is an acyl moiety substituted with an aliphatic, heteroaliphatic, aryl or heteroaryl moiety;
whereby each of the foregoing aliphatic or heteroaliphatic moieties may be independently substituted or unsubstituted, cyclic or acyclic, linear or branched, and wherein each of the foregoing aryl or heteroaryl moieties may be independently substituted or unsubstituted.

14. The compound of claim 1, wherein the compound has the structure:

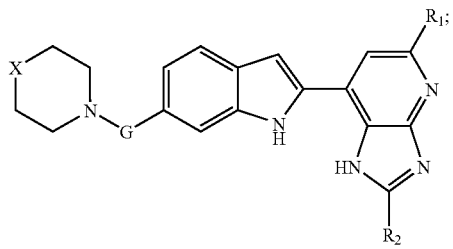

wherein $R_1$ and $R_2$ are as defined in claim 1;
G is $CH_2$ or —(C=O); and
X is O, S, C=O, S=O, C=$CR_4R_5$, $NR_4$, or $CR_4R_5$; wherein each occurrence of $R_4$ and $R_5$ is independently hydrogen, hydroxyl, halogen, cyano an aliphatic, heteroaliphatic, aryl, or heteroaryl moiety, or is an acyl moiety substituted with an aliphatic, heteroaliphatic, aryl or heteroaryl moiety;
whereby each of the foregoing aliphatic or heteroaliphatic moieties may be independently substituted or unsubstituted, cyclic or acyclic, linear or branched, and wherein each of the foregoing aryl or heteroaryl moieties may be independently substituted or unsubstituted.

15. The compound of claim 1, wherein the compound has the structure:

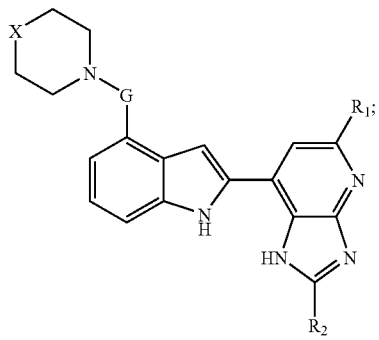

wherein $R_1$ and $R_2$ are as defined in claim 1;
G is $CH_2$ or —(C=O); and
X is O, S, C=O, S=O, C=$CR_4R_5$, $NR_4$, or $CR_4R_5$; wherein each occurrence of $R_4$ and $R_5$ is independently hydrogen, hydroxyl, halogen, cyano an aliphatic, heteroaliphatic, aryl, or heteroaryl moiety, or is an acyl moiety substituted with an aliphatic, heteroaliphatic, aryl or heteroaryl moiety;
whereby each of the foregoing aliphatic or heteroaliphatic moieties may be independently substituted or unsubstituted, cyclic or acyclic, linear or branched, and wherein each of the foregoing aryl or heteroaryl moieties may be independently substituted or unsubstituted.

16. The compound of claim 1, wherein the compound has the structure:

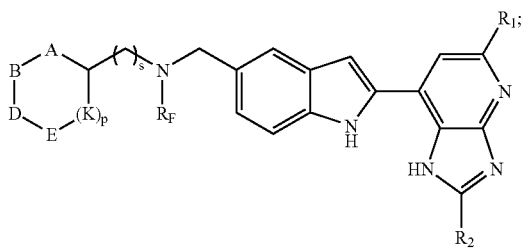

wherein R₁ and R₂ are as defined in claim 1;
p is an integer from 0-3;
s is an integer from 0-4;
A, B, D, E and each occurrence of K are independently absent, O, S, —C═O, —S═O, —C═CR₄R₅, —NR₄, or —CR₄R₅, wherein each occurrence of R and R₅ is independently hydrogen, hydroxyl, halogen, cyano, —OR_x, —SR_x, —NR_xR_y, an aliphatic, heteroaliphatic, aryl, or heteroaryl moiety, or is an acyl moiety substituted with an aliphatic, heteroaliphatic, aryl or heteroaryl moiety; and wherein A and B, B and D, D and E, E and K and any two adjacent K groups may be linked by a single or double bond as valency permits; wherein each occurrence of R_x and R_y is independently hydrogen, a protecting group, or an aliphatic, heteroaliphatic, aryl, heteroaryl, aliphaticaryl, heteroaliphatic aryl, aliphaticheteroaryl or heteroaliphaticheteroaryl moiety;
whereby each of the foregoing aliphatic or heteroaliphatic moieties may be independently substituted or unsubstituted, cyclic or acyclic, linear or branched, saturated or unsaturated and wherein each of the foregoing aryl, heteroaryl aliphaticaryl, heteroaliphatic aryl, aliphaticheteroaryl or heteroaliphaticheteroaryl moieties may be independently substituted or unsubstituted.

17. The compound of any one of claims 1-16, wherein R₁ is NH₂.

18. The compound of any one of claims 1-16, wherein R₁ is hydrogen.

19. The compound of any one of claims 1-16, wherein R₂ is NH₂, OH, C₁-C₆ alkyl or C₁-C₆ alkenyl, said alkyl and alkenyl groups optionally substituted with halogen or hydroxyl.

20. The compound of any one of claims 1-16, wherein R₂ is C₁-C₂ alkyl.

21. The compound of any one of claims 1-16, wherein R₂ is methyl.

22. The compound of any one of claims 1-16, wherein R₂ is hydrogen.

23. The compound of any one of claims 4-10, wherein one of R_F or R_G is hydrogen or lower alkyl; and the other is an alkyl, heteroalkyl, aryl, heteroaryl, alkylaryl or alkylheteroaryl, optionally independently substituted for each occurrence with one or more of halogen, alkoxy, thioalkyl, or substituted or unsubstituted alkyl, heteroalkyl, aryl, or heteroaryl, or wherein R_F and R_C taken together are a 3-, 4-, 5-, 6-, 7- or 8-membered substituted or unsubstituted, saturated or unsaturated cyclic or heterocyclic moiety.

24. The compound of any one of claims 4-10, wherein one of R_F or R_G is hydrogen or lower alkyl; and the other is an aryl, heteroaryl, alkylaryl or alkylheteroaryl moiety, optionally independently substituted for each occurrence with one or more of halogen, alkoxy, thioalkyl, or substituted or unsubstituted alkyl, heteroalkyl, aryl, or heteroaryl, or wherein R_F and R_G taken together are a 3-, 4-, 5-, 6-, 7- or 8-membered substituted or unsubstituted, saturated or unsaturated cyclic or heterocyclic moiety.

25. The compound of claim 24, wherein one of R_F or R_G is hydrogen or lower alkyl; and the other is phenyl, pyridyl, (alkyl)phenyl, or (alkyl)pyridyl, optionally substituted with one or more occurrences of halogen, trifluromethoxy, methoxy, trifluoromethyl, methylthio, or substituted or unsubstituted lower alkyl, lower heteroalkyl, aryl or heteroaryl.

26. The compound of any one of claims 4-10, wherein one of R_F or R_G is hydrogen or lower alkyl; and the other is a cyclic or acyclic, linear or branched, saturated or unsaturated aliphatic moiety optionally substituted with one or more of substituted or unsubstituted aryl, heteroaryl, amide, alkoxy, hydroxyl, thioalkyl, thiol, acyl or amino.

27. The compound of claim 11, wherein R_F is an alkyl, cycloalkyl, heteroalkyl, cycloheteroalkyl, aryl, heteroaryl, alkylaryl or alkylheteroaryl, optionally independently substituted for each occurrence with one or more of halogen, alkoxy, thioalkyl, or substituted or unsubstituted alkyl, heteroalkyl, aryl, or heteroaryl.

28. The compound of claim 12, wherein R_F is hydrogen, a protecting group, or an alkyl, cycloalkyl, heteroalkyl, cycloheteroalkyl, aryl, heteroaryl, alkylaryl or alkylheteroaryl, optionally independently substituted for each occurrence with one or more of halogen, alkoxy, thioalkyl, or substituted or unsubstituted alkyl, heteroalkyl, aryl, or heteroaryl.

29. The compound of claim 1, wherein said compound has the structure:

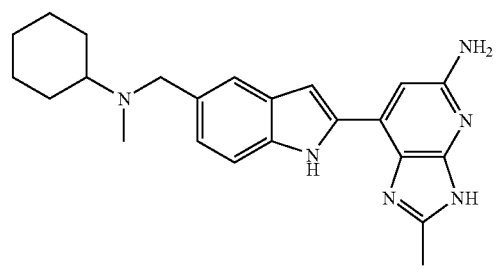

or a pharmaceutically acceptable salt thereof.

30. The compound of claim 1, wherein said compound is selected from the group consisting of:

| ER-# | Structure |
|---|---|
| 1 | 805600 (IC375) |
| 2 | 805894 (IC400) |
| 3 | 806006 |
| 4 | 805985 (IC403) |
| 5 | 805984 |
| 6 | 806002 |

| | ER-# | Structure |
|---|---|---|
| 7 | 805969 | 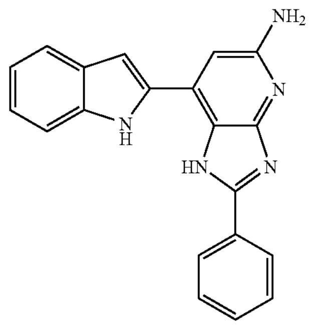 |
| 8 | 805971 | 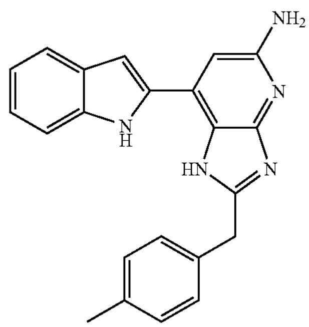 |
| 9 | 805996 | 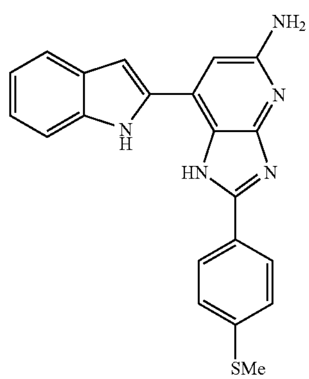 |
| 10 | 805639 (IC397) | 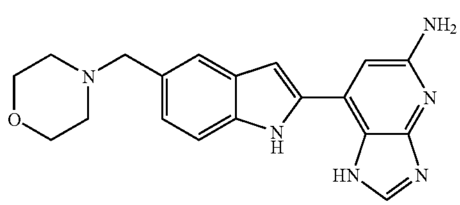 |
| 11 | 805895 (IC405) | 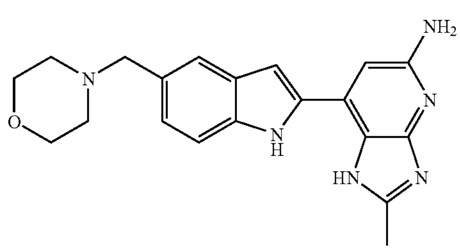 |

-continued
| ER-# | Structure |
|---|---|
| 12 806007 | 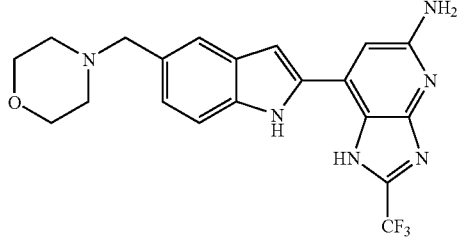 |
| 13 805976 | 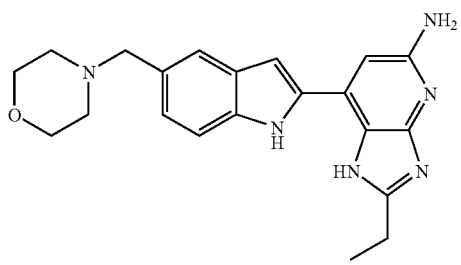 |
| 14 805975 | 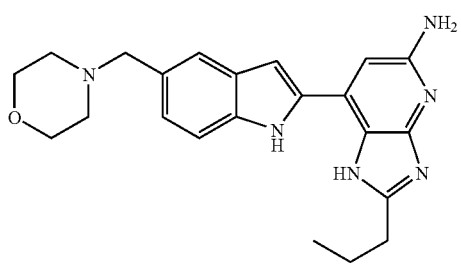 |
| 15 805999 | 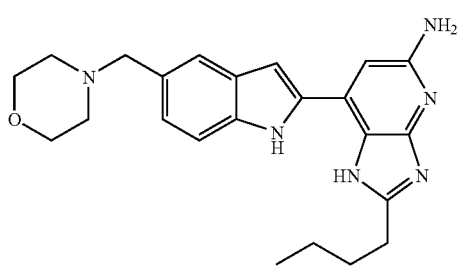 |
| 16 806011 | 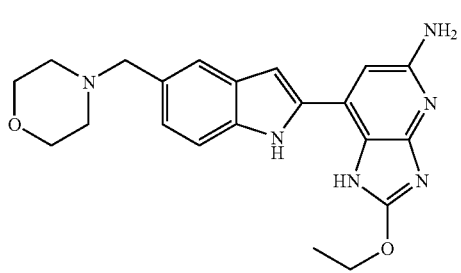 |

-continued

| ER-# | Structure |
|---|---|
| 17 | 805970 |
| 18 | 805972 |
| 19 | 805997 |
| 20 | 806010 |

-continued

| ER-# | Structure |
|---|---|
| 21 | 806014 |
| 22 | 806094 |
| 23 | 806095 |
| 26 | 806123 |
| 27 | 806136 |
| 28 | 806181 |

-continued

| ER-# | Structure |
|---|---|
| 29 | 806221 |
| 30 | 806220 |
| 31 | 806224 |
| 32 | 806228 |
| 33 | 806276 |
| 34 | 806275 |

-continued
| ER-# | Structure |
|---|---|
| 35 806274 | 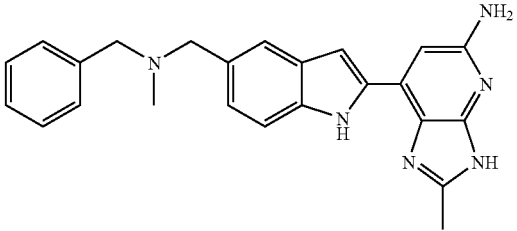 |
| 36 806273 | 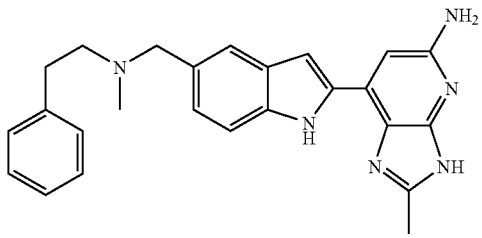 |
| 37 806286 | 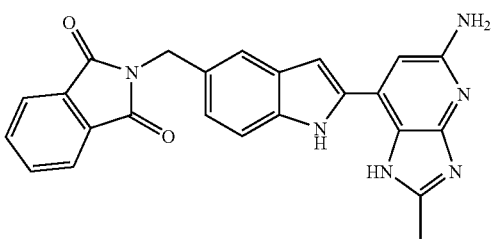 |
| 38 806287 | 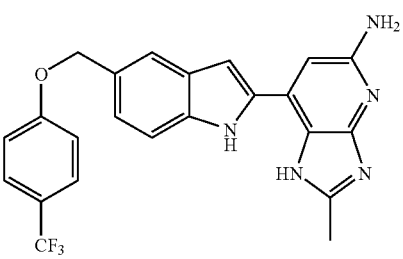 |
| 39 806311 | 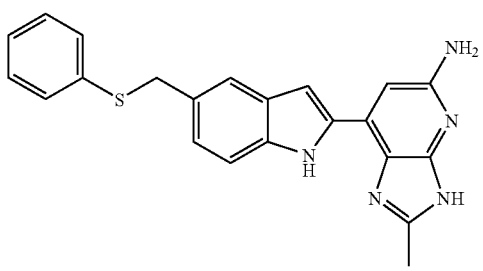 |
| 40 806317 | 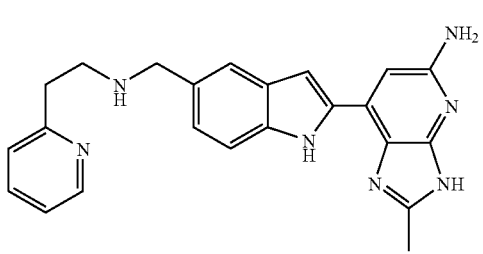 |

| ER-# | Structure |
|---|---|
| 41 | 806320 |
| 42 | 806329 |
| 43 | 806333 |
| 45 | 806336 |
| 46 | 806355 |
| 47 | 806358 |

-continued

| | ER-# | Structure |
|---|---|---|
| 48 | 806359 | 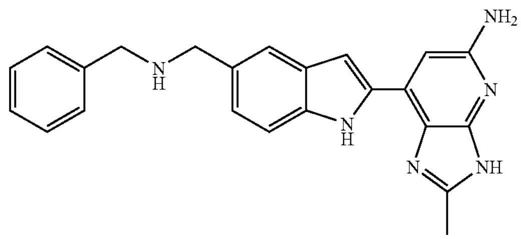 |
| 49 | 806363 | 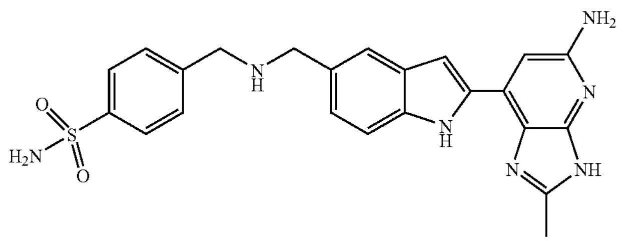 |
| 50 | 806362 | 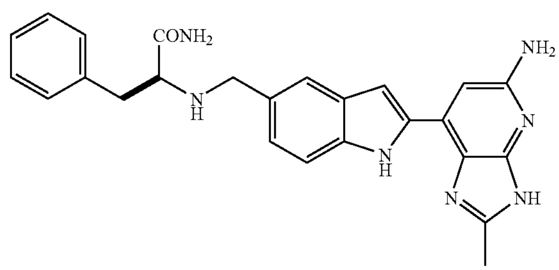 |
| 51 | 806361 | 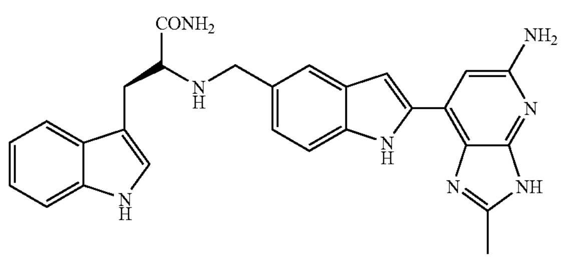 |
| 52 | 806368 | 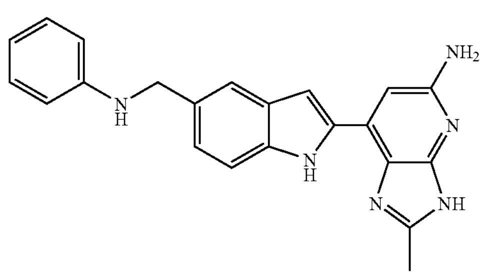 |
| 53 | 806372 | 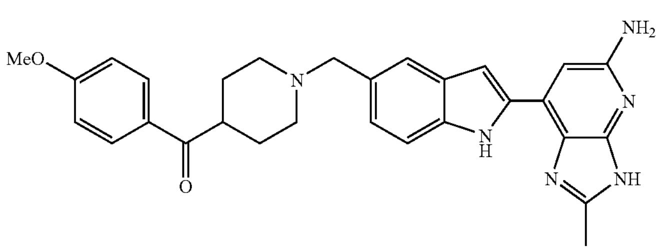 |

-continued

| ER-# | Structure |
|---|---|
| 54 | 806373 |
| 55 | 806374 |
| 56 | 806375 |
| 57 | 806383 |
| 58 | 806393 |
| 59 | 806401 |

-continued

| | ER-# | Structure |
|---|---|---|
| 60 | 806402 | 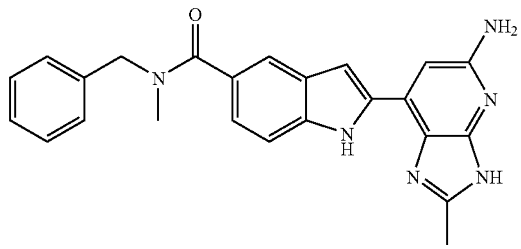 |
| 61 | 806404 | 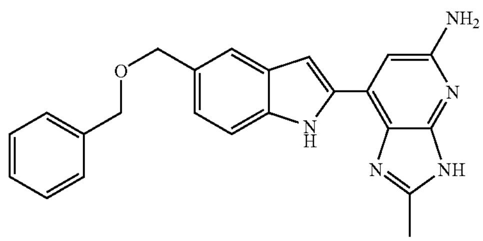 |
| 62 | 806417 | 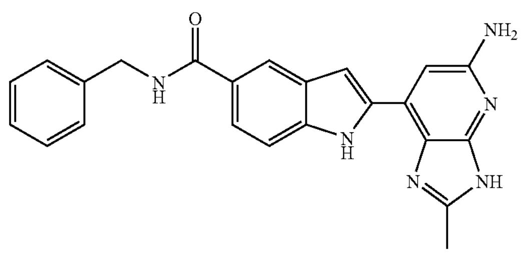 |
| 63 | 806419 | 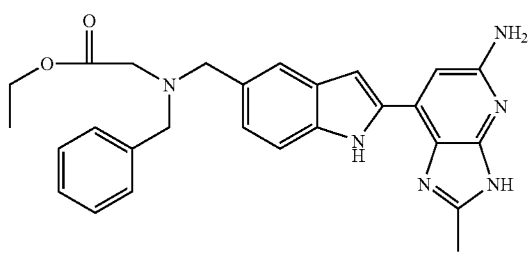 |
| 64 | 806420 | 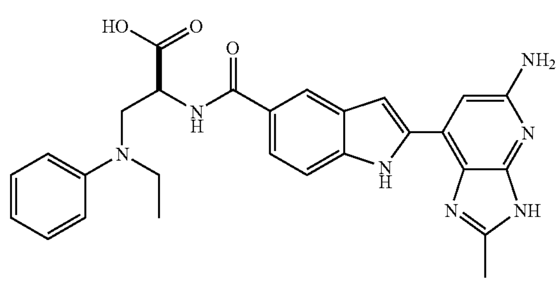 |
| 65 | 806421 | 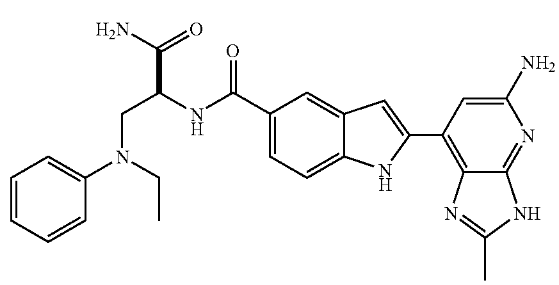 |

-continued

| ER-# | Structure |
|---|---|
| 66 | 806432 |
| 67 | 806435 |
| 68 | 806437 |
| 69 | 806569 |
| 70 | 806609 |
| 71 | 806610 |

-continued

| ER-# | Structure |
|---|---|
| 72 | 806644 |
| 73 | 806645 |
| 74 | 806646 |
| 75 | 806647 |
| 76 | 806653 |
| 77 | 806671 |

-continued

| ER-# | Structure |
|---|---|
| 78 806781 | |
| 79 806790 | |
| 80 806796 | |
| 81 806820 | |
| 82 806839 | |

| ER-# | Structure |
|---|---|
| 83 | 806840 |
| 84 | 806841 |
| 85 | 806842 |
| 86 | 806843 |
| 87 | 806844 |
| 88 | 806860 |

-continued
| ER-# | | Structure |
|---|---|---|
| 89 | 806874 | 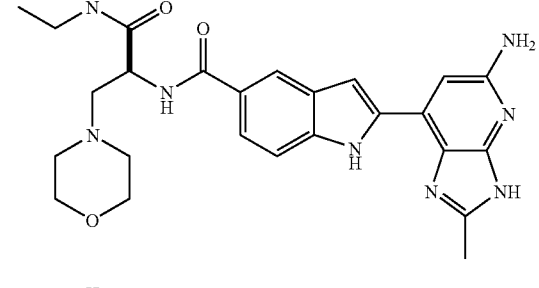 |
| 90 | 806875 | 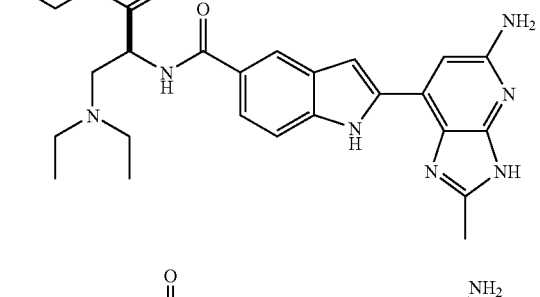 |
| 91 | 806878 | 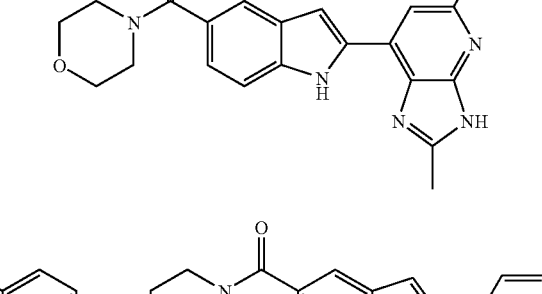 |
| 92 | 806899 | 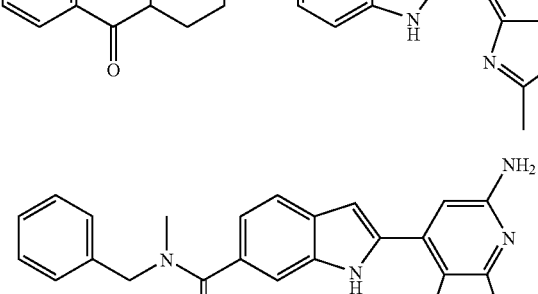 |
| 93 | 806900 | 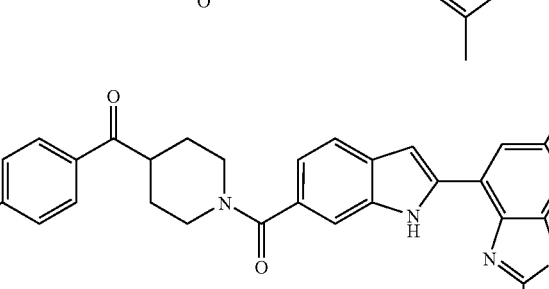 |
| 94 | 806901 | 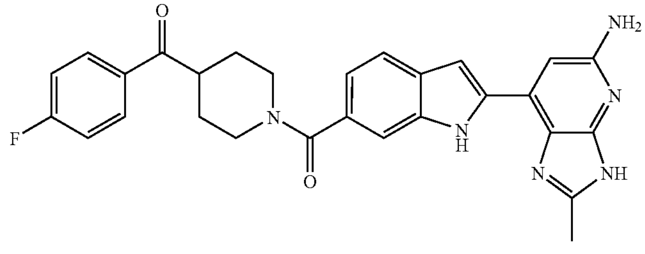 |

| ER-# | Structure |
|---|---|
| 95 | 806902 |
| 96 | 806903 |
| 97 | 806904 |
| 98 | 806905 |
| 99 | 806987 |
| 100 | 807014 |

-continued

| ER-# | Structure |
|---|---|
| 101 | 807015 |
| 102 | 807139 |
| 103 | 807140 |
| 104 | 807183 |
| 105 | 807240 |
| 106 | 807313 |

-continued
| ER-# | Structure |
|---|---|
| 107 | 807377  |
| 108 | 807392 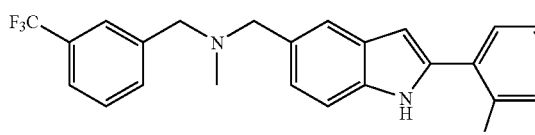 |
| 109 | 807400  |
| 110 | 807401 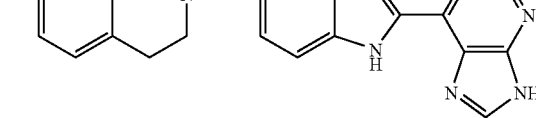<br>Trans racemic |
| 111 | 807399 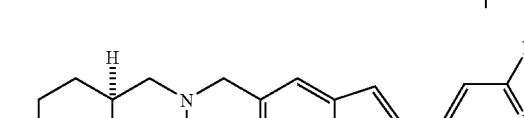<br>Cis racemic |
| 112 | 807447  |

| ER-# | Structure |
|---|---|
| 113 | 807448 |
| 114 | 807449 |
| 115 | 807450 |
| 116 | 807451 |
| 117 | 807452 |
| 118 | 807453 |

-continued

| ER-# | Structure |
|---|---|
| 119 | 807454 |
| 120 | 807457 |
| 121 | 807458 |
| 122 | 807459 |
| 123 | 807460 |
| 124 | 807462 |

-continued

| ER-# | Structure |
|---|---|
| 125 | 807463 |
| 126 | 807464 |
| 127 | 807465 |
| 128 | 807466 |
| 129 | 807467 |
| 130 | 807469 |

-continued

| ER-# | Structure |
|---|---|
| 131 | 807496 |
| 132 | 807497 |
| 133 | 807498 |
| 134 | 807505 |
| 135 | 807506 |
| 136 | 807528 |

-continued
| ER-# | | Structure |
|---|---|---|
| 137 | 807531 | 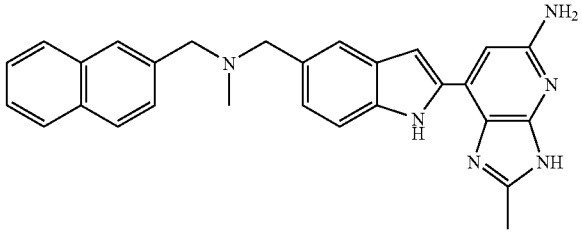 |
| 138 | 807532 | 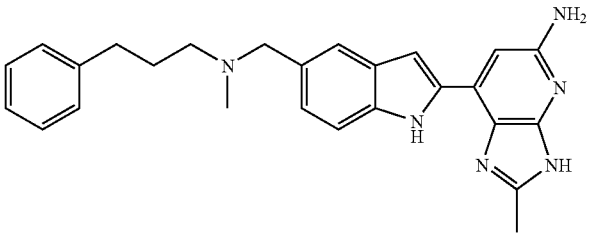 |
| 139 | 807543 | 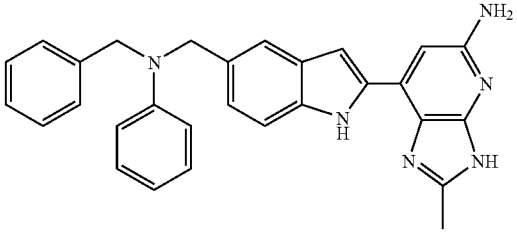 |
| 140 | 807544 | 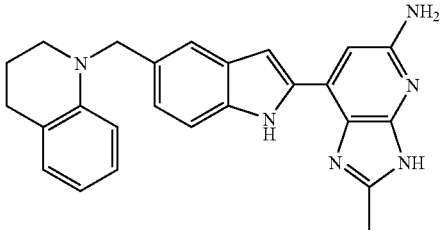 |
| 141 | 807546 | 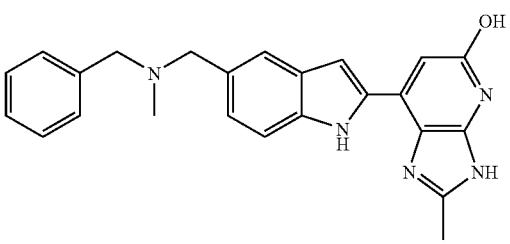 |
| 142 | 807548 | 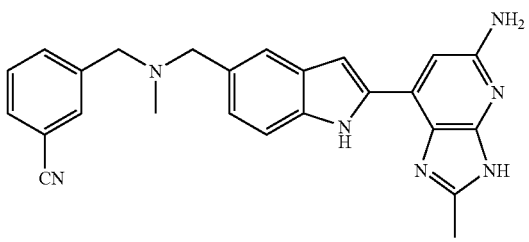 |

| ER-# | Structure |
|---|---|
| 143 | 807549 |
| 144 | 807550 |
| 145 | 807562 |
| 146 | 807571 |
| 147 | 807573 |

-continued

| ER-# | Structure |
|---|---|
| 148 | 807584 |
| 149 | 807585 |
| 150 | 807586 |
| 151 | 807587 |
| 152 | 807636 |
| 153 | 807649 |

-continued
| ER-# | Structure |
|---|---|
| 154 807660 | 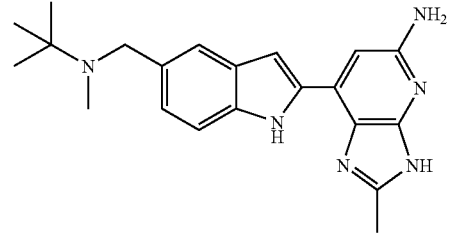 |
| 155 807662 | 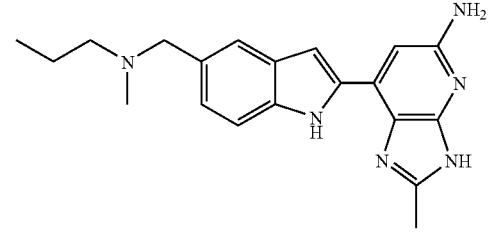 |
| 156 807663 | 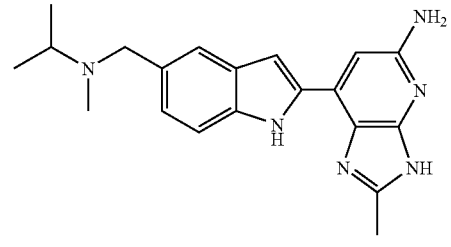 |
| 157 807703 | 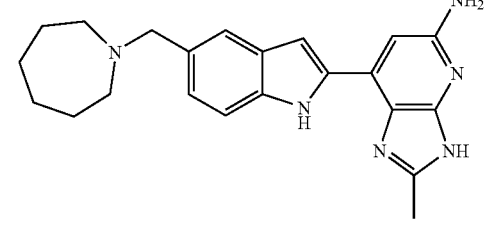 |
| 158 807704 | 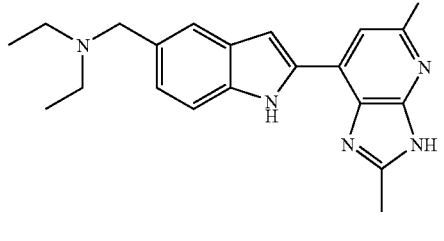 |
| 159 807748 | 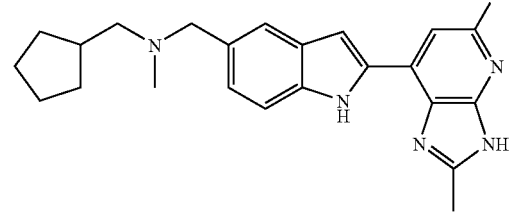 |

-continued

| ER-# | Structure |
|---|---|
| 160 807749 | |
| 161 807750 | |
| 162 807751 | |
| 163 807754 | |
| 164 807758 | |
| 165 807759 | |

| ER-# | Structure |
|---|---|
| 166 | 807762 |
| 167 | 807779 |
| 168 | 807787 |
| 169 | 807788 |
| 170 | 807789 |

-continued

| ER-# | | Structure |
|---|---|---|
| 171 | 807790 | 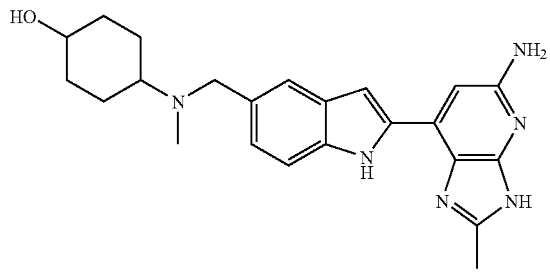 |
| 172 | 807794 | 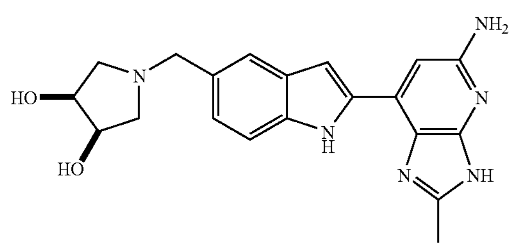 |
| 173 | 807835 | 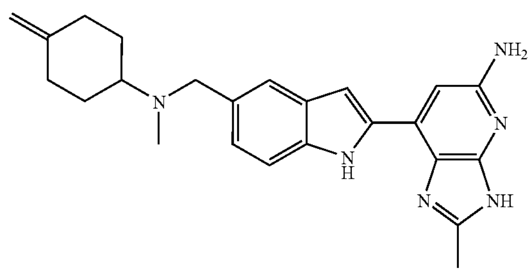 |
| 174 | 807836 | 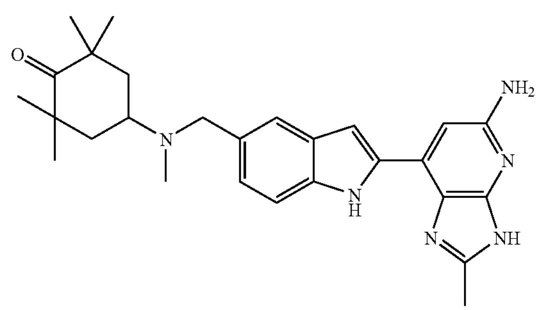 |
| 175 | 807837 | 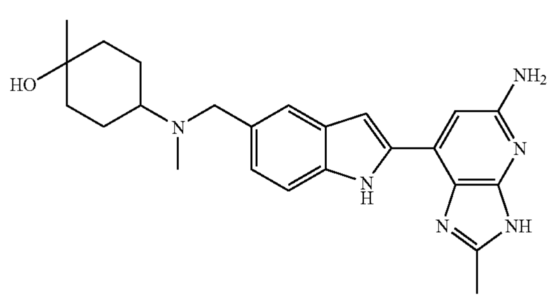 |

-continued

| ER-# | | Structure |
|---|---|---|
| 176 | 807862 | 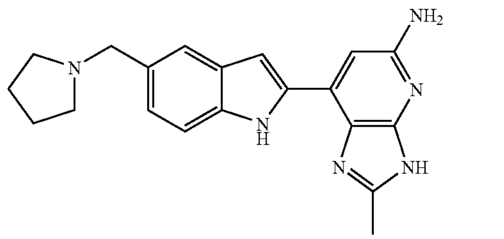 |
| 177 | 807865 | 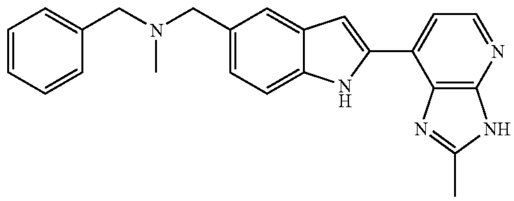 |
| 178 | 807876 | 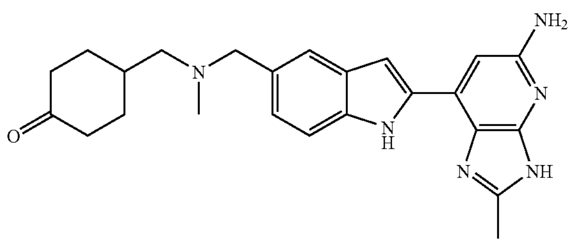 |
| 179 | 807892 | 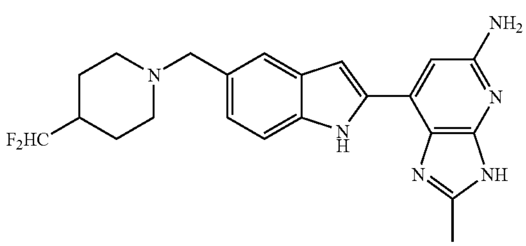 |
| 180 | 807920 | 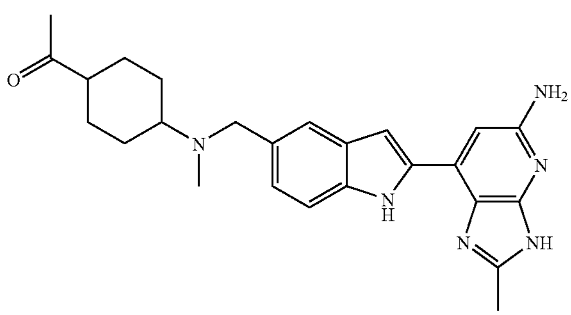 |
| 181 | 807930 | 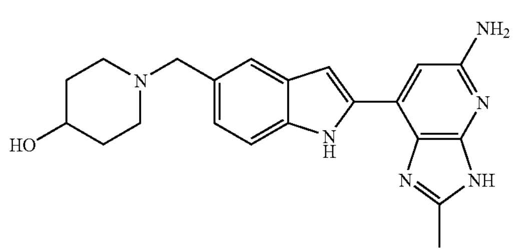 |

| ER-# | Structure |
|---|---|
| 182 | 807931 |
| 183 | 807952 |
| 184 | 807956 |
| 185 | 807962 |
| 186 | 807976 |

-continued
| ER-# | | Structure |
|---|---|---|
| 187 | 807977 | 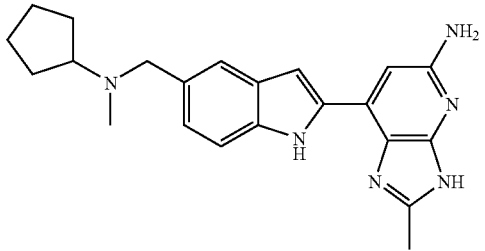 |
| 188 | 807978 | 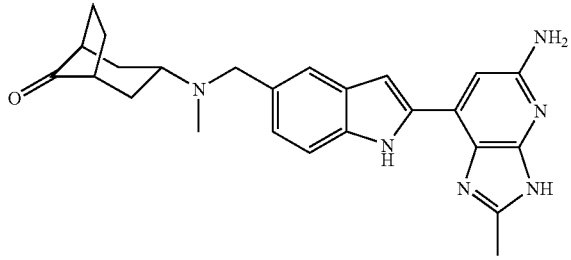 |
| 189 | 807980 | 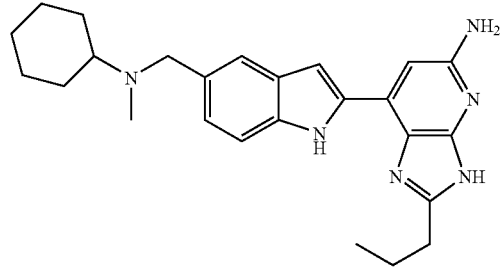 |
| 190 | 808009 | 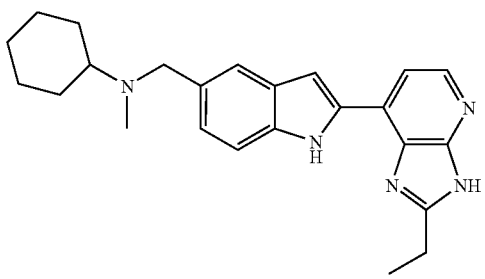 |
| 191 | 808028 | 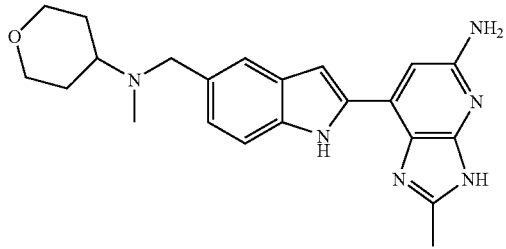 |

-continued

| ER-# | | Structure |
|---|---|---|
| 192 | 808036 | 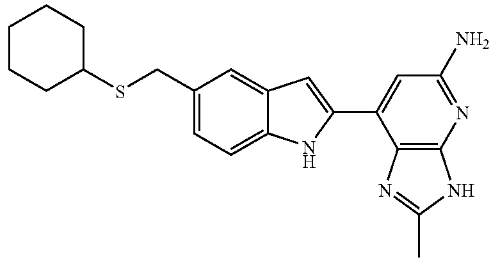 |
| 193 | 808039 | 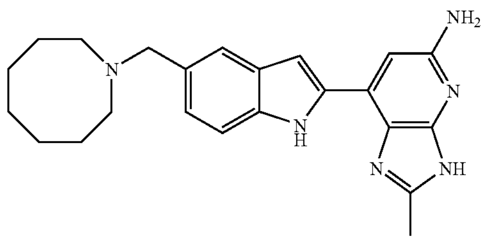 |
| 194 | 808040 | 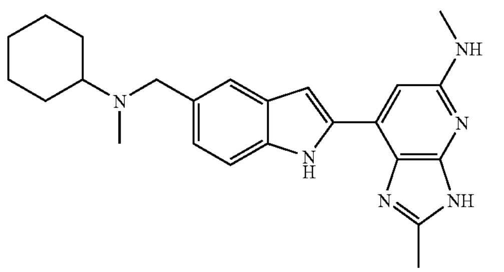 |
| 195 | 808041 | 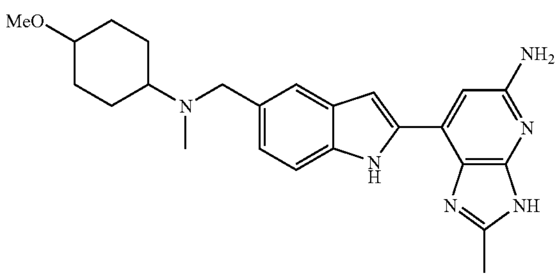 |
| 196 | 808069 | 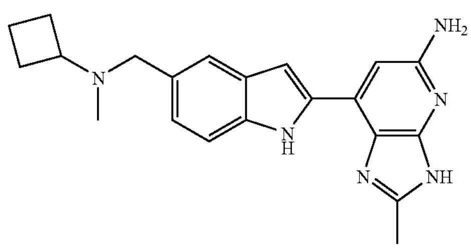 |
| 197 | 808078 | 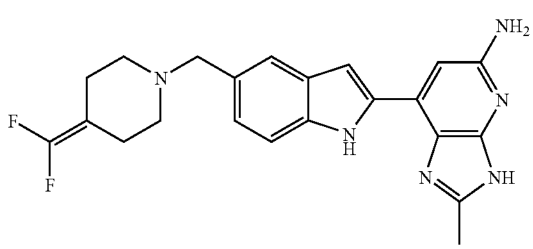 |

| ER-# | Structure |
|---|---|
| 198 | 808079 |
| 199 | 808080 |
| 200 | 808081 |
| 201 | 808082 |
| 202 | 808083 |
| 203 | 808084 |

-continued

| ER-# | | Structure |
|---|---|---|
| 204 | 808085 | 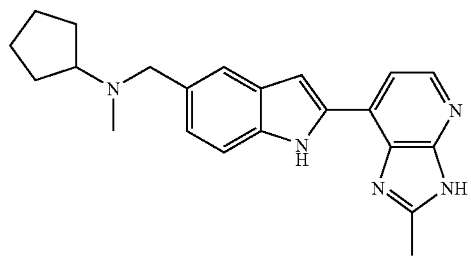 |
| 205 | 808086 | 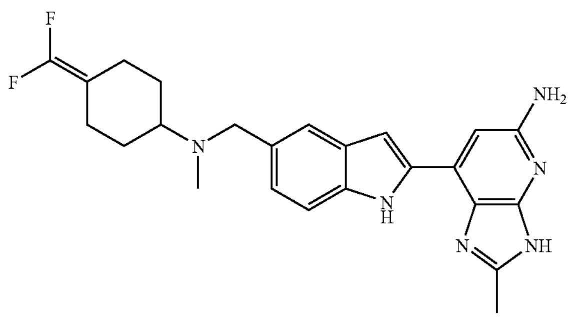 |
| 206 | 808101 | 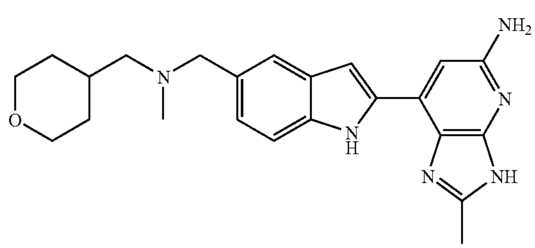 |
| 207 | 808102 | 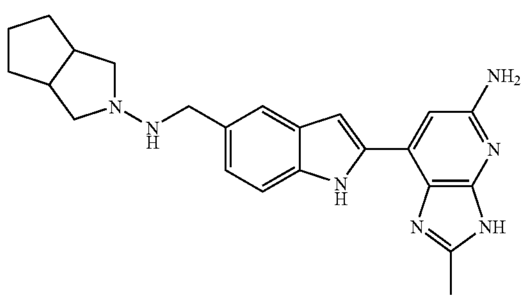 |
| 208 | 808103 | 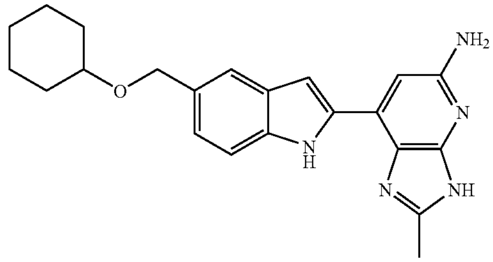 |

-continued

| | ER-# | Structure |
|---|---|---|
| 209 | 808107 | 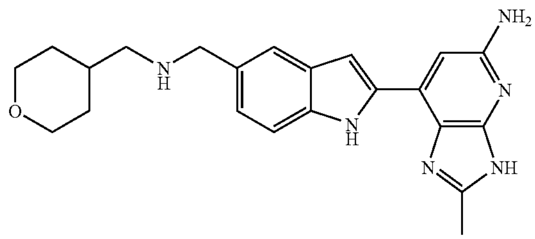 |
| 210 | 808128 | 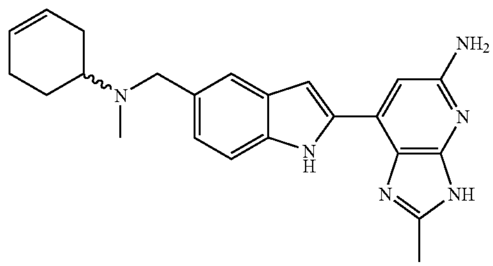 |
| 211 | 808151 | 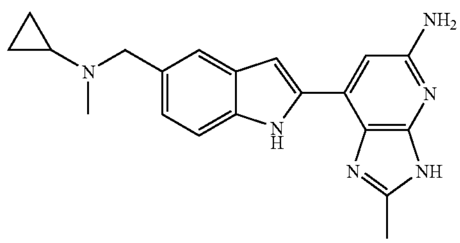 |
| 212 | 808152 | 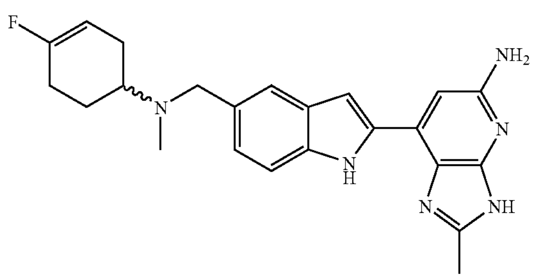 |
| 213 | 808153 | 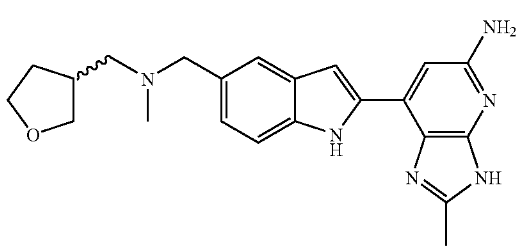 |
| 214 | 808160 | 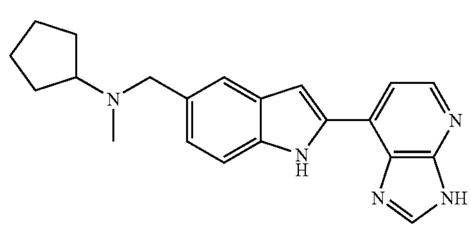 |

-continued

| ER-# | | Structure |
|---|---|---|
| 215 | 808164 | 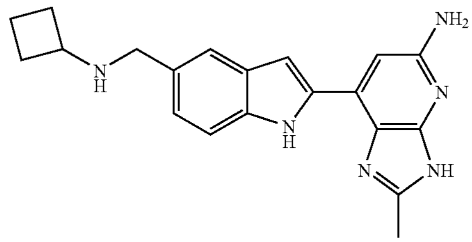 |
| 216 | 808247 | 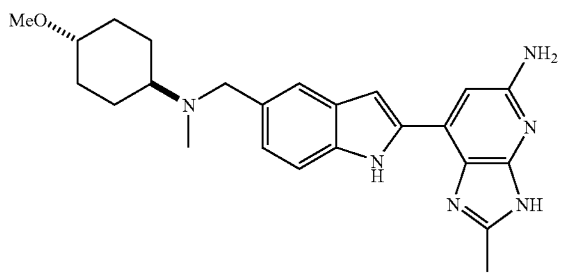 |
| 217 | 808254 | 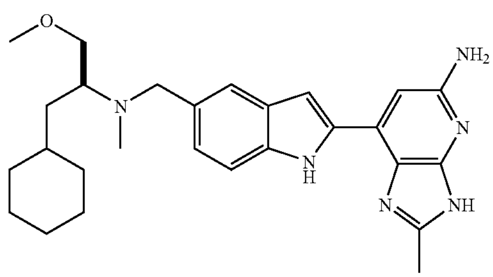 |
| 218 | 808255 | 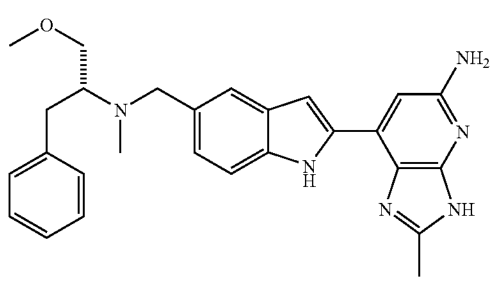 |
| 219 | 808256 | 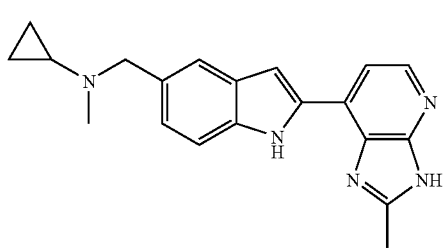 |

-continued
| ER-# | Structure |
|---|---|
| 220 | 808257 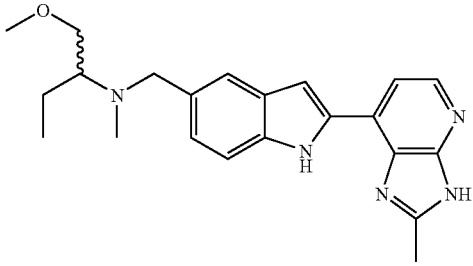 |
| 221 | 808259 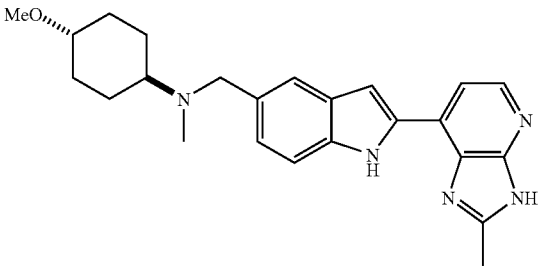 |
| 222 | 808260 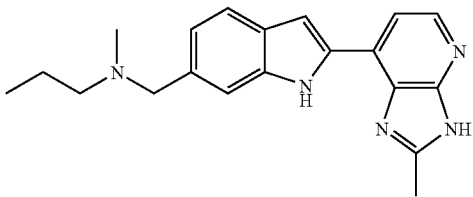 |
| 223 | 808261 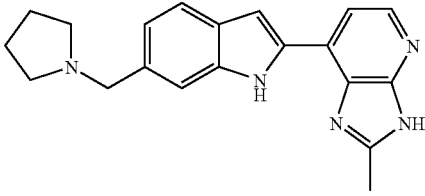 |
| 224 | 808262 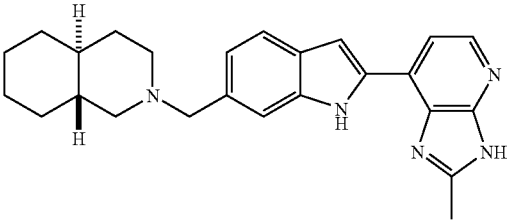 |
| 225 | 808266 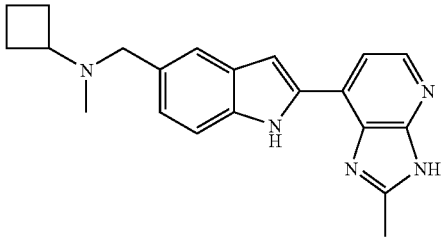 |

| ER-# | Structure |
|---|---|
| 226 808268 | |
| 227 808269 | |
| 228 808281 | |
| 229 808283 | |
| 230 808284 | |
| 231 808285 | |

| ER-# | Structure |
|---|---|
| 232 | 808286 |
| 233 | 808287 |
| 234 | 808288 |
| 235 | 808289 |
| 236 | 808290 |
| 237 | 808291 |

-continued

| ER-# | Structure |
|---|---|
| 238 | 808310 |
| 239 | 808311 |
| 240 | 808312 |
| 241 | 808313 |
| 242 | 808319 |

-continued

| ER-# | Structure |
|------|-----------|

243  808322

244  808346

245  808347

246  808355

247  808356

248  808361

| ER-# | Structure |
|---|---|
| 249 | 808362 |
| 250 | 808363 |
| 251 | 808364 |
| 252 | 808365 |
| 253 | 808370 |

-continued

| ER-# | Structure |
|---|---|
| 254 | 808371 |
| 255 | 808372 |
| 256 | 808385 |
| 257 | 808386 |
| 258 | 808387 |
| 259 | 808388 |

-continued

| ER-# | Structure |
|---|---|
| 260 | 808469 |
| 261 | 808470 |
| 262 | 808473 |
| 263 | 808496 |
| 264 | 808497 |
| 265 | 808498 |
| 266 | 808499 |

-continued
| ER-# | Structure |
|---|---|
| 267 | 808500 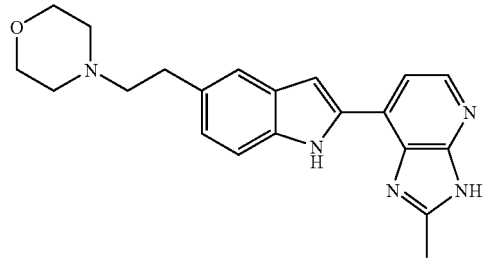 |
| 268 | 808501 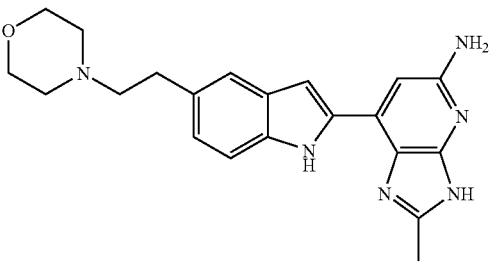 |
| 269 | 808513 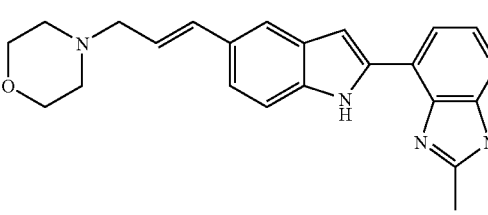 |
| 270 | 808514 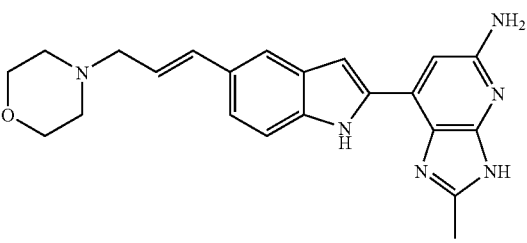 |
| 271 | 808541 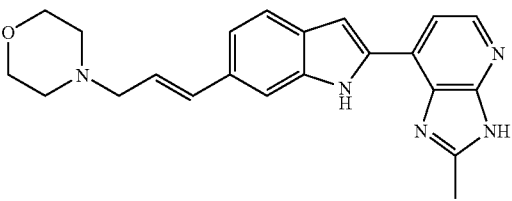 |
| 272 | 808542 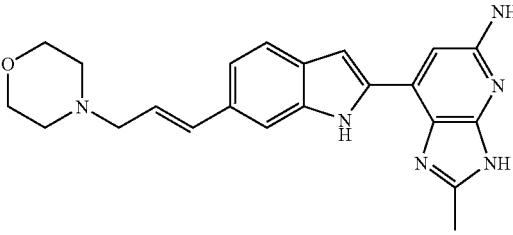 |

-continued

| ER-# | | Structure |
|---|---|---|
| 273 | 808543 | 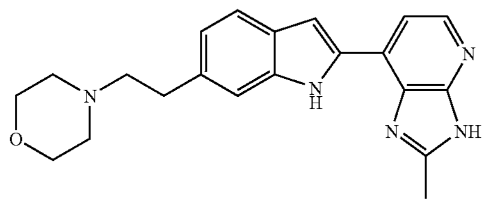 |
| 274 | 808544 | 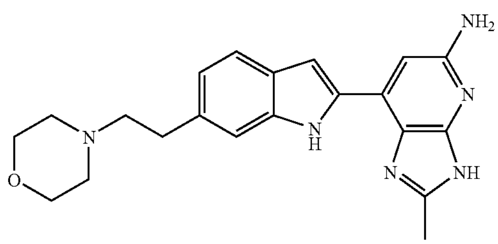 |
| 275 | 808548 | 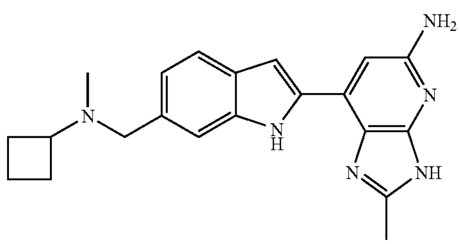 |
| 276 | 808571 | 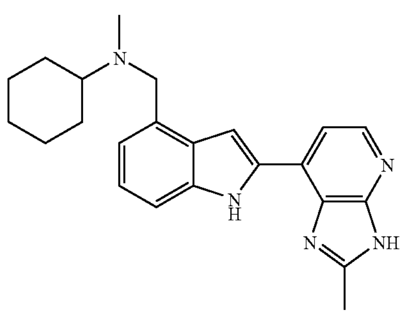 |
| 277 | 808576 | 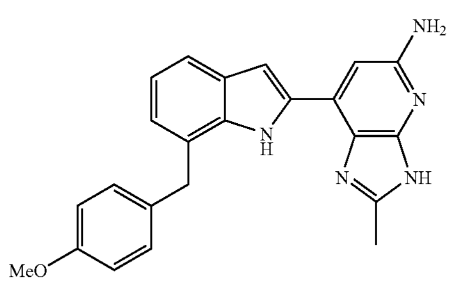 |
| 278 | 808600 | 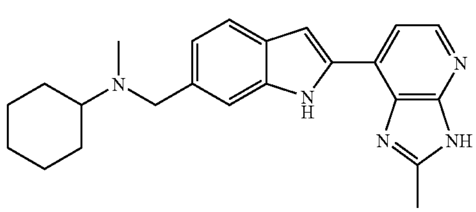 |

-continued

| ER-# | Structure |
|---|---|
| 278 | 808617 |
| 279 | 808620 |
| 280 | 808622 |
| 281 | 808623 |
| 282 | 808624 |
| 283 | 808627 |

-continued

| ER-# | Structure |
|---|---|
| 284 | 808628 |
| 285 | 808629 |
| 286 | 808631 |
| 287 | 808635 |
| 288 | 808636 |
| 289 | 808637 |

| -continued | |
|---|---|
| ER-# | Structure |

290 808658

291 808660

292 808661

293 808663

294 808665

-continued
| ER-# | Structure |
|---|---|
| 295 | 808672 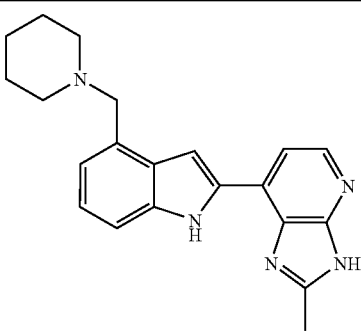 |
| 296 | 808673 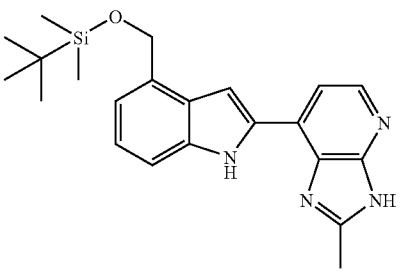 |
| 297 | 808675 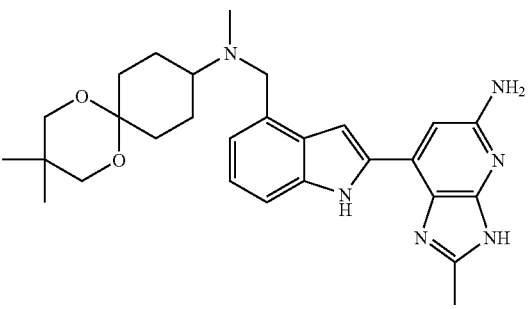 |
| 298 | 808691 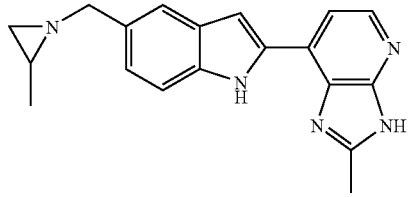 |
| 299 | 808692 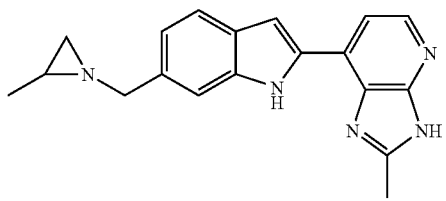 |

-continued
| ER-# | | Structure |
|---|---|---|
| 300 | 808702 | 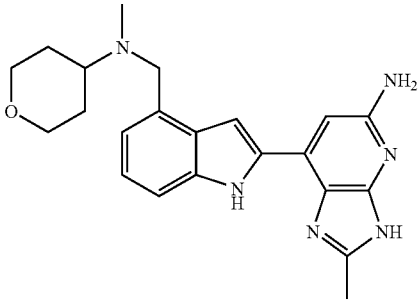 |
| 301 | 808703 | 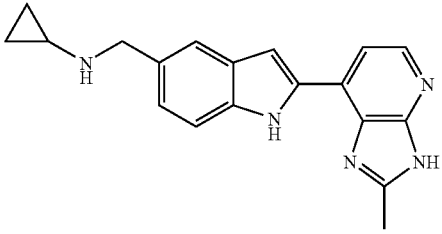 |
| 302 | 808704 | 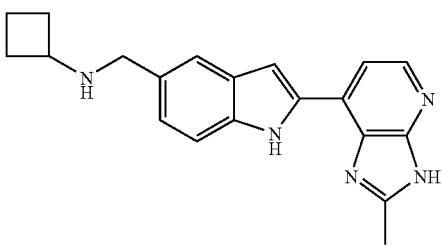 |
| 303 | 808705 | 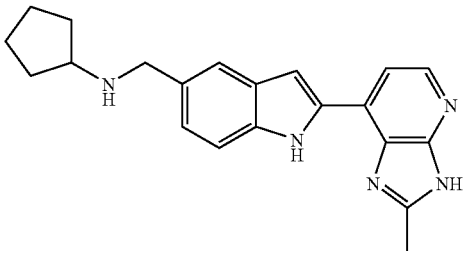 |
| 304 | 808711 | 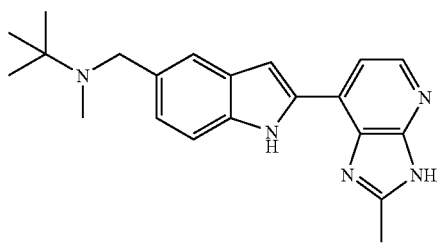 |
| 305 | 808712 | 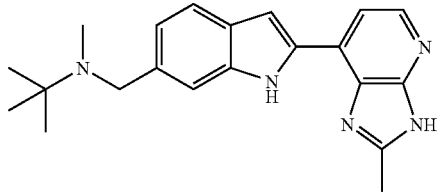 |

-continued

| ER-# | Structure |
|---|---|
| 306 | 808713 |
| 307 | 808714 |
| 308 | 808717 |
| 309 | 808719 |
| 310 | 808720 |
| 311 | 808833 |
| 312 | 808834 |

-continued

| ER-# | Structure |
|---|---|
| 313 | 808835 |
| 314 | 808836 |
| 315 | 808849 |
| 316 | 808983 |
| 317 | 808984 |
| 318 | 809047 |

-continued

| ER-# | Structure |
|---|---|
| 319 | 809187 |
| 320 | 809189 |
| 321 | 809190 |
| 322 | 809191 |
| 323 | 809192 |
| 324 | 809193 |

-continued
| ER-# | | Structure |
|---|---|---|
| 325 | 809196 | 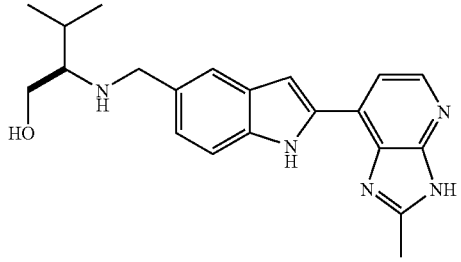 |
| 326 | 809197 | 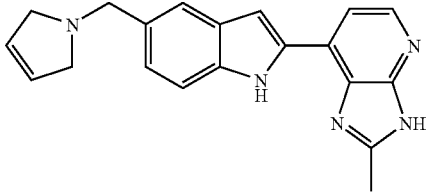 |
| 327 | 809198 | 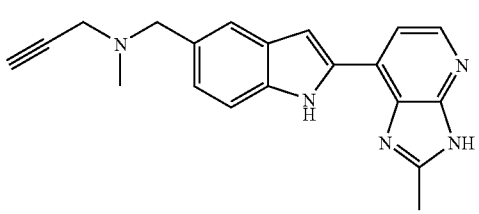 |
| 328 | 809199 | 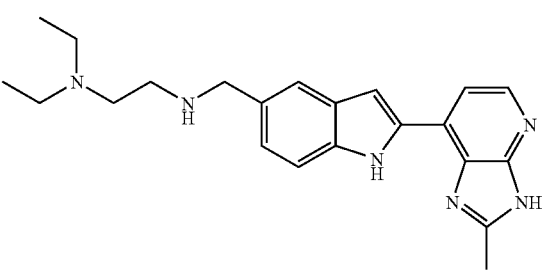 |
| 329 | 809200 | 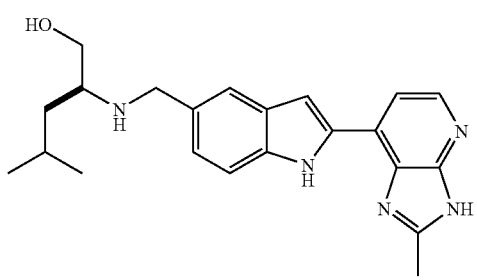 |
| 330 | 809201 | 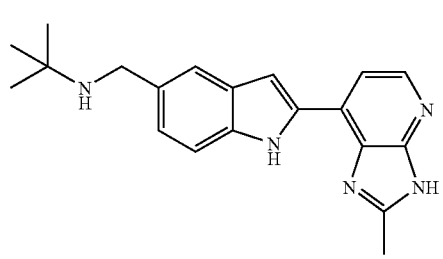 |

| ER-# | Structure |
|---|---|
| 331 809202 | |
| 332 809203 | |
| 333 809204 | |
| 334 809205 | |
| 335 809206 | |
| 336 809207 | |

-continued
| ER-# | Structure |
|---|---|
| 337 | 809208 | 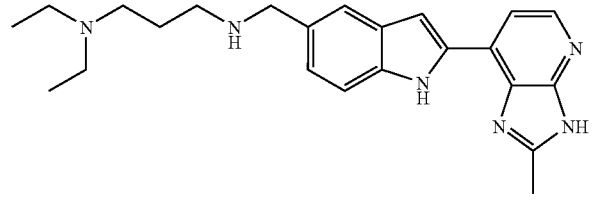 |
| 338 | 809209 | 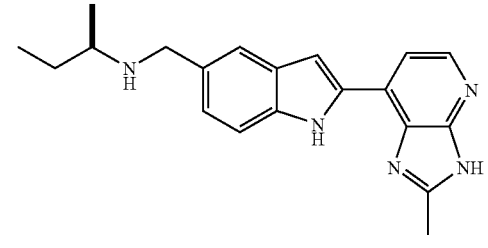 |
| 339 | 809210 | 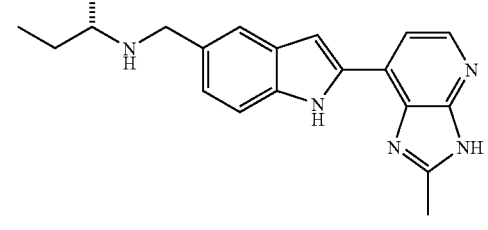 |
| 340 | 809211 | 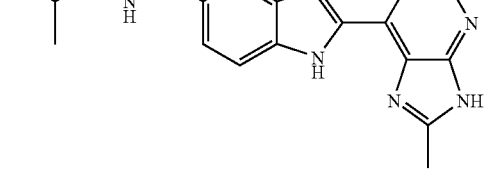 |
| 341 | 809212 | 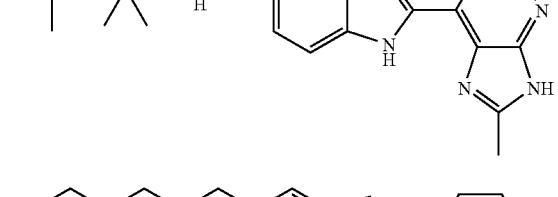 |
| 342 | 809213 | 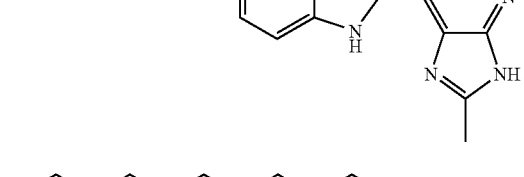 |
| 343 | 809214 | 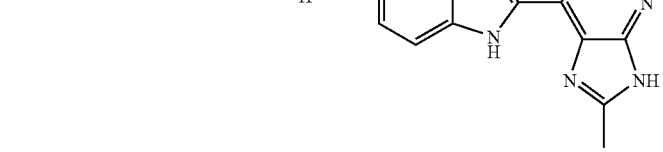 |

-continued

| ER-# | Structure |
|---|---|
| 344 | 809215 |
| 345 | 809216 |
| 346 | 809217 |
| 347 | 809218 |
| 348 | 809219 |
| 349 | 809220 |

-continued
| ER-# | Structure |
|---|---|
| 350 | 809221 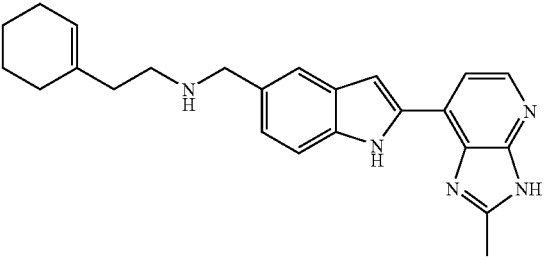 |
| 351 | 809222 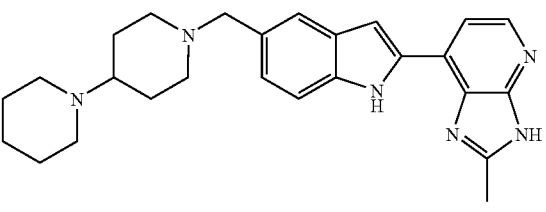 |
| 352 | 809223 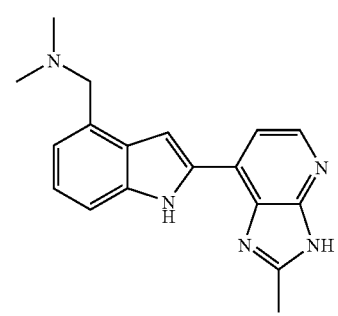 |
| 353 | 809224 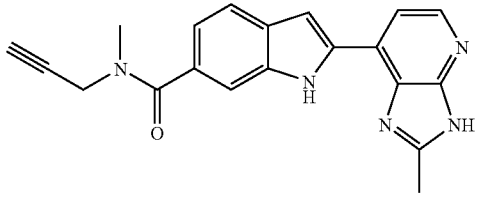 |
| 354 | 809225 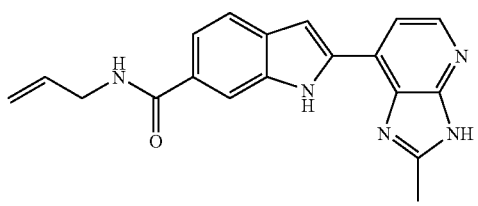 |
| 355 | 809226 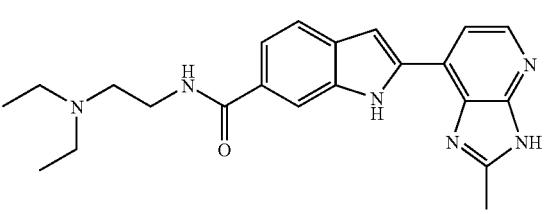 |

-continued

| ER-# | Structure |
|---|---|
| 356 | 809227 |
| 357 | 809228 |
| 358 | 809229 |
| 359 | 809230 |
| 360 | 809231 |
| 361 | 809232 |
| 362 | 809233 |

-continued

| ER-# | | Structure |
|---|---|---|
| 363 | 809234 | 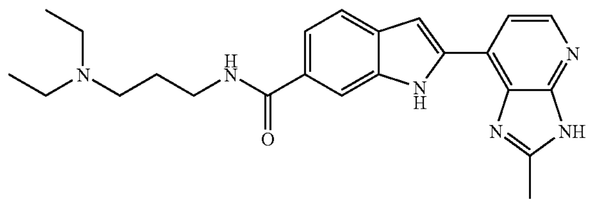 |
| 364 | 809235 | 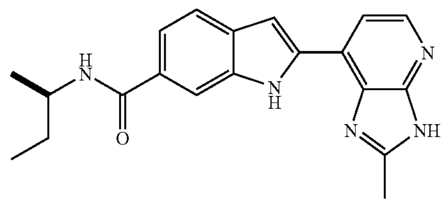 |
| 365 | 809236 | 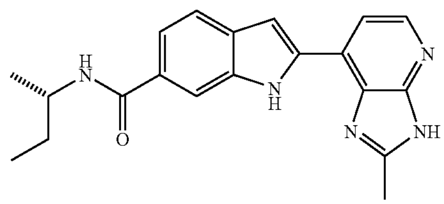 |
| 366 | 809237 | 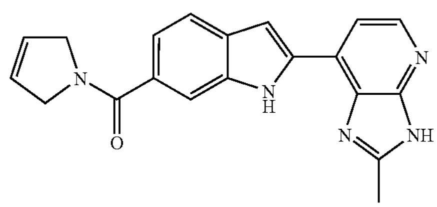 |
| 367 | 809238 | 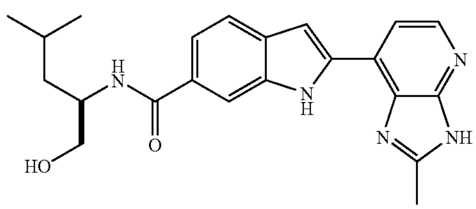 |
| 368 | 809251 | 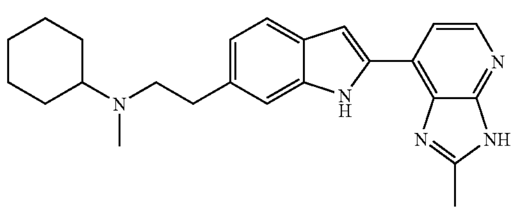 |
| 369 | 809252 | 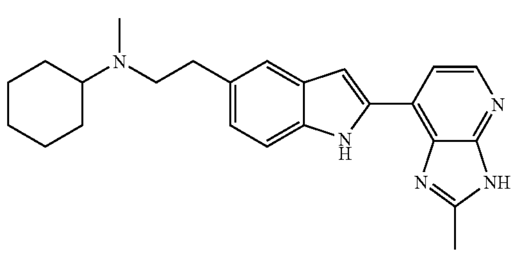 |

-continued

| ER-# | | Structure |
|---|---|---|
| 370 | IC261 | 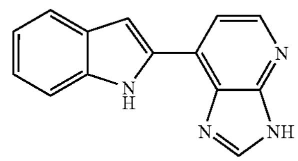 |
| 371 | IC375 | 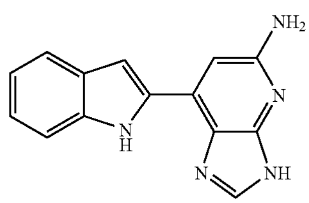 |
| 373 | IC395 | 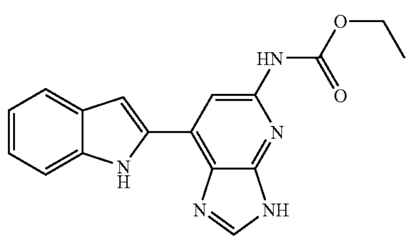 |
| 374 | IC396 | 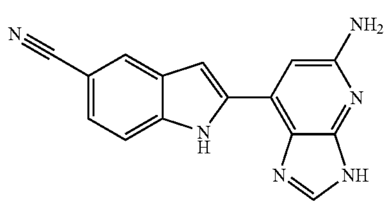 |
| 375 | IC400 | 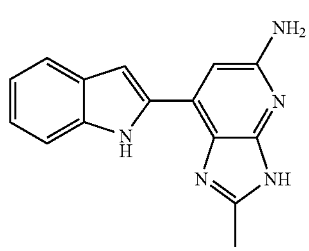 |
| 376 | IC401 | 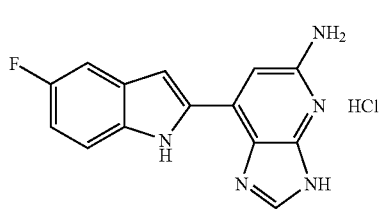 |
| 377 | IC402 | 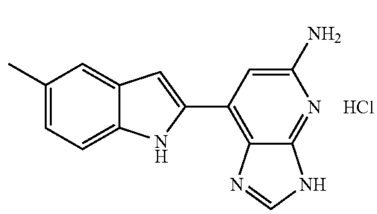 |

| ER-# | Structure |
|---|---|
| 378 IC403 | |
| 379 IC404 | |
| 380 IC415 | |
| 381 IC416 | |
or a pharmaceutically acceptable salt thereof.
31. A compound having the structure:
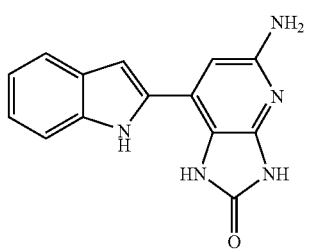
or a pharmaceutically acceptable salt thereof.
32. A compound having the structure of Formula II
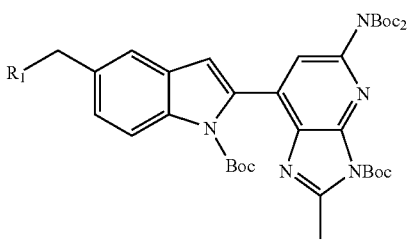
wherein $R_1$ is OH or O-TBS (t-butyldimethylsilyl ether).

33. A compound having the structure of Formula II
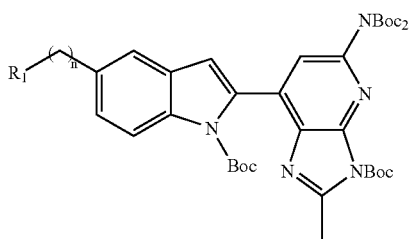
wherein:
n is 1 and $R_1$ is Cl; or
n is 0 and $R_1$ is —COOH.
34. A compound having the structure:
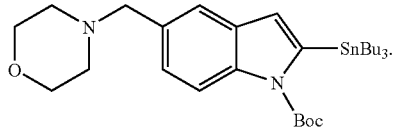
* * * * *

UNITED STATES PATENT AND TRADEMARK OFFICE
CERTIFICATE OF CORRECTION

PATENT NO.      : 7,314,936 B2                                    Page 1 of 1
APPLICATION NO. : 10/500840
DATED           : January 1, 2008
INVENTOR(S)     : Daun et al.

It is certified that error appears in the above-identified patent and that said Letters Patent is hereby corrected as shown below:

Column 327, Claim 16, Line 27:  Please correct "occurrence of R and $R_5$"
                                             To read -- occurrence of $R_4$ and $R_5$ --

Signed and Sealed this

Thirteenth Day of May, 2008

JON W. DUDAS
*Director of the United States Patent and Trademark Office*